US011773436B2

(12) United States Patent
Chang et al.

(10) Patent No.: US 11,773,436 B2
(45) Date of Patent: Oct. 3, 2023

(54) USING RANDOM PRIMING TO OBTAIN FULL-LENGTH V(D)J INFORMATION FOR IMMUNE REPERTOIRE SEQUENCING

(71) Applicant: Becton, Dickinson and Company, Franklin Lakes, NJ (US)

(72) Inventors: Christina Chang, San Jose, CA (US); Margaret Nakamoto, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 219 days.

(21) Appl. No.: 17/091,639

(22) Filed: Nov. 6, 2020

(65) Prior Publication Data
US 2021/0139970 A1    May 13, 2021

Related U.S. Application Data

(60) Provisional application No. 62/933,285, filed on Nov. 8, 2019.

(51) Int. Cl.
| | | |
|---|---|---|
| *C12Q 1/6806* | (2018.01) | |
| *C12Q 1/6865* | (2018.01) | |
| *C12Q 1/6867* | (2018.01) | |
| *C12Q 1/6874* | (2018.01) | |

(52) U.S. Cl.
CPC ......... *C12Q 1/6865* (2013.01); *C12Q 1/6867* (2013.01); *C12Q 1/6874* (2013.01); *C12Q 2521/101* (2013.01); *C12Q 2521/107* (2013.01); *C12Q 2565/1025* (2013.01)

(58) Field of Classification Search
CPC .................................................... C12Q 1/689
See application file for complete search history.

(56) References Cited

U.S. PATENT DOCUMENTS

| | | |
|---|---|---|
| 4,510,244 A | 4/1985 | Parks et al. |
| 4,725,536 A | 2/1988 | Fritsch et al. |
| 5,124,246 A | 6/1992 | Urdea et al. |
| 5,149,625 A | 9/1992 | Church et al. |
| 5,200,314 A | 4/1993 | Urdea |
| 5,308,990 A | 5/1994 | Takahashi et al. |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,830,712 A | 11/1998 | Rampersad et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,962,271 A | 10/1999 | Chenchik et al. |
| 5,962,272 A | 10/1999 | Chenchik et al. |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,064,755 A | 5/2000 | Some |
| 6,114,149 A | 9/2000 | Fry et al. |
| 6,117,631 A | 9/2000 | Nilsen |
| 6,124,092 A | 9/2000 | O'neill et al. |

(Continued)

FOREIGN PATENT DOCUMENTS

| | | |
|---|---|---|
| CA | 2474509 | 2/2003 |
| DE | 102008025656 | 12/2009 |

(Continued)

OTHER PUBLICATIONS

AccuPrime™ Pfx DNA polymerase brochure, Invitrogen, pp. 1-4 (Year: 2010).*
10X Genomics, Inc., 2019, User Guide: Visium Spatial Gene Expression Reagent Kits, www.10xGenomics.com, 76 pp.
2018 Top 10 Innovations, The Scientist Magazine® (2018). Available at: https://www.thescientist.com/features/2018-top-10-innovations-65140, 16 pp.

(Continued)

*Primary Examiner* — Teresa E Strzelecka
(74) *Attorney, Agent, or Firm* — Sheppard, Mullin, Richter & Hampton LLP

(57) ABSTRACT

Disclosed herein include systems, methods, compositions, and kits for labeling nucleic acid targets in a sample. In some embodiments, nucleic acid targets (e.g., mRNAs) are initially barcoded on the 3' end and are subsequently barcoded on the 5' end following a template switching reaction and intermolecular and/or intramolecular hybridization and extension. 5'- and/or 3'-barcoded nucleic acid targets can serve as templates for amplification reactions and/or random priming and extension reactions to generate a sequencing library. The method can comprise generating a full-length sequence of the nucleic acid target by aligning a plurality of sequencing reads. Immune repertoire profiling methods are also provided in some embodiments.

29 Claims, 32 Drawing Sheets

(56) References Cited

U.S. PATENT DOCUMENTS

| | | |
|---|---|---|
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,197,554 B1 | 3/2001 | Lin et al. |
| 6,214,558 B1 | 4/2001 | Shuber et al. |
| 6,235,475 B1 | 5/2001 | Brenner et al. |
| 6,235,483 B1 | 5/2001 | Wolber et al. |
| 6,265,163 B1 | 7/2001 | Albrecht et al. |
| 6,268,152 B1 | 7/2001 | Fodor et al. |
| 6,284,460 B1 | 9/2001 | Fodor et al. |
| 6,284,485 B1 | 9/2001 | Boyle et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,372,813 B1 | 4/2002 | Johnson et al. |
| 6,395,491 B1 | 5/2002 | Fodor et al. |
| 6,406,848 B1 | 6/2002 | Bridgham et al. |
| 6,436,675 B1 | 8/2002 | Welch et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,480,791 B1 | 11/2002 | Strathmann |
| 6,489,114 B2 | 12/2002 | Laayoun et al. |
| 6,489,116 B2 | 12/2002 | Wagner |
| 6,492,121 B2 | 12/2002 | Kurane et al. |
| 6,500,620 B2 | 12/2002 | Yu et al. |
| 6,512,105 B1 | 1/2003 | Hogan et al. |
| 6,514,699 B1 | 2/2003 | O'neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,787,308 B2 | 9/2004 | Balasubramanian et al. |
| 6,808,906 B2 | 10/2004 | Shen et al. |
| 6,849,404 B2 | 2/2005 | Park et al. |
| 6,852,488 B2 | 2/2005 | Fodor et al. |
| 6,858,412 B2 | 2/2005 | Willis et al. |
| 6,890,741 B2 | 5/2005 | Fan et al. |
| 6,946,251 B2 | 9/2005 | Kurn |
| 6,974,669 B2 | 12/2005 | Mirkin et al. |
| 7,022,479 B2 | 4/2006 | Wagner |
| 7,034,145 B2 | 4/2006 | Shen et al. |
| 7,155,050 B1 | 12/2006 | Sloge |
| 7,294,466 B2 | 11/2007 | McMillan |
| 7,323,309 B2 | 1/2008 | Mirkin et al. |
| 7,393,665 B2 | 7/2008 | Brenner |
| 7,407,757 B2 | 8/2008 | Brenner |
| 7,424,368 B2 | 9/2008 | Huang et al. |
| 7,432,055 B2 | 10/2008 | Pemov et al. |
| 7,470,515 B2 | 12/2008 | Rashtchian et al. |
| 7,473,767 B2 | 1/2009 | Dimitrov |
| 7,476,786 B2 | 1/2009 | Chan et al. |
| 7,537,897 B2 | 5/2009 | Brenner et al. |
| 7,544,473 B2 | 6/2009 | Brenner |
| 7,635,566 B2 | 12/2009 | Brenner |
| 7,638,612 B2 | 12/2009 | Rashtchian et al. |
| 7,718,403 B2 | 5/2010 | Kamberov et al. |
| 7,771,946 B2 | 8/2010 | Kurn |
| 7,822,555 B2 | 10/2010 | Huang et al. |
| 7,824,856 B2 | 11/2010 | Monforte |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,071,311 B2 | 12/2011 | Kurn |
| 8,110,351 B2 | 2/2012 | Bosnes |
| 8,114,681 B2 | 2/2012 | Martin et al. |
| 8,148,068 B2 | 4/2012 | Brenner |
| 8,168,385 B2 | 5/2012 | Brenner |
| 8,206,913 B1 | 6/2012 | Kamberov et al. |
| 8,241,850 B2 | 8/2012 | Brenner |
| 8,298,767 B2 | 10/2012 | Brenner et al. |
| 8,318,433 B2 | 11/2012 | Brenner |
| 8,367,051 B2 | 2/2013 | Matyjaszewski et al. |
| 8,420,324 B2 | 4/2013 | Rashtchian et al. |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,535,889 B2 | 9/2013 | Larson et al. |
| 8,563,274 B2 | 10/2013 | Brenner et al. |
| 8,603,749 B2 | 12/2013 | Gillevet et al. |
| 8,679,756 B1 | 3/2014 | Brenner et al. |
| 8,685,678 B2 | 4/2014 | Casbon et al. |
| 8,685,753 B2 | 4/2014 | Martin et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,110 B2 | 9/2014 | Wang et al. |
| 8,841,071 B2 | 9/2014 | Link |
| 8,856,410 B2 | 10/2014 | Park |
| 9,150,852 B2 | 10/2015 | Samuels et al. |
| 9,181,582 B2 | 11/2015 | Kurn |
| 9,188,586 B2 | 11/2015 | Fan et al. |
| 9,228,229 B2 | 1/2016 | Olson et al. |
| 9,262,376 B2 | 2/2016 | Tsuto |
| 9,297,047 B2 | 3/2016 | Furchak et al. |
| 9,371,598 B2 | 6/2016 | Chee |
| 9,582,877 B2 | 2/2017 | Fu et al. |
| 9,593,365 B2 | 3/2017 | Frisen et al. |
| 9,644,204 B2 | 5/2017 | Hindson et al. |
| 9,689,024 B2 | 6/2017 | Hindson et al. |
| 9,695,468 B2 | 7/2017 | Hindson et al. |
| 9,787,810 B1 | 10/2017 | Chiang |
| 9,850,515 B2 | 12/2017 | McCoy et al. |
| 9,856,530 B2 | 1/2018 | Hindson et al. |
| 9,868,979 B2 | 1/2018 | Chee et al. |
| 9,879,313 B2 | 1/2018 | Chee et al. |
| 9,905,005 B2 | 2/2018 | Fu et al. |
| 9,938,523 B2 | 4/2018 | LaBaer |
| 9,951,386 B2 | 4/2018 | Hindson et al. |
| 9,988,660 B2 | 6/2018 | Rashtchian et al. |
| 10,002,316 B2 | 6/2018 | Fodor et al. |
| 10,011,872 B1 | 7/2018 | Belgrader et al. |
| 10,017,761 B2 | 7/2018 | Weissman et al. |
| 10,023,910 B2 | 7/2018 | Drmanac et al. |
| 10,030,267 B2 | 7/2018 | Hindson et al. |
| 10,041,116 B2 | 8/2018 | Hindson et al. |
| 10,131,958 B1 | 11/2018 | Fan et al. |
| 10,138,518 B2 | 11/2018 | Chun |
| 10,151,003 B2 | 12/2018 | Fan et al. |
| 10,208,343 B2 | 2/2019 | Hindson et al. |
| 10,227,648 B2 | 3/2019 | Hindson et al. |
| 10,246,703 B2 | 4/2019 | Church et al. |
| 10,253,364 B2 | 4/2019 | Hindson et al. |
| 10,266,874 B2 | 4/2019 | Weissleder et al. |
| 10,273,541 B2 | 4/2019 | Hindson et al. |
| 10,288,608 B2 | 5/2019 | Kozlov et al. |
| 10,294,511 B2 | 5/2019 | Sanches-Kuiper et al. |
| 10,308,982 B2 | 6/2019 | Chee |
| 10,323,278 B2 | 6/2019 | Belgrader et al. |
| 10,337,061 B2 | 7/2019 | Hindson et al. |
| 10,344,329 B2 | 7/2019 | Hindson et al. |
| 10,450,607 B2 | 10/2019 | Hindson et al. |
| 10,550,429 B2 | 2/2020 | Harada et al. |
| RE47,983 E | 5/2020 | Gao et al. |
| 11,092,607 B2 | 8/2021 | Gaublomme et al. |
| 11,535,882 B2 | 12/2022 | Fu et al. |
| 2001/0024784 A1 | 9/2001 | Wagner |
| 2001/0036632 A1 | 11/2001 | Yu et al. |
| 2002/0019005 A1 | 2/2002 | Kamb |
| 2002/0051986 A1 | 5/2002 | Baez et al. |
| 2002/0065609 A1 | 5/2002 | Ashby |
| 2002/0072058 A1 | 6/2002 | Voelker et al. |
| 2002/0094116 A1 | 7/2002 | Forst et al. |
| 2002/0106666 A1 | 8/2002 | Hayashizaki |

(56) References Cited

U.S. PATENT DOCUMENTS

| | | |
|---|---|---|
| 2002/0132241 A1 | 9/2002 | Fan et al. |
| 2002/0168665 A1 | 11/2002 | Okawa |
| 2002/0172953 A1 | 11/2002 | Mirkin et al. |
| 2002/0187480 A1 | 12/2002 | Brandon |
| 2002/0192687 A1 | 12/2002 | Mirkin et al. |
| 2003/0003490 A1 | 1/2003 | Fan et al. |
| 2003/0013091 A1 | 1/2003 | Dimitrov |
| 2003/0032049 A1 | 2/2003 | Wagner |
| 2003/0049616 A1 | 3/2003 | Brenner et al. |
| 2003/0077611 A1 | 4/2003 | Slepnev |
| 2003/0082818 A1 | 5/2003 | Bahnson et al. |
| 2003/0087242 A1 | 5/2003 | Mirkin et al. |
| 2003/0104436 A1 | 6/2003 | Morris et al. |
| 2003/0165935 A1 | 9/2003 | Vann et al. |
| 2003/0175908 A1 | 9/2003 | Linnarsson |
| 2003/0186251 A1 | 10/2003 | Dunn et al. |
| 2003/0207296 A1 | 11/2003 | Park et al. |
| 2003/0207300 A1 | 11/2003 | Matray et al. |
| 2004/0047769 A1 | 3/2004 | Tanaami |
| 2004/0091864 A1 | 5/2004 | French et al. |
| 2004/0096368 A1 | 5/2004 | Davis et al. |
| 2004/0096892 A1 | 5/2004 | Wang et al. |
| 2004/0121342 A1 | 6/2004 | McKeown |
| 2004/0146901 A1 | 7/2004 | Morris et al. |
| 2004/0147435 A1 | 7/2004 | Hawiger et al. |
| 2004/0157243 A1 | 8/2004 | Huang et al. |
| 2004/0209298 A1 | 10/2004 | Kamberov et al. |
| 2004/0224325 A1 | 11/2004 | Knapp et al. |
| 2004/0259118 A1 | 12/2004 | Macevicz |
| 2005/0019776 A1 | 1/2005 | Callow et al. |
| 2005/0032110 A1 | 2/2005 | Shen et al. |
| 2005/0048500 A1 | 3/2005 | Lawton |
| 2005/0053952 A1 | 3/2005 | Hong et al. |
| 2005/0105077 A1 | 5/2005 | Padmanabhan et al. |
| 2005/0170373 A1 | 8/2005 | Monforte |
| 2005/0175993 A1 | 8/2005 | Wei |
| 2005/0196760 A1 | 9/2005 | Pemov et al. |
| 2005/0214825 A1 | 9/2005 | Stuelpnagel |
| 2005/0250146 A1 | 11/2005 | McMillan |
| 2005/0250147 A1 | 11/2005 | Macevicz |
| 2006/0002824 A1 | 1/2006 | Chang et al. |
| 2006/0035258 A1 | 2/2006 | Tadakamalla et al. |
| 2006/0040297 A1 | 2/2006 | Leamon et al. |
| 2006/0041385 A1 | 2/2006 | Bauer |
| 2006/0057634 A1 | 3/2006 | Rye |
| 2006/0073506 A1 | 4/2006 | Christians et al. |
| 2006/0211030 A1 | 9/2006 | Brenner |
| 2006/0257902 A1 | 11/2006 | Mendoza et al. |
| 2006/0263709 A1 | 11/2006 | Matsumura et al. |
| 2006/0263789 A1 | 11/2006 | Kincaid |
| 2006/0280352 A1 | 12/2006 | Muschler et al. |
| 2006/0281092 A1 | 12/2006 | Wile et al. |
| 2006/0286570 A1 | 12/2006 | Rowlen et al. |
| 2007/0020640 A1 | 1/2007 | Mccloskey et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0065823 A1 | 3/2007 | Dressman et al. |
| 2007/0065844 A1 | 3/2007 | Golub et al. |
| 2007/0105090 A1 | 5/2007 | Cassidy et al. |
| 2007/0117121 A1 | 5/2007 | Hutchison et al. |
| 2007/0117134 A1 | 5/2007 | Kou |
| 2007/0117177 A1 | 5/2007 | Luo et al. |
| 2007/0133856 A1 | 6/2007 | Dutta-Choudhury |
| 2007/0172873 A1 | 7/2007 | Brenner et al. |
| 2007/0178478 A1 | 8/2007 | Dhallan et al. |
| 2007/0202523 A1 | 8/2007 | Becker et al. |
| 2007/0281317 A1 | 12/2007 | Becker et al. |
| 2008/0038727 A1 | 2/2008 | Spier |
| 2008/0070303 A1 | 3/2008 | West et al. |
| 2008/0119736 A1 | 5/2008 | Dentinger |
| 2008/0194414 A1 | 8/2008 | Albert et al. |
| 2008/0261204 A1 | 10/2008 | Lexow |
| 2008/0268508 A1 | 10/2008 | Sowlay |
| 2008/0269068 A1 | 10/2008 | Church et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0053669 A1 | 2/2009 | Liu et al. |
| 2009/0061513 A1 | 3/2009 | Andersson Svahn et al. |
| 2009/0105959 A1 | 4/2009 | Braverman et al. |
| 2009/0131269 A1 | 5/2009 | Martin et al. |
| 2009/0137407 A1 | 5/2009 | Church et al. |
| 2009/0220385 A1 | 9/2009 | Brown et al. |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0290151 A1 | 11/2009 | Agrawal et al. |
| 2009/0298709 A1 | 12/2009 | Ma |
| 2009/0311694 A1 | 12/2009 | Gallagher et al. |
| 2010/0069250 A1 | 3/2010 | White, III |
| 2010/0105049 A1 | 4/2010 | Ehrich et al. |
| 2010/0105112 A1 | 4/2010 | Holtze et al. |
| 2010/0105886 A1 | 4/2010 | Woudenberg et al. |
| 2010/0120098 A1 | 5/2010 | Grunenwald et al. |
| 2010/0120630 A1 | 5/2010 | Huang et al. |
| 2010/0136544 A1 | 6/2010 | Agresti et al. |
| 2010/0159533 A1 | 6/2010 | Lipson et al. |
| 2010/0167354 A1 | 7/2010 | Kurn |
| 2010/0184076 A1 | 7/2010 | Lawton |
| 2010/0255471 A1 | 10/2010 | Clarke |
| 2010/0267028 A1 | 10/2010 | Pasche |
| 2010/0291666 A1 | 11/2010 | Collier et al. |
| 2010/0300895 A1 | 12/2010 | Nobile et al. |
| 2010/0323348 A1 | 12/2010 | Hamady et al. |
| 2010/0330574 A1 | 12/2010 | Whitman |
| 2011/0038507 A1 | 2/2011 | Hager |
| 2011/0059436 A1 | 3/2011 | Hardin et al. |
| 2011/0059556 A1 | 3/2011 | Strey |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0245111 A1 | 10/2011 | Chee |
| 2011/0263457 A1 | 10/2011 | Krutzik et al. |
| 2011/0294689 A1 | 12/2011 | Namsaraev |
| 2011/0312511 A1 | 12/2011 | Winquist et al. |
| 2012/0004132 A1 | 1/2012 | Zhang et al. |
| 2012/0010091 A1 | 1/2012 | Linnarson |
| 2012/0014977 A1 | 1/2012 | Furihata et al. |
| 2012/0034607 A1 | 2/2012 | Rothberg et al. |
| 2012/0040843 A1 | 2/2012 | Ducree et al. |
| 2012/0045844 A1 | 2/2012 | Rothberg et al. |
| 2012/0058520 A1 | 3/2012 | Hayashida |
| 2012/0058902 A1 | 3/2012 | Livingston et al. |
| 2012/0065081 A1 | 3/2012 | Chee |
| 2012/0071331 A1 | 3/2012 | Casbon |
| 2012/0087862 A1 | 4/2012 | Hood et al. |
| 2012/0142018 A1 | 6/2012 | Jiang |
| 2012/0149603 A1 | 6/2012 | Cooney et al. |
| 2012/0156675 A1 | 6/2012 | Lueerssen et al. |
| 2012/0163681 A1 | 6/2012 | Lohse |
| 2012/0165219 A1 | 6/2012 | Van Der Zaag et al. |
| 2012/0173159 A1 | 7/2012 | Davey et al. |
| 2012/0190020 A1 | 7/2012 | Oliphant et al. |
| 2012/0202293 A1 | 8/2012 | Martin et al. |
| 2012/0220022 A1 | 8/2012 | Ehrlich et al. |
| 2012/0220494 A1 | 8/2012 | Samuels et al. |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1 | 2/2013 | Shinozuka et al. |
| 2013/0116130 A1 | 5/2013 | Fu et al. |
| 2013/0190206 A1 | 7/2013 | Leonard |
| 2013/0203047 A1 | 8/2013 | Casbon et al. |
| 2013/0210643 A1 | 8/2013 | Casbon et al. |
| 2013/0210659 A1 | 8/2013 | Watson et al. |

(56) References Cited

U.S. PATENT DOCUMENTS

| | | |
|---|---|---|
| 2013/0224743 A1 | 8/2013 | Casbon et al. |
| 2013/0225418 A1 | 8/2013 | Watson |
| 2013/0225623 A1 | 8/2013 | Buxbaum et al. |
| 2013/0237458 A1 | 9/2013 | Casbon et al. |
| 2013/0267424 A1 | 10/2013 | Casbon et al. |
| 2013/0274117 A1 | 10/2013 | Church |
| 2013/0323732 A1 | 12/2013 | Anderson et al. |
| 2014/0004569 A1 | 1/2014 | Lambowitz et al. |
| 2014/0057799 A1 | 2/2014 | Johnson et al. |
| 2014/0066318 A1 | 3/2014 | Frisen et al. |
| 2014/0147860 A1 | 5/2014 | Kaduchak et al. |
| 2014/0155274 A1 | 6/2014 | Xie et al. |
| 2014/0155295 A1 | 6/2014 | Hindson et al. |
| 2014/0178438 A1 | 6/2014 | Sahin et al. |
| 2014/0194324 A1 | 7/2014 | Gormley et al. |
| 2014/0206079 A1 | 7/2014 | Malinoski et al. |
| 2014/0206547 A1 | 7/2014 | Wang |
| 2014/0216128 A1 | 8/2014 | Trotter et al. |
| 2014/0227684 A1 | 8/2014 | Hindson et al. |
| 2014/0227705 A1 | 8/2014 | Vogelstein et al. |
| 2014/0228239 A1 | 8/2014 | McCoy et al. |
| 2014/0228255 A1 | 8/2014 | Hindson et al. |
| 2014/0235506 A1 | 8/2014 | Hindson et al. |
| 2014/0243242 A1 | 8/2014 | Nicol et al. |
| 2014/0244742 A1 | 8/2014 | Yu et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0322716 A1 | 10/2014 | Robins |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0011396 A1 | 1/2015 | Schroeder et al. |
| 2015/0017654 A1 | 1/2015 | Gorfinkel et al. |
| 2015/0066385 A1 | 3/2015 | Schnall-levin et al. |
| 2015/0072867 A1 | 3/2015 | Soldatov et al. |
| 2015/0072873 A1 | 3/2015 | Heinz et al. |
| 2015/0099661 A1 | 4/2015 | Fodor et al. |
| 2015/0099673 A1 | 4/2015 | Fodor et al. |
| 2015/0111256 A1 | 4/2015 | Church et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0141292 A1 | 5/2015 | Fodor et al. |
| 2015/0152409 A1 | 6/2015 | Seitz et al. |
| 2015/0203897 A1 | 7/2015 | Robons et al. |
| 2015/0211050 A1 | 7/2015 | Iafrate et al. |
| 2015/0218620 A1 | 8/2015 | Behlke et al. |
| 2015/0225777 A1 | 8/2015 | Hindson et al. |
| 2015/0225778 A1 | 8/2015 | Hindson et al. |
| 2015/0247182 A1 | 9/2015 | Faham et al. |
| 2015/0253237 A1 | 9/2015 | Castellarnau et al. |
| 2015/0259734 A1 | 9/2015 | Asbury et al. |
| 2015/0275295 A1 | 10/2015 | Wang et al. |
| 2015/0298091 A1 | 10/2015 | Weitz |
| 2015/0299784 A1 | 10/2015 | Fan et al. |
| 2015/0307874 A1 | 10/2015 | Jaitin |
| 2015/0329852 A1 | 11/2015 | Nolan |
| 2015/0360193 A1 | 12/2015 | Fan et al. |
| 2015/0376609 A1 | 12/2015 | Hindson et al. |
| 2016/0017320 A1 | 1/2016 | Wang et al. |
| 2016/0026758 A1 | 1/2016 | Jabara et al. |
| 2016/0053253 A1 | 2/2016 | Salathia et al. |
| 2016/0055632 A1 | 2/2016 | Fu et al. |
| 2016/0060621 A1 | 3/2016 | Agresti et al. |
| 2016/0060682 A1 | 3/2016 | Pregibon et al. |
| 2016/0068889 A1 | 3/2016 | Gole et al. |
| 2016/0122751 A1 | 5/2016 | LaBaer |
| 2016/0122753 A1 | 5/2016 | Mikkelsen et al. |
| 2016/0138091 A1 | 5/2016 | Chee et al. |
| 2016/0145677 A1 | 5/2016 | Chee et al. |
| 2016/0145683 A1 | 5/2016 | Fan et al. |
| 2016/0153973 A1 | 6/2016 | Smith |
| 2016/0201125 A1 | 7/2016 | Samuels et al. |
| 2016/0208322 A1 | 7/2016 | Anderson et al. |
| 2016/0222378 A1 | 8/2016 | Fodor et al. |
| 2016/0232291 A1 | 8/2016 | Kyriazopoulou-Panagiotopoulou et al. |
| 2016/0244742 A1 | 8/2016 | Linnarsson et al. |
| 2016/0244828 A1 | 8/2016 | Mason |
| 2016/0265027 A1 | 9/2016 | Sanches-Kuiper et al. |
| 2016/0265069 A1 | 9/2016 | Fan et al. |
| 2016/0266094 A1 | 9/2016 | Ankrum et al. |
| 2016/0289669 A1 | 10/2016 | Fan et al. |
| 2016/0289670 A1 | 10/2016 | Samuels et al. |
| 2016/0298180 A1 | 10/2016 | Chee |
| 2016/0312276 A1 | 10/2016 | Fu et al. |
| 2016/0320720 A1 | 11/2016 | Murata et al. |
| 2016/0355879 A1 | 12/2016 | Kamberov et al. |
| 2016/0362730 A1 | 12/2016 | Alexander et al. |
| 2017/0044525 A1 | 2/2017 | Kaper et al. |
| 2017/0136458 A1 | 5/2017 | Dunne et al. |
| 2017/0154421 A1 | 6/2017 | Fu et al. |
| 2017/0192013 A1 | 7/2017 | Agresti et al. |
| 2017/0260584 A1 | 9/2017 | Zheng et al. |
| 2017/0275669 A1 | 9/2017 | Weissleder et al. |
| 2017/0314067 A1 | 11/2017 | Shum et al. |
| 2017/0342405 A1 | 11/2017 | Fu et al. |
| 2017/0342465 A1 | 11/2017 | Shum et al. |
| 2017/0342484 A1 | 11/2017 | Shum et al. |
| 2017/0344866 A1 | 11/2017 | Fan et al. |
| 2018/0016634 A1 | 1/2018 | Hindson et al. |
| 2018/0024139 A1 | 1/2018 | Peikon et al. |
| 2018/0030522 A1 | 2/2018 | Kamberov et al. |
| 2018/0037942 A1 | 2/2018 | Fu et al. |
| 2018/0057873 A1 | 3/2018 | Zhou et al. |
| 2018/0088112 A1 | 3/2018 | Fan et al. |
| 2018/0094312 A1 | 4/2018 | Hindson et al. |
| 2018/0094314 A1 | 4/2018 | Hindson et al. |
| 2018/0094315 A1 | 4/2018 | Hindson et al. |
| 2018/0105808 A1 | 4/2018 | Mikkelsen et al. |
| 2018/0112266 A1 | 4/2018 | Hindson et al. |
| 2018/0127743 A1 | 5/2018 | Vigneault et al. |
| 2018/0142292 A1 | 5/2018 | Hindson et al. |
| 2018/0163201 A1 | 6/2018 | Larson |
| 2018/0179590 A1 | 6/2018 | Belgrader et al. |
| 2018/0179591 A1 | 6/2018 | Belgrader et al. |
| 2018/0201923 A1 | 7/2018 | LaBaer |
| 2018/0201980 A1 | 7/2018 | Chee et al. |
| 2018/0208975 A1 | 7/2018 | Peterson et al. |
| 2018/0216174 A1 | 8/2018 | Shum et al. |
| 2018/0230527 A1 | 8/2018 | Fang et al. |
| 2018/0251825 A1 | 9/2018 | Stoeckius et al. |
| 2018/0258482 A1 | 9/2018 | Hindson et al. |
| 2018/0276332 A1 | 9/2018 | Fan et al. |
| 2018/0282803 A1 | 10/2018 | Belgrader et al. |
| 2018/0002738 A1 | 11/2018 | Wang et al. |
| 2018/0320241 A1 | 11/2018 | Nolan et al. |
| 2018/0340170 A1 | 11/2018 | Belhocine et al. |
| 2018/0346969 A1 | 12/2018 | Chang et al. |
| 2018/0346970 A1 | 12/2018 | Chang et al. |
| 2018/0371536 A1 | 12/2018 | Fu et al. |
| 2019/0010552 A1 | 1/2019 | Xu et al. |
| 2019/0025304 A1 | 1/2019 | Vigneault et al. |
| 2019/0032129 A1 | 1/2019 | Hindson et al. |
| 2019/0095578 A1 | 3/2019 | Shum et al. |
| 2019/0119726 A1 | 4/2019 | Shum et al. |
| 2019/0136316 A1 | 5/2019 | Hindson et al. |
| 2019/0136317 A1 | 5/2019 | Hindson et al. |
| 2019/0136319 A1 | 5/2019 | Hindson et al. |
| 2019/0161743 A1 | 5/2019 | Church et al. |
| 2019/0177788 A1 | 6/2019 | Hindson et al. |
| 2019/0177800 A1 | 6/2019 | Boutet et al. |

(56) References Cited

U.S. PATENT DOCUMENTS

| | | |
|---|---|---|
| 2019/0203270 A1 | 7/2019 | Amit et al. |
| 2019/0203291 A1 | 7/2019 | Hindson et al. |
| 2019/0211395 A1 | 7/2019 | Tsao et al. |
| 2019/0218276 A1 | 7/2019 | Regev et al. |
| 2019/0218607 A1 | 7/2019 | Love et al. |
| 2019/0221287 A1 | 7/2019 | Tsujimoto |
| 2019/0221292 A1 | 7/2019 | Tsujimoto |
| 2019/0256888 A1 | 8/2019 | Weissleder et al. |
| 2019/0256907 A1 | 8/2019 | Ryan et al. |
| 2019/0292592 A1 | 9/2019 | Shum et al. |
| 2019/0338353 A1 | 11/2019 | Belgrader et al. |
| 2019/0338357 A1 | 11/2019 | Fan et al. |
| 2019/0390253 A1 | 12/2019 | Kennedy et al. |
| 2020/0102598 A1 | 4/2020 | Xie et al. |
| 2020/0109437 A1 | 4/2020 | Chang et al. |
| 2020/0115753 A1 | 4/2020 | Shalek et al. |
| 2020/0149037 A1 | 5/2020 | Shum |
| 2021/0039582 A1 | 2/2021 | Patton et al. |
| 2021/0123044 A1 | 4/2021 | Zhang et al. |
| 2021/0132078 A1 | 5/2021 | Peikon et al. |
| 2021/0198754 A1 | 7/2021 | Fan et al. |
| 2021/0213413 A1 | 7/2021 | Saligrama et al. |
| 2021/0214770 A1 | 7/2021 | Prosen et al. |
| 2021/0214784 A1 | 7/2021 | Prosen et al. |
| 2021/0222163 A1 | 7/2021 | Wu et al. |
| 2021/0222244 A1 | 7/2021 | Martin et al. |
| 2021/0230582 A1 | 7/2021 | Fu et al. |
| 2021/0230583 A1 | 7/2021 | Lam et al. |
| 2021/0230666 A1 | 7/2021 | Wu et al. |
| 2021/0246492 A1 | 8/2021 | Song et al. |
| 2021/0263019 A1 | 8/2021 | Martin et al. |
| 2021/0355484 A1 | 11/2021 | Jensen et al. |
| 2021/0371909 A1 | 12/2021 | Lazaruk |
| 2021/0371914 A1 | 12/2021 | Stoeckius et al. |
| 2022/0010361 A1 | 1/2022 | Song et al. |
| 2022/0010362 A1 | 1/2022 | Campbell |
| 2022/0033810 A1 | 2/2022 | Song et al. |
| 2022/0154288 A1 | 5/2022 | Mortimer |
| 2022/0162773 A1 | 5/2022 | Sakofsky et al. |
| 2022/0348904 A1 | 5/2022 | Shum et al. |
| 2022/0178909 A1 | 6/2022 | Huang et al. |
| 2022/0214356 A1 | 7/2022 | Henikoff et al. |
| 2022/0219170 A1 | 7/2022 | Khurana et al. |
| 2022/0220549 A1 | 7/2022 | Shum et al. |
| 2022/0267759 A1 | 8/2022 | Sanjana et al. |
| 2022/0333185 A1 | 10/2022 | Fu et al. |

FOREIGN PATENT DOCUMENTS

| | | |
|---|---|---|
| EP | 1473080 | 11/2004 |
| EP | 1647600 | 4/2006 |
| EP | 1845160 | 10/2007 |
| EP | 2036989 | 3/2009 |
| EP | 1379693 | 5/2009 |
| EP | 2204456 | 7/2010 |
| EP | 2431465 | 3/2012 |
| EP | 2203749 | 8/2012 |
| EP | 2511708 | 10/2012 |
| EP | 2538220 | 12/2012 |
| EP | 2623613 | 8/2013 |
| EP | 1745155 | 10/2014 |
| EP | 2805769 | 11/2014 |
| EP | 2556171 | 9/2015 |
| EP | 2970958 | 12/2017 |
| EP | 3263715 | 1/2018 |
| EP | 2670863 B1 | 6/2018 |
| EP | 3136103 | 8/2018 |
| EP | 2954102 | 12/2018 |
| EP | 3428290 | 1/2019 |
| EP | 2970957 | 4/2019 |
| EP | 3058092 | 5/2019 |
| EP | 3256606 | 5/2019 |
| EP | 3327123 | 8/2019 |
| GB | 2293238 A | 3/1996 |
| JP | H04108385 | 4/1992 |
| JP | 2001078768 | 3/2001 |
| JP | 2005233974 | 9/2005 |
| JP | 2007504831 | 3/2007 |
| JP | 2008256428 | 10/2008 |
| JP | 2013039275 | 2/2013 |
| WO | WO1989001050 | 2/1989 |
| WO | WO1996024061 | 8/1996 |
| WO | WO1997010365 | 3/1997 |
| WO | WO1999015702 | 4/1999 |
| WO | WO1999028505 | 6/1999 |
| WO | WO2000058516 | 10/2000 |
| WO | WO2001048242 | 7/2001 |
| WO | WO2001053539 | 7/2001 |
| WO | WO2002018643 | 3/2002 |
| WO | WO2002046472 | 6/2002 |
| WO | WO2002056014 | 7/2002 |
| WO | WO2002059355 | 8/2002 |
| WO | WO2002070684 | 9/2002 |
| WO | WO2002072772 | 9/2002 |
| WO | WO2002079490 | 10/2002 |
| WO | WO2002083922 | 10/2002 |
| WO | WO2002101358 | 12/2002 |
| WO | WO2003031591 | 4/2003 |
| WO | WO2003035829 | 5/2003 |
| WO | WO2004017374 | 2/2004 |
| WO | WO2004021986 | 3/2004 |
| WO | WO2004033669 | 4/2004 |
| WO | WO2004066185 | 8/2004 |
| WO | WO2004081225 | 9/2004 |
| WO | WO2005017206 | 2/2005 |
| WO | WO2005021731 | 3/2005 |
| WO | WO2005042759 | 5/2005 |
| WO | WO2005071110 | 8/2005 |
| WO | WO2005080604 | 9/2005 |
| WO | WO2005111242 | 11/2005 |
| WO | WO2005111243 | 11/2005 |
| WO | WO2006026828 | 3/2006 |
| WO | WO2006071776 | 7/2006 |
| WO | WO2006102264 | 9/2006 |
| WO | WO2006137932 | 12/2006 |
| WO | WO2007087310 | 8/2007 |
| WO | WO2007087312 | 8/2007 |
| WO | WO2007147079 | 12/2007 |
| WO | WO2008047428 | 4/2008 |
| WO | WO2008051928 | 5/2008 |
| WO | WO2008057163 | 5/2008 |
| WO | WO2008096318 | 8/2008 |
| WO | WO2008104380 | 9/2008 |
| WO | WO2008147428 | 12/2008 |
| WO | WO2008150432 | 12/2008 |
| WO | WO2009048530 | 4/2009 |
| WO | WO2009148560 | 12/2009 |
| WO | WO2009152928 | 12/2009 |
| WO | WO2010059820 | 5/2010 |
| WO | WO2010117620 | 10/2010 |
| WO | WO2011091393 | 7/2011 |
| WO | WO2011106738 | 9/2011 |
| WO | WO2011123246 | 10/2011 |
| WO | WO2011127099 | 10/2011 |
| WO | WO2011143659 | 11/2011 |
| WO | WO2011155833 | 12/2011 |
| WO | WO2012038839 | 3/2012 |
| WO | WO2012041802 | 4/2012 |
| WO | WO2012042374 | 4/2012 |
| WO | WO2012047297 | 4/2012 |
| WO | WO2012048341 | 4/2012 |
| WO | WO2012083225 | 6/2012 |
| WO | WO2012099896 | 7/2012 |
| WO | WO2012103154 | 8/2012 |
| WO | WO2012108864 | 8/2012 |
| WO | WO2012112804 | 8/2012 |
| WO | WO2012129363 | 9/2012 |
| WO | WO2012140224 | 10/2012 |
| WO | WO2012142213 | 10/2012 |
| WO | WO2012148477 | 11/2012 |
| WO | WO2012148497 | 11/2012 |
| WO | WO2012149042 | 11/2012 |
| WO | WO2012156744 | 11/2012 |
| WO | WO2012162267 | 11/2012 |

(56) References Cited

FOREIGN PATENT DOCUMENTS

| | | |
|---|---|---|
| WO | WO2012177639 | 12/2012 |
| WO | WO2013019075 | 2/2013 |
| WO | WO2013070990 | 5/2013 |
| WO | WO2013096802 | 6/2013 |
| WO | WO2013117595 | 8/2013 |
| WO | WO2013130674 | 9/2013 |
| WO | WO2013148525 | 10/2013 |
| WO | WO2013173394 | 11/2013 |
| WO | WO2013176767 | 11/2013 |
| WO | WO2013177206 | 11/2013 |
| WO | WO2013188831 | 12/2013 |
| WO | WO2013188872 | 12/2013 |
| WO | WO2013191775 | 12/2013 |
| WO | WO2014015084 | 1/2014 |
| WO | WO2014015098 | 1/2014 |
| WO | WO2014018093 | 1/2014 |
| WO | WO2014018460 | 1/2014 |
| WO | WO2014028537 | 2/2014 |
| WO | WO2014031997 | 2/2014 |
| WO | WO2014065756 | 5/2014 |
| WO | WO2014093676 | 6/2014 |
| WO | WO2014108850 | 7/2014 |
| WO | WO2014124046 | 8/2014 |
| WO | WO2014124336 | 8/2014 |
| WO | WO2014124338 | 8/2014 |
| WO | WO2014126937 | 8/2014 |
| WO | WO2014144495 | 9/2014 |
| WO | WO2014145458 | 9/2014 |
| WO | WO2014176575 | 10/2014 |
| WO | WO2014200767 | 12/2014 |
| WO | WO2014201273 | 12/2014 |
| WO | WO2014204939 | 12/2014 |
| WO | WO2014210223 | 12/2014 |
| WO | WO2014210225 | 12/2014 |
| WO | WO2014210353 | 12/2014 |
| WO | WO2015002908 | 1/2015 |
| WO | WO2015031691 | 3/2015 |
| WO | WO2015035087 | 3/2015 |
| WO | WO2015044428 | 4/2015 |
| WO | WO2015047186 | 4/2015 |
| WO | WO2015057985 | 4/2015 |
| WO | WO2014071361 | 5/2015 |
| WO | WO2015061844 | 5/2015 |
| WO | WO2015103339 | 7/2015 |
| WO | WO2015117163 | 8/2015 |
| WO | WO2015134787 | 9/2015 |
| WO | WO2015160439 | 10/2015 |
| WO | WO2015168161 | 11/2015 |
| WO | WO2015179339 | 11/2015 |
| WO | WO2015200869 | 12/2015 |
| WO | WO2015200893 | 12/2015 |
| WO | WO2016044227 | 3/2016 |
| WO | WO2016049418 | 3/2016 |
| WO | WO2016061517 | 4/2016 |
| WO | WO2016100976 | 6/2016 |
| WO | WO2016118915 | 7/2016 |
| WO | WO2016126871 | 8/2016 |
| WO | WO2016130578 | 8/2016 |
| WO | WO2016160965 | 8/2016 |
| WO | WO2016138496 | 9/2016 |
| WO | WO2016138500 | 9/2016 |
| WO | WO2016145409 | 9/2016 |
| WO | WO2016149418 | 9/2016 |
| WO | WO2016160844 | 10/2016 |
| WO | WO2016168825 | 10/2016 |
| WO | WO2016172373 | 10/2016 |
| WO | WO2016190795 | 12/2016 |
| WO | WO2016191272 | 12/2016 |
| WO | WO2017032808 | 3/2017 |
| WO | WO2017040306 | 3/2017 |
| WO | WO2017044574 | 3/2017 |
| WO | WO2017053905 | 3/2017 |
| WO | WO2017079593 | 5/2017 |
| WO | WO2017087873 | 5/2017 |
| WO | WO2017096239 | 6/2017 |
| WO | WO2017097939 | 6/2017 |
| WO | WO2017117358 | 7/2017 |
| WO | WO2017125508 | 7/2017 |
| WO | WO2017139690 | 8/2017 |
| WO | WO2017164936 | 9/2017 |
| WO | WO2017173328 | 10/2017 |
| WO | WO2017205691 | 11/2017 |
| WO | WO2018017949 | 1/2018 |
| WO | WO2018020489 | 2/2018 |
| WO | WO2018031631 | 2/2018 |
| WO | WO2018058073 | 3/2018 |
| WO | WO2018064640 | 4/2018 |
| WO | WO2018075693 | 4/2018 |
| WO | WO2018111872 | 6/2018 |
| WO | WO2018115852 | 6/2018 |
| WO | WO2018119447 | 6/2018 |
| WO | WO2018132635 | 7/2018 |
| WO | WO2018140966 | 8/2018 |
| WO | WO2018144240 | 8/2018 |
| WO | WO2018144813 | 8/2018 |
| WO | WO2018174827 | 9/2018 |
| WO | WO2018217862 | 11/2018 |
| WO | WO2018218222 | 11/2018 |
| WO | WO2018222548 | 12/2018 |
| WO | WO2018226293 | 12/2018 |
| WO | WO2019055852 | 3/2019 |
| WO | WO2019076768 | 4/2019 |
| WO | WO2019084046 | 5/2019 |
| WO | WO2019099906 | 5/2019 |
| WO | WO2019113457 | 6/2019 |
| WO | WO2019113499 | 6/2019 |
| WO | WO2019113506 | 6/2019 |
| WO | WO2019113533 | 6/2019 |
| WO | WO2019118355 | 6/2019 |
| WO | WO2019126789 | 6/2019 |
| WO | WO2019157529 | 8/2019 |
| WO | WO2013137737 | 9/2019 |
| WO | WO2019178164 | 9/2019 |
| WO | WO2019213237 | 11/2019 |
| WO | WO2019213294 | 11/2019 |
| WO | WO2019218101 | 11/2019 |
| WO | WO2020028266 | 2/2020 |
| WO | WO2020033164 | 2/2020 |
| WO | WO2020037065 | 2/2020 |
| WO | WO2020046833 | 3/2020 |
| WO | WO2020072380 | 4/2020 |
| WO | WO2020097315 | 5/2020 |
| WO | WO2020123384 | 6/2020 |
| WO | WO2020131699 | 6/2020 |
| WO | WO2020154247 | 7/2020 |
| WO | WO2020159757 | 8/2020 |
| WO | WO2020167920 | 8/2020 |
| WO | WO2020214642 | 10/2020 |
| WO | WO2020242377 | 12/2020 |
| WO | WO2021092386 | 5/2021 |
| WO | WO2021142233 | 7/2021 |
| WO | WO2021146207 | 7/2021 |
| WO | WO2021146219 | 7/2021 |
| WO | WO2021146636 | 7/2021 |
| WO | WO2021155057 | 8/2021 |
| WO | WO2021155284 | 8/2021 |
| WO | WO2021163374 | 8/2021 |
| WO | WO2021168015 | 8/2021 |
| WO | WO2021168261 | 8/2021 |
| WO | WO20210178199 | 9/2021 |
| WO | WO2021247593 | 12/2021 |
| WO | WO2022015667 | 1/2022 |
| WO | WO2022026909 | 2/2022 |
| WO | WO2022040453 | 2/2022 |
| WO | WO2022143221 | 7/2022 |

OTHER PUBLICATIONS

Achim et al., "High-throughput spatial mapping of single-cell RNA-seq data to tissue of origin," Nature Biotechnology 2015, 33(5), 503-511.

Advisory Action dated Nov. 29, 2019 in U.S. Appl. No. 15/084,307.

Advisory Action dated Dec. 2, 2019 in U.S. Appl. No. 15/055,407.

Advisory Action dated Aug. 25, 2020 in U.S. Appl. No. 15/084,307.

(56) References Cited

OTHER PUBLICATIONS

Agasti et al., "Photocleavable DNA barcode-antibody conjugates allow sensitive and multiplexed protein analysis in single cell," J Am Chem Soc. 2012, 134(45), 18499-18502.
Alexandra M. Ewing of Richards, Layton and Finger, P.A., Entry of Appearance dated Jan. 18, 2019 in the USDC District of Delaware, C.A. No. 18-1800-RGA, 1 pp.
Alkan et al., "Personalized copy number and segmental duplication maps using next-generation sequencing," Nat Genet. 2009, 41(10):1061-1067.
Anderson, "Study Describes RNA Sequencing Applications for Molecular Indexing Methods," GenomeWeb 2014, 5 pp.
Ansorge, "Next-generation DNA sequencing techniques," New Biotechnology 2009, 25(4), 195-203.
Applied Biosystems, Apr. 2008, SOLiD™ System Barcoding, Application Note, 4 pp.
Argrawal et al., "Counting Single Native Biomolecules and Intact Viruses with Color-Coded Nanoparticles," Analytical Chemistry 2006, 78, 1061-1070.
Arslan et al., "An efficient algorithm for the stochastic simulation of the hybridization of DNA to microarrays," BMC Bioinformatics 2009, 10(411), 1-17.
Atanur et al., "The genome sequence ofthe spontaneously hypertensive rat: Analysis and functional significance." Genome Res. 2010, 20(6), 791-803.
Audic et al., "The Significance of Digital Gene Expression Profiles," Genome Res. Jul. 1997, 986-995.
Baek et al., "Development of Hydrogel TentaGel Shell-Core Beads for Ultra-high Throughput Solution Phase Screening of Encoded OBOC Combinatorial Small Molecule Libraries," J. Comb Chem. 2009, 11(1), 91-102.
BD Life Sciences, 2018, BD AbSeq antibody-oligo conjugates, www.bd.com/genomics, 2 pp.
BD Life Sciences, 2018, BD AbSeq on the BD Rhapsody system: Exploration of single-cell gene regulation by simultaneous digital mRNA and protein quantification, www.bd.com/genomics, 7 pp.
Bendall et al., "Single-Cell Mass Cytometry of Differential Immune and Drug Responses Across a Human Hematopoietic Continuum," Science 2011, 332(6030), 687-696.
Bionumbers, Aug. 21, 2010, "Useful fundamental Nos. in molecular biology," http://bionumbers.hms.harvard.edu/KeyNumbers/aspx, 1-4.
Biosciences Product Catalogue, Dynal® Catalog 1999, Oslo, Norway, 49-51.
BIOSCRIBE "Massively parallel sequencing technology for single-cell gene expression published" (press release), PhysOrg, Jan. 2, 2015.
Blainey, "The future is now: single-cell genomics of bacteria and archaea," FEMS Microbiol Rev. 2013, 37(3), 407-427.
Bogdanova et al., "Normalization of full-length enriched cDNA," Molecular Biosystems 2008, 4(3), 205-212.
Bonaldo et al., "Normalization and Subtraction: Two Approaches to facilitate Gene Discovery," Genome Res. Jun. 1996, 791-806.
Bontoux et al., "Integrating whole transcriptome assays on a lab-on-a-chip for single cell gene profiling", Lab on a Chip 2008, 8(3), 443-450.
Bose et al., "Scalable microfluidics for single-cell RNA printing and sequencing," Genome Biology 2015, 16(120), 1-16.
Brady et al., "Construction of cDNA libraries form single cells", Methods in Enzymology 1993, (225), 611-623.
Braha et al., "Simultaneous stochastic sensing of divalent metal ions," Nature Biotechnology 2000, 18, 1005-1007.
Bratke et al., "Differential expression of human granzymes A, B, and K in natural killer cells and during CD8+ T cell differentiation in peripheral blood," Eur J Immunol. 2005, 35, 2608-2616.
Brenner et al., "Gene expression analysis by massively parallel signature sequencing (MPSS) on microbead arrays," Nature Biotechnology 2000, 18, 630-634.
Brenner et al., "In vitro cloning of complex mixtures of DNA on microbeads: Physical separation of differentially expressed cDNAs," PNAS 2000, 97(4), 1665-1670.
Brinza et al., "Detection of somatic mutations at 0.1% frequency from cfDNA in peripheral blood with a multiplex next-generation sequencing assay," Conference Poster, AACR 107th Annual Meeting, Apr. 16-20, 2016, 1 p.
Brisco et al., "Quantification of RNA integrity and its use for measurement of transcript number," Nucleic Acids Research 2012, 40(18), e144, 1-9.
Brodin et al., "Challenges with Using Primer IDs to Improve Accuracy of Next Generation Sequencing," PLoS One 2015, 19(3), 1-12.
Buggenum et al., "A covalent and cleavable antibody DNA conjugation strategy for sensitive protein detection via immunoPCR," Scientific Reports 2016, 6(22675), 1-12.
Buschmann et al., Enhancing the detection of barcoded reads in high throughput DNA sequencing DNA by controlling the false discovery rate, BMC Bioinformatics, 15(1), 264, 1-16.
Bustin, "Absolute quantification of mRNA using real-time reverse transcription polymerase chain reaction assays," Journal of Molecular Endocrinology 2000, 25, 169-193.
Butkus, "Cellular research set to launch first gene expression platform using 'molecular indexing' technology," GenomeWeb, Jan. 5, 2014.
Cai, "Turning single cells in microarrays by super-resolution barcoding," Briefings in Functional Genomics 2012, 12(2), 75-80.
Cao et al., "Comprehensive single-cell transcriptional profiling of a multicellular organism," Science 2017, 357, 661-667.
Carr et al., "Inferring relative proportions of DNA variants from sequencing electropherograms," Bioinformatics 2009, 25(24), 3244-3250.
Caruccio et al., "Nextera (TM) Technology for NGS DNA Library Preparation: Simultaneous Fragmentation and Tagging by in Vitro Transposition," EpiBio 2009, 16(3), 4-6.
Casbon et al., "A method for counting PCR template molecules with application to next-generation sequencing," Nucleic Acids Res. 2011, 39(12), e81, 1-8.
Castellarnau et al., "Stochastic particle barcoding for single-cell tracking and multiparametric analysis," Small 2015, 11(4), 489-498.
Castle et al., "DNA copy number including telomeres and mitochondria, assayed using nextgeneration sequencing," BMC Genomics 2010, 11(244), 1-11.
Chamberlain et al., "Deletion screening ofthe Duchenne muscular dystrophy locus via multiplex DNA amplification," Nucleic Acids Res. 1988, 16(23), 11141-11156.
Chang et al., "Detection of Allelic Imbalance in Ascitic Supernatant by Digital Single Nucleotide Polymorphism Analysis," Clinical Cancer Research, 8, 2580-2585.
Chapin et al., "Rapid microRNA Profiling on Encoded Gel Microparticles," Angew Chem Int Ed Engl. 2011, 50(10), 2289-2293.
Chee et al., "Accessing genetic information with high-density DNA arrays," Science 1996, 274, 610-614.
Chee, "Enzymatic multiplex DNA sequencing," Nucleic Acids Research 1991, 19(12), 3301-3305.
Chen et al., "Spatially resolved, highly multiplexed RNA profiling in single cells," Science Express 2015, 348(6233), aaa6090, 1-36.
Church et al., "Multiplex DNA sequencing," Science 1988, 240(4849), 185-188.
Civil Cover Sheet filed Nov. 15, 2018 in the USDC for the District of Delaware, C.A. 18-1800-RGA, 1 pp.
Clontech Laboratories, Inc., "SMART™ PCR cDNA Synthesis Kit User Manual," Clontech 2007, 1-39.
Cloonan et al., "Stem cell transcriptome profiling via massive-scale mRNA sequencing", Nature Methods 2008, 5(7), 613-619.
Combined Search and Examination Report dated Aug. 6, 2014 in UK Patent Application No. 1408829.8.
Combined Search and Examination Report dated Feb. 21, 2017 in UK Patent Application No. 1609740.4.
Communication of a Notice of Opposition dated Jul. 21, 2016 in European Patent Application No. EP 10762102.1.
Complaint filed in Becton, *Dickinson and Company and Cellular Research Inc. v. 10X Genomics, Inc.* dated Nov. 15, 2018 in the USDC for the District of Delaware, C.A. 18-1800-RGA, 141 pp.

(56) References Cited

OTHER PUBLICATIONS

Costa et al., "Single-Tube Nested Real-Time PCR as a New Highly Sensitive Approach to Trace Hazelnut," Journal of Agricultural and Food Chemistry 2012, 60, 8103-8110.
Costello et al., "Discovery and characterization of artefactual mutations in deep coverage targeted capture sequencing data due to oxidative DNA damage during sample preparation," Nucleic Acids Res 2013,41(6), e67, 1-12.
Cotten et al., "Selection of proteins with desired properties from natural proteome libraries using mRNA display," Nature Protocols Jun. 2011, 1163-1182.
Cox, "Bar coding objects with DNA," Analyst 2001, 126, 545-547.
Craig et al., "Identification of genetic variants using bar-coded multiplexed sequencing," Nat Methods 2008, 5(10), 887-893.
Cusanovich et al., "Multiplex single-cell profiling of chromatin accessibility by combinatorial cellular indexing," Science 2015, 348(6237), 910-914.
Custom Antibody Services, Precision Antibody, accessed Apr. 16, 2014, 2 pp.
Daines et al., "High-throughput multiplex sequencing to discover copy number variants in *Drosophila*," Genetics 2009, 182(4), 182, 935-941.
Dalerba et al., "Single-cell dissection of transcriptional heterogeneity in human colon tumors," Nat Biotechnol. 2011, 29(12), 1120-1127.
D'Antoni et al., "Rapid quantitative analysis using a single molecule counting approach," Anal Biochem. 2006, 352, 97-109.
Daser et al., "Interrogation of genomes by molecular copy-number counting (MCC)," Nature Methods 2006, 3(6), 447-453.
Day et al., "Immobilization of polynucleotides on magnetic particles," Biochem. J. 1991, 278, 735-740.
Decision of Refusal dated Aug. 21, 2017 in Japanese Patent Application No. 2014-558975.
Defendant 10X Genomics, Inc.'s Letter to Judge Andrews in Response to Plaintiff's Letter of Supplemental Authority, dated Jul. 11, 2019 in the USDC for the District of Delaware, C.A. 18-1800-RGA, 2 pp.
Defendant 10X Genomics Motion for Admission Pro Hac Vice of Paul Ehrlich, Azra Hadzimehmedovic and Aaron Nathan, Pursuant to Local Rule 83.5, dated May 1, 2019 in the USDC for the District of Delaware, C.A. 18-1800-RGA, 5 pp.
Defendant 10X Genomics, Inc.'s Motion for Admission Pro Hac Vice Pursuant to Local Rule 83.5, dated Jan. 18, 2019 in the USDC District of Delaware, C.A. No. 18-1800-RGA, 5 pp.
Defendant 10X Genomics, Inc.'s Motion to Dismiss Pursuant to Federal Rule of Civil Procedure 12(b)(6), dated Jan. 18, 2019 in the USDC for the District of Delaware, C.A. 18-1800-RGA, 1 pp.
Defendant 10X Genomics, Inc.'s Motion to Dismiss the First Amended Complaint Pursuant to Federal Rule of Civil Procedure 12(b)(6), dated Mar. 1, 2019 in the USDC for the District of Delaware, C.A. 18-1800-RGA, 1 pp.
Defendant 10X Genomics Notice of Service for Initial Disclosures served to Opposing Counsel, dated Jun. 7, 2019 in the USDC for the District of Delaware, C.A. 18-1800-RGA, 2 pp.
Defendant 10X Genomic Inc.'s Notice of Service for Initial Requests for Production and Interrogatories Served to Becton, Dickinson, and Company and Cellular Research, Inc., dated May 31, 2019 in the USDC for the District of Delaware, C.A. 18-1800-RGA, 2 pp.
Defendant 10X Genomics Inc's, Notice of Service of Technical Documents, dated Jul. 8, 2019 in the USDC for the District of Delaware, C.A. 18-1800-RGA, 2 pp.
Defendant 10X Genomics, Inc.'s Opening Brief in Support of Its Motion to Dismiss Pursuant to Federal Rule of Civil Procedure 12(b)(6), dated Jan. 18, 2019 in the USDC District of Delaware, C.A. No. 1:18-cv-01800-RGA, 25 pp.
Defendant 10X Genomics, Inc.'s Opening Brief in Support of Its Motion to Dismiss Pursuant to Federal Rule of Civil Procedure 12(b)(6), dated Mar. 1, 2019 in the USDC District of Delaware, C.A. No. 18-1800 RGA, 26 pp.
Defendant 10X Genomics, Inc.'s [Proposed] Order for Partial Dismissal Pursuant to Federal Rules of Civil Procedure 12(b)(6), dated Jan. 18, 2019 in the USDC District of Delaware, C.A. No. 18-1800-RGA, 1 pp.
Defendant 10X Genomics, Inc's Proposed Order for Dismissal pursuant to Federal Rules of Civil Procedure 12(b)(6), filed Mar. 1, 2019 in the USDC for the District of Delaware, C.A. 18-1800-RGA, 1 pp.
Defendant 10X Genomics Reply Brief in Support of its Motion to Dismiss Pursuant to Federal Rule of Civil Procedure 12(b)(6), dated Apr. 12, 2019 in the USDC for the District of Delaware, C.A. No. 18-1800-RGA, 15 pp.
Defendant 10X Genomics Request for Oral Argument Under D. Del. LR 7.1.4, dated Apr. 18, 2019 in the USDC for the District of Delaware, C.A. 18-1800-RGA 2 pp.
Defendant 10X Genomics Response Letter to Judge Richard G. Andrews re Request for a Rule 16, dated Apr. 16, 2019 in the USDC for the District of Delaware, C.A. 18-1800-RGA, 2 pp.
Defendant 10X Genomics, Inc.'s Rule 7.1 Disclosure Statement, dated Jan. 18, 2019 in the USDC District of Delaware, C.A. No. 18-1800-RGA, 1 pp. 1.
Delley et al., "Combined aptamer and transcriptome sequencing of single cells," bioRxiv Jan. 10, 2017.
De Saizieu et al., "Bacterial transcript imaging by hybridization of total RNA to oligonucleotide arrays," Nature Biotechnology 1988, 16, 45-48.
Di Carlo et al., "Dynamic single-cell analysis for quantitative biology," Analytical Chemistry 2006, 78(23), 7918-7925.
Dirks et al., Triggered amplification by hybridization chain reaction., Proc Natl Acad Sci 2014, 101(43), 15275-15278.
Dube et al., "Mathematical Analysis of Copy Number Variation in a DNA Sample Using Digital PCR on a Nanofluidic Device," PLoS One 2008, 3(8) e2876.
Eberwine et al., "Analysis of gene expression in single live neurons," Proc. Natl. Acad. Sci. 1992, 89, 3010-3014.
Evanko et al., "Hybridization chain reaction," Nature Methods 2004, 1(3), 186-187.
Examination Report dated Oct. 24, 2017 in Australian Patent Application No. 2013226081.
Examination Report dated Jul. 20, 2018 in Australian Patent Application No. 2014312208.
Examination Report dated May 12, 2020 in Australian Patent Application No. 2018220004.
Examination Report dated Jul. 12, 2016 in European Patent Application No. 13755319.4.
Examination Report dated Apr. 10, 2017 in European Patent Application No. 14761937.3.
Examination Report dated Oct. 10, 2017 in European Patent Application No. 14761937.3.
Examination Report dated Mar. 16, 2018 in European Patent Application No. 13754428.4.
Examination Report dated Sep. 5, 2018 in European Patent Application No. 16710357.1.
Examination Report dated Sep. 26, 2018 in European Patent Application No. 16714081.3.
Examination Report dated Dec. 12, 2018 in European Patent Application No. 16719706.0.
Examination Report dated Jan. 2, 2019 in European Patent Application No. 16757986.1.
Examination Report dated Feb. 6, 2019 in European Patent Application No. 13754428.4.
Examination Report dated Apr. 26, 2019 in European Patent Application No. 16710357.1.
Examination Report dated Jun. 18, 2019 in European Patent Application No. 16710551.9.
Examination Report dated Jul. 24, 2019 in European Patent Application No. 16714081.3.
Examination Report dated Aug. 2, 2019 in European Patent Application No. 17202409.3.
Examination Report dated Oct. 11, 2019 in European Patent Application No. 16757986.1.
Examination Report dated Dec. 4, 2019 in European Patent Application No. 16719706.0.

(56) References Cited

OTHER PUBLICATIONS

Examination Report dated Feb. 19, 2020 in European Patent Application No. 16710551.9.
Examination Report dated Mar. 18, 2020 in European Patent Application No. 17202409.3.
Examination Report dated Jul. 6, 2020 in European Patent Application No. 17781265.8.
Examination Report dated Sep. 21, 2020 in European Patent Application No. 18703156.2.
Examination Report dated Mar. 18, 2019 in Singapore Patent Application No. 11201405274W.
Examination Report dated Jan. 27, 2016 in United Kingdom Patent Application No. 1408829.8.
Examination Report dated Feb. 19, 2016 in United Kingdom Patent Application No. GB1511591.8.
Examination Report dated Jun. 8, 2016 in United Kingdom Patent Application No. 1408829.8.
Examination Report dated Jun. 15, 2016 in United Kingdom Patent Application No. GB1511591.8.
Examination Report dated Jan. 3, 2018 in United Kingdom Patent Application No. 1609740.4.
Exhibit A filed Jul. 10, 2019 in the USDC for the District of Delaware, C.A. 18-1800-RGA, 25 pp.
Exhibits 12-32 filed Feb. 8, 2019 in the USDC for the District of Delaware, C.A. 18-1800-RGA, 795 pp.
Exhibits A-D filed Jan. 18, 2019 in the USDC District of Delaware, C.A. No. 1:18-cv-01800-RGA, 47 pp.
Exhibits A-E filed Mar. 1, 2019 in the USDC District of Delaware, C.A. No. 18-1800 RGA, 75 pp.
Extended European Search Report dated Jul. 17, 2015 in European Patent Application No. 13755319.4.
Extended European Search Report dated Dec. 14, 2015 in European Patent Application No. 13754428.4.
Extended European Search Report dated Feb. 8, 2018 in European Patent Application No. 17202409.3.
Extended European Search Report dated Jun. 11, 2018 in European Patent Application No. 16740872.3.
Extended European Search Report dated Mar. 22, 2019 in European Patent Application No. 18195513.9.
Fan et al., "Parallel Genotyping of Human SNPs Using Generic High-density Oligonucleotide Tag Arrays," Genome Research Oct. 2000, 853-860.
Fan et al., "Microfluidic digital PCR enables rapid prenatal diagnosis of fetal aneuploidy," Am Obstet Gynecol. 2009, 200, 543e1-543e7.
Fan, "Molecular counting: from noninvasive prenatal diagnostics to whole-genome haplotyping," Doctoral Dissertation, Stanford University 2010, 1-185.
Fan et al., "Non-invasive Prenatal Measurement of the Fetal Genome," Nature 2012, 487(7407), 320-324.
Fan et al., "Combinatorial labeling of single cells for gene expression cytometry," Science 2015, 347(6222), 1258366-1258369.
Feldhaus et al., "Oligonucleotide-conjugated beads for transdominant genetic experiments," Nucleic Acids Res. 2000, 28(2), 534-543.
Final Office Action dated Sep. 1, 2015 for U.S. Appl. No. 14/540,029.
Final Office Action dated Sep. 24, 2015 for U.S. Appl. No. 14/540,007.
Final Office Action dated Oct. 6, 2015 in U.S. Appl. No. 14/540,018.
Final Office Action dated Apr. 11, 2016 for U.S. Appl. No. 14/800,526.
Final Office Action dated Jul. 20, 2016 for U.S. Appl. No. 14/281,706.
Final Office Action dated Aug. 12, 2016 in U.S. Appl. No. 14/381,488.
Final Office Action dated Feb. 13, 2017 in U.S. Appl. No. 14/381,488.
Final Office Action dated May 8, 2017 in U.S. Appl. No. 15/224,460.
Final Office Action dated Oct. 16, 2017 in U.S. Appl. No. 15/409,355.
Final Office Action dated Nov. 16, 2017 in U.S. Appl. No. 14/381,488.
Final Office Action dated Jan. 25, 2018 in U.S. Appl. No. 14/381,526.
Final Office Action dated May 3, 2018 in U.S. Appl. No. 15/046,225.
Final Office Action dated May 10, 2018 in U.S. Appl. No. 14/381,488.
Final Office Action dated Jul. 5, 2018 in U.S. Appl. No. 15/004,618.
Final Office Action dated Jul. 20, 2018 in U.S. Appl. No. 15/217,886.
Final Office Action dated Nov. 16, 2018 in U.S. Appl. No. 15/134,967.
Final Office Action dated Feb. 19, 2019 in U.S. Appl. No. 14/381,526.
Final Office Action dated Mar. 1, 2019 in U.S. Appl. No. 16/012,584.
Final Office Action dated Apr. 22, 2019 in U.S. Appl. No. 15/987,851.
Final Office Action dated May 2, 2019 in U.S. Appl. No. 16/012,635.
Final Office Action dated May 3, 2019 in U.S. Appl. No. 15/937,713.
Final Office Action dated Sep. 18, 2019 in U.S. Appl. No. 15/055,407.
Final Office Action dated Oct. 2, 2019 in U.S. Appl. No. 15/084,307.
Final Office Action dated Dec. 4, 2019 in U.S. Appl. No. 15/596,364.
Final Office Action dated Jan. 8, 2020 in U.S. Appl. No. 15/459,977.
Final Office Action dated Jan. 16, 2020 in U.S. Appl. No. 16/012,584.
Final Office Action dated Jan. 29, 2020 in U.S. Appl. No. 14/381,488.
Final Office Action dated Feb. 4, 2020 in U.S. Appl. No. 15/715,028.
Final Office Action dated Mar. 9, 2020 in U.S. Appl. No. 15/987,851.
Final Office Action dated Apr. 28, 2020 in U.S. Appl. No. 15/134,967.
Final Office Action dated Jun. 5, 2020 in U.S. Appl. No. 15/084,307.
Final Office Action dated Aug. 19, 2020 in U.S. Appl. No. 15/875,816.
Final Office Action dated Sep. 14, 2020 in U.S. Appl. No. 16/789,358.
Final Office Action dated Sep. 22, 2020 in U.S. Appl. No. 16/789,311.
Final Office Action dated Sep. 25, 2020 in U.S. Appl. No. 15/055,407.
Final Office Action dated Dec. 7, 2020 in U.S. Appl. No. 16/012,584.
First Action Interview Pilot Program Pre-Interview Communication dated Oct. 15, 2018 in U.S. Appl. No. 15/987,851.
First Action Interview Office Action Summary dated Jan. 25, 2019 in U.S. Appl. No. 15/987,851.
Flanigon et al., "Multiplex protein detection with DNA readout via mass spectrometry," N Biotechnol. 2013, 30(2), 153-158.
Forster et al., "A human gut bacterial genome and culture collection for improved metagenomic analyses," Nature Biotechnology 2019, 37, 186-192.
Fox-Walsh et al., "A multiplex RNA-seq strategy to profile poly(A+) RNA: application to analysis of transcription response and 3' end formation," Genomics 2011, 98, 266-721.
Fu et al., "Counting individual DNA molecules by the stochastic attachment of diverse labels," Proc Natl Acad Sci 2011, 108(22), 9026-9031.
Fu et al., Digital Encoding of Cellular mRNAs Enabling Precise and Absolute Gene Expression Measurement by Single-Molecule Counting. Anal Chem. 2014, 86, 2867-2870.
Fu et al., "Molecular indexing enables quantitative targeted RNA sequencing and reveals poor efficiencies in standard library preparation," PNAS 2014, 111(5), 1891-1896.
Gerry et al., "Universal DNA Microarray Method for Multiplex Detection of Low Abundance Point Mutations," Journal of Molecular Biology 1999, 292, 251-262.
Gillespie, "Exact Stochastic Simulation of Coupled Chemical Reactions," Journal of Physical Chemistry 1977, 81(25), 2340-2361.
Gong et al., "Massively parallel detection of gene expression in single cells using subnanolitre wells," Lab Chip Oct. 2010, 2334-2337.
Gong et al., "Simple Method Prepare Oligonucleotide-Conjugated Antibodies and Its Application in Multiplex Protein Detection in Single Cells," Bioconjugate Chem. 2016, 27, 217-225.
Grant et al., "SNP genotyping on a genome-wide amplified DOP-PCR template," Nucleic Acids Res 2002, 30(22), e25, 1-6.
Gu et al., "Complete workflow for detection of low frequency somatic mutations from cell-free DNA using Ion Torrent™ platforms," Conference Poster, AACR 107th Annual Meeting, Apr. 16-20, 2016, 1 p.
Gu et al., "Depletion of abundant sequences by hybridization (DSH): using Cas9 to remove unwanted high-abundance species in sequencing libraries and molecular counting applications," Genome Biology 2016, 17(41) 1-13.
Gunderson et al., "Decoding Randomly Ordered DNA Arrays," Genome Research 2004, 14, 870-877.
Gundry et al., "Direct, genome-wide assessment of DNA mutations in single cells," Nucleic Acids Research 2011, 40(5), 2032-2040.
Gundry et al., "Direct mutation analysis by high-throughput sequencing: from germline to low-abundant, somatic variants," Mutat Res. 2012, 729(1-2), 1-15.
Hacia et al., "Determination of ancestral alleles for human single-nucleotide polymorphisms using high-density oligonucleotide arrays," Nature Genetics 1999, 22, 164-167.

(56) References Cited

OTHER PUBLICATIONS

Haff, "Improved Quantitative PCR Using Nested Primers," PCR Methods and Applications Mar. 1994, 332-337.
Hamady et al., "Error-correcting barcoded primers for pyrosequencing hundreds of samples in multiplex," Nat Methods 2008, 5(3), 235-237.
Han et al., "An approach to multiplexing an immunosorbent assay with antibody-oligonucleotide conjugates," Bioconjug Chem. 2010, 21(12), 2190-2196.
Harbers, "The current status of cDNA cloning," Genomics 2008, 91, 232-242.
Harrington et al., Cross-sectional characterization of HIV-1 env compartmentalization in cerebrospinal fluid over the full disease course, AIDS 2009, 23(8), 907-915.
Hartmann, "Gene expression profiling of single cells on large-scale oligonucleotide arrays", Nucleic Acids Research, (Oct. 2006) vol. 34, No. 21, p. e143, 1-12.
Hashimshony et al., "CEL-Seq: Single-Cell RNA-Seq by Multiplexed Linear Amplification," Cell Rep. 2012, 2(3), 666-673.
Hensel et al., "Simultaneous identification of bacterial virulence genes by negative selection," Science 1995, 269(5222), 400-403.
Hiatt et al., "Parallel, tag-directed assembly of locally derived short sequence reads," Nat Methods 2010, 7(2), 119-122.
Hiatt et al., "Single molecule molecular inversion probes for targeted, high-accuracy detection of low-frequency variation," Genome Res. 2013, 23(5), 843-854.
Holcomb et al., "Abstract 1853: Single-cell multiplexed profiling of protein-level changes induced by EGFR inhibitor gefitinib," Cancer Res 2016, 76(14 Suppl), Abstract 1853.
Hollas et al., "A stochastic approach to count RNA molecules using DNA sequencing methods," Algorithms in Bioinformatics. WABI 2003, Lecture Notes in Computer Science, 2812, 55-62.
How many species of bacteria are there? Wisegeek.org, accessed Jan. 21, 2014, 2 pp.
Hu et al., "Dissecting Cell-Type Composition and Activity-Dependent Transcriptional State in Mammalian Brains by Massively Parallel Single-Nucleus RNA-Seq," Molecular Cell 2017, 68, 1006-1015.
Hu et al., "Single Cell Multi-Omics Technology: Methodology and Application," Frontiers in Cell and Developmental Biology 2018, 6(28), 1-13.
Hug et al., Measure ofthe Number of Molecular of a Single mRNA Species in a Complex mRNA Preparation, Journal of Theoretical Biology 2003, 221, 615-624.
Ingolia et al., Genome-Wide Analysis in Vivo of Translation with Nucleotide Resolution Using Ribosome Profiling, Science 2009, 324(5924), 218-223.
International Preliminary Report on Patentability dated Mar. 26, 2019 in PCT Application No. PCT/US2017/053331.
International Preliminary Report on Patentability dated Aug. 6, 2019 in PCT Application No. PCT/US2018/014385.
International Preliminary Report on Patentability dated Nov. 3, 2020 in PCT Application No. PCT/US2019/030175.
International Preliminary Report on Patentability dated Nov. 3, 2020 in PCT Application No. PCT/US2019/030245.
International Search Report and Written Opinion dated May 7, 2012 for PCT Application No. PCT/IB2011/003160.
International Search Report and Written Opinion dated Jun. 6, 2012 in PCT Application No. PCT/US2011/065291.
International Search Report and Written Opinion dated Jun. 14, 2013 in PCT Application No. PCT/US2013/028103.
International Search Report and Written Opinion dated Aug. 16, 2013 for PCT Application No. PCT/US2013/027891.
International Search Report and Written Opinion dated Dec. 19, 2014 in PCT Application No. PCT/US2014/059542.
International Search Report and Written Opinion dated Feb. 3, 2015 in PCT Application No. PCT/US2014/053301.
International Search Report and Written Opinion dated May 3, 2016 in PCT Application No. PCT/US2016/018354.
International Search Report and Written Opinion dated Jun. 9, 2016 in PCT Application No. PCT/US2016/022712.
International Search Report and Written Opinion dated Jun. 17, 2016 in PCT Application No. PCT/US2016/019962.
International Search Report and Written Opinion dated Jun. 20, 2016 in PCT Application No. PCT/US2016/014612.
International Search Report and Written Opinion dated Aug. 9, 2016 in PCT Application No. PCT/US2016/019971.
International Search Report and Written Opinion dated Sep. 27, 2016 in PCT Application No. PCT/US2016/034473.
International Search Report and Written Opinion dated Sep. 28, 2016 in PCT Application No. PCT/US2016/028694.
International Search Report and Written Opinion dated Dec. 5, 2016 in PCT Application No. PCT/US2016/024783.
International Search Report and Written Opinion dated Jan. 31, 2017 in PCT Application No. PCT/US2016/050694.
International Search Report and Written Opinion dated Aug. 7, 2017 in PCT Application No. PCT/US2017/034576.
International Search Report and Written Opinion dated Sep. 8, 2017 in PCT Application No. PCT/US2017/030097.
International Search Report and Written Opinion dated Mar. 20, 2018 in PCT Application No. PCT/US2017/053331.
International Search Report and Written Opinion dated Mar. 28, 2018 in PCT Application No. PCT/US2018/014385.
International Search Report and Written Opinion dated Jul. 16, 2018 in PCT Application No. PCT/US2018/024602.
International Search Report and Written Opinion dated Jun. 24, 2019 in PCT Application No. PCT/US2019/030175.
International Search Report and Written Opinion dated Oct. 8, 2019 in PCT Application No. PCT/US2019/043949.
International Search Report and Written Opinion dated Oct. 16, 2019 in PCT Application No. PCT/US2019/030245.
International Search Report and Written Opinion dated Nov. 27, 2019 in PCT Application No. PCT/US2019/046549.
International Search Report and Written Opinion dated Dec. 4, 2019 in PCT Application No. PCT/US2019/053868.
International Search Report and Written Opinion dated Jan. 27, 2020 in PCT Application No. PCT/US2019/048179.
International Search Report and Written Opinion dated Mar. 30, 2020 in PCT Application No. PCT/US2019/060243.
International Search Report and Written Opinion dated Mar. 30, 2020 in PCT Application No. PCT/US2019/065237.
International Search Report and Written Opinion dated May 18, 2020 in PCT Application No. PCT/US2020/014339.
International Search Report and Written Opinion dated Jun. 30, 2020 in PCT Application No. PCT/US2020/017890.
International Search Report and Written Opinion dated Nov. 12, 2020 in PCT Application No. PCT/US2020/042880.
Invitation to Pay Fees dated Mar. 16, 2016 in PCT Application No. PCT/US2016/019971.
Invitation to Pay Fees dated May 16, 2018 in PCT Application No. PCT/US2018/024602.
Invitation to Pay Fees dated Nov. 26, 2019 in PCT Application No. PCT/US2019/048179.
Invitation to Pay Additional Search Fees dated May 7, 2020 in PCT Application No. PCT/US2020/017890.
Invitation to Respond to Written Opinion dated May 26, 2017 in Singapore Patent Application No. 11201405274W.
Islam et al., "Characterization ofthe single-cell transcriptional landscape by highly multiplex RNA-seq," Genome Research 2011, 21, 1160-1167.
Islam et al., "Highly multiplexed and strand specific single-cell RNA 5' end sequencing," Nature Protocols 2012, 7(5), 813-828.
Islam et al., "Quantitative single-cell RNA-seq with unique molecular identifiers," Nature Methods 2014, 11(2), 163-168.
Jabara, "Capturing the cloud: High throughput sequencing of multiple individual genomes from a retroviral population," Biology Lunch Bunch Series, Training Initiatives in Biomedical & Biological Sciences ofthe University of North Carolina at Chapel Hill 2010.
Jabara et al., "Accurate sampling and deep sequencing ofthe HIV-1 protease gene using a Primer ID," PNAS 2011, 108(50), 20166-20171.

(56) References Cited

OTHER PUBLICATIONS

Jason J. Rawnsley of Richards, Layton and Finger, P.A., Entry of Appearance dated Jan. 18, 2019 in the USDC District of Delaware, C.A. No. 18-1800-RGA, 1 pp.

Jiang et al., "Synthetic spike-in standards for RNA-seq experiments," Genome Res. 2011, 21, 1543-1551.

Joint Stipulation and Order to Extend Time to Respond to Plaintiff's First Amended Complaint, dated Feb. 21, 2019 in the USDC for the District of Delaware, C.A. 18-1800-RGA, 2 pp.

Joint Stipulation and Order to Request Extended Time to File Opposition to Defendant's Motion to Dismiss dated, Mar. 8, 2019 in the USDC District of Delaware, C.A. No. 18-1800 RGA, 2 pp.

Joint Stipulation and Order to Request Extended Time to Submit a proposed Protective Order, dated Jun. 7, 2019 in the USDC for the District of Delaware, C.A. 18-1800-RGA, 1 pp.

Joint Stipulation and Order to Extended Time to Submit Agreed Document Production Protocol, filed Jun. 28, 2019 in the USDC for the District of Delaware, C.A. 18-1800 (RGA), 1 pp.

Joint Stipulation and Order to Request Extended Time to Submit Agreed Document Production Protocol, dated Jul. 11, 2019 in the USDC for the District of Delaware, C.A. 18-1800 (RGA), 1 pp.

Junker et al., "Single-Cell Transcriptomics Enters the Age of Mass Production," Molecular Cell 2015, 58, 563-564.

Kanagawa, "Bias and artifacts in multi-template polymerase chain reactions (PCR)," Journal of Bioscience and Bioengineering 2003, 96(4), 317-323.

Kang et al., "Targeted sequencing with enrichment PCR: a novel diagnostic method for the detection of EGFR mutations," Oncotarget 2015, 6(15), 13742-13749.

Kang et al., "Application of multi-omics in single cells," Ann Biotechnol. 2018, 2(1007), 1-8.

Karrer et al., "In situ isolation of mRNA from individual plant cells: creation of cell-specific cDNA libraries," Proc. Natl. Acad. Sci. USA 1995, 92, 3814-3818.

Kausch et al., "Organelle Isolation by Magnetic Immunoabsorption," BioTechniques 1999, 26(2), 336-343.

Kebschull et al., "Sources of PCR-induced distortions in high-throughput sequencing data sets," Nucleic Acids Research Jan. 15, 2015.

Keys et al., Primer ID Informs Next-Generation Sequencing Platforms and Reveals Preexisting Drug Resistance Mutations in the HIV-1 Reverse Transcriptase Coding Domain, AIDS Research and Human Retroviruses 2015, 31(6), 658-668.

Kim et al., Polony Multiplex Analysis of Gene Expression (PMAGE) in Mouse Hypertrophic Cardiomyopathy, Science 2007, 316(5830), 1481-1484.

Kinde et al., "Detection and quantification of rare mutations with massively parallel sequencing," Proc. Natl Acad Sci 2011, 108(23), 9530-0535.

Kirsebom et al., "Stimuli-Responsive Polymers in the 21st Century: Elaborated Architecture to Achieve High Sensitivity, Fast Response, and Robust Behavior," Journal of Polymer Science: Part B: Polymer Physics 2011, 49, 173-178.

Kivioja et al., "Counting absolute numbers of molecules using unique molecular identifiers," Nature Proceedings Jan. 18, 2011.

Klein et al., Droplet Barcoding for Single-Cell Transcriptomics Applied to Embryonic Stem Cells, Cell 2015, 161, 1187-1201.

Ko et al., "RNA-conjugated template-switching RT-PCR method for generating an *Escherichia coli* cDNA library for small RNAs," Journal of Microbiological Methods 2006, 64, 297-304.

Koboldt et al., VarScan: variant detection in massively parallel sequencing of individual and pooled samples, Bioinformatics 2009, 25(17), 2283-2285.

Kolodziejczyk et al., The Technology and Biology of Single-Cell RNA Sequencing, Molecular Cell 2015, 58, 610-620.

Konig et al., "iCLIP reveals the function of hnRNAP particles in splicing at individual nucleotide resolution," Nature Structural & Molecular Biology 2010, 17(7), 909-916.

Kooiker & Xue, "cDNA Library Preparation," Cereal Genomics 2013, 1099, 29-40.

Kotake et al., "A simple nested RT-PCR method for quantitation of the relative amounts of multiple cytokine mRNAs in small tissue samples," Journal of Immunological Methods 1996, 199, 193-203.

Kozarewa & Turner, "96-Plex Molecular Barcoding for the Illumina Genome Analyzer," High-Throughput Next Generation Sequencing. Methods in Molecular Biology (Methods and Applications) 2011, 733, 24 pp. DOI: 10.1007/978-1-61779-089-8_20.

Kozlov et al., "A high-complexity, multiplexed solution-phase assay for profiling protease activity on microarrays," Comb Chem High Throughput Screen 2008, 11(1), 24-35.

Kurimoto et al., "An improved single-cell cDNA amplification method for efficient high-density oligonucleotide microarray analysis," Nucleic Acids Res. 2006, 34(5), e42, 1-17.

Kurimoto et al., "Global single-cell cDNA amplification to provide a template for representative high-density oligonucleotide microarray analysis," Nature Protocols 2007, 2(3), 739-752.

Lamble et al., "Improved workflows for high throughput library preparation using the transposome-based nextera system," BMC Biotechnology 2013, 13, 104, 1-10.

Larson et al., "A single molecule view of gene expression," Trends Cell Biol. 2009, 19(11), 630-637.

Lass-Napiorkowska et al., "Detection methodology based on target molecule-induced sequencespecific binding to a single-stranded oligonucleotide," Anal Chem. 2012, 84(7), 3382-3389.

Leamon et al., A massively parallel PicoTiterPlate based platform for discrete picoliter-scale polymerase chain reactions, Electrophoresis 2003, 24, 3769-3777.

Lee et al., "Large-scale arrays of picolitre chambers for single-cell analysis of large cell populations," Lab Chip Oct. 2010, 2952-2958.

Lee et al., "Highly Multiplexed Subcellular RNA Sequencing in Situ," Science 2014, 343,1360-1363.

Lee et al., "Universal process-inert encoding architecture for polymer microparticles," Nature Materials 2014, 13(5), 524-529.

Letter regarding the opposition procedure dated Jul. 22, 2015 for European Patent Application No. 11810645.9.

Letter to Judge Richard G. Andrews Requesting a Rule 16 Conference, dated Apr. 15, 2019 in the USDC for the District of Delaware, C.A. 18-1800 (RGA), 1 pp.

Letter to Judge Andrews regarding Agreement on Proposed Scheduling Order, dated May 7, 2019 in the USDC for the District of Delaware, C.A. 18-1800-RGA, 1 pp.

Letter to Judge Andrews regarding Notice of Supplemental Authority, dated Jul. 10, 2019 in the USDC for the District of Delaware, C.A. 18-1800(RGA), 2pp.

Lin et al., "Self-Assembled Combinatorial Encoding Nanoarrays for Multiplexed Biosensin," Nano Lett. Jul. 2007, (2), 507-512.

Liu et al., "Single-cell transcriptome sequencing: recent advances and remaining challenges," F1000Research 2016, 5(F1000 Faculty Rev)(182), 1-9.

Lizardi et al., "Mutation detection and single-molecule counting using isothermal rolling-circle amplification," Nat Genet. 1998, 19, 225-232.

Lockhart et al., "Expression monitoring by hybridization to high-density oligonucleotide arrays," Nature Biotechnology 1996, 14, 1675-1680.

Lovatt et al., "Transcriptome in vivo analysis (TIVA) of spatially defined single cells in live tissue," Nat Methods 2014, 11(2), 190-196.

Loy et al., "A rapid library preparation method with custom assay designs for detection of variants at 0.1% allelic frequency in liquid biopsy samples," Oct. 2, 2018, 1 p.

Lucito et al., "Representational Oligonucleotide Microarray Analysis: A High-Resolution Method to Detect Genome Copy Number Variation," Genome Research 2003, 13, 2291-2305.

Lundberg et al., "Practical innovations for high-throughput amplicon sequencing," Nature Methods 2013, 10(10), 999-1007.

Lundberg et al., "Supplementary Information for: Practical innovations for high-throughput amplicon sequencing," Nature Methods Jan. 24, 2013.

Maamar et al., "Noise in Gene Expression Determines Cell Fate in Bacillus subtilis," Science 2007, 317, 526-529.

MacAulay et al., "Single Cell Genomics: Advances and Future Perspectives," PLoS Genetics 2014, 10(1), 1-9.

(56) References Cited

OTHER PUBLICATIONS

MacAulay et al., "G&T-seq: parallel sequencing of single-cell genomes and transcriptomes," Nature Methods Jan. 7, 2015.
Macosko et al., "Highly parallel genome-wide expression profiling of individual cells using nanoliter droplets," Cell 2015, 161, 1202-1214.
Maeda et al., "Development of a DNA barcode tagging method for monitoring dynamic changes in gene expression by using an ultra high-throughput sequencer," BioTechniques 2008, 45(1), 95-97.
Makrigiorgos et al., "A PCR-Based amplification method retaining quantities difference between two complex genomes," Nature Biotech 2002, 20(9), 936-939.
Marcus et al., "Microfluidic single-cell mRNA isolation and analysis," Anal Chem. 2006, 78, 3084-3089.
Mardis, "Next-generation DNA sequencing methods", Annu. Rev. Genomics Hum. Genet. Sep. 2008, 387-402.
Marguerat et al., "Next-generation sequencing: applications beyond genomes," Biochem. Soc. Trans. 2008, 36(5), 1091-1096.
Marguiles et al., Genome sequencing in microfabricated high-density picolitre reactors, Nature 2005, 437, 376-380.
Martinez et al., "A microfluidic approach to encapsulate living cells in uniform alginate hydrogel microparticles," Macromol. Biosci Dec. 2012, 946-951.
Massachusetts General Hospital, Overview of Illumina Chemistry, http://nextgen.mgh.harvard.edu/IlluminaChemistry.html, downloaded Jan. 28, 2020, 2 pp.
McCloskey et al., "Encoding PCR products with batch-stamps and barcodes," Biochem Genet. 2007, 45(11-12), 761-767.
Medvedev et al., "Detecting copy number variation with mated short reads," Genome Res. 2010, 20, 1613-1622.
Mei et al., "Identification of recurrent regions of Copy-Number Variants across multiple individuals," BMC Bioinformatics Nov. 2010, 147, 1-14.
Merriam-Webster, definition of associate: http://www.merriam-webster.com/dictionary/associate, accessed Apr. 5, 2016.
Meyer et al., "Parallel tagged sequencing on the 454 platform," Nature Protocols 2008, 3(2), 267-278.
Miller et al., Directed evolution by in vitro compartmentalization, Nature Methods 2006, 3(7), 561-570.
Miner et al., "Molecular barcodes detect redundancy and contamination in hairpin-bisulfite PCR," Nucleic Acids Research 2004, 32(17), e135, 1-4.
Mortazavi et al., "Mapping and quantifying mammalian transcriptomes by RNA-Seq," Nat. Methods 2008, 5(7), 621-628.
Motion and Order for Admission Pro Hac Vice Pursuant to Local Rule 83.5, dated Jan. 24, 2019 in the USDC District of Delaware, C.A. No. 18-1800-RGA, 7 pp.
Nadai et al., Protocol for nearly full-length sequencing of HIV-1 RNA from plasma, PLoS One 2008, 3(1), e1420, 1-6.
Nagai et al., "Development of a microchamber array for picoleter PCR," Anal. Chem. 2001, 73, 1043-1047.
Navin et al., "The first five years of single-cell cancer genomics and beyond," Genome Research 2015, 25, 1499-1507.
Newell et al., Cytometry by time-of-flight shows combinatorial cytokine expression and virus-specific cell niches within a continuum of CD8+ T cell phenotypes. Immunity 2012, 36(1), 142-152.
Non-Final Office Action dated Oct. 3, 2013 in U.S. Appl. No. 12/969,581.
Non-Final Office Action dated Feb. 18, 2015 for U.S. Appl. No. 14/540,007.
Non-Final Office Action dated Feb. 26, 2015 for U.S. Appl. No. 14/540,029.
Non-Final Office Action dated Mar. 19, 2015 in U.S. Appl. No. 14/540,018.
Non-Final Office Action dated May 7, 2015 for U.S. Appl. No. 13/327,526.
Non-Final Office Action dated Dec. 3, 2015 for U.S. Appl. No. 14/281,706.
Non-Final Office Action dated Dec. 31, 2015 for U.S. Appl. No. 14/800,526.
Non-Final Office Action dated Apr. 11, 2016 in U.S. Appl. No. 14/472,363.
Non-Final Office Action dated May 10, 2016 in U.S. Appl. No. 14/381,488.
Non-Final Office Action dated May 13, 2016 in U.S. Appl. No. 14/508,911.
Non-Final Office Action dated Aug. 17, 2016 for U.S. Appl. No. 14/800,526.
Non-Final Office Action dated Sep. 26, 2016 in U.S. Appl. No. 15/167,807.
Non-Final Office Action dated Oct. 11, 2016 in U.S. Appl. No. 15/224,460.
Non-Final Office Action dated Jan. 19, 2017 in U.S. Appl. No. 15/055,445.
Non-Final Office Action dated Mar. 24, 2017 in U.S. Appl. No. 15/409,355.
Non-Final Office Action dated Jun. 2, 2017 in U.S. Appl. No. 14/381,526.
Non-Final Office Action dated Jun. 7, 2017 in U.S. Appl. No. 14/381,488.
Non-Final Office Action dated Jul. 28, 2017 in U.S. Appl. No. 14/975,441.
Non-Final Office Action dated Sep. 8, 2017 in U.S. Appl. No. 15/046,225.
Non-Final Office Action dated Sep. 8, 2017 in U.S. Appl. No. 15/134,967.
Non-Final Office Action dated Nov. 1, 2017 in U.S. Appl. No. 15/667,125.
Non-Final Office Action dated Nov. 9, 2017 in U.S. Appl. No. 15/004,618.
Non-Final Office Action dated Jan. 9, 2018 in U.S. Appl. No. 15/217,896.
Non-Final Office Action dated Jan. 12, 2018 in U.S. Appl. No. 15/217,886.
Non-Final Office Action dated Mar. 8, 2018 in U.S. Appl. No. 15/608,780.
Non-Final Office Action dated Apr. 6, 2018 in U.S. Appl. No. 15/603,239.
Non-Final Office Action dated Jul. 25, 2018 in U.S. Appl. No. 15/108,268.
Non-Final Office Action dated Oct. 4, 2018 in U.S. Appl. No. 15/260,106.
Non-Final Office Action dated Oct. 25, 2018 in U.S. Appl. No. 16/012,584.
Non-Final Office Action dated Nov. 5, 2018 in U.S. Appl. No. 16/038,790.
Non-Final Office Action dated Nov. 26, 2018 in U.S. Appl. No. 15/937,713.
Non-Final Office Action dated Jan. 7, 2019 in U.S. Appl. No. 15/055,407.
Non-Final Office Action dated Jan. 14, 2019 in U.S. Appl. No. 16/219,553.
Non-Final Office Action dated Mar. 19, 2019 in U.S. Appl. No. 15/046,225.
Non-Final Office Action dated May 15, 2019 in U.S. Appl. No. 15/084,307.
Non-Final Office Action dated May 23, 2019 in U.S. Appl. No. 15/459,977.
Non-Final Office Action dated Jun. 17, 2019 in U.S. Appl. No. 14/381,488.
Non-Final Office Action dated Jul. 9, 2019 in U.S. Appl. No. 15/596,364.
Non-Final Office Action dated Aug. 20, 2019 for U.S. Appl. No. 15/715,028.
Non-Final Office Action dated Sep. 18, 2019 in U.S. Appl. No. 16/194,819.
Non-Final Office Action dated Nov. 29, 2019 in U.S. Appl. No. 15/937,713.
Non-Final Office Action dated Jan. 17, 2020 in U.S. Appl. No. 15/084,307.
Non-Final Office Action dated Feb. 5, 2020 in U.S. Appl. No. 15/875,816.

(56) References Cited

OTHER PUBLICATIONS

Non-Final Office Action dated Mar. 12, 2020 in U.S. Appl. No. 16/789,358.
Non-Final Office Action dated Mar. 17, 2020 in U.S. Appl. No. 15/055,407.
Non-Final Office Action dated Mar. 26, 2020 in U.S. Appl. No. 16/012,635.
Non-Final Office Action dated Mar. 26, 2020 in U.S. Appl. No. 16/789,311.
Non-Final Office Action dated Jun. 8, 2020 in U.S. Appl. No. 15/715,028.
Non-Final Office Action dated Aug. 4, 2020 in U.S. Appl. No. 15/459,977.
Non-Final Office Action dated Aug. 19, 2020 in U.S. Appl. No. 16/374,626.
Non-Final Office Action dated Aug. 25, 2020 in U.S. Appl. No. 14/381,488.
Non-Final Office Action dated Dec. 4, 2020 in U.S. Appl. No. 16/677,012.
Non-Final Office Action dated Dec. 9, 2020 in U.S. Appl. No. 16/788,743.
Notice of Allowability dated Jun. 19, 2014 for U.S. Appl. No. 12/969,581.
Notice of Allowance dated Mar. 21, 2014 for U.S. Appl. No. 12/969,581.
Notice of Allowance dated Aug. 22, 2014 for U.S. Appl. No. 12/969,581.
Notice of Allowance dated Dec. 15, 2015 for U.S. Appl. No. 14/540,007.
Notice of Allowance dated Dec. 21, 2015 in U.S. Appl. No. 14/540,018.
Notice of Allowance dated Jan. 21, 2016 for U.S. Appl. No. 13/327,526.
Notice of Allowance dated Jan. 9, 2019 in U.S. Appl. No. 15/603,239.
Notice of Allowance dated Mar. 20, 2019 in U.S. Appl. No. 16/219,553.
Notice of Allowance dated Mar. 21, 2019 in U.S. Appl. No. 15/993,468.
Notice of Allowance dated May 28, 2019 in U.S. Appl. No. 16/219,553.
Notice of Allowance dated Sep. 24, 2019 in U.S. Appl. No. 15/217,886.
Notice of Allowance dated Nov. 11, 2019 in Japanese Patent Application No. 2017-245295.
Notice of Allowance dated Nov. 29, 2019 in U.S. Appl. No. 16/012,635.
Notice of Allowance dated Dec. 27, 2019 in U.S. Appl. No. 15/260,106.
Notice of Allowance dated Mar. 5, 2020 in U.S. Appl. No. 15/217,886.
Notice of Allowance dated Mar. 27, 2020 in U.S. Appl. No. 15/596,364.
Notice of Allowance dated Mar. 30, 2020 in U.S. Appl. No. 15/937,713.
Notice of Allowance dated Apr. 15, 2020 in U.S. Appl. No. 16/012,635.
Notice of Allowance dated Sep. 23, 2020 in Korean Patent Application No. 10-2016-7008144.
Notice of Allowance dated Oct. 29, 2020 in U.S. Appl. No. 15/987,851.
Notice, Consent, and Reference of a Civil Action to a Magistrate Judge (Rule 73.1), filed Nov. 15, 2018 in the USDC for the District of Delaware, C.A. 18-1800-RGA, 3 pp.
Notice of Opposition dated Jul. 9, 2015 for European Patent Application No. 11810645.9.
Notice of Opposition dated Jul. 27, 2016 for European Patent Application No. 10762102.1.
Notice of Reasons for Rejection dated Dec. 28, 2016 in Japanese Patent Application No. 2014-558975.
Notice of Reasons for Rejection dated Apr. 2, 2018 in Japanese Patent Application No. 2014-558975.
Notice of Reasons for Rejection dated Jul. 30, 2018 in Japanese Patent Application No. 2016-537867.
Notice of Reasons for Rejection dated Aug. 31, 2018 in Japanese Patent Application No. 2016-520632.
Notice of Reasons for Rejection dated Dec. 5, 2018 in Japanese Patent Application No. 2017-245295.
Notice of Reason for Rejection dated Nov. 21, 2019 in Korean Patent Application No. 10-2016-7008144.
Notice of Reasons for Rejection dated Feb. 25, 2020 in Japanese Patent Application No. 2019-014564.
Notice of Reasons for Rejection dated May 11, 2020 in Japanese Patent Application No. 2017-549390.
Notice of Service of Disclosures to Opposing Counsel, dated Jun. 10, 2019 in the USDC for the District of Delaware, C.A. 18-1800 (RGA), 3 pp.
Notice of Service of Interrogatories and First Request of Documents and Things to Defendant 10X Genomics, Inc., dated Jul. 5, 2019 in the USDC for the District of Delaware, C.A. 18-1800 (RGA), 3 pp.
Notification Prior to Examination dated Nov. 27, 2019 in Israeli Patent Application No. 265478.
Novak et al., "Single-Cell Multiplex Gene Detection and Sequencing with Microfluidically Generated Agarose Emulsions," Angew. Chem. Int. Ed. 2011, 50, 390-395.
Office Action dated Jun. 6, 2016 in Chinese Patent Application No. 201380022187.9.
Office Action dated Dec. 27, 2016 in Chinese Patent Application No. 201380022187.9.
Office Action dated Feb. 17, 2017 in Canadian Patent Application No. 2,865,575.
Office Action dated Jul. 14, 2017 in Chinese Patent Application No. 201380022187.9.
Office Action dated Dec. 19, 2017 in Chinese Patent Application No. 201480061859.1.
Office Action dated Feb. 15, 2018 in Canadian Patent Application No. 2,865,575.
Office Action dated Sep. 7, 2018 in Chinese Patent Application No. 201480061859.1.
Office Action dated Dec. 13, 2018 in Canadian Patent Application No. 2,865,575.
Office Action dated Jan. 2, 2019 in Chinese Patent Application No. 201480059505.3.
Office Action dated Mar. 4, 2020 in Canadian Patent Application No. 2,865,575.
Office Action dated Jun. 22, 2020 in Chinese Patent Application No. 201680007351.2.
Office Action dated Jun. 22, 2020 in Chinese Patent Application No. 201680007652.5.
Office Action dated Jun. 23, 2020 in Chinese Patent Application No. 2016800157452.
Office Action dated Jul. 20, 2020 in Japanese Patent Application No. 2018-512152.
Office Action dated Oct. 29, 2020 in Chinese Patent Application No. 2018800377201.
Office Action dated Nov. 12, 2020 in European Patent Application No. 18716877.8.
Office Action dated Dec. 3, 2020 in European Patent Application No. 16719706.0.
Office Action dated Jan. 4, 2021 in Japanese Patent Application No. 2017-549390.
Ogino et al., "Quantification of PCR bias caused by a single nucleotide polymorphism in SMN gene dosage analysis," J Mol Diagn. 2002, 4(4), 185-190.
Opposition to Defendant's Motion to Dismiss Pursuant to Federal Rule of Civil Procedure 12(b)(6) dated Feb. 15, 2019, in the USDC for the District of Delaware, C.A. 18-800-RGA, 3 pp.
Oral Order by Judge Andrews Canceling Scheduling Conference set for May 8, 2019.
Order Setting Rule 16(b) Conference as Ordered by Judge Andrews Pursuant to Fed. R. Civ. P. 16(b), ruling dated Apr. 17, 2019 in the USDC District of Delaware, C.A. 18-1800-RGA, 1 pp.
Order Scheduling ADR Mediation Teleconference, filed May 13, 2019 in the USDC for the District of Delaware, C.A. 18-1800-RGA, 4pp.

(56) References Cited

OTHER PUBLICATIONS

Ozkumur et al., "Inertial Focusing for Tumor Antigen-Dependent and -Independent Sorting of Rare Circulating Tumor Cells," Science Translational Medicine 2013, 5(179), 1-20.
Parameswaran et al., "A pyrosequencing-tailored nucleotide barcode design unveils opportunities for large-scale sample multiplexing," Nucleic Acids Res. 2007, 35(19), e130, 1-9.
Park et al., "Discovery of common Asian copy number variants using integrated high-resolution array CGH and massively parallel DNA sequencing," Nat Genet. 2010, 42(5), 400-405.
Patanjali et al., "Construction of a uniform-abundance (normalized) CNDA library," Proceedings of the National Academy of Sciences 1991, 88(5), 1943-1947.
Peng et al., "Reducing amplification artifacts in high multiplex amplicon sequencing by using molecular barcodes," BMC Genomics 2015, 16(589), 1-12.
Perez-Rentero et al., "Synthesis of Oligonucleotides Carrying Thiol Groups Using a Simple Reagent Derived fromThreoninol," Molecules 2012, 17, 10026-10045.
Peterson et al., "Multiplexed quantification of proteins and transcripts in single cells," Nature Biotechnology 2017, 35, 936-939.
Pfaffl et al., "Determination of stable housekeeping genes, differentially regulated target genes and sample integrity: BestKeeper—Excel-based tool using pair-wise correlations," Biotechnology Letters, 26(6), 505-515.
Picelli et al., "Tn5 transposase and tagmentation procedures for massively scaled sequencing projects," Genome Research 2014, 24(12), 2033-2040.
Picelli et al., "Single-cell RNA-sequencing: The future of genome biology is now," RNA Biology 2017, 14(5), 637-650.
Pihlak et al., "Rapid genome sequencing with short universal tiling probes," Nature Biotechnology 2008, 26, 1-9.
Pinkel et al., "Comparative Genomic Hybridization," Annual Review of Genomics and Human Genetics Jun. 2005, 331-354.
Plaintiff's Brief in Opposition to Defendant's Motion to Dismiss Pursuant to Fed. R. Civ. P. 12(b)(6), filed Mar. 29, 2019 in the USDC District of Delaware, C.A. No. 18-1800 (RGA), 27 pp.
Plaintiff's First Amended Complaint filed on Feb. 8, 2019, in the USDC for the District of Delaware, C.A. 18-1800-RGA, 178 pp.
Pleasance et al., "A small-cell lung cancer genome with complex signatures of tobacco exposure," Nature 2010, 463(7278), 184-190.
Plessy et al., "Population transcriptomics with single-cell resolution: a new field made possible by microfluidics: a technology for high throughput transcript counting and data-driven definition of cell types," Bioessays 2012, 35, 131-140.
Pre-interview communication dated Nov. 27, 2018 in U.S. Appl. No. 16/012,635.
Preissl et al., "Single-nucleus analysis of accessible chromatin in developing mouse forebrain reveals cell-type-specific transcriptional regulation," Nature Neuroscience 2018, 21(3), 432-439.
Proposed Stipulated Protective Order Pursuant to Rule 26(c) ofthe Federal Rules of Civil Procedure, filed Jun. 20, 2019 In the USDC for the District of Delaware, C.A. 18-1800 (RGA), 26 pp.
Qiu et al., "DNA Sequence-Based "BarCodes" for Tracking the Origins of Expressed Sequence Tags from a Maize cDNA Library Constructed Using Multiple mRNA Sources," Plant Physiol. 2003, 133, 475-481.
Raj et al., "Stochastic mRNA synthesis in mammalian cells," PLoS Biol. 2006, 4(10) 1707-1719.
Raj et al., "Imaging individual mRNA molecules using multiple singly labeled probes," Nature Methods 2008, 5(10), 877-879.
Raj et al., "Single-Molecule Approaches to Stochastic Gene Expression," Annu Rev Biophys 2009, 38, 255-270.
Rajeevan et al., "Global amplification of sense RNA: a novel method to replicate and archive mRNA for gene expression analysis," Genomics 2003, 82, 491-497.
Report on the Filing or Determination of an Action Regarding a Patent or Trademark filed Nov. 15, 2018 in the USDC for the District of Delaware, C.A. 18-1800-RGA, 2 pp.

Restriction Requirement dated Mar. 15, 2016 in U.S. Appl. No. 14/381,488.
Restriction Requirement dated Mar. 17, 2016 in U.S. Appl. No. 14/472,363.
Restriction Requirement dated Mar. 29, 2019 in U.S. Appl. No. 15/715,028.
Restriction Requirement dated Jun. 19, 2019 in U.S. Appl. No. 15/596,364.
Restriction Requirement dated Sep. 20, 2019 in U.S. Appl. No. 15/875,816.
Rhee et al., "Simultaneous detection of mRNA and protein stem cell markers in live cells," BMC Biotechnology 2009, 9(30), 1-10.
Roche Diagnostics GmbH, "Genome Sequencer 20 System: First to the Finish," 2006, 1-40.
Rule 7.1 Disclosure Statement dated Nov. 15, 2018 in the USDC for the District of Delaware, C.A. 18-1800-RGA, 1 pp.
Sah et al., "Complete Genome Sequence of a 2019 Novel Coronavirus (SARS-CoV-2) Strain Isolated in Nepal," Microbiol Resour Announc. 2020, 9(11), e00169-20, 3 pp.
Sano et al., "Immuno-PCR: Very Sensitive Antigen Detection by Means of Specific Antibody—DNA Conjugates," Science 1992, 258, 120-122.
Sasagawa et al., "Quartz-Seq: a highly reproducible and sensitive single-cell RNA sequencing method, reveals non-genetic gene-expression heterogeneity," Genome Biology 2013, 14, R31.
Sasuga et al., Single-cell chemical lysis method for analyses of intracellular molecules using an array of picoliter-scale microwells, Anal Chem 2008, 80(23), 9141-9149.
Satija et al., Spatial reconstruction of single-cell gene expression data, Nature Biotechnology 2015, 33(5), 495-508.
Scheduling Order pursuant to Local Rule 16.1(b), filed May 7, 2019 in the USDC for the District of Delaware, C.A. 18-1800-RGA, 10 pp.
Scheduling Order Signed by Judge Andrews, dated May 8, 2019 in the USDC for the District of Delaware, C.A. 18-1800-RGA, 10 pp.
Schmitt et al., "Detection of ultra-rare mutations by next-generation sequencing," Proc Natl Acad Sci 2012, 109(36), 1-6.
Search and Examination Report dated Aug. 26, 2015 in United Kingdom Patent Application No. 1511591.8.
Search Report and Written Opinion dated Jan. 26, 2016 in Singapore Patent Application No. 1120140527W.
Search Report and Written Opinion dated Aug. 26, 2020 in Singapore Patent Application No. 10201806890V.
Sebat et al., "Large-Scale Copy Number Polymorphism in the Human Genome," Science 2004, 305, 525-528.
Shahi et al., "Abseq: ultrahigh-throughput single cell protein profiling with droplet microfluidic barcoding," Scientific Reports 2017, 7(44447), 1-10.
Shalek et al., "Single-cell transcriptomics reveals bimodality in expression and splicing in immune cells," Nature 2013, 498(7453), 236-240.
Shendure et al., "Next-generation DNA sequencing," Nature Biotechnology 2008, 26(10), 1135-1145.
Shiroguchi et al., "Digital RNA sequencing minimizes sequence-dependent bias and amplification noise with optimized single-molecule barcodes," Proc Natl Acad Sci 2012, 109(4):1347-1352.
S.H.KO, "An 'equalized cDNA library' by the reassociation of short double-stranded cDNAs," Nucleic Acids Res. 1990, 18(19), 5705-5711.
Shoemaker et al., "Quantitative phenotypic analysis of yeast deletion mutants using a highly parallel molecular bar-coding strategy," Nature Genetics 1996, 14, 450-456.
Shortreed et al., "A thermodynamic approach to designing structure-free combinatorial DNA word sets," Nucleic Acids Res. 2005, 33(15), 4965-4977.
Shum et al., "Quantitation of mRNA Transcripts and Proteins Using the BD Rhapsody™ Single-Cell Analysis System," Adv Exp Med Biol. 2019,1129, 63-79.
Simpson et al., "Copy number variant detection in inbred strains from short read sequence data," Bioinformatics 2010, 26(4), 565-567.

(56) References Cited

OTHER PUBLICATIONS

Smith et al., "Highly-multiplexed barcode sequencing: an efficient method for parallel analysis of pooled samples," Nucleic Acids Research 2010, 38(13), e142, 1-7.
Soares et al., "Construction and characterization of a normalized cDNA library," Proc. Natl., Acad. Sci. 1994, 91, 9228-9232.
Sogin et al., "Microbial diversity in the deep sea and the underexplored "rare biosphere"," PNAS 2008, 103(32), 12115-12120.
Sommer et al., "Minimal homology requirements for PCR primers," Nucleic Acids Research 1989, 17(16), 6749.
Song et al., "Design rules for size-based cell sorting and sheathless cell focusing by hydrophoresis," Journal of Chromatography A 2013, 1302, 191-196.
Soumillon et al., "Characterization of directed differentiation by high-throughput single-cell RNA-Seq," bioRxiv Jan. 13, 2014.
Speicher et al., "The new cytogenetics: blurring the boundaries with molecular biology," Nature Reviews Genetics 2005, 6(10), 782-792.
Statement of Opposition of Strawman Limited filed against European Patent No. EP2414548B1 on Jul. 19, 2016.
Statement of Opposition dated Jul. 21, 2016 filed against European Patent No. EP2414548B1.
Statement of Opposition filed against European Patent No. EP2414548B1 on Jul. 26, 2016.
Statement regarding Third-Party Submission filed on Jun. 6, 2018 for U.S. Appl. No. 15/847,752.
Stipulated Protective Order Pursuant to Rule 26(c) ofthe Federal Rules of Civil Procedure, dated Jun. 21, 2019 in the USDC for the District of Delaware, C.A. 18-1800 (RGA), 26 pp.
Stipulation and Order to Extend Time to File Opposition to Motion to Dismiss, and Reply in Support of the Motion, dated Jan. 28, 2019 in the USDC for the District of Delaware, C.A. 18-1800-RGA, 2 pp.
Stoeckius et al., "Large-scale simultaneous measurement of epitopes and transcriptomes in single cells," Nature Methods 2017, 14(9), 865-868.
Stratagene 1988 Catalog, Gene Characterization Kits, 39.
Subkhankulova et al., "Comparative evaluation of linear and exponential amplification techniques for expression profiling at the single cell level," Genome Biology 2006, 7(3), 1-16.
Submission dated Jan. 15, 2018 in preparation for upcoming oral proceedings in opposition against European Patent No. EP2414548B1.
Summons in a Civil Action to Defendant 10X Genomics, Inc. filed Nov. 16, 2018 in the USDC for the District of Delaware, Civil Action No. 18-1800, 2 pp.
Summons to Attend Oral Proceedings dated Nov. 16, 2020 in European Patent Application No. 17202409.3.
Sun et al., "Ultra-deep profiling of alternatively spliced *Drosophila dscam* isoforms by circularization-assisted multi-segment sequencing," EMBO J. 2013, 32(14), 2029-2038.
Takahashi et al., "Novel technique of quantitative nested real-time PCR assay for *Mycobacterium tuberculosis* DNA," Journal of Clinical Microbiology 2006, 44, 1029-1039.
Tan et al., "Genome-wide comparison of DNA hydroxymethylation in mouse embryonic stem cells and neural progenitor cells by a new comparative hMeDIP-seq method," Nucleic Acids Res. 2013, 41(7), e84, 1-12.
Tang et al., "RNA-Seq analysis to capture the transcriptome landscape of a single cell," Nature Protocols 2010, 5(3), 516-535.
Taudien et al., "Haplotyping and copy number estimation ofthe highly polymorphic human beta-defensin locus on 8p23 by 454 amplicon sequencing," BMC Genomics Nov. 2010, 252, 1-14.
The Tibbs Times, UNC bioscience newsletter, Apr. 1-17, 2010.
Third-Party Submission filed on May 21, 2018 for U.S. Appl. No. 15/847,752.
Tomaz et al., "Differential methylation as a cause of allele dropout at the imprinted GNAS locus," Genet Test Mol Biomarkers 2010, 14(4), 455-460.
Treutlein et al., Reconstructing lineage hierarchies ofthe distal lung epithelium using single-cell RNA-seq, Nature 2014, 509, 371-375.
Ullal et al., "Cancer cell profiling by barcoding allows multiplexed protein analysis in fine needle aspirates," Sci Transl Med. 2014, 6(219), 22 pp.
Unopposed Motion to Extend Time for Defendant's Response, dated Dec. 4, 2018 in the USDC for the District of Delaware, C.A. 18-1800-(RGA), 2 pp.
Vandesompele et al., "Accurate normalization of real-time quantitative RT-PCR data by geometric averaging of multiple internal control genes," Genome Biology 2002, 3(7), 1-12.
Velculescu et al., "Serial Analysis of Gene Expression," Science 1995, 270(5235), 484-487.
Velculescu et al., "Characterization ofthe Yeast Transcriptome," Cell 1997, 88, 243-251.
Vogelstein et al., "Digital PCR," Proc. Natl. Acad. Sci. 1999, 96, 9236-9241.
Vollbrecht et al., "Validation and comparison of two NGS assays for the detection of EGFR T790M resistance mutation in liquid biopsies of NSCLC patients," Oncotarget 2018, 9(26), 18529-18539.
Walker et al., "Isothermal in vitro amplification of DNA by a restriction enzyme/DNA polymerase system," Proc Natl Acad Sci 1992, 89, 392-396.
Walsh et al., "Detection of inherited mutations for breast and ovarian cancer using genomic capture and massively parallel sequencing," Proc Natl Acad Sci 2010, 107(28), 12629-12633.
Wang et al., "Combining Gold Nanoparticles with Real-Time Immuno-PCR for Analysis of HIV p24 Antigens," Proceedings of ICBBE 2007, 1198-1201.
Wang et al., "RNA-Seq: a revolutionary tool for transcriptomics," Nature Reviews Genetics 2009, 10(1), 57-63.
Wang et al., "iCLIP predicts the dual splicing effects of TIA-RNA interactions," PLoS Biol 2010, 8(10), e1000530, 1-16.
Wang et al., "Advances and applications of single-cell sequencing technologies," Molecular Cell 2015, 58, 598-609.
Warren et al., "Transcription factor profiling in individual hematopoietic progenitors by digital RT-PCR," PNAS 2006, 103(47), 17807-17812.
Weber et al., "A real-time polymerase chain reaction assay for quantification of allele ratios and correction of amplification bias," Anal Biochem. 2003, 320, 252-258.
Weibrecht et al., "Proximity ligation assays: a recent addition to the proteomics toolbox," Expert Rev. Proteomics 2010, 7(3), 401-409.
Weiner et al., "Kits and their unique role in molecular biology: a brief retrospective," BioTechniques 2008, 44(5), 701-704.
White et al., "High-throughput microfluidic single-cell RT-qPCR," PNAS 2011, 108(34), 13999-14004.
Wittes et al., "Searching for Evidence of Altered Gene Expression: a Comment on Statistical Analysis of Microarray Data," Journal of the National Cancer Institute 1999, 91(5), 400-401.
Wodicka et al., "Genome-wide expression monitoring in *Saccharomyces cerevisiae*," Nature Biotechnology 1997, 15, 1359-1367.
Wojdacz et al., "Primer design versus PCR bias in methylation independent PCR amplifications," Epigenetics 2009, 4(4), 231-234.
Wood et al., "Using next-generation sequencing for high resolution multiplex analysis of copy number variation from nanogram quantities of DNA from formalin-fixed paraffin-embedded specimens," Nucleic Acids Res. 2010, 38(14), 1-14.
Written Submission of Publications dated Jun. 14, 2018 in Japanese Patent Application No. 2016-537867.
Wu et al., "Quantitative assessment of single-cell RNA-sequencing methods," Nat Methods 2014, 11(1), 41-46.
Yandell et al., "A probabilistic disease-gene finder for personal genomes," Genome Res. 2011, 21(9), 1529-1542.
Ye et al., Fluorescent microsphere-based readout technology for multiplexed human single nucleotide polymorphism analysis and bacterial identification, Human Mutation 2001, 17(4), 305-316.
Yoon et al., Sensitive and accurate detection of copy number variants using read depth of coverage, Genome Res. 2009, 19, 1586-1592.
Zagordi et al., "Error correction of next-generation sequencing data and reliable estimation of HIV quasispecies," Nucleic Acids Research 2010, 38(21), 7400-7409.

(56) References Cited

OTHER PUBLICATIONS

Zhang et al., "The impact of next-generation sequencing on genomics," J Genet Genomics 2011, 38(3), 95-109.
Zhang et al., "DNA-based hybridization chain reaction for amplified bioelectronic signal and ultrasensitive detection of proteins," Anal Chem. 2012, 84, 5392-5399.
Zhao et al., "Homozygous Deletions and Chromosome Amplifications in Human Lung Carcinomas Revealed by Single Nucleotide Polymorphism Array Analysis," Cancer Research 2005, 65(13), 5561-5570.
Zheng et al., "Haplotyping germline and cancer genomes with high-throughput linked-read sequencing," Nature Biotechnology 2016, 34(3), 303-311.
Zhou et al., "Counting alleles reveals a connection between chromosome 18q loss and vascular invasion," Nature Biotechnology 2001, 19, 78-81.
Zhou et al., "Photocleavable Peptide-Oligonucleotide Conjugates for Protein Kinase Assays by MALDI-TOF MS," Mol. BioSyst. Aug. 2012, 2395-2404.
Zhu et al., "Reverse Transcriptase Template Switching: A SMART Approach for Full-Length cDNA Library Construction," BioTechniques 2001, 30(4), 892-897.
Adey et al., "Rapid, low-input, low-bias construction of shotgun fragment libraries by high-density in vitro transposition," Genome Biology 2010, 11(R19), in 17 pages.
Ahern, "Biochemical, Reagent Kits Offer Scientists Good Return on Investment," The Scientist 1995, 9(15), in 5 pages.
Bolivar et al., "Targeted next-generation sequencing of endometrial cancer and matched circulating tumor DNA: identification of plasma-based, tumor-associated mutations in early stage patients," Modern Pathology 2019, 32(3), 405-414.
Brouilette et al., "A Simple and Novel Method for RNA-seq Library Preparation of Single Cell cDNA Analysis by Hyperactive Tn5 Transposase," Developmental Dynamics 2012, 241, 1584-1590.
Buenrosto et al., "Transposition of native chromatin for multimodal regulatory analysis and personal epigenomics," Nat Methods 2013, 10(12), 1213-1218.
Buenrosto et al., "ATAC-seq: A Method for Assaying Chromatin Accessibility Genome-Wide," Curr Protoc Mol Biol 2016, 109, 1-21.
Chang et al., "Single-cell protein and gene expression profiling of stem memory T cells by BD Ab-seq," Annual Joint Meeting of the American Society for Cell Biology and the European Molecular Biology Organization 2017, 28(26), p. 1896.
Chen et al., "High-throughput sequencing of the transcriptome and chromatin accessibility in the same cell," Nature Biotechnology 2019, 37, 1452-1457.
Dengl et al., "Engineered hapten-binding antibody derivatives for modulation of pharmacokinetic properties of small molecules and targeted payload delivery," Immunol Rev. 2016, 270, 165-177.
Examination Report dated Mar. 25, 2021 in European Patent Application No. 17781265.8.
Examination Report dated Oct. 8, 2021 in European Patent Application No. 18716877.8.
Examination Report dated Nov. 18, 2021 in European Patent Application No. 19724003.9.
Examination Report dated Nov. 24, 2021 in European Patent Application No. 19762517.1.
Examination Report dated Dec. 6, 2021 in European Patent Application No. 18703156.2.
Examination Report dated Dec. 9, 2021 in European Patent Application No. 19723988.2.
Examination Report dated Apr. 7, 2022 in Singapore Patent Application No. 10201806890V.
Examination Report dated Apr. 8, 2022 in Australian Patent Application No. 2018281745.
Extended European Search Report dated May 6, 2021 in European Patent Application No. 20207621.2.
Extended European Search Report dated May 28, 2021 in European Patent Application No. 20209777.0.
Final Office Action dated Feb. 11, 2021 in U.S. Appl. No. 15/134,967.
Final Office Action dated Mar. 16, 2021 in U.S. Appl. No. 15/715,028.
Final Office Action dated Mar. 25, 2021 in U.S. Appl. No. 16/374,626.
Final Office Action dated Jun. 15, 2021 in U.S. Appl. No. 15/084,307.
Final Office Action dated Jul. 15, 2021 in U.S. Appl. No. 16/836,750.
Final Office Action dated Aug. 10, 2021 in U.S. Appl. No. 16/012,584.
Final Office Action dated Aug. 27, 2021 in U.S. Appl. No. 15/055,407.
Final Office Action dated Sep. 24, 2021 in U.S. Appl. No. 16/788,743.
Final Office Action dated Oct. 1, 2021 in U.S. Appl. No. 16/677,012.
Final Office Action dated Nov. 2, 2021 in U.S. Appl. No. 16/789,311.
Final Office Action dated Jan. 18, 2022 in U.S. Appl. No. 16/588,405.
Final Office Action dated Feb. 23, 2022 in U.S. Appl. No. 16/707,780.
Final Office Action dated Mar. 15, 2022 in U.S. Appl. No. 16/374,626.
Final Office Action dated Mar. 25, 2022 in U.S. Appl. No. 16/551,620.
Final Office Action dated Apr. 12, 2022 in U.S. Appl. No. 15/084,307.
Final Office Action dated May 26, 2022 in U.S. Appl. No. 16/747,737.
Final Office Action dated Jun. 14, 2022 in U.S. Appl. No. 15/055,407.
Final Office Action dated Aug. 23, 2022 in U.S. Appl. No. 16/012,584.
Fitzgerald and Grivel, "A Universal Nanoparticle Cell Secretion Capture Assay," Cytometry Part A 2012, 83A(2), 205-211.
Gertz et al., "Transposase mediated construction of RNA-seq libraries," Genome Research 2012, 22, 134-141.
Goodridge et al., "Synthesis of Albumin and Malic Enzyme in Wheat-Germ Lysates and *Xenopus laevis* Oocytes Programmed with Chicken-Liver Messenger RNA," Eur. J. Biochem. 1979, 96, 1-8.
Gratton et al., "Cell-permeable peptides improve cellular uptake and therapeutic gene delivery of replication-deficient viruses in cells and in vivo," Nature Medicine 2003, 9(3), 357-362.
International Search Report and Written Opinion dated Jan. 19, 2021 in PCT Application No. PCT/US2020/059419.
International Search Report and Written Opinion dated Apr. 9, 2021 in PCT Application No. PCT/US2021/013137.
International Search Report and Written Opinion dated Apr. 21, 2021 in PCT Application No. PCT/US2021/015571.
International Search Report and Written Opinion dated May 4, 2021 in PCT Application No. PCT/US2021/013109.
International Search Report and Written Opinion dated May 11, 2021 in PCT Application No. PCT/US2021/013748.
International Search Report and Written Opinion dated Jul. 15, 2021 in PCT Application No. PCT/US2021/019475.
International Search Report and Written Opinion dated Jul. 20, 2021 in PCT Application No. PCT/US2021/015898.
International Search Report and Written Opinion dated Aug. 31, 2021 in PCT Application No. PCT/US2021/035270.
International Search Report and Written Opinion dated Sep. 22, 2021, in PCT Application No. PCT/US2021/013747.
International Search Report and Written Opinion dated Sep. 27, 2021, in PCT Application No. PCT/US2021/013747.
International Search Report and Written Opinion dated Oct. 12, 2021, in PCT Application No. PCT/US2021/041327.
International Search Report and Written Opinion dated Oct. 29, 2021, in PCT Application No. PCT/US2021/032319.
International Search Report and Written Opinion dated Dec. 6, 2021, in PCT Application No. PCT/US2021/046750.
International Search Report and Written Opinion dated Nov. 12, 2021, in PCT Application No. PCT/US2021/044036.
International Search Report and Written Opinion dated Mar. 10, 2022, in PCT Application No. PCT/US2021/060206.
International Search Report and Written Opinion dated Apr. 12, 2022, in PCT Application No. PCT/US2021/059573.
International Search Report and Written Opinion dated Mar. 11, 2022, in PCT Application No. PCT/US2021/060197.
International Search Report and Written Opinion dated Apr. 5, 2022, in PCT Application No. PCT/US2021/062473.
International Search Report and Written Opinion dated Jun. 8, 2022, in PCT Application No. PCT/US2022/021015.
International Search Report and Written Opinion dated Jul. 29, 2022, in PCT Application No. PCT/US2022/029023.
International Search Report and Written Opinion dated Jul. 29, 2022, in PCT Application No. PCT/US2022/029057.
Invitation to Pay Fees dated May 25, 2021 in PCT Application No. PCT/US2021/01598.

(56) References Cited

OTHER PUBLICATIONS

Invitation to Pay Additional Search Fees dated Sep. 8, 2021 in PCT Application No. PCT/US2021/032319.
Invitation to Provide Informal Clarification dated Jun. 9, 2021 in PCT Application No. PCT/US2021/019475.
Jacobsen et al., "33rd Annual Meeting & Pre-Conference Programs of the Society for Immunotherapy of Cancer," Journal for Immunotherapy of Cancer 2018, 6(S1), 7-11.
Janeway et al., "Structural variation in immunoglobulin constant regions," Immunology: The Immune System in Health and Disease 1999, 101-103.
Lake et al., "Integrative single-cell analysis of transcriptional and epigenetic states in the human adult brain," Nature Biotechnology 2018, 36(1), 70-80.
Lan et al., "Droplet barcoding for massively parallel single-molecule deep sequencing," Nature Communications 2016, 7(11784), in 10 pages.
Livingstone, "rRNA depletion, poly(A) enrichment, or exonuclease treatment?" Tebu-Bio Blog 2015, in 1 page.
Lutz et al., "Isolation and analysis of high quality nuclear DNA with reduced organellar DNA for plant genome sequencing and resequencing," BMC Biotechnology 2011, 11(54), in 9 pages.
Mair et al., "A Targeted Multi-omic Analysis Approach Measures Protein Expression and Low-Abundance Transcripts on the Single-Cell Level", Cell Reports 2020, 31(1), 107499, in 20 pages.
Minnoye et al., "Chromatin accessibility profiling methods," Nature Reviews Method Primers Jan. 24, 2021.
Monneron, "One-step Isolation and Characterization of Nuclear Membranes, 1974 Electron Microscopy and Composition of Biological Membranes and Envelops," The Royal Publishing Society 1974, 268, 101-108.
Non-Final Office Action dated Jan. 19, 2021 in U.S. Appl. No. 16/836,750.
Non-Final Office Action dated Feb. 2, 2021 in U.S. Appl. No. 16/535,080.
Non-Final Office Action dated Feb. 25, 2021 in U.S. Appl. No. 15/055,407.
Non-Final Office Action dated Feb. 25, 2021 in U.S. Appl. No. 15/084,307.
Non-Final Office Action dated Mar. 29, 2021 in U.S. Appl. No. 16/789,358.
Non-Final Office Action dated Apr. 14, 2021 in U.S. Appl. No. 16/789,311.
Non-Final Office Action dated Apr. 20, 2021 in U.S. Appl. No. 15/875,816.
Non-Final Office Action dated May 18, 2021 in U.S. Appl. No. 16/535,080.
Non-Final Office Action dated Jun. 9, 2021 in U.S. Appl. No. 16/588,405.
Non-Final Office Action dated Aug. 17, 2021 in U.S. Appl. No. 16/551,620.
Non-Final Office Action dated Aug. 19, 2021 in U.S. Appl. No. 16/781,814.
Non-Final Office Action dated Aug. 31, 2021 in U.S. Appl. No. 15/715,028.
Non-Final Office Action dated Sep. 1, 2021 in U.S. Appl. No. 16/789,358.
Non-Final Office Action dated Sep. 14, 2021 in U.S. Appl. No. 16/707,780.
Non-Final Office Action dated Sep. 28, 2021 in U.S. Appl. No. 16/400,885.
Non-Final Office Action dated Sep. 30, 2021 in U.S. Appl. No. 16/374,626.
Non-Final Office Action dated Oct. 1, 2021 in U.S. Appl. No. 16/677,012.
Non-Final Office Action dated Oct. 8, 2021 in U.S. Appl. No. 16/400,866.
Non-Final Office Action dated Dec. 15, 2021 in U.S. Appl. No. 15/875,816.
Non-Final Office Action dated Dec. 21, 2021 in U.S. Appl. No. 15/055,407.
Non-Final Office Action dated Jan. 6, 2022 in U.S. Appl. No. 15/084,307.
Non-Final Office Action dated Feb. 2, 2022 in U.S. Appl. No. 16/747,737.
Non-Final Office Action dated Feb. 9, 2022 in U.S. Appl. No. 16/525,054.
Non-Final Office Action dated Apr. 5, 2022 in U.S. Appl. No. 16/400,885.
Non-Final Office Action dated Apr. 8, 2022 in U.S. Appl. No. 16/232,287.
Non-Final Office Action dated May 3, 2022 in U.S. Appl. No. 16/012,584.
Non-Final Office Action dated May 11, 2022 in U.S. Appl. No. 16/588,405.
Non-Final Office Action dated May 19, 2022 in U.S. Appl. No. 16/459,444.
Non-Final Office Action dated Jul. 7, 2022 in U.S. Appl. No. 16/788,743.
Non-Final Office Action dated Jul. 7, 2022 in U.S. Appl. No. 16/677,012.
Non-Final Office Action dated Jul. 18, 2022 in U.S. Appl. No. 16/551,620.
Non-Final Office Action dated Jul. 27, 2022 in U.S. Appl. No. 16/747,737.
Non-Final Office Action dated Oct. 13, 2022 in U.S. Appl. No. 17/147,272.
Notice of Allowance dated Jan. 13, 2021 in U.S. Appl. No. 14/381,488.
Notice of Allowance dated Jan. 13, 2021 in U.S. Appl. No. 15/459,977.
Notice of Allowance dated Apr. 26, 2021 in Japanese Patent Application No. 2019-014564.
Notice of Allowance dated Aug. 16, 2021 in Japanese Patent Application No. 2018-512152.
Notice of Allowance dated Nov. 16, 2021 in U.S. Appl. No. 16/836,750.
Notice of Allowance dated Jan. 24, 2022 in Korean U.S. Appl. No. 16/836,750.
Notice of Allowance dated Feb. 9, 2022 in U.S. Appl. No. 16/781,814.
Notice of Allowance dated Feb. 11, 2022 in Chinese Patent Application No. 201680007351.2.
Notice of Allowance dated Feb. 16, 2022 in U.S. Appl. No. 15/875,816.
Notice of Allowance dated Feb. 21, 2022 in Korean Patent Application No. 10-2020-7033213.
Notice of Allowance dated Apr. 11, 2022 in U.S. Appl. No. 15/134,967.
Notice of Allowance dated Apr. 25, 2022 in Korean Patent Application No. 10-2018-7008560.
Notice of Allowance dated Apr. 27, 2022 in U.S. Appl. No. 16/400,886.
Notice of Allowance dated May 9, 2022 in Australian Patent Application No. 2018281745.
Notice of Allowance dated May 15, 2022 in Japanese Patent Application No. 2019-540515.
Notice of Allowance dated May 23, 2022 in U.S. Appl. No. 15/715,028.
Notice of Allowance dated May 26, 2022 in Korean Patent Application No. 10-2019-7038794.
Notice of Allowance dated Jun. 6, 2022 in U.S. Appl. No. 16/789,358.
Notice of Allowance dated Jul. 20, 2022 in U.S. Appl. No. 16/707,780.
Notice of Allowance dated Aug. 9, 2022 in U.S. Appl. No. 16/232,287.
Notice of Allowance dated Sep. 26, 2022, 2022 in U.S. Appl. No. 16/232,287.
Notice of Allowance dated Oct. 17, 2022, 2022 in U.S. Appl. No. 16/400,885.
Notice of Allowance dated Oct. 20, 2022 in Australian Patent Application No. 2019204928.
Notice of Allowance dated Oct. 21, 2022 in European Patent Application No. 19762517.1.
Notice of Allowance dated Oct. 24, 2022 in European Patent Application No. 20708266.0.

(56) References Cited

OTHER PUBLICATIONS

Notice of Allowance dated Oct. 25, 2022 in European Patent Application No. 19724003.9.
Notice of Allowance dated Nov. 7, 2022 in U.S. Appl. No. 16/012,584.
Novus Biologicals, "Fixation and Permeability in ICC IF," Novus Biologicals Jan. 3, 2021.
Nowak et al., "Does the KIR2DS5 gene protect from some human diseases?," PLoS One 2010, 5(8), in 6 pages.
Office Action dated Jan. 6, 2021 in Chinese Patent Application No. 201680052330.2.
Office Action dated Jan. 14, 2021 in Japanese Patent Application No. 2019-014564.
Office Action dated Jan. 15, 2021 in Korean Patent Application No. 10-2020-7033213.
Office Action dated Jan. 26, 2021 in Chinese Patent Application No. 201680007351.2.
Office Action dated Feb. 4, 2021 in Canadian Patent Application No. 2,865,575.
Office Action dated Feb. 20, 2021 in Chinese Patent Application No. 201680022865.5.
Office Action dated Mar. 1, 2021 in Chinese Patent Application No. 201680007652.5.
Office Action dated Mar. 2, 2021 in Chinese Patent Application No. 2016800157452.
Office Action dated Mar. 8, 2021 in Japanese Patent Application No. 2018-512152.
Office Action dated Mar. 16, 2021 in Chinese Patent Application No. 2018800377201.
Office Action dated May 10, 2021 in Japanese Patent Application No. 2019-566787.
Office Action dated May 21, 2021 in Chinese Patent Application No. 201680007351.2.
Office Action dated Jul. 26, 2021 in Korean Patent Application No. 10-2019-7011635.
Office Action dated Jul. 28, 2021 in Korean Patent Application No. 10-2020-7033213.
Office Action dated Aug. 13, 2021 in Chinese Patent Application No. 2017800587991.
Office Action dated Aug. 27, 2021 in Chinese Patent Application No. 2016800076525.
Office Action dated Aug. 30, 2021 in Japanese Patent Application No. 2019-540515.
Office Action dated Aug. 31, 2021, in Korean Patent Application No. 10-2019-7038794.
Office Action dated Sep. 14, 2021, in Chinese Patent Application No. 2016800523302.
Office Action dated Oct. 21, 2021, in Chinese Patent Application No. 2016800073512.
Office Action dated Nov. 2, 2021, in Japanese Patent Application No. 2017-549390.
Office Action dated Dec. 23, 2021, in Japanese Patent Application No. 2019-566787.
Office Action dated Dec. 17, 2021 in Korean Patent Application No. 10-2018-7008560.
Office Action dated Jan. 13, 2022 in Chinese Patent Application 2017800587991.
Office Action dated Feb. 9, 2022 in Japanese Patent Application No. 2019-540515.
Office Action dated Mar. 7, 2022 in Korean Patent Application No. 10-2022-7004715.
Office Action dated May 17, 2022 in Australian Patent Application No. 2019024928.
Office Action dated May 24, 2022 in European Patent Application No. 20708266.0.
Office Action dated Jun. 28, 2022 in European Patent Application No. 16719706.0.
Office Action dated Aug. 2, 2022 in European Patent Application No. 19765601.0.
Office Action dated Aug. 1, 2022 in Korean Patent Application No. 10-2022-7017261.
O'Shea et al., "Analysis of T Cell Receptor Beta Chain CDR3 Size Using RNA Extracted from Formalin Fixed Paraffin Wax Embedded Tissue," Journal of Clinical Pathology 1997, 50(10), 811-814.
Prevette et al., "Polycation-Induced Cell Membrane Permeability Does Not Enhance Cellular Uptake or Expression Efficiency of Delivered DNA," Molecular Pharmaceutics 2010, 7(3), 870-883.
Pringle et al., "In Situ Hybridization Demonstration of Poly-Adenylated RNA Sequences in Formalin-Fixed Parafin Sections Using a Biotinylated Oligonucleotide Poly d(T) Probe," Journal of Pathology 1989, 158, 279-286.
Quail et al., "SASI-Seq: sample assurance Spike-Ins, and highly differentiating 384 barcoding for Illumina sequencing," BMC Genomics 2014, 15(110), in 13 pages.
Restriction Requirement dated Jun. 4, 2021 in U.S. Appl. No. 16/551,620.
Restriction Requirement dated Aug. 8, 2022 in U.S. Appl. No. 17/163,177.
Restriction Requirement dated Aug. 19, 2022 in U.S. Appl. No. 17/147,283.
Restriction Requirement dated Sep. 16, 2022 in U.S. Appl. No. 17/151,050.
Restriction Requirement dated Sep. 19, 2022 in U.S. Appl. No. 16/934,530.
Restriction Requirement dated Oct. 21, 2022 in U.S. Appl. No. 17/320,052.
Restriction Requirement dated Nov. 8, 2022 in U.S. Appl. No. 17/157,872.
Schouten et al., "Relative quantification of 40 nucleic acid sequences by multiplex ligation-dependent probe amplification," Nucleic Acids Research 2002, 30(12), e57.
Shapiro et al., "Single-cell sequencing-based technologies will revolutionize whole-organism science," Nature Reviews Genetics 2013, 14, 618-629.
Song et al., DNase-seq: a high-resolution technique for mapping active gene regulatory elements across the genome from mammalian cells, Cold Spring Harb Protoc, Feb. 2010, in 13 pages.
Sos et al., "Characterization of chromatin accessibility with a transposome hypersensitive sites sequencing (THS-seq) assay," Genome Biology 2016, 17(20), in 15 pages.
Stoeckius et al., "Cell Hashing with barcoded antibodies enables multiplexing and doublet detection for single cell genomics," Genome Biology 2018, 19(224), 1-12.
Takara Bio, "SMARTer Human BCR IgG IgM H/K/L Profiling Kit User Manual," Takara Bio USA Inc. Jan. 22, 2019.
TotalSeq™—A0251 anti-human Hashtag 1 Antibody, BioLegend®, Jul. 1-10, 2018.
Trzupek et al., "Discovery of CD8O and CD86 as recent activation markers on regulatory T cells by protein-RNA single-cell analysis", Genome Medicine 2020, 12(1), in 22 pages.
Vestheim et al., "Application of Blocking Oligonucleotides to Improve Signal-to-Noise Ratio in a PCR," Methods in Molecular Biology 2011, 687, 265-274.
Wang et al., "Tagmentation-based whole-genome bisulfite sequencing," Nature Protocols 2013, 8(10), 2022-2032.
Yang & Zhao, "Quantitative Analysis of Nonoxynol-9 in Blood," Contraception 1991, 43(2), 161-166.
Zeberg et al., "The major genetic risk factor for severe COVID-19 is inherited from Neanderthals," Nature 2020, 587(7835), 1-13.
Zhang et al., "Immunoaffinity Purification of Plasma Membrane with Secondary Antibody Superparamagnetic Beads," Journal of Proteome, Jun. 2006, 34-43.
Zhao et al., "Methylated DNA Immunoprecipitation and High-Throughput Sequencing (MeDIP-seq) Using Low Amounts of Genomic DNA," Cellular Reprogramming 2014, 16(3), in 20 pages.
De Simone et al., "Single Cell T Cell Receptor Sequencing: Techniques and Future Challenges," Frontiers in Immunology 2018, 9(1638), 1-7.
Dovgan et al., "Antibody—Oligonucleotide Conjugates as Therapeutic, Imaging, and Detection Agents," Bioconjugate Chem. 2019, 30, 2483-2501.

(56) References Cited

OTHER PUBLICATIONS

Erickson et al., "AbSeq Protocol Using the Nano-Well Cartridge-Based Rhapsody Platform to Generate Protein and Transcript Expression Data on the Single-Cell Level," STAR Protocols 2020, in 31 pages.
Final Office Action dated Nov. 15, 2022 in U.S. Appl. No. 16/525,054.
Final Office Action dated Nov. 16, 2022 in U.S. Appl. No. 16/588,405.
Final Office Action dated Jan. 25, 2023 in U.S. Appl. No. 16/789,311.
Final Office Action dated Jan. 26, 2023 in U.S. Appl. No. 16/459,444.
International Search Report and Written Opinion dated Dec. 5, 2022, in PCT Application No. PCT/US2022/075774.
International Search Report and Written Opinion dated Dec. 15, 2022, in PCT Application No. PCT/US2022/075655.
International Search Report and Written Opinion dated Dec. 20, 2022, in PCT Application No. PCT/US2022/075661.
International Search Report and Written Opinion dated Dec. 22, 2022, in PCT Application No. PCT/US2022/075577.
International Search Report and Written Opinion dated Jan. 9, 2023, in PCT Application No. PCT/US2022/076366.
Lee et al., "Comparison of Surface Markers between Human and Rabbit Mesenchymal Stem Cells," PLoS ONE 2014, 9(11), in 10 pages.
Non-Final Office Action dated Nov. 17, 2022 in U.S. Appl. No. 16/551,638.
Non-Final Office Action dated Dec. 8, 2022 in U.S. Appl. No. 16/934,530.
Non-Final Office Action dated Dec. 21, 2022 in U.S. Appl. No. 15/055,407.
Non-Final Office Action dated Jan. 10, 2023 in U.S. Appl. No. 17/163,177.
Non-Final Office Action dated Jan. 23, 2023 in U.S. Appl. No. 17/183,840.
Non-Final Office Action dated Jan. 24, 2023 in U.S. Appl. No. 17/157,872.
Notice of Allowance dated Apr. 26, 2022 in Chinese Patent Application No. 201780058799.1.
Notice of Allowance dated Jan. 10, 2023 in U.S. Appl. No. 16/588,405.
Notice of Allowance dated Jan. 31, 2023 in U.S. Appl. No. 16/747,737.
Office Action dated May 5, 2022 in European Patent Application No. 19787547.9.
Restriction Requirement dated Dec. 23, 2022 in U.S. Appl. No. 17/531,618.
Restriction Requirement dated Jan. 20, 2023 in U.S. Appl. No. 17/373,519.

* cited by examiner

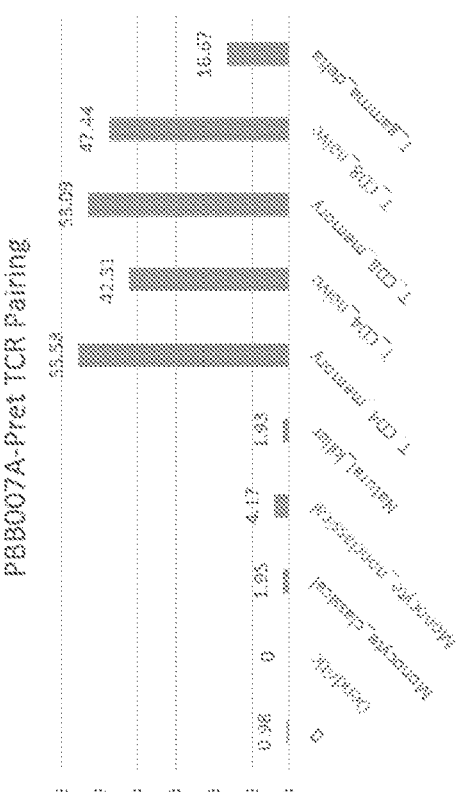
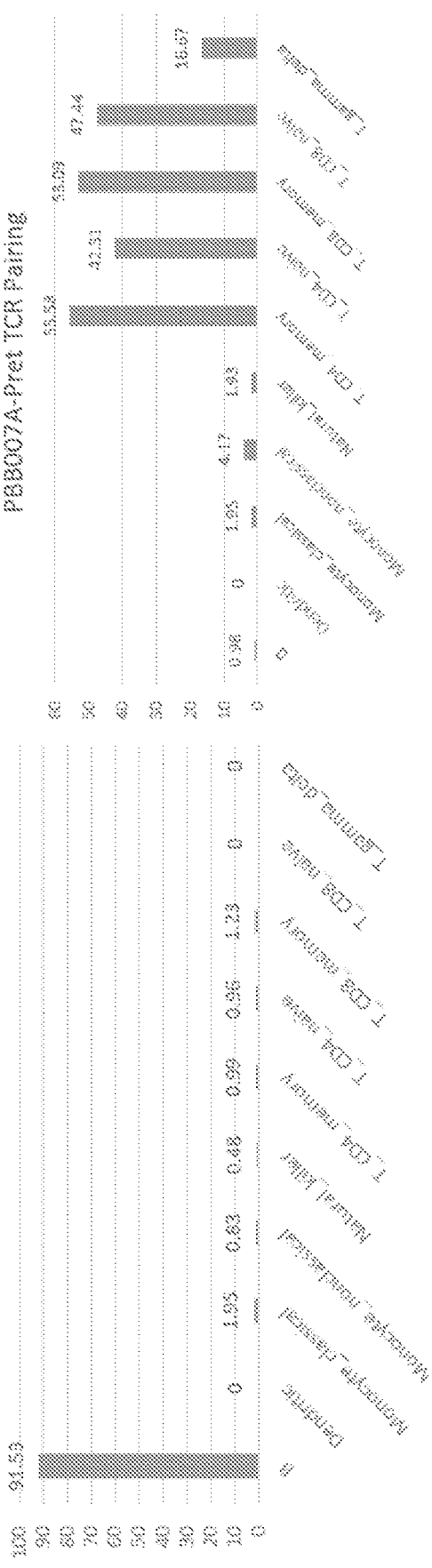
FIG. 12A  FIG. 12B  FIG. 12C  FIG. 12D

USING RANDOM PRIMING TO OBTAIN FULL-LENGTH V(D)J INFORMATION FOR IMMUNE REPERTOIRE SEQUENCING

RELATED APPLICATIONS

This application claims the benefit under 35 U.S.C. § 119(e) of U.S. Provisional Patent Application Ser. No. 62/933,285, filed Nov. 8, 2019, the content of this related application is incorporated herein by reference in its entirety for all purposes.

BACKGROUND

Field

The present disclosure relates generally to the field of molecular biology, and for particular to multiomics analyses using molecular barcoding.

Description of the Related Art

Methods and techniques of molecular barcoding are useful for single cell transcriptomics analysis, including deciphering gene expression profiles to determine the states of cells using, for example, reverse transcription, polymerase chain reaction (PCR) amplification, and next generation sequencing (NGS). Molecular barcoding is also useful for single cell proteomics analysis. There is a need for methods and techniques for full-length expression profiling of nucleic acid targets (e.g., V(D)J-containing transcripts). There is a need for compositions and methods that can enable both identification and counting of nucleic acid targets (e.g., V(D)J-containing transcripts).

SUMMARY

Disclosed herein include methods for labeling nucleic acid targets in a sample. In some embodiments, the method comprises: contacting copies of a nucleic acid target with a plurality of oligonucleotide barcodes, wherein each oligonucleotide barcode comprises a first universal sequence, a molecular label (e.g., a first molecular label), and a target-binding region capable of hybridizing to the nucleic acid target; generating a plurality of barcoded nucleic acid molecules each comprising the target-binding region and a complement of the target-binding region; hybridizing the complement of the target-binding region of each barcoded nucleic acid molecule with the target-binding region of one or more of: (i) an oligonucleotide barcode of the plurality of oligonucleotide barcodes, (ii) the barcoded nucleic acid molecule itself, and (iii) a different barcoded nucleic acid molecule of the plurality of barcoded nucleic acid molecules; extending 3'-ends of the plurality of barcoded nucleic acid molecules to generate a plurality of extended barcoded nucleic acid molecules each comprising the first molecular label and a second molecular label; amplifying the plurality of extended barcoded nucleic acid molecules using a target-specific primer capable of hybridizing to a sequence of the nucleic acid target and a primer comprising the first universal sequence, thereby generating a first plurality of barcoded amplicons comprising the sequence of the nucleic acid target, or a portion thereof; hybridizing random primers to the first plurality of barcoded amplicons and extending the random primers to generate a plurality of extension products, wherein the random primers comprise a second universal sequence, or a complement thereof; and amplifying the plurality of extension products using primers capable of hybridizing to the first universal sequence and the second universal sequence, or complements thereof, thereby generating a second plurality of barcoded amplicons. In some embodiments, the method comprises: determining the copy number of the nucleic acid target in the sample based on the number of first molecular labels with distinct sequences, second molecular labels with distinct sequences, or a combination thereof, associated with the second plurality of barcoded amplicons, or products thereof. In some embodiments, the method does not comprise fragmentation, tagmentation, or both.

Disclosed herein include methods of determining the numbers of nucleic acid targets in a sample. In some embodiments, the method comprises: contacting copies of a nucleic acid target with a plurality of oligonucleotide barcodes, wherein each oligonucleotide barcode comprises a first universal sequence, a molecular label (e.g., a first molecular label), and a target-binding region capable of hybridizing to the nucleic acid target; generating a plurality of barcoded nucleic acid molecules each comprising the target-binding region and a complement of the target-binding region; hybridizing the complement of the target-binding region of each barcoded nucleic acid molecule with the target-binding region of one or more of: (i) an oligonucleotide barcode of the plurality of oligonucleotide barcodes, (ii) the barcoded nucleic acid molecule itself, and (iii) a different barcoded nucleic acid molecule of the plurality of barcoded nucleic acid molecules; extending 3'-ends of the plurality of barcoded nucleic acid molecules to generate a plurality of extended barcoded nucleic acid molecules each comprising the first molecular label and a second molecular label; amplifying the plurality of extended barcoded nucleic acid molecules using a target-specific primer capable of hybridizing to a sequence of the nucleic acid target and a primer comprising the first universal sequence, thereby generating a first plurality of barcoded amplicons comprising the sequence of the nucleic acid target, or a portion thereof; hybridizing random primers to the first plurality of barcoded amplicons and extending the random primers to generate a plurality of extension products, wherein the random primers comprise a second universal sequence, or a complement thereof; amplifying the plurality of extension products using primers capable of hybridizing to the first universal sequence and the second universal sequence, or complements thereof, thereby generating a second plurality of barcoded amplicons; and determining the copy number of the nucleic acid target in the sample based on the number of first molecular labels with distinct sequences, second molecular labels with distinct sequences, or a combination thereof, associated with the second plurality of barcoded amplicons, or products thereof.

In some embodiments, determining the copy number of the nucleic acid target in the sample comprises: (a) determining the copy number of the nucleic acid target in the sample based on the number of second molecular labels with distinct sequences associated with the second plurality of barcoded amplicons, or products thereof, and/or (b) determining the copy number of the nucleic acid target in the sample based on the number of first molecular labels with distinct sequences associated with the second plurality of barcoded amplicons, or products thereof. In some embodiments, the method comprises: denaturing the plurality of barcoded nucleic acid molecules prior to hybridizing the complement of the target-binding region of each barcoded nucleic acid molecule with the target-binding region of: (i) an oligonucleotide barcode of the plurality of oligonucleotide barcodes, (ii) the barcoded nucleic acid molecule itself, and/or (iii) a different barcoded nucleic acid molecule of the plurality of barcoded nucleic acid molecules.

In some embodiments, the method comprises: denaturing the plurality of extended barcoded nucleic acid molecules prior to amplifying the plurality of extended barcoded nucleic acid molecules. In some embodiments, the sequence of each of the plurality of nucleic acid targets comprises a subsequence of each of the plurality of nucleic acid targets. In some embodiments, the sequence of the nucleic acid target in the plurality of barcoded nucleic acid molecules comprises a subsequence of the nucleic acid target. In some embodiments, the first molecular label is hybridized to the second molecular label after extending the 3'-ends of the plurality of barcoded nucleic acid molecules. In some embodiments, the extended barcoded nucleic acid molecules each comprise the first molecular label, the second molecular label, the target-binding region, and the complement of the target-binding region. In some embodiments, the complement of the target-binding region is complementary to a portion of the target-binding region. In some embodiments, the target-binding region comprises a gene-specific sequence, a poly(dT) sequence, or both.

In some embodiments, generating a plurality of barcoded nucleic acid molecules each comprising the target-binding region and a complement of the target-binding region comprises: (i) barcoding copies of a nucleic acid target in a sample using the plurality of oligonucleotide barcodes to generate a plurality of barcoded nucleic acid molecules each comprising a sequence complementary to at least a portion of the nucleic acid target, a first molecular label, and the target-binding region; and (ii) attaching an oligonucleotide comprising a complement of the target binding region to the plurality of barcoded nucleic acid molecules to generate a plurality of barcoded nucleic acid molecules each comprising the target-binding region and a complement of the target-binding region.

In some embodiments, generating a plurality of barcoded nucleic acid molecules each comprising the target-binding region and a complement of the target-binding region comprises: (i) barcoding copies of a nucleic acid target in a sample using the plurality of oligonucleotide barcodes to generate a plurality of barcoded nucleic acid molecules each comprising a sequence complementary to at least a portion of the nucleic acid target, a first molecular label, and the target-binding region; (ii) amplifying the plurality of barcoded nucleic acid molecules to generate a plurality of amplified barcoded nucleic acid molecules; and (iii) attaching an oligonucleotide comprising a complement of the target binding region to plurality of amplified barcoded nucleic acid molecules to generate a plurality of barcoded nucleic acid molecules each comprising the target-binding region and a complement of the target-binding region.

In some embodiments, barcoding copies of a nucleic acid target in a sample comprises extending the plurality of oligonucleotide barcodes hybridized to the copies of the nucleic acid target to generate the plurality of barcoded nucleic acid molecules. In some embodiments, extending the plurality of oligonucleotide barcodes hybridized to the copies of the nucleic acid target comprises reverse transcribing the copies of the nucleic acid target hybridized to the plurality of oligonucleotide barcodes. In some embodiments, attaching the oligonucleotide comprising the complement of the target binding region comprises ligating the oligonucleotide comprising the complement of the target binding region to the plurality of barcoded nucleic acid molecules and/or amplified barcoded nucleic acid molecules. In some embodiments, the target-binding region comprises a poly(dT) sequence, and wherein attaching the oligonucleotide comprising the complement of the target binding region comprises adding a plurality of adenosine monophosphates to the plurality of barcoded nucleic acid molecules and/or amplified barcoded nucleic acid molecules using a terminal deoxynucleotidyl transferase.

In some embodiments, generating a plurality of barcoded nucleic acid molecules each comprising the target-binding region and a complement of the target-binding region comprises: extending the plurality of oligonucleotide barcodes hybridized to the copies of the nucleic acid target in the presence of a reverse transcriptase and a template switch oligonucleotide comprising the target-binding region, or a portion thereof, to generate a plurality of barcoded nucleic acid molecules each comprising a sequence complementary to at least a portion of the nucleic acid target, a first molecular label, the target-binding region, and a complement of the target-binding region. In some embodiments, the reverse transcriptase is capable of terminal transferase activity. In some embodiments, the template switch oligonucleotide comprises one or more 3' ribonucleotides, for example three 3' ribonucleotides. In some embodiments, the 3' ribonucleotides comprise guanine. In some embodiments, the reverse transcriptase comprises a viral reverse transcriptase, for example murine leukemia virus (MLV) reverse transcriptase or a Moloney murine leukemia virus (MMLV) reverse transcriptase. In some embodiments, the method comprises extending the plurality of oligonucleotide barcodes hybridized to the copies of the nucleic acid target in the presence of one or more of ethylene glycol, polyethylene glycol, 1,2-propanediol, dimethyl sulfoxide (DMSO), glycerol, formamide, 7-deaza-GTP, acetamide, tetramethylammonium chloride salt, betaine, or any combination thereof.

In some embodiments, hybridizing the complement of the target-binding region of a barcoded nucleic acid molecule with the target-binding region of the barcoded nucleic acid molecule itself comprises intramolecular hybridization of the target-binding region and the complement of the target-binding region within a barcoded nucleic acid molecule to form a stem loop. In some embodiments, the second molecular label is the complement of the first molecular label.

In some embodiments, hybridizing the complement of the target-binding region of a barcoded nucleic acid molecule with the target-binding region of an oligonucleotide barcode of the plurality of oligonucleotide barcodes comprises intermolecular hybridization of the complement of the target-binding region of a barcoded nucleic acid molecule with the target-binding region of an oligonucleotide barcode of the plurality of oligonucleotide barcodes. In some embodiments, the second molecular label is a different from the first molecular label, and wherein the second molecular label is not a complement of the first molecular label. In some embodiments, the method comprises extending the 3' ends of the oligonucleotide barcodes hybridized to the complement of the target-binding region of the barcoded nucleic acid molecule to generate a plurality of extended barcoded nucleic acid molecules each comprising a complement of the first molecular label and a second molecular label. In some embodiments, the sequence of the second molecular label is different from the sequence of the first molecular label, wherein the wherein the second molecular label is not a complement of the first molecular label.

In some embodiments, hybridizing the complement of the target-binding region of a barcoded nucleic acid molecule with the target-binding region of a different barcoded nucleic acid molecule of the plurality of barcoded nucleic acid molecules comprises intermolecular hybridization of the complement of the target-binding region of a barcoded nucleic acid molecule with the target-binding region of a different barcoded nucleic acid molecule of the plurality of barcoded nucleic acid molecules. In some embodiments, the sequence of the second molecular label is different from the sequence of the first molecular label, and wherein the second molecular label is not a complement of the first molecular label.

In some embodiments, the sample comprises a single cell, a plurality of cells, a plurality of single cells, a tissue, a tumor sample, or any combination thereof. In some embodiments, a single cell comprises an immune cell or a circulating tumor cell. In some embodiments, the immune cell is a B cell or a T cell. In some embodiments, the target-specific primer specifically hybridizes to an immune receptor. In some embodiments, the target-specific primer specifically hybridizes to a constant region of an immune receptor, a variable region of an immune receptor, a diversity region of an immune receptor, the junction of a variable region and diversity region of an immune receptor, or a combination thereof. In some embodiments, the immune receptor is a T cell receptor (TCR) and/or a B cell receptor (BCR) receptor. In some embodiments, the TCR comprises TCR alpha chain, TCR beta chain, TCR gamma chain, TCR delta chain, or any combination thereof. In some embodiments, the BCR receptor comprises BCR heavy chain and/or BCR light chain.

In some embodiments, extending 3'-ends of the plurality of barcoded nucleic acid molecules comprises extending 3'-ends of the plurality of barcoded nucleic acid molecules using a DNA polymerase lacking at least one of 5' to 3' exonuclease activity and 3' to 5' exonuclease activity. In some embodiments, the DNA polymerase comprises a Klenow Fragment. In some embodiments, the method comprises obtaining sequence information of the second plurality of barcoded amplicons, or products thereof. In some embodiments, obtaining the sequence information comprises attaching sequencing adaptors to the second plurality of barcoded amplicons, or products thereof. In some embodiments, amplifying the plurality of extension products comprises adding sequences of binding sites of sequencing primers and/or sequencing adaptors, complimentary sequences thereof, and/or portions thereof, to the plurality of extension products. In some embodiments, the sequencing adaptors comprise the P5 sequence, the P7 sequence, a complimentary sequence thereof, or a portion thereof. In some embodiments, the sequencing primers comprise a Read 1 sequencing primer, a Read 2 sequencing primer, a complimentary sequence thereof, or a portion thereof. In some embodiments, obtaining sequence information of the second plurality of barcoded amplicons, or products thereof, comprises: obtaining sequencing data comprising a plurality of sequencing reads of the second plurality of barcoded amplicons, or products thereof, wherein each of the plurality of sequencing reads comprise (1) a cell label sequence, (2) a molecular label sequence, and/or (3) a subsequence of the nucleic acid target.

In some embodiments, the method comprises: for each unique cell label sequence, which indicates a single cell of the sample: aligning each of the plurality of sequencing reads of the nucleic acid target to generate an aligned sequence of the nucleic acid target. In some embodiments, the aligned sequence of the nucleic acid target comprises at least 50% of the cDNA sequence of the nucleic acid target, at least 70% of the cDNA sequence of the nucleic acid target, at least 90% of the cDNA sequence of the nucleic acid target, or the full length of the cDNA sequence of the nucleic acid target. In some embodiments, the nucleic acid target is an immune receptor. In some embodiments, the immune receptor comprises BCR light chain, BCR heavy chain, TCR alpha chain, TCR beta chain, TCR gamma chain, TCR delta chain, or any combination thereof. In some embodiments, the aligned sequence of the nucleic acid target comprises the complementarity determining region 1 (CDR1), the complementarity determining region 2 (CDR2), the complementarity determining region 3 (CDR3), the variable region, the full length of the variable region, or a combination thereof. In some embodiments, the aligned sequence of the nucleic acid target comprises the variable region, the diversity region, the junction of a variable region diversity region and/or the constant region, or any combination thereof.

In some embodiments, obtaining the sequence information comprises obtaining the sequence information of the BCR light chain and the BCR heavy chain of a single cell. In some embodiments, the sequence information of the BCR light chain and the BCR heavy chain comprises the sequence of the complementarity determining region 1 (CDR1), the CDR2, the CDR3, or any combination thereof, of the BCR light chain and/or the BCR heavy chain. In some embodiments, the method comprises: pairing the BCR light chain and the BCR heavy chain of the single cell based on the obtained sequence information. In some embodiments, the sample comprises a plurality of single cells, the method comprising pairing the BCR light chain and the BCR heavy chain of at least 50% of said single cells based on the obtained sequence information.

In some embodiments, obtaining the sequence information comprises obtaining the sequence information of the TCR alpha chain and the TCR beta chain of a single cell. In some embodiments, the sequence information of the TCR alpha chain and the TCR beta chain comprises the sequence of the complementarity determining region 1 (CDR1), the CDR2, the CDR3, or any combination thereof, of the TCR alpha chain and/or the TCR beta chain. In some embodiments, the method comprises: pairing the TCR alpha chain and the TCR beta chain of the single cell based on the obtained sequence information. In some embodiments, the sample comprises a plurality of single cells, the method comprising pairing the TCR alpha chain and the TCR beta chain of at least 50% of said single cells based on the obtained sequence information.

In some embodiments, obtaining the sequence information comprises obtaining the sequence information of the TCR gamma chain and the TCR delta chain of a single cell. In some embodiments, the sequence information of the TCR gamma chain and the TCR delta chain comprises the sequence of the complementarity determining region 1 (CDR1), the CDR2, the CDR3, or any combination thereof, of the TCR gamma chain and/or the TCR delta chain. In some embodiments, the method comprises: pairing the TCR gamma chain and the TCR delta chain of the single cell based on the obtained sequence information. In some embodiments, the sample comprises a plurality of single cells, the method comprising pairing the TCR gamma chain and the TCR delta chain of at least 50% of said single cells based on the obtained sequence information.

In some embodiments, the complement of the target-binding region comprises the reverse complementary sequence of the target-binding region or the complementary sequence of the target-binding region. In some embodiments, the complement of the molecular label comprises a reverse complementary sequence of the molecular label or a complementary sequence of the molecular label. In some embodiments, the plurality of barcoded nucleic acid molecules comprises barcoded deoxyribonucleic acid (DNA) molecules, barcoded ribonucleic acid (RNA) molecules, or a combination thereof. In some embodiments, the nucleic acid target comprises a nucleic acid molecule. In some embodiments, the nucleic acid molecule comprises ribonucleic acid (RNA), messenger RNA (mRNA), microRNA, small interfering RNA (siRNA), RNA degradation product, RNA comprising a poly(A) tail, or any combination thereof. In some embodiments, the mRNA encodes an immune receptor. In some embodiments, the nucleic acid target comprises a cellular component binding reagent, and/or the nucleic acid molecule is associated with the cellular component binding reagent. In some embodiments, the method comprises dissociating the nucleic acid molecule and the cellular component binding reagent.

In some embodiments, at least 10 of the plurality of oligonucleotide barcodes comprise different molecular label sequences. In some embodiments, each molecular label of the plurality of oligonucleotide barcodes comprises at least 6 nucleotides. In some embodiments, the plurality of oligonucleotide barcodes are associated with a solid support. In some embodiments, the plurality of oligonucleotide barcodes associated with the same solid support each comprise an identical sample label. In some embodiments, each sample label of the plurality of oligonucleotide barcodes comprises at least 6 nucleotides. In some embodiments, the plurality of oligonucleotide barcodes each comprise a cell label. In some embodiments, each cell label of the plurality of oligonucleotide barcodes comprises at least 6 nucleotides. In some embodiments, oligonucleotide barcodes associated with the same solid support comprise the same cell label. In some embodiments, oligonucleotide barcodes associated with different solid supports comprise different cell labels. In some embodiments, the plurality of extended barcoded nucleic acid molecules each comprises a cell label and a complement of the cell label. In some embodiments, the complement of the cell label comprises a reverse complementary sequence of the cell label, or a complementary sequence of the cell label.

In some embodiments, the solid support comprises a synthetic particle, a planar surface, or a combination thereof. In some embodiments, the sample comprises a single cell, the method comprising associating a synthetic particle comprising the plurality of the oligonucleotide barcodes with the single cell in the sample. The method can comprise lysing the single cell after associating the synthetic particle with the single cell. In some embodiments, lysing the single cell comprises heating the sample, contacting the sample with a detergent, changing the pH of the sample, or any combination thereof. In some embodiments, the synthetic particle and the single cell are in the same partition. In some embodiments, the partition is a well or a droplet. In some embodiments, at least one of the plurality of oligonucleotide barcodes is immobilized or partially immobilized on the synthetic particle, or at least one of the plurality of oligonucleotide barcodes is enclosed or partially enclosed in the synthetic particle. In some embodiments, the synthetic particle is disruptable. In some embodiments, the synthetic particle is a disruptable hydrogel particle. In some embodiments, the synthetic particle comprises a bead. In some embodiments, the bead comprises a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. In some embodiments, the synthetic particle comprises a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. In some embodiments, each of the plurality of oligonucleotide barcodes comprises a linker functional group, the synthetic particle comprises a solid support functional group, and the support functional group and the linker functional group are associated with each other. In some embodiments, the linker functional group and the support functional group are individually selected from the group consisting of C6, biotin, streptavidin, primary amine(s), aldehyde(s), ketone(s), and any combination thereof.

Disclosed herein include kits. In some embodiments, the kit comprises: a plurality of oligonucleotide barcodes, wherein each of the plurality of oligonucleotide barcodes comprises a molecular label and a target-binding region, and wherein at least 10 of the plurality of oligonucleotide barcodes comprise different molecular label sequences; a reverse transcriptase; a template switching oligonucleotide comprising the target-binding region, or a portion thereof; and a DNA polymerase lacking at least one of 5' to 3' exonuclease activity and 3' to 5' exonuclease activity.

In some embodiments, the reverse transcriptase comprises a viral reverse transcriptase, for example a murine leukemia virus (MLV) reverse transcriptase or a Moloney murine leukemia virus (MMLV) reverse transcriptase. In some embodiments, the template switch oligonucleotide comprises one or more 3' ribonucleotides. In some embodiments, the template switch oligonucleotide comprises three 3' ribonucleotides. In some embodiments, the 3' ribonucleotides comprise guanine. The kit can comprise one or more of ethylene glycol, polyethylene glycol, 1,2-propanediol, dimethyl sulfoxide (DMSO), glycerol, formamide, 7-deaza-GTP, acetamide, tetramethylammonium chloride salt, betaine, or any combination thereof.

Disclosed herein include kits. In some embodiments, the kit comprises: a plurality of oligonucleotide barcodes, wherein each of the plurality of oligonucleotide barcodes comprises a molecular label and a target-binding region, and wherein at least 10 of the plurality of oligonucleotide barcodes comprise different molecular label sequences; a terminal deoxynucleotidyl transferase; and a DNA polymerase lacking at least one of 5' to 3' exonuclease activity and 3' to 5' exonuclease activity. In some embodiments, the DNA polymerase comprises a Klenow Fragment. The kit can comprise a buffer, a cartridge, or both. The kit can comprise one or more reagents for a reverse transcription reaction and/or an amplification reaction. In some embodiments, the target-binding region comprises a gene-specific sequence, an oligo(dT) sequence, a random multimer, or any combination thereof. In some embodiments, the oligonucleotide barcode comprises an identical sample label and/or an identical cell label. In some embodiments, each sample label and/or cell label of the plurality of oligonucleotide barcodes comprise at least 6 nucleotides. In some embodiments, each molecular label of the plurality of oligonucleotide barcodes comprises at least 6 nucleotides.

In some embodiments, at least one of the plurality of oligonucleotide barcodes is immobilized or partially immobilized on, or enclosed or partially enclosed in, the synthetic particle. In some embodiments, the synthetic particle is disruptable (e.g., a disruptable hydrogel particle). In some embodiments, the synthetic particle comprises a bead. In some embodiments, the bead comprises a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. In some embodiments, the synthetic particle comprises a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. In some embodiments, each of the plurality of oligonucleotide barcodes comprises a linker functional group, the synthetic particle comprises a solid support functional group, and the support functional group and the linker functional group are associated with each other. In some embodiments, the linker functional group and the support functional group are individually selected from the group consisting of C6, biotin, streptavidin, primary amine(s), aldehyde(s), ketone(s), and any combination thereof.

BRIEF DESCRIPTION OF THE DRAWINGS

FIGS. 12A-12D depict data related to the random priming-based methods provided herein. BCR pairing (FIGS. 12A-12B) and TCR pairing (FIGS. 12C-12D) obtained with a random-priming based approach provided herein (FIGS. 12A and 12C) as compared to a currently available method (FIGS. 12B and 12D) are shown.

DETAILED DESCRIPTION

Figure 1:
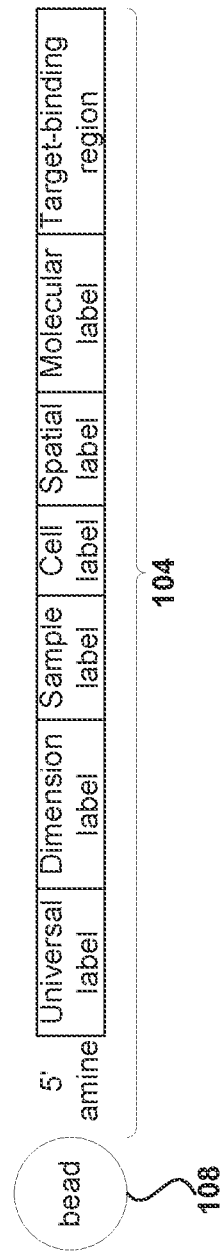
FIG. 1 illustrates a non-limiting exemplary barcode.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Quantifying small numbers of nucleic acids, for example messenger ribonucleotide acid (mRNA) molecules, is clinically important for determining, for example, the genes that are expressed in a cell at different stages of development or under different environmental conditions. However, it can also be very challenging to determine the absolute number of nucleic acid molecules (e.g., mRNA molecules), especially when the number of molecules is very small. One method to determine the absolute number of molecules in a sample is digital polymerase chain reaction (PCR). Ideally, PCR produces an identical copy of a molecule at each cycle. However, PCR can have disadvantages such that each molecule replicates with a stochastic probability, and this probability varies by PCR cycle and gene sequence, resulting in amplification bias and inaccurate gene expression measurements. Stochastic barcodes with unique molecular labels (also referred to as molecular indexes (MIs)) can be used to count the number of molecules and correct for amplification bias. Stochastic barcoding, such as the Precise™ assay (Cellular Research, Inc. (Palo Alto, Calif.)) and Rhapsody™ assay (Becton, Dickinson and Company (Franklin Lakes, N.J.)), can correct for bias induced by PCR and library preparation steps by using molecular labels (MLs) to label mRNAs during reverse transcription (RT).

The Precise™ assay can utilize a non-depleting pool of stochastic barcodes with large number, for example 6561 to 65536, unique molecular label sequences on poly(T) oligonucleotides to hybridize to all poly(A)-mRNAs in a sample during the RT step. A stochastic barcode can comprise a universal PCR priming site. During RT, target gene molecules react randomly with stochastic barcodes. Each target molecule can hybridize to a stochastic barcode resulting to generate stochastically barcoded complementary ribonucleotide acid (cDNA) molecules). After labeling, stochastically barcoded cDNA molecules from microwells of a microwell plate can be pooled into a single tube for PCR amplification and sequencing. Raw sequencing data can be analyzed to produce the number of reads, the number of stochastic barcodes with unique molecular label sequences, and the numbers of mRNA molecules.

Disclosed herein include methods of labeling nucleic acid targets in a sample. In some embodiments, the method comprises: contacting copies of a nucleic acid target with a plurality of oligonucleotide barcodes, wherein each oligonucleotide barcode comprises a first universal sequence, a molecular label, and a target-binding region capable of hybridizing to the nucleic acid target; generating a plurality of barcoded nucleic acid molecules each comprising the target-binding region and a complement of the target-binding region; hybridizing the complement of the target-binding region of each barcoded nucleic acid molecule with the target-binding region of one or more of: (i) an oligonucleotide barcode of the plurality of oligonucleotide barcodes, (ii) the barcoded nucleic acid molecule itself, and (iii) a different barcoded nucleic acid molecule of the plurality of barcoded nucleic acid molecules; extending 3'-ends of the plurality of barcoded nucleic acid molecules to generate a plurality of extended barcoded nucleic acid molecules each comprising the first molecular label and a second molecular label; amplifying the plurality of extended barcoded nucleic acid molecules using a target-specific primer capable of hybridizing to a sequence of the nucleic acid target and a primer comprising the first universal sequence, thereby generating a first plurality of barcoded amplicons comprising the sequence of the nucleic acid target, or a portion thereof; hybridizing random primers to the first plurality of barcoded amplicons and extending the random primers to generate a plurality of extension products, wherein the random primers comprise a second universal sequence, or a complement thereof; and amplifying the plurality of extension products using primers capable of hybridizing to the first universal sequence and the second universal sequence, or complements thereof, thereby generating a second plurality of barcoded amplicons.

Disclosed herein include methods of determining the numbers of nucleic acid targets in a sample. In some embodiments, the method comprises: contacting copies of a nucleic acid target with a plurality of oligonucleotide barcodes, wherein each oligonucleotide barcode comprises a first universal sequence, a molecular label (e.g., a first molecular label), and a target-binding region capable of hybridizing to the nucleic acid target; generating a plurality of barcoded nucleic acid molecules each comprising the target-binding region and a complement of the target-binding region; hybridizing the complement of the target-binding region of each barcoded nucleic acid molecule with the target-binding region of one or more of: (i) an oligonucleotide barcode of the plurality of oligonucleotide barcodes, (ii) the barcoded nucleic acid molecule itself, and (iii) a different barcoded nucleic acid molecule of the plurality of barcoded nucleic acid molecules; extending 3'-ends of the plurality of barcoded nucleic acid molecules to generate a plurality of extended barcoded nucleic acid molecules each comprising the first molecular label and a second molecular label; amplifying the plurality of extended barcoded nucleic acid molecules using a target-specific primer capable of hybridizing to a sequence of the nucleic acid target and a primer comprising the first universal sequence, thereby generating a first plurality of barcoded amplicons comprising the sequence of the nucleic acid target, or a portion thereof; hybridizing random primers to the first plurality of barcoded amplicons and extending the random primers to generate a plurality of extension products, wherein the random primers comprise a second universal sequence, or a complement thereof; amplifying the plurality of extension products using primers capable of hybridizing to the first universal sequence and the second universal sequence, or complements thereof, thereby generating a second plurality of barcoded amplicons; and determining the copy number of the nucleic acid target in the sample based on the number of first molecular labels with distinct sequences, second molecular labels with distinct sequences, or a combination thereof, associated with the second plurality of barcoded amplicons, or products thereof.

Disclosed herein include kits. In some embodiments, the kit comprises: a plurality of oligonucleotide barcodes, wherein each of the plurality of oligonucleotide barcodes comprises a molecular label and a target-binding region, and wherein at least 10 of the plurality of oligonucleotide barcodes comprise different molecular label sequences; a reverse transcriptase; a template switching oligonucleotide comprising the target-binding region, or a portion thereof; and a DNA polymerase lacking at least one of 5' to 3' exonuclease activity and 3' to 5' exonuclease activity.

Disclosed herein include kits. In some embodiments, the kit comprises: a plurality of oligonucleotide barcodes, wherein each of the plurality of oligonucleotide barcodes comprises a molecular label and a target-binding region, and wherein at least 10 of the plurality of oligonucleotide barcodes comprise different molecular label sequences; a terminal deoxynucleotidyl transferase; and a DNA polymerase lacking at least one of 5' to 3' exonuclease activity and 3' to 5' exonuclease activity.

Definitions

Unless defined otherwise, technical and scientific terms used herein have the same meaning as commonly understood by one of ordinary skill in the art to which the present disclosure belongs. See, e.g., Singleton et al., Dictionary of Microbiology and Molecular Biology 2nd ed., J. Wiley & Sons (New York, N.Y. 1994); Sambrook et al., Molecular Cloning, A Laboratory Manual, Cold Spring Harbor Press (Cold Spring Harbor, N.Y. 1989). For purposes of the present disclosure, the following terms are defined below.

As used herein, the term "adaptor" can mean a sequence to facilitate amplification or sequencing of associated nucleic acids. The associated nucleic acids can comprise target nucleic acids. The associated nucleic acids can comprise one or more of spatial labels, target labels, sample labels, indexing label, or barcode sequences (e.g., molecular labels). The adaptors can be linear. The adaptors can be pre-adenylated adaptors. The adaptors can be double- or single-stranded. One or more adaptor can be located on the 5' or 3' end of a nucleic acid. When the adaptors comprise known sequences on the 5' and 3' ends, the known sequences can be the same or different sequences. An adaptor located on the 5' and/or 3' ends of a polynucleotide can be capable of hybridizing to one or more oligonucleotides immobilized on a surface. An adaptor can, in some embodiments, comprise a universal sequence. A universal sequence can be a region of nucleotide sequence that is common to two or more nucleic acid molecules. The two or more nucleic acid molecules can also have regions of different sequence. Thus, for example, the 5' adaptors can comprise identical and/or universal nucleic acid sequences and the 3' adaptors can comprise identical and/or universal sequences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize to such a universal sequence. The target nucleic acid sequence-bearing molecules may be modified to attach universal adaptors (e.g., non-target nucleic acid sequences) to one or both ends of the different target nucleic acid sequences. The one or more universal primers attached to the target nucleic acid can provide sites for hybridization of universal primers. The one or more universal primers attached to the target nucleic acid can be the same or different from each other.

As used herein the term "associated" or "associated with" can mean that two or more species are identifiable as being co-located at a point in time. An association can mean that two or more species are or were within a similar container. An association can be an informatics association. For example, digital information regarding two or more species can be stored and can be used to determine that one or more of the species were co-located at a point in time. An association can also be a physical association. In some embodiments, two or more associated species are "tethered", "attached", or "immobilized" to one another or to a common solid or semisolid surface. An association may refer to covalent or non-covalent means for attaching labels to solid or semi-solid supports such as beads. An association may be a covalent bond between a target and a label. An association can comprise hybridization between two molecules (such as a target molecule and a label).

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, a "complementary" sequence can refer to a "complement" or a "reverse complement" of a sequence. It is understood from the disclosure that if a molecule can hybridize to another molecule it may be complementary, or partially complementary, to the molecule that is hybridizing.

As used herein, the term "digital counting" can refer to a method for estimating a number of target molecules in a sample. Digital counting can include the step of determining a number of unique labels that have been associated with targets in a sample. This methodology, which can be stochastic in nature, transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "non-depleting reservoirs" can refer to a pool of barcodes (e.g., stochastic barcodes) made up of many different labels. A non-depleting reservoir can comprise large numbers of different barcodes such that when the non-depleting reservoir is associated with a pool of targets each target is likely to be associated with a unique barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of barcodes detected then allows calculation of the number of target molecules present in the original collection or sample. When the ratio of the number of copies of a target molecule present to the number of unique barcodes is low, the labeled target molecules are highly unique (i.e., there is a very low probability that more than one target molecule will have been labeled with a given label).

As used herein, the term "nucleic acid" refers to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g., altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g., rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkyl phosphotriesters, methyl and other alkyl phosphonate such as 3'-alkylene phosphonates, 5'-alkylene phosphonates, chiral phosphonates, phosphinates, phosphoramidates including 3'-amino phosphoramidate and aminoalkyl phosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (e.g., morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C, 4'-C-oxymethylene linkage thereby forming a bicyclic sugar moiety. The linkage can be a methylene ($-CH_2$), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases, (e.g., adenine (A) and guanine (G)), and the pyrimidine bases, (e.g., thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C\equiv C-CH3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g., 9-(2-aminoethoxy)-H-pyrimido(5,4-(b) (1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g., 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo[2,3-d]pyrimidin-2-one).

As used herein, the term "sample" can refer to a composition comprising targets. Suitable samples for analysis by the disclosed methods, devices, and systems include cells, tissues, organs, or organisms.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of barcodes (e.g., stochastic barcodes) may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A bead can be non-spherical in shape. A plurality of solid supports spaced in an array may not comprise a substrate. A solid support may be used interchangeably with the term "bead."

As used herein, the term "stochastic barcode" can refer to a polynucleotide sequence comprising labels of the present disclosure. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "gene-specific stochastic barcode" can refer to a polynucleotide sequence comprising labels and a target-binding region that is gene-specific. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "stochastic barcoding" can refer to the random labeling (e.g., barcoding) of nucleic acids. Stochastic barcoding can utilize a recursive Poisson strategy to associate and quantify labels associated with targets. As used herein, the term "stochastic barcoding" can be used interchangeably with "stochastic labeling."

As used here, the term "target" can refer to a composition which can be associated with a barcode (e.g., a stochastic barcode). Exemplary suitable targets for analysis by the disclosed methods, devices, and systems include oligonucleotides, DNA, RNA, mRNA, microRNA, tRNA, and the like. Targets can be single or double stranded. In some embodiments, targets can be proteins, peptides, or polypeptides. In some embodiments, targets are lipids. As used herein, "target" can be used interchangeably with "species."

As used herein, the term "reverse transcriptases" can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transcriptases, and group II intron reverse transcriptases. Examples of group II intron reverse transcriptases include the *Lactococcus lactis* Ll.LtrB intron reverse transcriptase, the *Thermosynechococcus elongatus* TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

The terms "universal adaptor primer," "universal primer adaptor" or "universal adaptor sequence" are used interchangeably to refer to a nucleotide sequence that can be used to hybridize to barcodes (e.g., stochastic barcodes) to generate gene-specific barcodes. A universal adaptor sequence can, for example, be a known sequence that is universal across all barcodes used in methods of the disclosure. For example, when multiple targets are being labeled using the methods disclosed herein, each of the target-specific sequences may be linked to the same universal adaptor sequence. In some embodiments, more than one universal adaptor sequences may be used in the methods disclosed herein. For example, when multiple targets are being labeled using the methods disclosed herein, at least two of the target-specific sequences are linked to different universal adaptor sequences. A universal adaptor primer and its complement may be included in two oligonucleotides, one of which comprises a target-specific sequence and the other comprises a barcode. For example, a universal adaptor sequence may be part of an oligonucleotide comprising a target-specific sequence to generate a nucleotide sequence that is complementary to a target nucleic acid. A second oligonucleotide comprising a barcode and a complementary sequence of the universal adaptor sequence may hybridize with the nucleotide sequence and generate a target-specific barcode (e.g., a target-specific stochastic barcode). In some embodiments, a universal adaptor primer has a sequence that is different from a universal PCR primer used in the methods of this disclosure.

Barcodes

Barcoding, such as stochastic barcoding, has been described in, for example, US 2015/0299784, WO 2015/031691, and Fu et al, Proc Natl Acad Sci U.S.A. 2011 May 31; 108(22):9026-31, the content of these publications is incorporated hereby in its entirety. In some embodiments, the barcode disclosed herein can be a stochastic barcode which can be a polynucleotide sequence that may be used to stochastically label (e.g., barcode, tag) a target. Barcodes can be referred to stochastic barcodes if the ratio of the number of different barcode sequences of the stochastic barcodes and the number of occurrence of any of the targets to be labeled can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. Barcodes can be referred to as stochastic barcodes if the ratio of the number of different barcode sequences of the stochastic barcodes and the number of occurrence of any of the targets to be labeled is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1. Barcode sequences of stochastic barcodes can be referred to as molecular labels.

A barcode, for example a stochastic barcode, can comprise one or more labels. Exemplary labels can include a universal label, a cell label, a barcode sequence (e.g., a molecular label), a sample label, a plate label, a spatial label, and/or a pre-spatial label. FIG. 1 illustrates an exemplary barcode 104 with a spatial label. The barcode 104 can comprise a 5' amine that may link the barcode to a solid support 105. The barcode can comprise a universal label, a dimension label, a spatial label, a cell label, and/or a molecular label. The order of different labels (including but not limited to the universal label, the dimension label, the spatial label, the cell label, and the molecule label) in the barcode can vary. For example, as shown in FIG. 1, the universal label may be the 5'-most label, and the molecular label may be the 3'-most label. The spatial label, dimension label, and the cell label may be in any order. In some embodiments, the universal label, the spatial label, the dimension label, the cell label, and the molecular label are in any order. The barcode can comprise a target-binding region. The target-binding region can interact with a target (e.g., target nucleic acid, RNA, mRNA, DNA) in a sample. For example, a target-binding region can comprise an oligo (dT) sequence which can interact with poly(A) tails of mRNAs. In some instances, the labels of the barcode (e.g., universal label, dimension label, spatial label, cell label, and barcode sequence) may be separated by 1, 2, 3, 4, 5, 6, 7, 8, 9, 10, 11, 12, 13, 14, 15, 16, 17, 18, 19, or 20 or more nucleotides.

A label, for example the cell label, can comprise a unique set of nucleic acid sub-sequences of defined length, e.g., seven nucleotides each (equivalent to the number of bits used in some Hamming error correction codes), which can be designed to provide error correction capability. The set of error correction sub-sequences comprise seven nucleotide sequences can be designed such that any pairwise combination of sequences in the set exhibits a defined "genetic distance" (or number of mismatched bases), for example, a set of error correction sub-sequences can be designed to exhibit a genetic distance of three nucleotides. In this case, review of the error correction sequences in the set of sequence data for labeled target nucleic acid molecules (described more fully below) can allow one to detect or correct amplification or sequencing errors. In some embodiments, the length of the nucleic acid sub-sequences used for creating error correction codes can vary, for example, they can be, or be about 1, 2, 3, 4, 5, 6, 7, 8, 9, 10, 15, 20, 30, 31, 40, 50, or a number or a range between any two of these values, nucleotides in length. In some embodiments, nucleic acid sub-sequences of other lengths can be used for creating error correction codes.

The barcode can comprise a target-binding region. The target-binding region can interact with a target in a sample. The target can be, or comprise, ribonucleic acids (RNAs), messenger RNAs (mRNAs), microRNAs, small interfering RNAs (siRNAs), RNA degradation products, RNAs each comprising a poly(A) tail, or any combination thereof. In some embodiments, the plurality of targets can include deoxyribonucleic acids (DNAs).

In some embodiments, a target-binding region can comprise an oligo(dT) sequence which can interact with poly(A) tails of mRNAs. One or more of the labels of the barcode (e.g., the universal label, the dimension label, the spatial label, the cell label, and the barcode sequences (e.g., molecular label)) can be separated by a spacer from another one or two of the remaining labels of the barcode. The spacer can be, for example, 1, 2, 3, 4, 5, 6, 7, 8, 9, 10, 11, 12, 13, 14, 15, 16, 17, 18, 19, or 20, or more nucleotides. In some embodiments, none of the labels of the barcode is separated by spacer.

Universal Labels

A barcode can comprise one or more universal labels. In some embodiments, the one or more universal labels can be the same for all barcodes in the set of barcodes attached to a given solid support. In some embodiments, the one or more universal labels can be the same for all barcodes attached to a plurality of beads. In some embodiments, a universal label can comprise a nucleic acid sequence that is capable of hybridizing to a sequencing primer. Sequencing primers can be used for sequencing barcodes comprising a universal label. Sequencing primers (e.g., universal sequencing primers) can comprise sequencing primers associated with high-throughput sequencing platforms. In some embodiments, a universal label can comprise a nucleic acid sequence that is capable of hybridizing to a PCR primer. In some embodiments, the universal label can comprise a nucleic acid sequence that is capable of hybridizing to a sequencing primer and a PCR primer. The nucleic acid sequence of the universal label that is capable of hybridizing to a sequencing or PCR primer can be referred to as a primer binding site. A universal label can comprise a sequence that can be used to initiate transcription of the barcode. A universal label can comprise a sequence that can be used for extension of the barcode or a region within the barcode. A universal label can be, or be about, 1, 2, 3, 4, 5, 10, 15, 20, 25, 30, 35, 40, 45, 50, or a number or a range between any two of these values, nucleotides in length. For example, a universal label can comprise at least about 10 nucleotides. A universal label can be at least, or be at most, 1, 2, 3, 4, 5, 10, 15, 20, 25, 30, 35, 40, 45, 50, 100, 200, or 300 nucleotides in length. In some embodiments, a cleavable linker or modified nucleotide can be part of the universal label sequence to enable the barcode to be cleaved off from the support.

Dimension Labels

A barcode can comprise one or more dimension labels. In some embodiments, a dimension label can comprise a nucleic acid sequence that provides information about a dimension in which the labeling (e.g., stochastic labeling) occurred. For example, a dimension label can provide information about the time at which a target was barcoded. A dimension label can be associated with a time of barcoding (e.g., stochastic barcoding) in a sample. A dimension label can be activated at the time of labeling. Different dimension labels can be activated at different times. The dimension label provides information about the order in which targets, groups of targets, and/or samples were barcoded. For example, a population of cells can be barcoded at the G0 phase of the cell cycle. The cells can be pulsed again with barcodes (e.g., stochastic barcodes) at the G1 phase of the cell cycle. The cells can be pulsed again with barcodes at the S phase of the cell cycle, and so on. Barcodes at each pulse (e.g., each phase of the cell cycle), can comprise different dimension labels. In this way, the dimension label provides information about which targets were labelled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be labeled before and/or after treatment with a drug and/or therapy. The changes in the number of copies of distinct targets can be indicative of the sample's response to the drug and/or therapy.

A dimension label can be activatable. An activatable dimension label can be activated at a specific time point. The activatable label can be, for example, constitutively activated (e.g., not turned off). The activatable dimension label can be, for example, reversibly activated (e.g., the activatable dimension label can be turned on and turned off). The dimension label can be, for example, reversibly activatable at least 1, 2, 3, 4, 5, 6, 7, 8, 9, 10, or more times. The dimension label can be reversibly activatable, for example, at least 1, 2, 3, 4, 5, 6, 7, 8, 9, 10 or more times. In some embodiments, the dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging), and introduction of a non-natural nucleotide.

The dimension label can, in some embodiments, be identical for all barcodes (e.g., stochastic barcodes) attached to a given solid support (e.g., a bead), but different for different solid supports (e.g., beads). In some embodiments, at least 60%, 70%, 80%, 85%, 90%, 95%, 97%, 99% or 100%, of barcodes on the same solid support can comprise the same dimension label. In some embodiments, at least 60% of barcodes on the same solid support can comprise the same dimension label. In some embodiments, at least 95% of barcodes on the same solid support can comprise the same dimension label.

There can be as many as $10^6$ or more unique dimension label sequences represented in a plurality of solid supports (e.g., beads). A dimension label can be, or be about 1, 2, 3, 4, 5, 10, 15, 20, 25, 30, 35, 40, 45, 50, or a number or a range between any two of these values, nucleotides in length. A dimension label can be at least, or be at most, 1, 2, 3, 4, 5, 10, 15, 20, 25, 30, 35, 40, 45, 50, 100, 200, or 300, nucleotides in length. A dimension label can comprise between about 5 to about 200 nucleotides. A dimension label can comprise between about 10 to about 150 nucleotides. A dimension label can comprise between about 20 to about 125 nucleotides in length.

Spatial Labels

A barcode can comprise one or more spatial labels. In some embodiments, a spatial label can comprise a nucleic acid sequence that provides information about the spatial orientation of a target molecule which is associated with the barcode. A spatial label can be associated with a coordinate in a sample. The coordinate can be a fixed coordinate. For example, a coordinate can be fixed in reference to a substrate. A spatial label can be in reference to a two or three-dimensional grid. A coordinate can be fixed in reference to a landmark. The landmark can be identifiable in space. A landmark can be a structure which can be imaged. A landmark can be a biological structure, for example an anatomical landmark. A landmark can be a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g., a well, a container, or a droplet). In some embodiments, multiple spatial labels are used together to encode one or more positions in space.

The spatial label can be identical for all barcodes attached to a given solid support (e.g., a bead), but different for different solid supports (e.g., beads). In some embodiments, the percentage of barcodes on the same solid support comprising the same spatial label can be, or be about, 60%, 70%, 80%, 85%, 90%, 95%, 97%, 99%, 100%, or a number or a range between any two of these values. In some embodiments, the percentage of barcodes on the same solid support comprising the same spatial label can be at least, or be at most, 60%, 70%, 80%, 85%, 90%, 95%, 97%, 99%, or 100%. In some embodiments, at least 60% of barcodes on the same solid support can comprise the same spatial label. In some embodiments, at least 95% of barcodes on the same solid support can comprise the same spatial label.

There can be as many as $10^6$ or more unique spatial label sequences represented in a plurality of solid supports (e.g., beads). A spatial label can be, or be about, 1, 2, 3, 4, 5, 10, 15, 20, 25, 30, 35, 40, 45, 50, or a number or a range between any two of these values, nucleotides in length. A spatial label can be at least or at most 1, 2, 3, 4, 5, 10, 15, 20, 25, 30, 35, 40, 45, 50, 100, 200, or 300 nucleotides in length. A spatial label can comprise between about 5 to about 200 nucleotides, for example, between about 10 to about 150 nucleotides, or between about 20 to about 125 nucleotides in length.

Cell Labels

A barcode (e.g., a stochastic barcode) can comprise one or more cell labels. In some embodiments, a cell label can comprise a nucleic acid sequence that provides information for determining which target nucleic acid originated from which cell. In some embodiments, the cell label is identical for all barcodes attached to a given solid support (e.g., a bead), but different for different solid supports (e.g., beads). In some embodiments, the percentage of barcodes on the same solid support comprising the same cell label can be, or be about 60%, 70%, 80%, 85%, 90%, 95%, 97%, 99%, 100%, or a number or a range between any two of these values. In some embodiments, the percentage of barcodes on the same solid support comprising the same cell label can be, or be about 60%, 70%, 80%, 85%, 90%, 95%, 97%, 99%, or 100%. For example, at least 60% or at least 95% of barcodes on the same solid support can comprise the same cell label.

There can be as many as $10^6$ or more unique cell label sequences represented in a plurality of solid supports (e.g., beads). A cell label can be, or be about, 1, 2, 3, 4, 5, 10, 15, 20, 25, 30, 35, 40, 45, 50, or a number or a range between any two of these values, nucleotides in length. A cell label can be at least, or be at most, 1, 2, 3, 4, 5, 10, 15, 20, 25, 30, 35, 40, 45, 50, 100, 200, or 300 nucleotides in length. For example, a cell label can comprise between about 5 to about 200 nucleotides, between about 10 to about 150 nucleotides, or between about 20 to about 125 nucleotides in length.

Barcode Sequences

A barcode can comprise one or more barcode sequences. In some embodiments, a barcode sequence can comprise a nucleic acid sequence that provides identifying information for the specific type of target nucleic acid species hybridized to the barcode. A barcode sequence can comprise a nucleic acid sequence that provides a counter (e.g., that provides a rough approximation) for the specific occurrence of the target nucleic acid species hybridized to the barcode (e.g., target-binding region).

In some embodiments, a diverse set of barcode sequences are attached to a given solid support (e.g., a bead). In some embodiments, there can be, or be about, $10^2$, $10^3$, $10^4$, $10^5$, $10^6$, $10^7$, $10^8$, $10^9$, or a number or a range between any two of these values, unique molecular label sequences. For example, a plurality of barcodes can comprise about 6561 barcodes sequences with distinct sequences. As another example, a plurality of barcodes can comprise about 65536 barcode sequences with distinct sequences. In some embodiments, there can be at least, or be at most, $10^2$, $10^3$, $10^4$, $10^5$, $10^6$, $10^7$, $10^8$, or $10^9$, unique barcode sequences. The unique molecular label sequences can be attached to a given solid support (e.g., a bead). In some embodiments, the unique molecular label sequence is partially or entirely encompassed by a particle (e.g., a hydrogel bead).

The length of a barcode can be different in different implementations. For example, a barcode can be, or be about, 1, 2, 3, 4, 5, 10, 15, 20, 25, 30, 35, 40, 45, 50, or a number or a range between any two of these values, nucleotides in length. As another example, a barcode can be at least, or be at most, 1, 2, 3, 4, 5, 10, 15, 20, 25, 30, 35, 40, 45, 50, 100, 200, or 300 nucleotides in length.

Molecular Labels

A barcode (e.g., a stochastic barcode) can comprise one or more molecular labels. Molecular labels can include barcode sequences. In some embodiments, a molecular label can comprise a nucleic acid sequence that provides identifying information for the specific type of target nucleic acid species hybridized to the barcode. A molecular label can comprise a nucleic acid sequence that provides a counter for the specific occurrence of the target nucleic acid species hybridized to the barcode (e.g., target-binding region).

In some embodiments, a diverse set of molecular labels are attached to a given solid support (e.g., a bead). In some embodiments, there can be, or be about, $10^2$, $10^3$, $10^4$, $10^5$, $10^6$, $10^7$, $10^8$, $10^9$, or a number or a range between any two of these values, of unique molecular label sequences. For example, a plurality of barcodes can comprise about 6561 molecular labels with distinct sequences. As another example, a plurality of barcodes can comprise about 65536 molecular labels with distinct sequences. In some embodiments, there can be at least, or be at most, $10^2$, $10^3$, $10^4$, $10^5$, $10^6$, $10^7$, $10^8$, or $10^9$, unique molecular label sequences. Barcodes with unique molecular label sequences can be attached to a given solid support (e.g., a bead).

For barcoding (e.g., stochastic barcoding) using a plurality of stochastic barcodes, the ratio of the number of different molecular label sequences and the number of occurrence of any of the targets can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. In some embodiments, the ratio of the number of different molecular label sequences and the number of occurrence of any of the targets is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1.

A molecular label can be, or be about, 1, 2, 3, 4, 5, 10, 15, 20, 25, 30, 35, 40, 45, 50, or a number or a range between any two of these values, nucleotides in length. A molecular label can be at least, or be at most, 1, 2, 3, 4, 5, 10, 15, 20, 25, 30, 35, 40, 45, 50, 100, 200, or 300 nucleotides in length.

Target-Binding Region

A barcode can comprise one or more target binding regions, such as capture probes. In some embodiments, a target-binding region can hybridize with a target of interest. In some embodiments, the target binding regions can comprise a nucleic acid sequence that hybridizes specifically to a target (e.g., target nucleic acid, target molecule, e.g., a cellular nucleic acid to be analyzed), for example a specific gene sequence. In some embodiments, a target binding region can comprise a nucleic acid sequence that can attach (e.g., hybridize) to a specific location of a specific target nucleic acid. In some embodiments, the target binding region can comprise a nucleic acid sequence that is capable of specific hybridization to a restriction enzyme site overhang (e.g., an EcoRI sticky-end overhang). The barcode can then ligate to any nucleic acid molecule comprising a sequence complementary to the restriction site overhang.

In some embodiments, a target binding region can comprise a non-specific target nucleic acid sequence. A non-specific target nucleic acid sequence can refer to a sequence that can bind to multiple target nucleic acids, independent of the specific sequence of the target nucleic acid. For example, target binding region can comprise a random multimer sequence, or an oligo(dT) sequence that hybridizes to the poly(A) tail on mRNA molecules. A random multimer sequence can be, for example, a random dimer, trimer, quatramer, pentamer, hexamer, septamer, octamer, nonamer, decamer, or higher multimer sequence of any length. In some embodiments, the target binding region is the same for all barcodes attached to a given bead. In some embodiments, the target binding regions for the plurality of barcodes attached to a given bead can comprise two or more different target binding sequences. A target binding region can be, or be about, 5, 10, 15, 20, 25, 30, 35, 40, 45, 50, or a number or a range between any two of these values, nucleotides in length. A target binding region can be at most about 5, 10, 15, 20, 25, 30, 35, 40, 45, 50 or more nucleotides in length.

In some embodiments, a target-binding region can comprise an oligo(dT) which can hybridize with mRNAs comprising polyadenylated ends. A target-binding region can be gene-specific. For example, a target-binding region can be configured to hybridize to a specific region of a target. A target-binding region can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these values, nucleotides in length. A target-binding region can be at least, or be at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30, nucleotides in length. A target-binding region can be about 5-30 nucleotides in length. When a barcode comprises a gene-specific target-binding region, the barcode can be referred to herein as a gene-specific barcode.

Orientation Property

A stochastic barcode (e.g., a stochastic barcode) can comprise one or more orientation properties which can be used to orient (e.g., align) the barcodes. A barcode can comprise a moiety for isoelectric focusing. Different barcodes can comprise different isoelectric focusing points. When these barcodes are introduced to a sample, the sample can undergo isoelectric focusing in order to orient the barcodes into a known way. In this way, the orientation property can be used to develop a known map of barcodes in a sample. Exemplary orientation properties can include, electrophoretic mobility (e.g., based on size of the barcode), isoelectric point, spin, conductivity, and/or self-assembly. For example, barcodes with an orientation property of self-assembly, can self-assemble into a specific orientation (e.g., nucleic acid nanostructure) upon activation.

Affinity Property

A barcode (e.g., a stochastic barcode) can comprise one or more affinity properties. For example, a spatial label can comprise an affinity property. An affinity property can include a chemical and/or biological moiety that can facilitate binding of the barcode to another entity (e.g., cell receptor). For example, an affinity property can comprise an antibody, for example, an antibody specific for a specific moiety (e.g., receptor) on a sample. In some embodiments, the antibody can guide the barcode to a specific cell type or molecule. Targets at and/or near the specific cell type or molecule can be labeled (e.g., stochastically labeled). The affinity property can, in some embodiments, provide spatial information in addition to the nucleotide sequence of the spatial label because the antibody can guide the barcode to a specific location. The antibody can be a therapeutic antibody, for example a monoclonal antibody or a polyclonal antibody. The antibody can be humanized or chimeric. The antibody can be a naked antibody or a fusion antibody.

The antibody can be a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

The antibody fragment can be, for example, a portion of an antibody such as F(ab')2, Fab', Fab, Fv, sFv and the like. In some embodiments, the antibody fragment can bind with the same antigen that is recognized by the full-length antibody. The antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (CD8, CD34, CD45), and therapeutic antibodies.

Universal Adaptor Primer

A barcode can comprise one or more universal adaptor primers. For example, a gene-specific barcode, such as a gene-specific stochastic barcode, can comprise a universal adaptor primer. A universal adaptor primer can refer to a nucleotide sequence that is universal across all barcodes. A universal adaptor primer can be used for building gene-specific barcodes. A universal adaptor primer can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these nucleotides in length. A universal adaptor primer can be at least, or be at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 nucleotides in length. A universal adaptor primer can be from 5-30 nucleotides in length.

Linker

When a barcode comprises more than one of a type of label (e.g., more than one cell label or more than one barcode sequence, such as one molecular label), the labels may be interspersed with a linker label sequence. A linker label sequence can be at least about 5, 10, 15, 20, 25, 30, 35, 40, 45, 50 or more nucleotides in length. A linker label sequence can be at most about 5, 10, 15, 20, 25, 30, 35, 40, 45, 50 or more nucleotides in length. In some instances, a linker label sequence is 12 nucleotides in length. A linker label sequence can be used to facilitate the synthesis of the barcode. The linker label can comprise an error-correcting (e.g., Hamming) code.

Solid Supports

Barcodes, such as stochastic barcodes, disclosed herein can, in some embodiments, be associated with a solid support. The solid support can be, for example, a synthetic particle. In some embodiments, some or all of the barcode sequences, such as molecular labels for stochastic barcodes (e.g., the first barcode sequences) of a plurality of barcodes (e.g., the first plurality of barcodes) on a solid support differ by at least one nucleotide. The cell labels of the barcodes on the same solid support can be the same. The cell labels of the barcodes on different solid supports can differ by at least one nucleotide. For example, first cell labels of a first plurality of barcodes on a first solid support can have the same sequence, and second cell labels of a second plurality of barcodes on a second solid support can have the same sequence. The first cell labels of the first plurality of barcodes on the first solid support and the second cell labels of the second plurality of barcodes on the second solid support can differ by at least one nucleotide. A cell label can be, for example, about 5-20 nucleotides long. A barcode sequence can be, for example, about 5-20 nucleotides long. The synthetic particle can be, for example, a bead.

The bead can be, for example, a silica gel bead, a controlled pore glass bead, a magnetic bead, a Dynabead, a sephadex/sepharose bead, a cellulose bead, a polystyrene bead, or any combination thereof. The bead can comprise a material such as polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, or any combination thereof.

In some embodiments, the bead can be a polymeric bead, for example a deformable bead or a gel bead, functionalized with barcodes or stochastic barcodes (such as gel beads from 10× Genomics (San Francisco, Calif.). In some implementation, a gel bead can comprise a polymer-based gels. Gel beads can be generated, for example, by encapsulating one or more polymeric precursors into droplets. Upon exposure of the polymeric precursors to an accelerator (e.g., tetramethylethylenediamine (TEMED)), a gel bead may be generated.

In some embodiments, the particle can be disruptable (e.g., dissolvable, degradable). For example, the polymeric bead can dissolve, melt, or degrade, for example, under a desired condition. The desired condition can include an environmental condition. The desired condition may result in the polymeric bead dissolving, melting, or degrading in a controlled manner. A gel bead may dissolve, melt, or degrade due to a chemical stimulus, a physical stimulus, a biological stimulus, a thermal stimulus, a magnetic stimulus, an electric stimulus, a light stimulus, or any combination thereof.

Analytes and/or reagents, such as oligonucleotide barcodes, for example, may be coupled/immobilized to the interior surface of a gel bead (e.g., the interior accessible via diffusion of an oligonucleotide barcode and/or materials used to generate an oligonucleotide barcode) and/or the outer surface of a gel bead or any other microcapsule described herein. Coupling/immobilization may be via any form of chemical bonding (e.g., covalent bond, ionic bond) or physical phenomena (e.g., Van der Waals forces, dipole-dipole interactions, etc.). In some embodiments, coupling/immobilization of a reagent to a gel bead or any other microcapsule described herein may be reversible, such as, for example, via a labile moiety (e.g., via a chemical cross-linker, including chemical cross-linkers described herein). Upon application of a stimulus, the labile moiety may be cleaved and the immobilized reagent set free. In some embodiments, the labile moiety is a disulfide bond. For example, in the case where an oligonucleotide barcode is immobilized to a gel bead via a disulfide bond, exposure of the disulfide bond to a reducing agent can cleave the disulfide bond and free the oligonucleotide barcode from the bead. The labile moiety may be included as part of a gel bead or microcapsule, as part of a chemical linker that links a reagent or analyte to a gel bead or microcapsule, and/or as part of a reagent or analyte. In some embodiments, at least one barcode of the plurality of barcodes can be immobilized on the particle, partially immobilized on the particle, enclosed in the particle, partially enclosed in the particle, or any combination thereof.

In some embodiments, a gel bead can comprise a wide range of different polymers including but not limited to: polymers, heat sensitive polymers, photosensitive polymers, magnetic polymers, pH sensitive polymers, salt-sensitive polymers, chemically sensitive polymers, polyelectrolytes, polysaccharides, peptides, proteins, and/or plastics. Polymers may include but are not limited to materials such as poly(N-isopropylacrylamide) (PNIPAAm), poly(styrene sulfonate) (PSS), poly(allyl amine) (PAAm), poly(acrylic acid) (PAA), poly(ethylene imine) (PEI), poly(diallyldimethyl-ammonium chloride) (PDADMAC), poly(pyrolle) (PPy), poly(vinylpyrrolidone) (PVPON), poly(vinyl pyridine) (PVP), poly(methacrylic acid) (PMAA), poly(methyl methacrylate) (PMMA), polystyrene (PS), poly(tetrahydrofuran) (PTHF), poly(phthaladehyde) (PTHF), poly(hexyl viologen) (PHV), poly(L-lysine) (PLL), poly(L-arginine) (PARG), poly(lactic-co-glycolic acid) (PLGA).

Numerous chemical stimuli can be used to trigger the disruption, dissolution, or degradation of the beads. Examples of these chemical changes may include, but are not limited to, pH-mediated changes to the bead wall, disintegration of the bead wall via chemical cleavage of crosslink bonds, triggered depolymerization of the bead wall, and bead wall switching reactions. Bulk changes may also be used to trigger disruption of the beads.

Bulk or physical changes to the microcapsule through various stimuli also offer many advantages in designing capsules to release reagents. Bulk or physical changes occur on a macroscopic scale, in which bead rupture is the result of mechano-physical forces induced by a stimulus. These processes may include, but are not limited to pressure induced rupture, bead wall melting, or changes in the porosity of the bead wall.

Biological stimuli may also be used to trigger disruption, dissolution, or degradation of beads. Generally, biological triggers resemble chemical triggers, but many examples use biomolecules, or molecules commonly found in living systems such as enzymes, peptides, saccharides, fatty acids, nucleic acids and the like. For example, beads may comprise polymers with peptide cross-links that are sensitive to cleavage by specific proteases. More specifically, one example may comprise a microcapsule comprising GFLGK peptide cross links. Upon addition of a biological trigger such as the protease Cathepsin B, the peptide cross links of the shell well are cleaved and the contents of the beads are released. In other cases, the proteases may be heat-activated. In another example, beads comprise a shell wall comprising cellulose. Addition of the hydrolytic enzyme chitosan serves as biologic trigger for cleavage of cellulosic bonds, depolymerization of the shell wall, and release of its inner contents.

The beads may also be induced to release their contents upon the application of a thermal stimulus. A change in temperature can cause a variety changes to the beads. A change in heat may cause melting of a bead such that the bead wall disintegrates. In other cases, the heat may increase the internal pressure of the inner components of the bead such that the bead ruptures or explodes. In still other cases, the heat may transform the bead into a shrunken dehydrated state. The heat may also act upon heat-sensitive polymers within the wall of a bead to cause disruption of the bead.

Inclusion of magnetic nanoparticles to the bead wall of microcapsules can allow triggered rupture of the beads as well as guide the beads in an array. A device of this disclosure may comprise magnetic beads for either purpose. In some embodiments, incorporation of $Fe_3O_4$ nanoparticles into polyelectrolyte containing beads triggers rupture in the presence of an oscillating magnetic field stimulus.

A bead may also be disrupted, dissolved, or degraded as the result of electrical stimulation. Similar to magnetic particles described in the previous section, electrically sensitive beads can allow for both triggered rupture of the beads as well as other functions such as alignment in an electric field, electrical conductivity or redox reactions. In one example, beads containing electrically sensitive material are aligned in an electric field such that release of inner reagents can be controlled. In other examples, electrical fields may induce redox reactions within the bead wall itself that may increase porosity.

A light stimulus may also be used to disrupt the beads. Numerous light triggers are possible and may include systems that use various molecules such as nanoparticles and chromophores capable of absorbing photons of specific ranges of wavelengths. For example, metal oxide coatings can be used as capsule triggers. UV irradiation of polyelectrolyte capsules coated with $SiO_2$ may result in disintegration of the bead wall. In yet another example, photo switchable materials such as azobenzene groups may be incorporated in the bead wall. Upon the application of UV or visible light, chemicals such as these undergo a reversible cis-to-trans isomerization upon absorption of photons. In this aspect, incorporation of photon switches can result in a bead wall that may disintegrate or become more porous upon the application of a light trigger.

Figure 2:
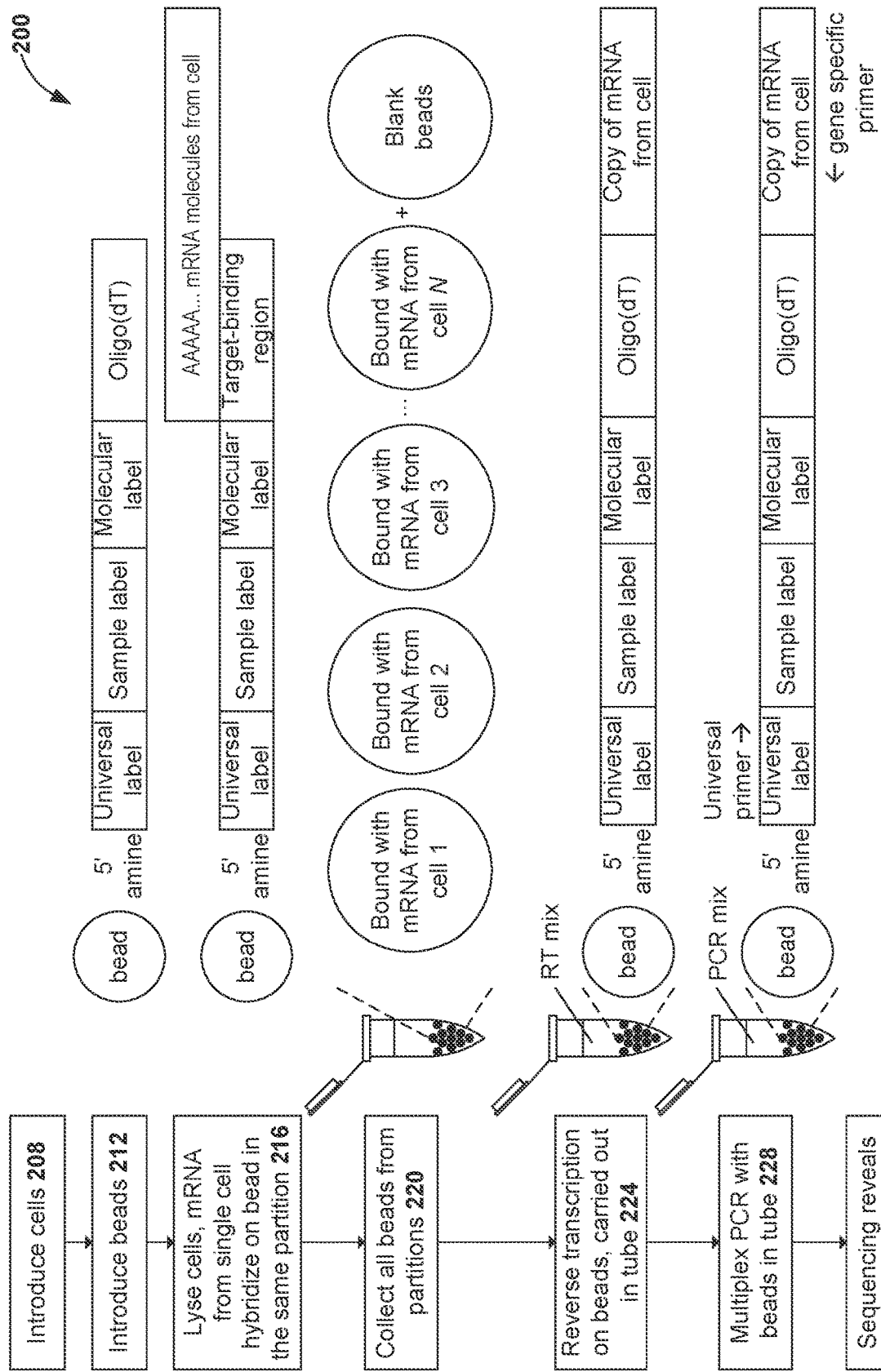
FIG. 2 shows a non-limiting exemplary workflow of barcoding and digital counting.

For example, in a non-limiting example of barcoding (e.g., stochastic barcoding) illustrated in FIG. 2, after introducing cells such as single cells onto a plurality of microwells of a microwell array at block 208, beads can be introduced onto the plurality of microwells of the microwell array at block 212. Each microwell can comprise one bead. The beads can comprise a plurality of barcodes. A barcode can comprise a 5' amine region attached to a bead. The barcode can comprise a universal label, a barcode sequence (e.g., a molecular label), a target-binding region, or any combination thereof.

The barcodes disclosed herein can be associated with (e.g., attached to) a solid support (e.g., a bead). The barcodes associated with a solid support can each comprise a barcode sequence selected from a group comprising at least 100 or 1000 barcode sequences with unique sequences. In some embodiments, different barcodes associated with a solid support can comprise barcode with different sequences. In some embodiments, a percentage of barcodes associated with a solid support comprises the same cell label. For example, the percentage can be, or be about 60%, 70%, 80%, 85%, 90%, 95%, 97%, 99%, 100%, or a number or a range between any two of these values. As another example, the percentage can be at least, or be at most 60%, 70%, 80%, 85%, 90%, 95%, 97%, 99%, or 100%. In some embodiments, barcodes associated with a solid support can have the same cell label. The barcodes associated with different solid supports can have different cell labels selected from a group comprising at least 100 or 1000 cell labels with unique sequences.

The barcodes disclosed herein can be associated to (e.g., attached to) a solid support (e.g., a bead). In some embodiments, barcoding the plurality of targets in the sample can be performed with a solid support including a plurality of synthetic particles associated with the plurality of barcodes. In some embodiments, the solid support can include a plurality of synthetic particles associated with the plurality of barcodes. The spatial labels of the plurality of barcodes on different solid supports can differ by at least one nucleotide. The solid support can, for example, include the plurality of barcodes in two dimensions or three dimensions. The synthetic particles can be beads. The beads can be silica gel beads, controlled pore glass beads, magnetic beads, Dynabeads, Sephadex/Sepharose beads, cellulose beads, polystyrene beads, or any combination thereof. The solid support can include a polymer, a matrix, a hydrogel, a needle array device, an antibody, or any combination thereof. In some embodiments, the solid supports can be free floating. In some embodiments, the solid supports can be embedded in a semi-solid or solid array. The barcodes may not be associated with solid supports. The barcodes can be individual nucleotides. The barcodes can be associated with a substrate.

As used herein, the terms "tethered," "attached," and "immobilized," are used interchangeably, and can refer to covalent or non-covalent means for attaching barcodes to a solid support. Any of a variety of different solid supports can be used as solid supports for attaching pre-synthesized barcodes or for in situ solid-phase synthesis of barcode.

In some embodiments, the solid support is a bead. The bead can comprise one or more types of solid, porous, or hollow sphere, ball, bearing, cylinder, or other similar configuration which a nucleic acid can be immobilized (e.g., covalently or non-covalently). The bead can be, for example, composed of plastic, ceramic, metal, polymeric material, or any combination thereof. A bead can be, or comprise, a discrete particle that is spherical (e.g., microspheres) or have a non-spherical or irregular shape, such as cubic, cuboid, pyramidal, cylindrical, conical, oblong, or disc-shaped, and the like. In some embodiments, a bead can be non-spherical in shape.

Beads can comprise a variety of materials including, but not limited to, paramagnetic materials (e.g., magnesium, molybdenum, lithium, and tantalum), superparamagnetic materials (e.g., ferrite ($Fe_3O_4$; magnetite) nanoparticles), ferromagnetic materials (e.g., iron, nickel, cobalt, some alloys thereof, and some rare earth metal compounds), ceramic, plastic, glass, polystyrene, silica, methylstyrene, acrylic polymers, titanium, latex, Sepharose, agarose, hydrogel, polymer, cellulose, nylon, or any combination thereof.

In some embodiments, the bead (e.g., the bead to which the labels are attached) is a hydrogel bead. In some embodiments, the bead comprises hydrogel.

Some embodiments disclosed herein include one or more particles (for example, beads). Each of the particles can comprise a plurality of oligonucleotides (e.g., barcodes). Each of the plurality of oligonucleotides can comprise a barcode sequence (e.g., a molecular label sequence), a cell label, and a target-binding region (e.g., an oligo(dT) sequence, a gene-specific sequence, a random multimer, or a combination thereof). The cell label sequence of each of the plurality of oligonucleotides can be the same. The cell label sequences of oligonucleotides on different particles can be different such that the oligonucleotides on different particles can be identified. The number of different cell label sequences can be different in different implementations. In some embodiments, the number of cell label sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, a number or a range between any two of these values, or more. In some embodiments, the number of cell label sequences can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. In some embodiments, no more than 1, 2, 3, 4, 5, 6, 7, 8, 9, 10, 20, 30, 40, 50, 60, 70, 80, 90, 100, 200, 300, 400, 500, 600, 700, 800, 900, 1000, or more of the plurality of the particles include oligonucleotides with the same cell sequence. In some embodiment, the plurality of particles that include oligonucleotides with the same cell sequence can be at most 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or more. In some embodiments, none of the plurality of the particles has the same cell label sequence.

The plurality of oligonucleotides on each particle can comprise different barcode sequences (e.g., molecular labels). In some embodiments, the number of barcode sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values. In some embodiments, the number of barcode sequences can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. For example, at least 100 of the plurality of oligonucleotides comprise different barcode sequences. As another example, in a single particle, at least 100, 500, 1000, 5000, 10000, 15000, 20000, 50000, a number or a range between any two of these values, or more of the plurality of oligonucleotides comprise different barcode sequences. Some embodiments provide a plurality of the particles comprising barcodes. In some embodiments, the ratio of an occurrence (or a copy or a number) of a target to be labeled and the different barcode sequences can be at least 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, or more. In some embodiments, each of the plurality of oligonucleotides further comprises a sample label, a universal label, or both. The particle can be, for example, a nanoparticle or microparticle.

The size of the beads can vary. For example, the diameter of the bead can range from 0.1 micrometer to 50 micrometers. In some embodiments, the diameter of the bead can be, or be about, 0.1, 0.5, 1, 2, 3, 4, 5, 6, 7, 8, 9, 10, 20, 30, 40, or 50 micrometers, or a number or a range between any two of these values.

The diameter of the bead can be related to the diameter of the wells of the substrate. In some embodiments, the diameter of the bead can be, or be about, 10%, 20%, 30%, 40%, 50%, 60%, 70%, 80%, 90%, 100%, or a number or a range between any two of these values, longer or shorter than the diameter of the well. The diameter of the beads can be related to the diameter of a cell (e.g., a single cell entrapped by a well of the substrate). In some embodiments, the diameter of the bead can be at least, or be at most, 10%, 20%, 30%, 40%, 50%, 60%, 70%, 80%, 90%, or 100% longer or shorter than the diameter of the well. The diameter of the beads can be related to the diameter of a cell (e.g., a single cell entrapped by a well of the substrate). In some embodiments, the diameter of the bead can be, or be about, 10%, 20%, 30%, 40%, 50%, 60%, 70%, 80%, 90%, 100%, 150%, 200%, 250%, 300%, or a number or a range between any two of these values, longer or shorter than the diameter of the cell. In some embodiments, the diameter of the beads can be at least, or be at most, 10%, 20%, 30%, 40%, 50%, 60%, 70%, 80%, 90%, 100%, 150%, 200%, 250%, or 300% longer or shorter than the diameter of the cell.

A bead can be attached to and/or embedded in a substrate. A bead can be attached to and/or embedded in a gel, hydrogel, polymer and/or matrix. The spatial position of a bead within a substrate (e.g., gel, matrix, scaffold, or polymer) can be identified using the spatial label present on the barcode on the bead which can serve as a location address.

Examples of beads can include, but are not limited to, streptavidin beads, agarose beads, magnetic beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, silica beads, silica-like beads, anti-biotin microbeads, anti-fluorochrome microbeads, and BcMag™ Carboxyl-Terminated Magnetic Beads.

A bead can be associated with (e.g., impregnated with) quantum dots or fluorescent dyes to make it fluorescent in one fluorescence optical channel or multiple optical channels. A bead can be associated with iron oxide or chromium oxide to make it paramagnetic or ferromagnetic. Beads can be identifiable. For example, a bead can be imaged using a camera. A bead can have a detectable code associated with the bead. For example, a bead can comprise a barcode. A bead can change size, for example, due to swelling in an organic or inorganic solution. A bead can be hydrophobic. A bead can be hydrophilic. A bead can be biocompatible.

A solid support (e.g., a bead) can be visualized. The solid support can comprise a visualizing tag (e.g., fluorescent dye). A solid support (e.g., a bead) can be etched with an identifier (e.g., a number). The identifier can be visualized through imaging the beads.

A solid support can comprise an insoluble, semi-soluble, or insoluble material. A solid support can be referred to as "functionalized" when it includes a linker, a scaffold, a building block, or other reactive moiety attached thereto, whereas a solid support may be "nonfunctionalized" when it lacks such a reactive moiety attached thereto. The solid support can be employed free in solution, such as in a microtiter well format; in a flow-through format, such as in a column; or in a dipstick.

The solid support can comprise a membrane, paper, plastic, coated surface, flat surface, glass, slide, chip, or any combination thereof. A solid support can take the form of resins, gels, microspheres, or other geometric configurations. A solid support can comprise silica chips, microparticles, nanoparticles, plates, arrays, capillaries, flat supports such as glass fiber filters, glass surfaces, metal surfaces (steel, gold silver, aluminum, silicon and copper), glass supports, plastic supports, silicon supports, chips, filters, membranes, microwell plates, slides, plastic materials including multi-well plates or membranes (e.g., formed of polyethylene, polypropylene, polyamide, polyvinylidenedifluoride), and/or wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms.

The solid support can comprise a polymer matrix (e.g., gel, hydrogel). The polymer matrix may be able to permeate intracellular space (e.g., around organelles). The polymer matrix may able to be pumped throughout the circulatory system.

Substrates and Microwell Array

As used herein, a substrate can refer to a type of solid support. A substrate can refer to a solid support that can comprise barcodes or stochastic barcodes of the disclosure. A substrate can, for example, comprise a plurality of microwells. For example, a substrate can be a well array comprising two or more microwells. In some embodiments, a microwell can comprise a small reaction chamber of defined volume. In some embodiments, a microwell can entrap one or more cells. In some embodiments, a microwell can entrap only one cell. In some embodiments, a microwell can entrap one or more solid supports. In some embodiments, a microwell can entrap only one solid support. In some embodiments, a microwell entraps a single cell and a single solid support (e.g., a bead). A microwell can comprise barcode reagents of the disclosure.

Methods of Barcoding

The disclosure provides for methods for estimating the number of distinct targets at distinct locations in a physical sample (e.g., tissue, organ, tumor, cell). The methods can comprise placing barcodes (e.g., stochastic barcodes) in close proximity with the sample, lysing the sample, associating distinct targets with the barcodes, amplifying the targets and/or digitally counting the targets. The method can further comprise analyzing and/or visualizing the information obtained from the spatial labels on the barcodes. In some embodiments, a method comprises visualizing the plurality of targets in the sample. Mapping the plurality of targets onto the map of the sample can include generating a two-dimensional map or a three-dimensional map of the sample. The two-dimensional map and the three-dimensional map can be generated prior to or after barcoding (e.g., stochastically barcoding) the plurality of targets in the sample. Visualizing the plurality of targets in the sample can include mapping the plurality of targets onto a map of the sample. Mapping the plurality of targets onto the map of the sample can include generating a two-dimensional map or a three-dimensional map of the sample. The two-dimensional map and the three-dimensional map can be generated prior to or after barcoding the plurality of targets in the sample. in some embodiments, the two-dimensional map and the three-dimensional map can be generated before or after lysing the sample. Lysing the sample before or after generating the two-dimensional map or the three-dimensional map can include heating the sample, contacting the sample with a detergent, changing the pH of the sample, or any combination thereof.

In some embodiments, barcoding the plurality of targets comprises hybridizing a plurality of barcodes with a plurality of targets to create barcoded targets (e.g., stochastically barcoded targets). Barcoding the plurality of targets can comprise generating an indexed library of the barcoded targets. Generating an indexed library of the barcoded targets can be performed with a solid support comprising the plurality of barcodes (e.g., stochastic barcodes).

Contacting a Sample and a Barcode

The disclosure provides for methods for contacting a sample (e.g., cells) to a substrate of the disclosure. A sample comprising, for example, a cell, organ, or tissue thin section, can be contacted to barcodes (e.g., stochastic barcodes). The cells can be contacted, for example, by gravity flow wherein the cells can settle and create a monolayer. The sample can be a tissue thin section. The thin section can be placed on the substrate. The sample can be one-dimensional (e.g., forms a planar surface). The sample (e.g., cells) can be spread across the substrate, for example, by growing/culturing the cells on the substrate.

When barcodes are in close proximity to targets, the targets can hybridize to the barcode. The barcodes can be contacted at a non-depletable ratio such that each distinct target can associate with a distinct barcode of the disclosure. To ensure efficient association between the target and the barcode, the targets can be cross-linked to barcode.

Cell Lysis

Following the distribution of cells and barcodes, the cells can be lysed to liberate the target molecules. Cell lysis can be accomplished by any of a variety of means, for example, by chemical or biochemical means, by osmotic shock, or by means of thermal lysis, mechanical lysis, or optical lysis. Cells can be lysed by addition of a cell lysis buffer comprising a detergent (e.g., SDS, Li dodecyl sulfate, Triton X-100, Tween-20, or NP-40), an organic solvent (e.g., methanol or acetone), or digestive enzymes (e.g., proteinase K, pepsin, or trypsin), or any combination thereof. To increase the association of a target and a barcode, the rate of the diffusion of the target molecules can be altered by for example, reducing the temperature and/or increasing the viscosity of the lysate.

In some embodiments, the sample can be lysed using a filter paper. The filter paper can be soaked with a lysis buffer on top of the filter paper. The filter paper can be applied to the sample with pressure which can facilitate lysis of the sample and hybridization of the targets of the sample to the substrate.

In some embodiments, lysis can be performed by mechanical lysis, heat lysis, optical lysis, and/or chemical lysis. Chemical lysis can include the use of digestive enzymes such as proteinase K, pepsin, and trypsin. Lysis can be performed by the addition of a lysis buffer to the substrate. A lysis buffer can comprise Tris HCl. A lysis buffer can comprise at least about 0.01, 0.05, 0.1, 0.5, or 1 M or more Tris HCl. A lysis buffer can comprise at most about 0.01, 0.05, 0.1, 0.5, or 1 M or more Tris HCL. A lysis buffer can comprise about 0.1 M Tris HCl. The pH of the lysis buffer can be at least about 1, 2, 3, 4, 5, 6, 7, 8, 9, 10, or more. The pH of the lysis buffer can be at most about 1, 2, 3, 4, 5, 6, 7, 8, 9, 10, or more. In some embodiments, the pH of the lysis buffer is about 7.5. The lysis buffer can comprise a salt (e.g., LiCl). The concentration of salt in the lysis buffer can be at least about 0.1, 0.5, or 1 M or more. The concentration of salt in the lysis buffer can be at most about 0.1, 0.5, or 1 M or more. In some embodiments, the concentration of salt in the lysis buffer is about 0.5M. The lysis buffer can comprise a detergent (e.g., SDS, Li dodecyl sulfate, triton X, tween, NP-40). The concentration of the detergent in the lysis buffer can be at least about 0.0001%, 0.0005%, 0.001%, 0.005%, 0.01%, 0.05%, 0.1%, 0.5%, 1%, 2%, 3%, 4%, 5%, 6%, or 7%, or more. The concentration of the detergent in the lysis buffer can be at most about 0.0001%, 0.0005%, 0.001%, 0.005%, 0.01%, 0.05%, 0.1%, 0.5%, 1%, 2%, 3%, 4%, 5%, 6%, or 7%, or more. In some embodiments, the concentration of the detergent in the lysis buffer is about 1% Li dodecyl sulfate. The time used in the method for lysis can be dependent on the amount of detergent used. In some embodiments, the more detergent used, the less time needed for lysis. The lysis buffer can comprise a chelating agent (e.g., EDTA, EGTA). The concentration of a chelating agent in the lysis buffer can be at least about 1, 5, 10, 15, 20, 25, or 30 mM or more. The concentration of a chelating agent in the lysis buffer can be at most about 1, 5, 10, 15, 20, 25, or 30 mM or more. In some embodiments, the concentration of chelating agent in the lysis buffer is about 10 mM. The lysis buffer can comprise a reducing reagent (e.g., beta-mercaptoethanol, DTT). The concentration of the reducing reagent in the lysis buffer can be at least about 1, 5, 10, 15, or 20 mM or more. The concentration of the reducing reagent in the lysis buffer can be at most about 1, 5, 10, 15, or 20 mM or more. In some embodiments, the concentration of reducing reagent in the lysis buffer is about 5 mM. In some embodiments, a lysis buffer can comprise about 0.1M TrisHCl, about pH 7.5, about 0.5M LiCl, about 1% lithium dodecyl sulfate, about 10 mM EDTA, and about 5 mM DTT.

Lysis can be performed at a temperature of about 4, 10, 15, 20, 25, or 30° C. Lysis can be performed for about 1, 5, 10, 15, or 20 or more minutes. A lysed cell can comprise at least about 100000, 200000, 300000, 400000, 500000, 600000, or 700000 or more target nucleic acid molecules. A lysed cell can comprise at most about 100000, 200000, 300000, 400000, 500000, 600000, or 700000 or more target nucleic acid molecules.

Attachment of Barcodes to Target Nucleic Acid Molecules

Following lysis of the cells and release of nucleic acid molecules therefrom, the nucleic acid molecules can randomly associate with the barcodes of the co-localized solid support. Association can comprise hybridization of a barcode's target recognition region to a complementary portion of the target nucleic acid molecule (e.g., oligo(dT) of the barcode can interact with a poly(A) tail of a target). The assay conditions used for hybridization (e.g., buffer pH, ionic strength, temperature, etc.) can be chosen to promote formation of specific, stable hybrids. In some embodiments, the nucleic acid molecules released from the lysed cells can associate with the plurality of probes on the substrate (e.g., hybridize with the probes on the substrate). When the probes comprise oligo(dT), mRNA molecules can hybridize to the probes and be reverse transcribed. The oligo(dT) portion of the oligonucleotide can act as a primer for first strand synthesis of the cDNA molecule. For example, in a non-limiting example of barcoding illustrated in FIG. 2, at block 216, mRNA molecules can hybridize to barcodes on beads. For example, single-stranded nucleotide fragments can hybridize to the target-binding regions of barcodes.

Attachment can further comprise ligation of a barcode's target recognition region and a portion of the target nucleic acid molecule. For example, the target binding region can comprise a nucleic acid sequence that can be capable of specific hybridization to a restriction site overhang (e.g., an EcoRI sticky-end overhang). The assay procedure can further comprise treating the target nucleic acids with a restriction enzyme (e.g., EcoRI) to create a restriction site overhang. The barcode can then be ligated to any nucleic acid molecule comprising a sequence complementary to the restriction site overhang. A ligase (e.g., T4 DNA ligase) can be used to join the two fragments.

For example, in a non-limiting example of barcoding illustrated in FIG. 2, at block 220, the labeled targets from a plurality of cells (or a plurality of samples) (e.g., target-barcode molecules) can be subsequently pooled, for example, into a tube. The labeled targets can be pooled by, for example, retrieving the barcodes and/or the beads to which the target-barcode molecules are attached.

The retrieval of solid support-based collections of attached target-barcode molecules can be implemented by use of magnetic beads and an externally-applied magnetic field. Once the target-barcode molecules have been pooled, all further processing can proceed in a single reaction vessel. Further processing can include, for example, reverse transcription reactions, amplification reactions, cleavage reactions, dissociation reactions, and/or nucleic acid extension reactions. Further processing reactions can be performed within the microwells, that is, without first pooling the labeled target nucleic acid molecules from a plurality of cells.

Reverse Transcription

The disclosure provides for a method to create a target-barcode conjugate using reverse transcription (e.g., at block 224 of FIG. 2). The target-barcode conjugate can comprise the barcode and a complementary sequence of all or a portion of the target nucleic acid (i.e., a barcoded cDNA molecule, such as a stochastically barcoded cDNA molecule). Reverse transcription of the associated RNA molecule can occur by the addition of a reverse transcription primer along with the reverse transcriptase. The reverse transcription primer can be an oligo(dT) primer, a random hexanucleotide primer, or a target-specific oligonucleotide primer. Oligo(dT) primers can be, or can be about, 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, reverse transcription of the labeled-RNA molecule can occur by the addition of a reverse transcription primer. In some embodiments, the reverse transcription primer is an oligo(dT) primer, random hexanucleotide primer, or a target-specific oligonucleotide primer. Generally, oligo(dT) primers are 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

Reverse transcription can occur repeatedly to produce multiple labeled-cDNA molecules. The methods disclosed herein can comprise conducting at least about 1, 2, 3, 4, 5, 6, 7, 8, 9, 10, 11, 12, 13, 14, 15, 16, 17, 18, 19, or 20 reverse transcription reactions. The method can comprise conducting at least about 25, 30, 35, 40, 45, 50, 55, 60, 65, 70, 75, 80, 85, 90, 95, or 100 reverse transcription reactions.

Amplification

One or more nucleic acid amplification reactions (e.g., at block 228 of FIG. 2) can be performed to create multiple copies of the labeled target nucleic acid molecules. Amplification can be performed in a multiplexed manner, wherein multiple target nucleic acid sequences are amplified simultaneously. The amplification reaction can be used to add sequencing adaptors to the nucleic acid molecules. The amplification reactions can comprise amplifying at least a portion of a sample label, if present. The amplification reactions can comprise amplifying at least a portion of the cellular label and/or barcode sequence (e.g., a molecular label). The amplification reactions can comprise amplifying at least a portion of a sample tag, a cell label, a spatial label, a barcode sequence (e.g., a molecular label), a target nucleic acid, or a combination thereof. The amplification reactions can comprise amplifying 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range or a number between any two of these values, of the plurality of nucleic acids. The method can further comprise conducting one or more cDNA synthesis reactions to produce one or more cDNA copies of target-barcode molecules comprising a sample label, a cell label, a spatial label, and/or a barcode sequence (e.g., a molecular label).

In some embodiments, amplification can be performed using a polymerase chain reaction (PCR). As used herein, PCR can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some embodiments, the amplification does not produce circularized transcripts.

In some embodiments, the methods disclosed herein further comprise conducting a polymerase chain reaction on the labeled nucleic acid (e.g., labeled-RNA, labeled-DNA, labeled-cDNA) to produce a labeled amplicon (e.g., a stochastically labeled amplicon). The labeled amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample label, a spatial label, a cell label, and/or a barcode sequence (e.g., a molecular label). The labeled amplicon can be a single-stranded molecule. The single-stranded molecule can comprise DNA, RNA, or a combination thereof. The nucleic acids of the disclosure can comprise synthetic or altered nucleic acids.

Amplification can comprise use of one or more non-natural nucleotides. Non-natural nucleotides can comprise photolabile or triggerable nucleotides. Examples of non-natural nucleotides can include, but are not limited to, peptide nucleic acid (PNA), morpholine and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise, for example, 1, 2, 3, 4, 5, 6, 7, 8, 9, 10, 11, 12, 13, 14, or 15 or more nucleotides. The one or more primers can comprise at least 1, 2, 3, 4, 5, 6, 7, 8, 9, 10, 11, 12, 13, 14, or 15 or more nucleotides. The one or more primers can comprise less than 12-15 nucleotides. The one or more primers can anneal to at least a portion of the plurality of labeled targets (e.g., stochastically labeled targets). The one or more primers can anneal to the 3' end or 5' end of the plurality of labeled targets. The one or more primers can anneal to an internal region of the plurality of labeled targets. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled targets. The one or more primers can comprise a fixed panel of primers. The one or more primers can comprise at least one or more custom primers. The one or more primers can comprise at least one or more control primers. The one or more primers can comprise at least one or more gene-specific primers.

The one or more primers can comprise a universal primer. The universal primer can anneal to a universal primer binding site. The one or more custom primers can anneal to a first sample label, a second sample label, a spatial label, a cell label, a barcode sequence (e.g., a molecular label), a target, or any combination thereof. The one or more primers can comprise a universal primer and a custom primer. The custom primer can be designed to amplify one or more targets. The targets can comprise a subset of the total nucleic acids in one or more samples. The targets can comprise a subset of the total labeled targets in one or more samples. The one or more primers can comprise at least 96 or more custom primers. The one or more primers can comprise at least 960 or more custom primers. The one or more primers can comprise at least 9600 or more custom primers. The one or more custom primers can anneal to two or more different labeled nucleic acids. The two or more different labeled nucleic acids can correspond to one or more genes.

Any amplification scheme can be used in the methods of the present disclosure. For example, in one scheme, the first round PCR can amplify molecules attached to the bead using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and barcode sequence (e.g., molecular label) on read 1, the gene on read 2, and the sample index on index 1 read.

In some embodiments, nucleic acids can be removed from the substrate using chemical cleavage. For example, a chemical group or a modified base present in a nucleic acid can be used to facilitate its removal from a solid support. For example, an enzyme can be used to remove a nucleic acid from a substrate. For example, a nucleic acid can be removed from a substrate through a restriction endonuclease digestion. For example, treatment of a nucleic acid containing a dUTP or ddUTP with uracil-d-glycosylase (UDG) can be used to remove a nucleic acid from a substrate. For example, a nucleic acid can be removed from a substrate using an enzyme that performs nucleotide excision, such as a base excision repair enzyme, such as an apurinic/apyrimidinic (AP) endonuclease. In some embodiments, a nucleic acid can be removed from a substrate using a photocleavable group and light. In some embodiments, a cleavable linker can be used to remove a nucleic acid from the substrate. For example, the cleavable linker can comprise at least one of biotin/avidin, biotin/streptavidin, biotin/neutravidin, Ig-protein A, a photolabile linker, acid or base labile linker group, or an aptamer.

When the probes are gene-specific, the molecules can hybridize to the probes and be reverse transcribed and/or amplified. In some embodiments, after the nucleic acid has been synthesized (e.g., reverse transcribed), it can be amplified. Amplification can be performed in a multiplex manner, wherein multiple target nucleic acid sequences are amplified simultaneously. Amplification can add sequencing adaptors to the nucleic acid.

In some embodiments, amplification can be performed on the substrate, for example, with bridge amplification. cDNAs can be homopolymer tailed in order to generate a compatible end for bridge amplification using oligo(dT) probes on the substrate. In bridge amplification, the primer that is complementary to the 3' end of the template nucleic acid can be the first primer of each pair that is covalently attached to the solid particle. When a sample containing the template nucleic acid is contacted with the particle and a single thermal cycle is performed, the template molecule can be annealed to the first primer and the first primer is elongated in the forward direction by addition of nucleotides to form a duplex molecule consisting of the template molecule and a newly formed DNA strand that is complementary to the template. In the heating step of the next cycle, the duplex molecule can be denatured, releasing the template molecule from the particle and leaving the complementary DNA strand attached to the particle through the first primer. In the annealing stage of the annealing and elongation step that follows, the complementary strand can hybridize to the second primer, which is complementary to a segment of the complementary strand at a location removed from the first primer. This hybridization can cause the complementary strand to form a bridge between the first and second primers secured to the first primer by a covalent bond and to the second primer by hybridization. In the elongation stage, the second primer can be elongated in the reverse direction by the addition of nucleotides in the same reaction mixture, thereby converting the bridge to a double-stranded bridge. The next cycle then begins, and the double-stranded bridge can be denatured to yield two single-stranded nucleic acid molecules, each having one end attached to the particle surface via the first and second primers, respectively, with the other end of each unattached. In the annealing and elongation step of this second cycle, each strand can hybridize to a further complementary primer, previously unused, on the same particle, to form new single-strand bridges. The two previously unused primers that are now hybridized elongate to convert the two new bridges to double-strand bridges.

The amplification reactions can comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids.

Amplification of the labeled nucleic acids can comprise PCR-based methods or non-PCR based methods. Amplification of the labeled nucleic acids can comprise exponential amplification of the labeled nucleic acids. Amplification of the labeled nucleic acids can comprise linear amplification of the labeled nucleic acids. Amplification can be performed by polymerase chain reaction (PCR). PCR can refer to a reaction for the in vitro amplification of specific DNA sequences by the simultaneous primer extension of complementary strands of DNA. PCR can encompass derivative forms of the reaction, including but not limited to, RT-PCR, real-time PCR, nested PCR, quantitative PCR, multiplexed PCR, digital PCR, suppression PCR, semi-suppressive PCR and assembly PCR.

In some embodiments, amplification of the labeled nucleic acids comprises non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), a Qβ replicase (Qβ), use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and/or ramification extension amplification (RAM).

In some embodiments, the methods disclosed herein further comprise conducting a nested polymerase chain reaction on the amplified amplicon (e.g., target). The amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample tag or molecular identifier label. Alternatively, the amplicon can be a single-stranded molecule. The single-stranded molecule can comprise DNA, RNA, or a combination thereof. The nucleic acids of the present invention can comprise synthetic or altered nucleic acids.

In some embodiments, the method comprises repeatedly amplifying the labeled nucleic acid to produce multiple amplicons. The methods disclosed herein can comprise conducting at least about 1, 2, 3, 4, 5, 6, 7, 8, 9, 10, 11, 12, 13, 14, 15, 16, 17, 18, 19, or 20 amplification reactions. Alternatively, the method comprises conducting at least about 25, 30, 35, 40, 45, 50, 55, 60, 65, 70, 75, 80, 85, 90, 95, or 100 amplification reactions.

Amplification can further comprise adding one or more control nucleic acids to one or more samples comprising a plurality of nucleic acids. Amplification can further comprise adding one or more control nucleic acids to a plurality of nucleic acids. The control nucleic acids can comprise a control label.

Amplification can comprise use of one or more non-natural nucleotides. Non-natural nucleotides can comprise photolabile and/or triggerable nucleotides. Examples of non-natural nucleotides include, but are not limited to, peptide nucleic acid (PNA), morpholine and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise one or more oligonucleotides. The one or more oligonucleotides can comprise at least about 7-9 nucleotides. The one or more oligonucleotides can comprise less than 12-15 nucleotides. The one or more primers can anneal to at least a portion of the plurality of labeled nucleic acids. The one or more primers can anneal to the 3' end and/or 5' end of the plurality of labeled nucleic acids. The one or more primers can anneal to an internal region of the plurality of labeled nucleic acids. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled nucleic acids. The one or more primers can comprise a fixed panel of primers, at least one or more custom primers, at least one or more control primers, or a combination thereof. The one or more primers can comprise at least one or more housekeeping gene primers. The one or more primers can comprise a universal primer. The universal primer can anneal to a universal primer binding site. The one or more custom primers can anneal to the first sample tag, the second sample tag, the molecular identifier label, the nucleic acid or a product thereof. The one or more primers can comprise a universal primer and a custom primer. The custom primer can be designed to amplify one or more target nucleic acids. The target nucleic acids can comprise a subset of the total nucleic acids in one or more samples. In some embodiments, the primers are the probes attached to the array of the disclosure.

In some embodiments, barcoding (e.g., stochastically barcoding) the plurality of targets in the sample further comprises generating an indexed library of the barcoded targets (e.g., stochastically barcoded targets) or barcoded fragments of the targets. The barcode sequences of different barcodes (e.g., the molecular labels of different stochastic barcodes) can be different from one another. Generating an indexed library of the barcoded targets includes generating a plurality of indexed polynucleotides from the plurality of targets in the sample. For example, for an indexed library of the barcoded targets comprising a first indexed target and a second indexed target, the label region of the first indexed polynucleotide can differ from the label region of the second indexed polynucleotide by, by about, by at least, or by at most, 1, 2, 3, 4, 5, 6, 7, 8, 9, 10, 20, 30, 40, 50, or a number or a range between any two of these values, nucleotides. In some embodiments, generating an indexed library of the barcoded targets includes contacting a plurality of targets, for example mRNA molecules, with a plurality of oligonucleotides including a poly(T) region and a label region; and conducting a first strand synthesis using a reverse transcriptase to produce single-strand labeled cDNA molecules each comprising a cDNA region and a label region, wherein the plurality of targets includes at least two mRNA molecules of different sequences and the plurality of oligonucleotides includes at least two oligonucleotides of different sequences. Generating an indexed library of the barcoded targets can further comprise amplifying the single-strand labeled cDNA molecules to produce double-strand labeled cDNA molecules; and conducting nested PCR on the double-strand labeled cDNA molecules to produce labeled amplicons. In some embodiments, the method can include generating an adaptor-labeled amplicon.

Barcoding (e.g., stochastic barcoding) can include using nucleic acid barcodes or tags to label individual nucleic acid (e.g., DNA or RNA) molecules. In some embodiments, it involves adding DNA barcodes or tags to cDNA molecules as they are generated from mRNA. Nested PCR can be performed to minimize PCR amplification bias. Adaptors can be added for sequencing using, for example, next generation sequencing (NGS). The sequencing results can be used to determine cell labels, molecular labels, and sequences of nucleotide fragments of the one or more copies of the targets, for example at block 232 of FIG. 2.

Figure 3:
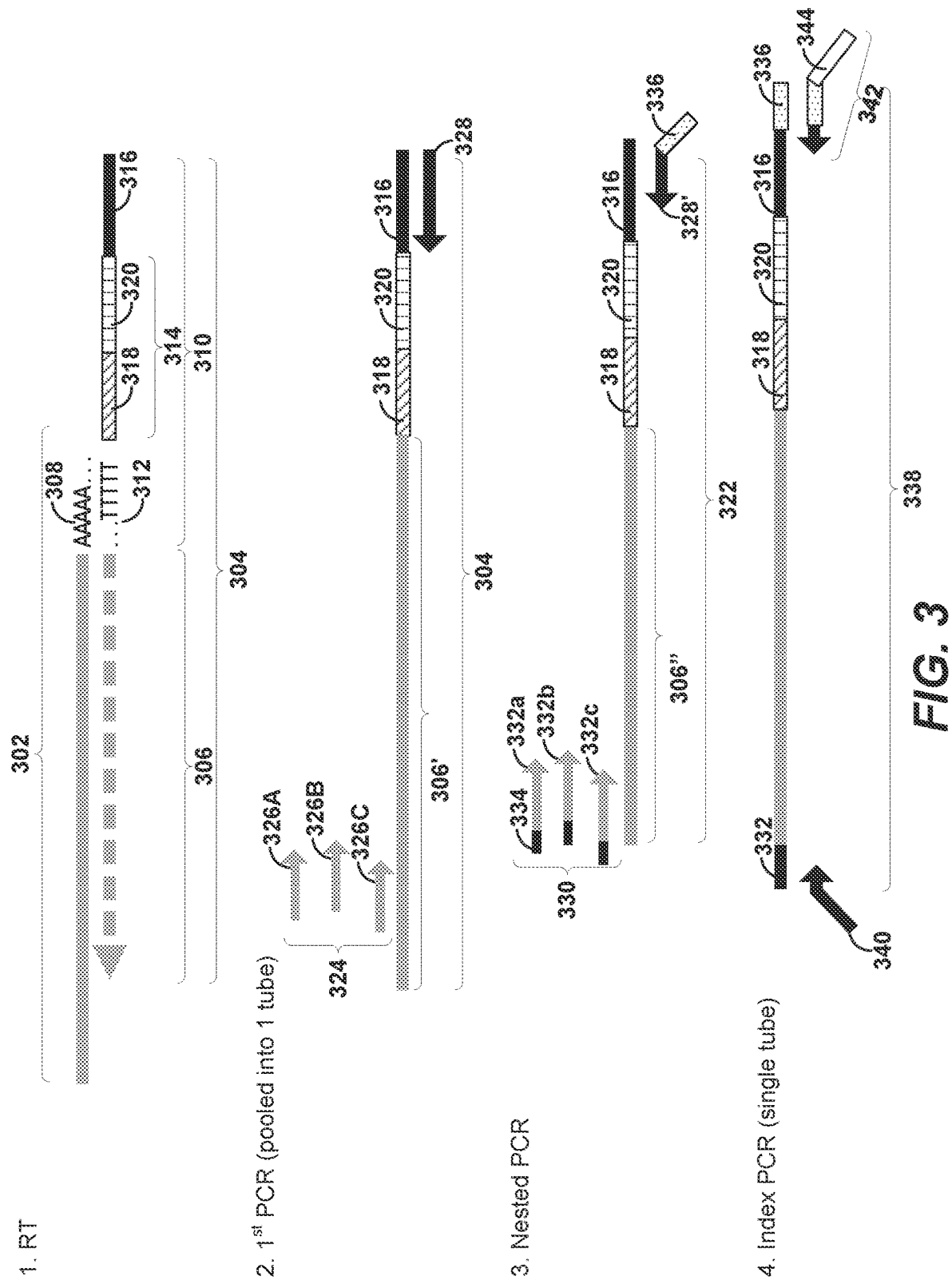
FIG. 3 is a schematic illustration showing a non-limiting exemplary process for generating an indexed library of targets barcoded at the 3'-ends from a plurality of targets.

FIG. 3 is a schematic illustration showing a non-limiting exemplary process of generating an indexed library of the barcoded targets (e.g., stochastically barcoded targets), such as barcoded mRNAs or fragments thereof. As shown in step 1, the reverse transcription process can encode each mRNA molecule with a unique molecular label sequence, a cell label sequence, and a universal PCR site. In particular, RNA molecules 302 can be reverse transcribed to produce labeled cDNA molecules 304, including a cDNA region 306, by hybridization (e.g., stochastic hybridization) of a set of barcodes (e.g., stochastic barcodes) 310 to the poly(A) tail region 308 of the RNA molecules 302. Each of the barcodes 310 can comprise a target-binding region, for example a poly(dT) region 312, a label region 314 (e.g., a barcode sequence or a molecule), and a universal PCR region 316.

In some embodiments, the cell label sequence can include 3 to 20 nucleotides. In some embodiments, the molecular label sequence can include 3 to 20 nucleotides. In some embodiments, each of the plurality of stochastic barcodes further comprises one or more of a universal label and a cell label, wherein universal labels are the same for the plurality of stochastic barcodes on the solid support and cell labels are the same for the plurality of stochastic barcodes on the solid support. In some embodiments, the universal label can include 3 to 20 nucleotides. In some embodiments, the cell label comprises 3 to 20 nucleotides.

In some embodiments, the label region 314 can include a barcode sequence or a molecular label 318 and a cell label 320. In some embodiments, the label region 314 can include one or more of a universal label, a dimension label, and a cell label. The barcode sequence or molecular label 318 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The cell label 320 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The universal label can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. Universal labels can be the same for the plurality of stochastic barcodes on the solid support and cell labels are the same for the plurality of stochastic barcodes on the solid support. The dimension label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length.

In some embodiments, the label region 314 can comprise, comprise about, comprise at least, or comprise at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different labels, such as a barcode sequence or a molecular label 318 and a cell label 320. Each label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length. A set of barcodes or stochastic barcodes 310 can contain, contain about, contain at least, or can be at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, barcodes or stochastic barcodes 310. And the set of barcodes or stochastic barcodes 310 can, for example, each contain a unique label region 314. The labeled cDNA molecules 304 can be purified to remove excess barcodes or stochastic barcodes 310. Purification can comprise Ampure bead purification.

As shown in step 2, products from the reverse transcription process in step 1 can be pooled into 1 tube and PCR amplified with a $1^{st}$ PCR primer pool and a $1^{st}$ universal PCR primer. Pooling is possible because of the unique label region 314. In particular, the labeled cDNA molecules 304 can be amplified to produce nested PCR labeled amplicons 322. Amplification can comprise multiplex PCR amplification. Amplification can comprise a multiplex PCR amplification with 96 multiplex primers in a single reaction volume. In some embodiments, multiplex PCR amplification can utilize, utilize about, utilize at least, or utilize at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, multiplex primers in a single reaction volume. Amplification can comprise using a $1^{st}$ PCR primer pool 324 comprising custom primers 326A-C targeting specific genes and a universal primer 328. The custom primers 326 can hybridize to a region within the cDNA portion 306' of the labeled cDNA molecule 304. The universal primer 328 can hybridize to the universal PCR region 316 of the labeled cDNA molecule 304.

As shown in step 3 of FIG. 3, products from PCR amplification in step 2 can be amplified with a nested PCR primers pool and a $2^{nd}$ universal PCR primer. Nested PCR can minimize PCR amplification bias. In particular, the nested PCR labeled amplicons 322 can be further amplified by nested PCR. The nested PCR can comprise multiplex PCR with nested PCR primers pool 330 of nested PCR primers 332a-c and a $2^{nd}$ universal PCR primer 328' in a single reaction volume. The nested PCR primer pool 328 can contain, contain about, contain at least, or contain at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different nested PCR primers 330. The nested PCR primers 332 can contain an adaptor 334 and hybridize to a region within the cDNA portion 306" of the labeled amplicon 322. The universal primer 328' can contain an adaptor 336 and hybridize to the universal PCR region 316 of the labeled amplicon 322. Thus, step 3 produces adaptor-labeled amplicon 338. In some embodiments, nested PCR primers 332 and the $2^{nd}$ universal PCR primer 328' may not contain the adaptors 334 and 336. The adaptors 334 and 336 can instead be ligated to the products of nested PCR to produce adaptor-labeled amplicon 338.

As shown in step 4, PCR products from step 3 can be PCR amplified for sequencing using library amplification primers. In particular, the adaptors 334 and 336 can be used to conduct one or more additional assays on the adaptor-labeled amplicon 338. The adaptors 334 and 336 can be hybridized to primers 340 and 342. The one or more primers 340 and 342 can be PCR amplification primers. The one or more primers 340 and 342 can be sequencing primers. The one or more adaptors 334 and 336 can be used for further amplification of the adaptor-labeled amplicons 338. The one or more adaptors 334 and 336 can be used for sequencing the adaptor-labeled amplicon 338. The primer 342 can contain a plate index 344 so that amplicons generated using the same set of barcodes or stochastic barcodes 310 can be sequenced in one sequencing reaction using next generation sequencing (NGS).

Barcoding on 5' Ends of Nucleic Acid Targets

Disclosed herein includes systems, methods, compositions, and kits for attachment of barcodes (e.g., stochastic barcodes) with molecular labels (or molecular indices) to the 5'-ends of nucleic acid targets being barcoded or labeled (e.g., deoxyribonucleic acid molecules, and ribonucleic acid molecules). The 5'-based transcript counting methods disclosed herein can complement, or supplement, for example, 3'-based transcript counting methods (e.g., Rhapsody™ assay (Becton, Dickinson and Company (Franklin Lakes, N.J.)), Chromium™ Single Cell 3' Solution (10× Genomics (San Francisco, Calif.))). The barcoded nucleic acid targets can be used for sequence identification, transcript counting, alternative splicing analysis, mutation screening, and/or full-length sequencing in a high throughput manner. Transcript counting on the 5'-end (5' relative to the target nucleic acid targets being labeled) can reveal alternative splicing isoforms and variants (including, but not limited to, splice variants, single nucleotide polymorphisms (SNPs), insertions, deletions, substitutions) on, or closer to, the 5'-ends of nucleic acid molecules. In some embodiments, the method can involve intramolecular hybridization.

Figure 4A:
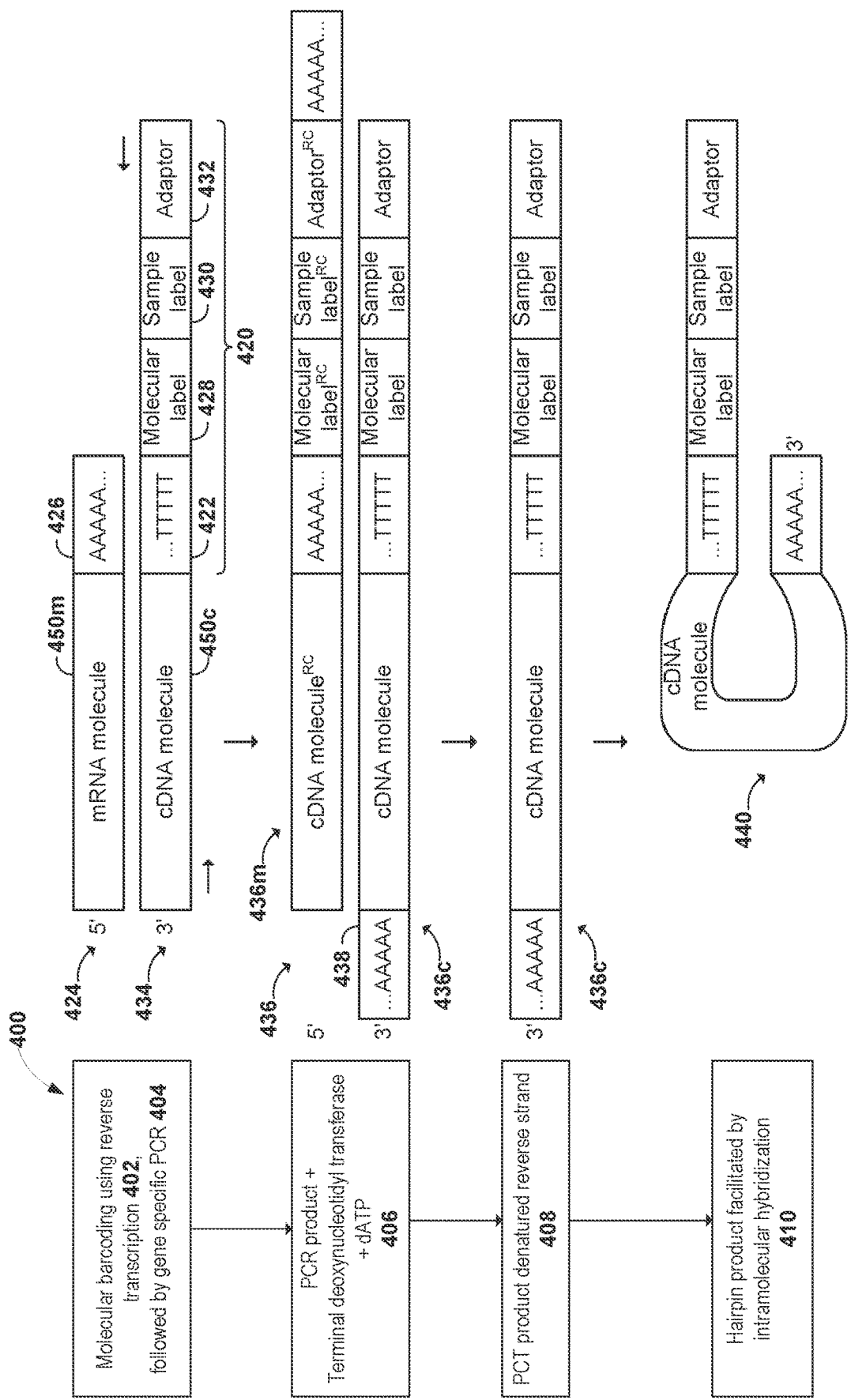
FIGS. 4A-4B show a schematic illustration of a non-limiting exemplary method of gene-specific labeling nucleic acid targets on the 5'-ends.
Figure 4B:
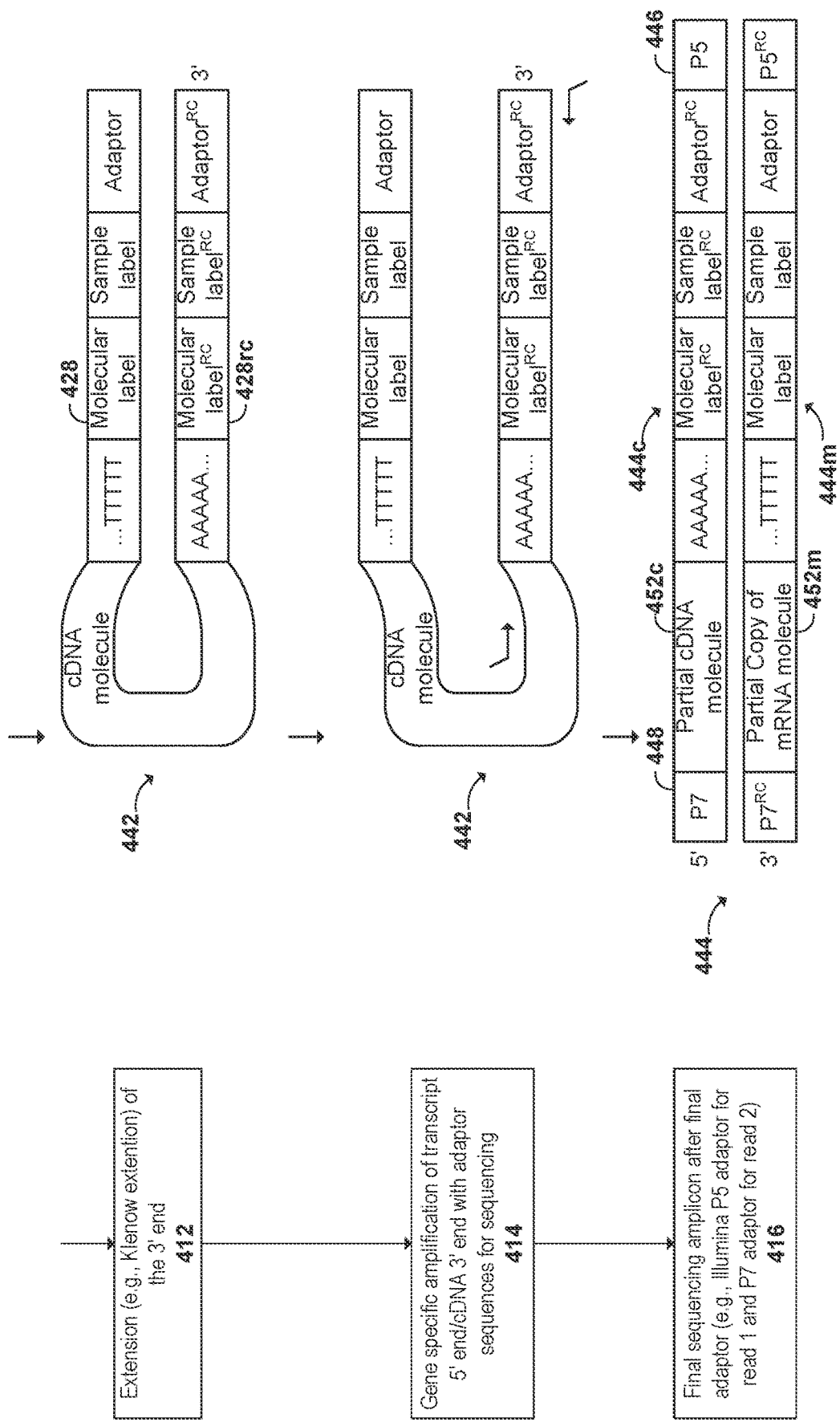

FIGS. 4A-4B show a schematic illustration of a non-limiting exemplary method 400 of gene-specific labeling nucleic acid targets on the 5'-ends. A barcode 420 (e.g., a stochastic barcode) with a target binding region (e.g., a poly(dT) tail 422) can bind to poly-adenylated RNA transcripts 424 via the poly(dA) tail 426, or other nucleic acid targets, for labeling or barcoding (e.g., unique labeling). The barcodes 420 can include molecular labels (MLs) 428 and sample labels (SLs) 430 for labeling the transcripts 424 and tracking sample origins of the RNA transcripts 424, respectively, along with one or more additional sequences (e.g., consensus sequences, such as an adaptor sequence 432), flanking the molecular label 428/sample label 430 region of each barcode 420 for subsequent reactions. The repertoire of sequences of the molecular labels in the barcodes per sample can be sufficiently large for stochastic labeling of RNA transcripts.

After cDNA synthesis at block 402 to generate barcoded cDNA molecules 434 comprising the RNA transcripts 424 (or a portion thereof), a gene specific method can be used for 5' molecular barcoding. After gene specific amplification at block 404, which can be optional, a terminal transferase and deoxyadenosine triphosphates (dATPs) can be added at block 406 to facilitate 3' poly(dA) tailing to generate amplicons 436 with a poly(A) tail 438. A short denaturation step at block 408 allows the separation of forward 436m and reverse strands 436c (e.g., barcoded cDNA molecules with poly(dA) tails) of the amplicon 436. The reverse strand 436c of the amplicon 436 can hybridize intra-molecularly via its poly(dA) tail 438 on the 3' end and the poly(dT) region 422 end of the strand to form a hairpin or stem loop 440 at block 410. An polymerase (e.g., a Klenow fragment) can then be used to extend from the poly(dA) tail 438 to duplicate the barcode to form extended barcoded reverse strand 442 at block 412. Gene specific amplification at block 414 (e.g., optionally) can then be performed to amplify genes of interest to produce amplicons 444 with barcodes on the 5' end (relative to the RNA transcripts 424) for sequencing at block 416. In some embodiments, the method 400 includes one or both of gene specific amplification of barcoded cDNA molecule 434 at block 404 and gene specific amplification of extended barcoded reverse strand 442 at block 414.

Figure 5A:
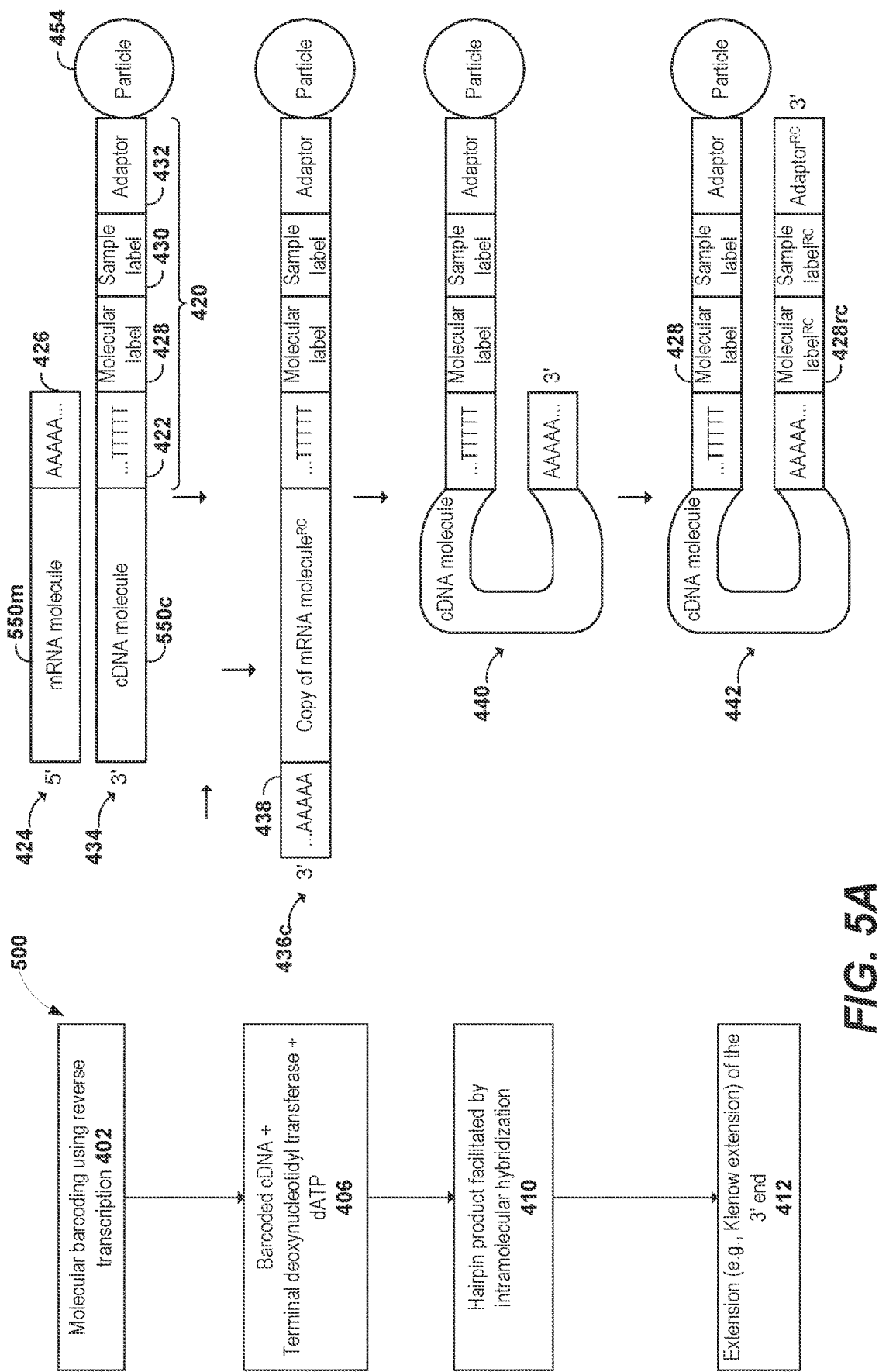
FIGS. 5A-5B show a schematic illustration of a non-limiting exemplary method of labeling nucleic acid targets on the 5'-ends for whole transcriptome analysis.
Figure 5B:
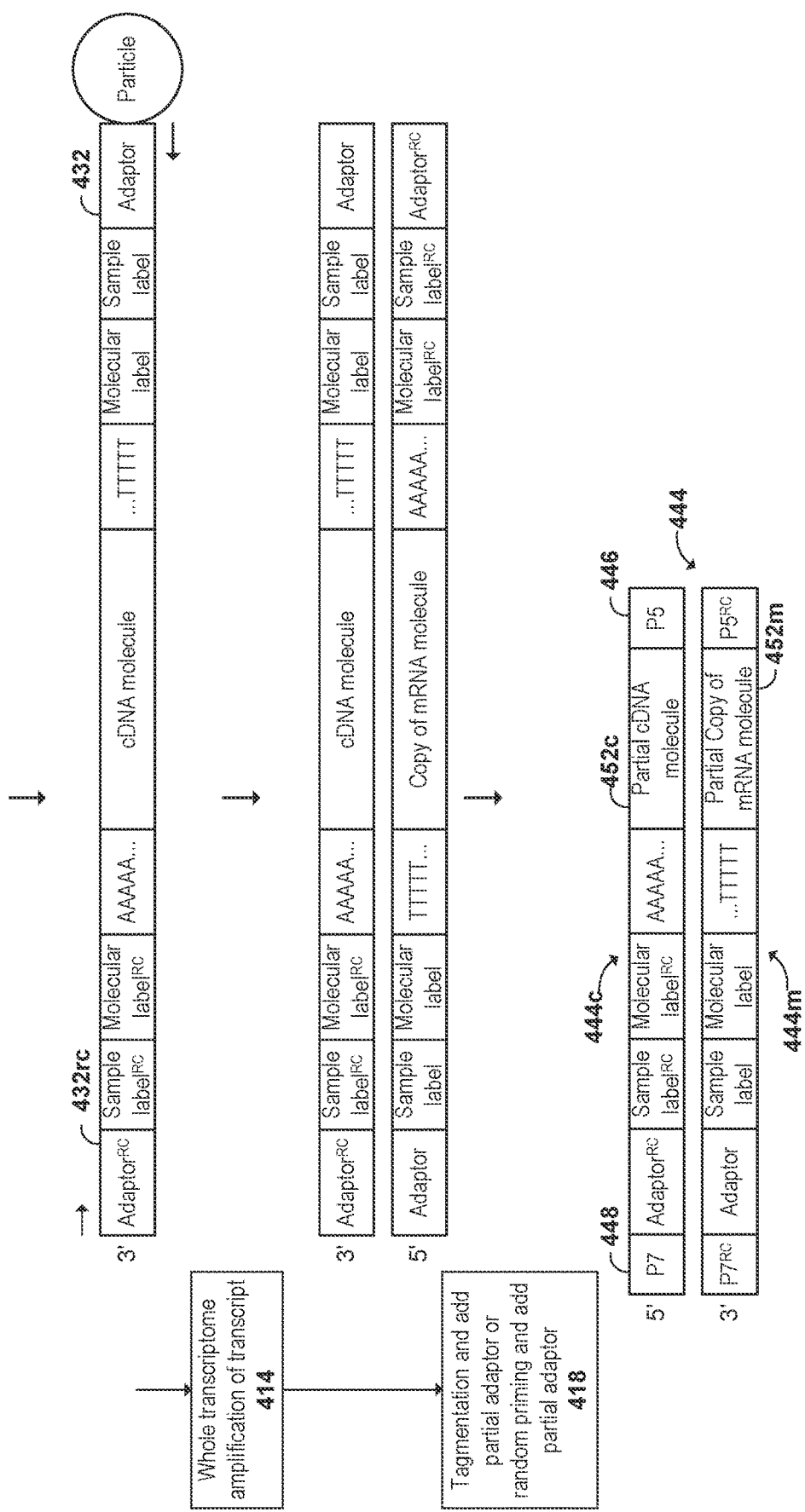

FIGS. 5A-5B show a schematic illustration of a non-limiting exemplary method 500 of labeling nucleic acid targets on the 5'-ends for whole transcriptome analysis. A barcode 420 (e.g., a stochastic barcode) with a target binding region (e.g., a poly(dT) tail 422) can bind to poly-adenylated RNA transcripts 424 via the poly(dA) tail 426, or other nucleic acid targets, for labeling or barcoding (e.g., unique labeling). For example, a barcode 420 with a target binding region can bind to a nucleic acid target for labeling or barcoding. A barcode 420 can include a molecular label (ML) 428 and a sample label (SL) 430. Molecular labels 428 and sample labels 430 can be used for labeling the transcripts 424, or nucleic acid targets (e.g., antibody oligonucleotides, whether associated with antibodies or have dissociated from antibodies) and tracking sample origins of the transcripts 424, respectively, along with one or more additional sequences (e.g., consensus sequences, such as an adaptor sequence 432), flanking the molecular label 428/sample label 430 region of each barcode 420 for subsequent reactions. The repertoire of sequences of the molecular labels 428 in the barcodes per sample can be sufficiently large for stochastic labeling of RNA transcripts 424, or nucleic acid targets.

After cDNA synthesis to generate barcoded cDNA molecules 434 at block 402, a terminal transferase enzyme can be used for A-tailing of the 3' end of the barcoded cDNA molecules 434 (equivalent to the 5' end of RNA transcripts labeled) to generate cDNA molecules 436c each with a 3' poly(dA) tail 438 at block 406. Intramolecular hybridization of the cDNA molecules 436c with 3' poly(dA) tails 438 can be initiated (e.g., with a heat and cooling cycle, or by diluting the barcoded cDNA molecules 436c with poly(dA) tails 438) such that the new 3' poly(dA) tail 438 is annealed with the poly(dT) tail 422 of the same labeled cDNA molecule to generate a barcoded cDNA molecule a hairpin or stem loop structure 440 at block 410. A polymerase (e.g., Klenow enzyme) with dNTP can be added to facilitate a 3' extension beyond the new 3' poly(dA) tail 438 to duplicate the barcodes (e.g., molecular labels 428 that are on the 5'-ends of the labeled cDNA molecules with stem loops 440 at block 412. A whole transcriptome amplification (WTA) can be performed at block 414 using mirrored adaptors 432, 432rc or primers containing sequences (or subsequences) of the adaptors 432, 432rc. Methods, such as tagmentation or random priming, can be used to generate smaller fragments of amplicons 444 with sequencing adaptors (e.g., P5 446 and P7 448 sequence) for sequencing at block 418 (e.g., using an Illumina (San Diego, Calif., U.S.) sequencer). In some embodiments, sequencing adaptors for other sequencing methods or sequencers (e.g., sequencers from Pacific Biosciences of California, Inc. (Menlo Park, Calif., US) or Oxford Nanopore Technologies Limited (Oxford, UK)) can be directly ligated to generate amplicons for sequencing.

Disclosed herein includes methods for determining the numbers of a nucleic acid target in a sample. In some embodiments, the method comprises: contacting copies of a nucleic acid target 424 in a sample to a plurality of oligonucleotide barcodes 420, wherein each of the plurality of oligonucleotide barcodes 420 comprises a molecular label sequence 428 and a target-binding region (e.g., a poly(dT) sequence 422) capable of hybridizing to the nucleic acid target 424, and wherein at least 10 of the plurality of oligonucleotide barcodes 420 comprise different molecular label sequences 428; extending the copies of the nucleic acid target 424 hybridized to the oligonucleotide barcodes 420 to generate a plurality of nucleic acid molecules 434 each comprising a sequence complementary 450c to at least a portion of the nucleic acid target 424 at block 402; amplifying the plurality of barcoded nucleic acid molecules 434 at block 404 to generate a plurality of amplified barcoded nucleic acid molecules 436; attaching an oligonucleotide comprising the complement 438 of the target-binding region 422 to the plurality of amplified barcoded nucleic acid molecules 436 to generate a plurality of barcoded nucleic acid molecules 436c each comprising the target-binding region 422 and a complement 438 of the target-binding region at block 406; hybridizing the target-binding region 422 and the complement 438 of the target-binding region 422 within each of the plurality of barcoded nucleic acid molecules 436c to form a stem loop 440 at block 410; extending 3'-ends of the plurality of barcoded nucleic acid molecules each with the stem loop 440 at block 412 to extend the stem loop 440 to generate a plurality of extended barcoded nucleic acid molecules 442 each comprising the molecular label 428 and a complement 428rc of the molecular label; amplifying the plurality of extended barcoded nucleic acid molecules 442 at block 414 to generate a plurality of single-labeled nucleic acid molecules 444c each comprising the complement 428rc of the molecular label; and determining the number of the nucleic acid target in the sample based on the number of complements 428rc of molecular labels with distinct sequences associated with the plurality of single-labeled nucleic acid molecules.

In some embodiments, the molecular label 428 is hybridized to the complement 428rc of the molecular label after extending the 3'-ends of the plurality of barcoded nucleic acid molecules with the stem loops 440. The method can comprise denaturing the plurality of extended barcoded nucleic acid molecules 442 prior to amplifying the plurality of extended barcoded nucleic acid molecules 442 to generate the plurality of single-labeled nucleic acid molecules 444c (which can be part of the amplicons 444c). Contacting copies of the nucleic acid target 424 in the sample can comprise contacting copies of a plurality of nucleic acid targets 424 to a plurality of oligonucleotide barcodes 420. Extending the copies of the nucleic acid target 424 can comprise extending the copies of the plurality nucleic acid targets 424 hybridized to the oligonucleotide barcodes 420 to generate a plurality of barcoded nucleic acid molecules 436c each comprising a sequence complementary 450c to at least a portion of one of the plurality of nucleic acid targets 424. Determining the number of the nucleic acid target 424 can comprise determining the number of each of the plurality of nucleic acid targets 424 in the sample based on the number of the complements 428rc of the molecular labels with distinct sequences associated with single-labeled nucleic acid molecules of the plurality of single-labeled nucleic acid molecules 444c comprising a sequence 452c of the each of the plurality of nucleic acid targets 424. The sequence 452c of the each of the plurality of nucleic acid targets can comprise a subsequence (including a complement or a reverse complement) of the each of the plurality of nucleic acid targets 424.

Disclosed herein includes methods for determining the numbers of targets in a sample. In some embodiments, the method comprises: barcoding 402 copies of a nucleic acid target 424 in a sample using a plurality of oligonucleotide barcodes 420 to generate a plurality of barcoded nucleic acid molecules 434 each comprising a sequence 450c (e.g., a complementary sequence, a reverse complementary sequence, or a combination thereof) of the nucleic acid target 424, a molecular label 428, and a target-binding region (e.g., a poly(dT) region 422), and wherein at least 10 of the plurality of oligonucleotide barcodes 420 comprise different molecular label sequences 428; attaching 406 an oligonucleotide comprising a complement 438 of the target-binding region 422 to the plurality of barcoded nucleic acid molecules 434 to generate a plurality of barcoded nucleic acid molecules 436 each comprising the target-binding region 422 and the complement 438 of the target-binding region 422; hybridizing 410 the target-binding region 422 and the complement 438 of the target-binding region within each of the plurality of barcoded nucleic acid molecules 436c to form a stem loop 440; extending 412 3'-ends of the plurality of barcoded nucleic acid molecules to extend the stem loop 440 to generate a plurality of extended barcoded nucleic acid molecules 442 each comprising the molecular label 428 and a complement 428rc of the molecular label; and determining the number of the nucleic acid target 424 in the sample based on the number of complements 428rc of molecular labels with distinct sequences associated with the plurality of extended barcoded nucleic acid molecules 442.

Disclosed herein includes methods for attaching oligonucleotide barcodes to a target in a sample. In some embodiments, the method comprises: barcoding 402 copies of a nucleic acid target 424 in a sample using a plurality of oligonucleotide barcodes 420 to generate a plurality of barcoded nucleic acid molecules 434 each comprising a sequence 450c of the nucleic acid target 424, a molecular label 428, and a target-binding region 422, and wherein at least 10 of the plurality of oligonucleotide barcodes 420 comprise different molecular label sequences 428; attaching an oligonucleotide comprising a complement 438 of the target binding region 422 to the plurality of barcoded nucleic acid molecules 434 to generate a plurality of barcoded nucleic acid molecules 436c each comprising the target-binding region 422 and the complement 438 of the target-binding region 422; hybridizing 410 the target-binding region 422 and the complement 438 of the target-binding region 422 within each of the plurality of barcoded nucleic acid molecules 436c to form a stem loop 440; and extending 412 3'-ends of the plurality of barcoded nucleic acid molecules to extend the stem loop 440 to generate a plurality of extended barcoded nucleic acid molecules 442 each comprising the molecular label 428 and a complement 428rc of the molecular label 428. In some embodiments, the method comprises: determining the number of the nucleic acid target 424 in the sample based on the number of molecular labels 428 with distinct sequences, complements 428rc thereof, or a combination thereof, associated with the plurality of extended barcoded nucleic acid molecules 442. For example, the number of the nucleic acid target 424 can be determined based on one or both of the molecular labels 428 with distinct sequences, complements 428rc thereof.

In some embodiments, the method comprises: barcoding 402 the copies of the plurality of targets 424 comprises: contacting copies of the nucleic acid target 424 to the plurality of oligonucleotide barcodes 420, wherein each of the plurality of oligonucleotide barcodes 420 comprises the target-binding region 422 capable of hybridizing to the nucleic acid target 424; and extending 402 the copies of the nucleic acid target 424 hybridized to the oligonucleotide barcodes 420 to generate the plurality of barcoded nucleic acid molecules 434.

In some embodiments, the method comprises: amplifying 404 the plurality of barcoded nucleic acid molecules 434 to generate a plurality of amplified barcoded nucleic acid molecules 436c, wherein attaching the oligonucleotide comprising the complement 438 of the target-binding region 422 comprises: attaching the oligonucleotide comprising the complement 438 of the target binding region to the plurality of amplified barcoded nucleic molecules to generate a plurality of barcoded nucleic acid molecules 436r each comprising the target-binding region 422 and a complement 438 of the target-binding region.

Gene Specific Analysis. In some embodiments, the method (e.g., the method 400) comprises: amplifying 414 the plurality of extended barcoded nucleic acid molecules 442 to generate a plurality of single-labeled nucleic acid molecules 444c each comprising the complement 428rc of the molecular label 428. The single-labeled nucleic acid molecules 444c can be generated when the amplicons 444 containing them are denatured. Determining the number of the nucleic acid target 424 in the sample can comprise: determining the number of the nucleic acid target 424 in the sample based on the number of complements 428rc of molecular labels 428 with distinct sequences associated with the plurality of single-labeled nucleic acid molecules 444c.

Whole Transcriptome Analysis. In some embodiments, the method (e.g., the method 500) comprises: amplifying 414 the plurality of extended barcoded nucleic acid molecules 442 to generate copies 444c of the plurality of extended barcoded nucleic acid molecules. Determining the number of the nucleic acid target 424 in the sample comprises: determining the number of the nucleic acid target 424 in the sample based on the number of complements 428rc of molecular labels 428 with distinct sequences associated with the copies 444c of plurality of extended barcoded nucleic acid molecules. The copies 444c of the plurality of extended barcoded nucleic acid molecules can be formed when amplicons 444 containing them are denatured.

In some embodiments, the sequence of the nucleic acid target in the plurality of barcoded nucleic acid molecules comprises a subsequence 452c of the nucleic acid target. The target-binding region can comprise a gene-specific sequence. Attaching 406 the oligonucleotide comprising the complement 438 of the target binding region 422 can comprise ligating the oligonucleotide comprising the complement 438 of the target binding region 422 to the plurality of barcoded nucleic acid molecules 434.

In some embodiments, the target-binding region can comprise a poly(dT) sequence 422. Attaching the oligonucleotide comprising the complement 438 of the target binding region 422 comprises: adding a plurality of adenosine monophosphates to the plurality of barcoded nucleic acid molecules 434 using a terminal deoxynucleotidyl transferase.

In some embodiments, extending the copies of the nucleic acid target 424 hybridized to the oligonucleotide barcodes 420 can comprise reverse transcribing the copies of the nucleic acid target 424 hybridized to the oligonucleotide barcodes 420 to generate a plurality of barcoded complementary deoxyribonucleic acid (cDNA) molecules 434. Extending the copies of the nucleic acid target 424 hybridized to the oligonucleotide barcodes 420 can comprise extending 402 the copies of the nucleic acid target 424 hybridized to the oligonucleotide barcodes 420 using a DNA polymerase lacking at least one of 5' to 3' exonuclease activity and 3' to 5' exonuclease activity. The DNA polymerase can comprise a Klenow Fragment.

In some embodiments, the method comprises: obtaining sequence information of the plurality of extended barcoded nucleic acid molecules 442. Obtaining the sequence information can comprise attaching sequencing adaptors (e.g., the P5 446 and P7 448 adaptor) to the plurality of extended barcoded nucleic acid molecules 442.

In some embodiments, the complement 438 of the target-binding region can comprise the reverse complementary sequence of the target-binding region. The complement 438 of the target-binding region can comprise the complementary sequence of the target-binding region. The complement 428rc of the molecular label can comprise a reverse complementary sequence of the molecular label. The complement of the molecular label can comprise a complementary sequence of the molecular label.

In some embodiments, the plurality of barcoded nucleic acid molecules 434 can comprise barcoded deoxyribonucleic acid (DNA) molecules. The barcoded nucleic acid molecules 434 can comprise barcoded ribonucleic acid (RNA) molecules. The nucleic acid target 424 can comprise a nucleic acid molecule. The nucleic acid molecule can comprise ribonucleic acid (RNA), messenger RNA (mRNA), microRNA, small interfering RNA (siRNA), RNA degradation product, RNA comprising a poly(A) tail, or any combination thereof.

Antibody Oligonucleotides. In some embodiments, the nucleic acid target can comprise a cellular component binding reagent. Cellular binding reagents associated with nucleic acid targets (e.g., antibody oligonucleotides, such as sample indexing oligonucleotides) have been described in US2018/0088112; and U.S. application Ser. No. 15/937,713, filed on Mar. 27, 2018; the content of each of these applications is incorporated herein by reference in its entirety. In some embodiments, multiomics information, such as genomics, chromatin accessibility, methylomics, transcriptomics, and proteomics, of single cells can be obtained using 5' barcoding methods of the disclosure. The nucleic acid molecule can be associated with the cellular component binding reagent. The method can comprise: dissociating the nucleic acid molecule and the cellular component binding reagent.

In some embodiments, each molecular label 428 of the plurality of oligonucleotide barcodes 420 comprises at least 6 nucleotides. The oligonucleotide barcode 420 can comprise an identical sample label 430. Each sample label 430 of the plurality of oligonucleotide barcodes 420 can comprise at least 6 nucleotides. The oligonucleotide barcode 420 can comprise an identical cell label. Each cell label of the plurality of oligonucleotide barcodes 420 can comprise at least 6 nucleotides.

In some embodiments, at least one of the plurality of barcoded nucleic acid molecules 436c is associated with a solid support when hybridizing 410 the target-binding region and the complement of the target-binding region within each of the plurality of barcoded nucleic acid molecules to form the stem loop. At least one of the plurality of barcoded nucleic acid molecules 436c can dissociate from a solid support when hybridizing 410 the target-binding region 422 and the complement 438 of the target-binding region 422 within each of the plurality of barcoded nucleic acid molecules 436c to form the stem loop 440. At least one of the plurality of barcoded nucleic acid molecules 436c can be associated with a solid support when hybridizing 410 the target-binding region 422 and the complement 438 of the target-binding region within each of the plurality of barcoded nucleic acid molecules 436c to form the stem loop 440.

In some embodiments, at least one of the plurality of barcoded nucleic acid molecules is associated with a solid support when extending 412 the 3'-ends of the plurality of barcoded nucleic acid molecules to extend the stem loop 440 to generate the plurality of extended barcoded nucleic acid molecules 442 each comprising the molecular label 428 and a complement 428rc of the molecular label. At least one of the plurality of barcoded nucleic acid molecules can dissociate from a solid support when extending 412 the 3'-ends of the plurality of barcoded nucleic acid molecules to extend the stem loop 440 to generate the plurality of extended barcoded nucleic acid molecules 442 each comprising the molecular label 428 and a complement 428rc of the molecular label. At least one of the plurality of barcoded nucleic acid molecules 436c can be associated with a solid support when extending 412 the 3'-ends of the plurality of barcoded nucleic acid molecules to extend the stem loop 440 to generate the plurality of extended barcoded nucleic acid molecules 442 each comprising the molecular label 428 and a complement 428rc of the molecular label. The solid support can comprise a synthetic particle 454. The solid support can comprise a planar surface or a substantially planar surface (e.g., a slide, such as a microscope slide or a coverslip).

In some embodiments, at least one of the plurality of barcoded nucleic acid molecules 436c is in solution when hybridizing 410 the target-binding region 422 and the complement 438 of the target-binding region 422 within each of the plurality of barcoded nucleic acid molecules 436c to form the stem loop 440. For example, when the concentration of the plurality of barcoded nucleic acid molecules 436c in solution is sufficiently low, such intramolecular hybridization can occur. At least one of the plurality of barcoded nucleic acid molecules can be in solution when extending 412 the 3'-ends of the plurality of barcoded nucleic acid molecules to extend the stem loop 440 to generate the plurality of extended barcoded nucleic acid molecules 442 each comprising the molecular label 428 and a complement 428rc of the molecular label.

In some embodiments, the sample comprises a single cell, the method comprising associating a synthetic particle 454 comprising the plurality of the oligonucleotide barcodes 420 with the single cell in the sample. The method can comprise: lysing the single cell after associating the synthetic particle 454 with the single cell. Lysing the single cell can comprise heating the sample, contacting the sample with a detergent, changing the pH of the sample, or any combination thereof. The synthetic particle and the single cell can be in the same well. The synthetic particle and the single cell can be in the same droplet.

In some embodiments, at least one of the plurality of oligonucleotide barcodes 420 can be immobilized on the synthetic particle 454. At least one of the plurality of oligonucleotide barcodes 420 can be partially immobilized on the synthetic particle 454. At least one of the plurality of oligonucleotide barcodes 420 can be enclosed in the synthetic particle 454. At least one of the plurality of oligonucleotide barcodes 420 can be partially enclosed in the synthetic particle 454. The synthetic particle 454 can be disruptable. The synthetic particle 454 can comprise a bead. The bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The synthetic particle 454 can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The synthetic particle 454 can comprise a disruptable hydrogel particle. Each of the plurality of oligonucleotide barcodes can comprise a linker functional group. The synthetic particle 454 can comprise a solid support functional group. The support functional group and the linker functional group can be associated with each other. The linker functional group and the support functional group can be individually selected from the group consisting of C6, biotin, streptavidin, primary amine(s), aldehyde(s), ketone(s), and any combination thereof.

Kits for Barcoding on 5' Ends of Nucleic Acid Targets

Disclosed herein includes kits for attaching oligonucleotide barcodes 420 to a target 424 in a sample, determining the numbers of targets 424 in a sample, and/or determining the numbers of a nucleic acid target 424 in a sample. In some embodiments, the kit includes: a plurality of oligonucleotide barcodes 420, wherein each of the plurality of oligonucleotide barcodes 420 comprises a molecular label 428 and a target-binding region (e.g., a poly(dT) sequence 422), and wherein at least 10 of the plurality of oligonucleotide barcodes 420 comprise different molecular label sequences 428; a terminal deoxynucleotidyl transferase or a ligase; and a DNA polymerase lacking at least one of 5' to 3' exonuclease activity and 3' to 5' exonuclease activity. The DNA polymerase can comprise a Klenow Fragment. The kit can comprise a buffer and/or a cartridge. The kit can comprise one or more reagents for a reverse transcription reaction. The kit can comprise one or more reagents for an amplification reaction.

In some embodiments, the target-binding region comprises a gene-specific sequence, an oligo(dT) sequence, a random multimer, or any combination thereof. The oligonucleotide barcode can comprise an identical sample label and/or an identical cell label. Each sample label and/or cell label of the plurality of oligonucleotide barcodes can comprise at least 6 nucleotides. Each molecular label of the plurality of oligonucleotide barcodes can comprise at least 6 nucleotides.

In some embodiments, at least one of the plurality of oligonucleotide barcodes 420 is immobilized on the synthetic particle 454. At least one of the plurality of oligonucleotide barcodes 420 can be partially immobilized on the synthetic particle 454. At least one of the plurality of oligonucleotide barcodes 420 can be enclosed in the synthetic particle 454. At least one of the plurality of oligonucleotide barcodes 420 can be partially enclosed in the synthetic particle 454. The synthetic particle 454 can be disruptable. The synthetic particle 454 can comprise a bead. The bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The synthetic particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The synthetic particle 454 can comprise a disruptable hydrogel particle. Each of the plurality of oligonucleotide barcodes can comprise a linker functional group. The synthetic particle 454 can comprise a solid support functional group. The support functional group and the linker functional group can be associated with each other. The linker functional group and the support functional group can be individually selected from the group consisting of C6, biotin, streptavidin, primary amine(s), aldehyde(s), ketone(s), and any combination thereof.

Full-Length Expression Profiling

Figure 9A:
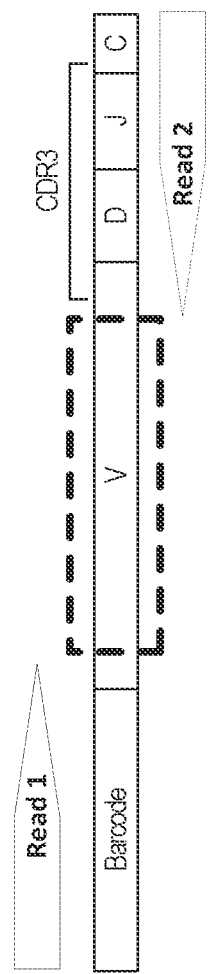
FIGS. 9A-9B show non-limiting exemplary schematics of the expression profiling of an immune receptor mRNA.

High-throughput single-cell RNA-sequencing has transformed the understanding of complex and heterogenous biological samples. However, most methods enable only 3' analysis of the mRNA transcript information, which may limit analysis of splice variants, alternative transcription start sites and highly variable loci due to rearrangement such as the VDJ junction of T cell and B cell receptors and antibodies. Methods for determining the sequences of a nucleic acid target (e.g., the V(D)J region of an immune receptor) using 5' barcoding and/or 3' barcoding are described in U.S. patent application Ser. No. 16/588,405, filed on Sep. 30, 2019; the content of which is incorporated herein by reference in its entirety. FIG. 9A is a non-limiting exemplary schematic of the 5' expression profiling of an immune receptor mRNA. While 5' expression profiling of the V(D)J region of an immune receptor can improve TCR/BCR coverage, and can yield CDR3 sequence information, this approach can miss the V region (indicated by dotted box in FIG. 9A). For both T and B cells, currently available C priming-based approaches can read into V(D)J but misses upstream V region. Thus, currently available methods can limit the ability to get full length nucleic acid target (e.g., V(D)J-containing transcript) information. A particular problem in the art is that we need to know the VDJ sequence as a longer read because there are many VDJ due to the numerous recombination events possible. There is a need for methods of both counting of sequences (e.g., V(D)J-containing transcripts) and identification of said sequences (in particular full-length sequence identification).

There are provided, in some embodiments, methods to obtain full-length V(D)J information (e.g., by Illumina sequencing on the Rhapsody system) using a random priming approach. T and B cell receptors contain V segments, D segments (for TCR beta and BCR heavy chain only), J segments as well as a constant region at the 3' prime end of the mRNA. CDR3, which is made of the V(D)J junction, contains the bulk of the repertoire diversity and is short enough to be sequenced on the Illumina short read platform. However, full-length V segment information is also useful and cannot be easily obtained without long read sequencing technologies, as Illumina short read capability limits ability to get full-length V(D)J information. The methods provided herein can employ random priming and extension to generate a library that contains both full-length V(D)J amplicons as well as shorter amplicons that only contain partial V segment sequences, which would enables a user to obtain both CDR3 information as well as full-length V segment sequence from a single library and sequencing run compatible with Illumina sequencers. Thus, some embodiments of the methods provided herein yield full-length immune receptor mRNA sequences.

Currently available 5' VDJ assays can acquire full-length information using a fragmentation approach, which is also possible on Rhapsody, but requires higher cost enzymes and reagents. Additionally, more enzymatic steps are involved with this fragmentation-based approach (e.g., fragmentation, end repair, a-tailing, ligation) versus the random priming approach provided herein (involving only random priming and extension). Fragmentation can also necessitate the use of enzymes to add primer sites, while some embodiments of the random priming-based methods provided herein do not require ligation of known primer site(s).

Figure 7:
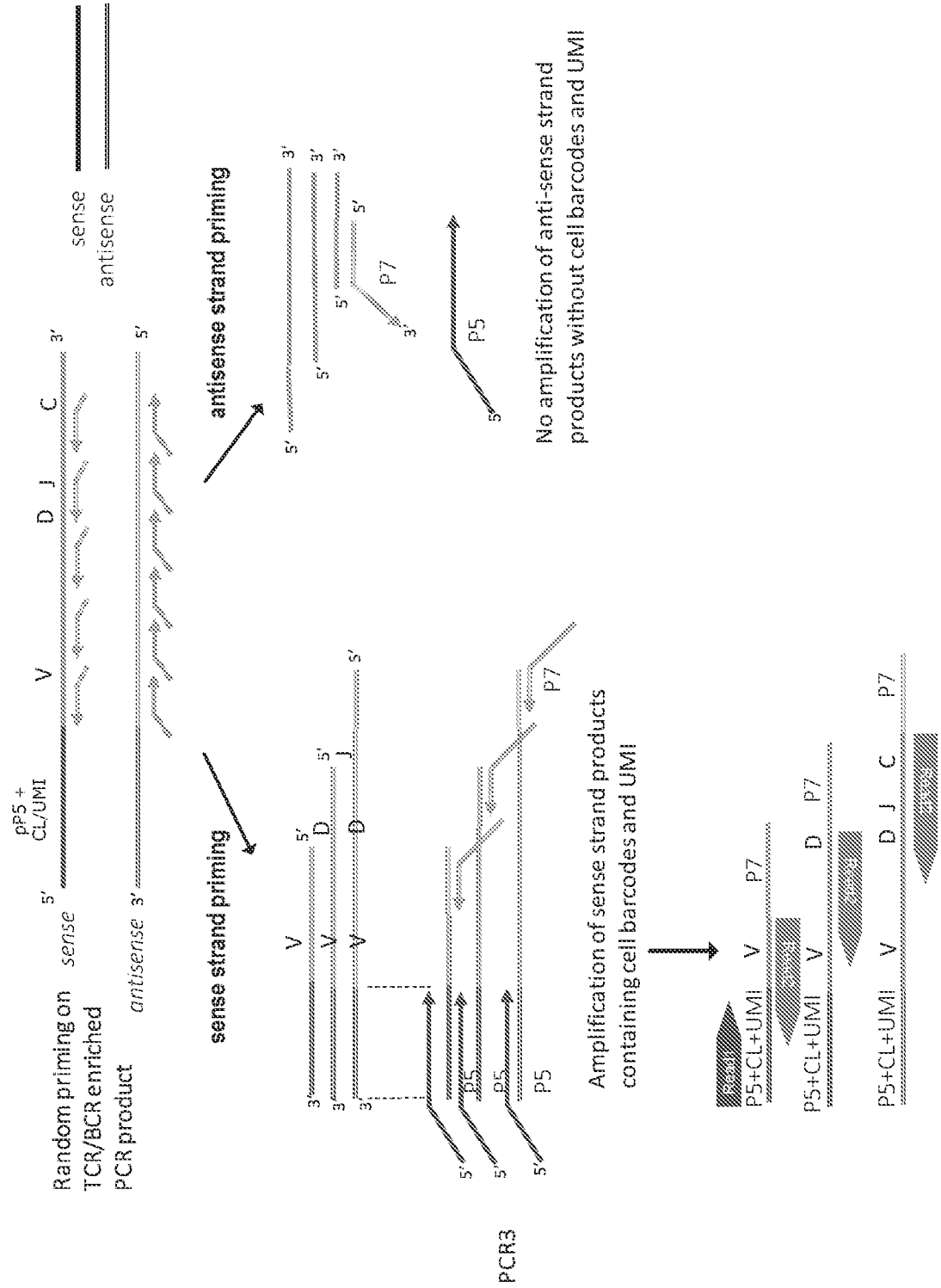
FIG. 7 is a schematic illustration of a non-limiting exemplary workflow of performing full-length expression profiling.
Figure 8:
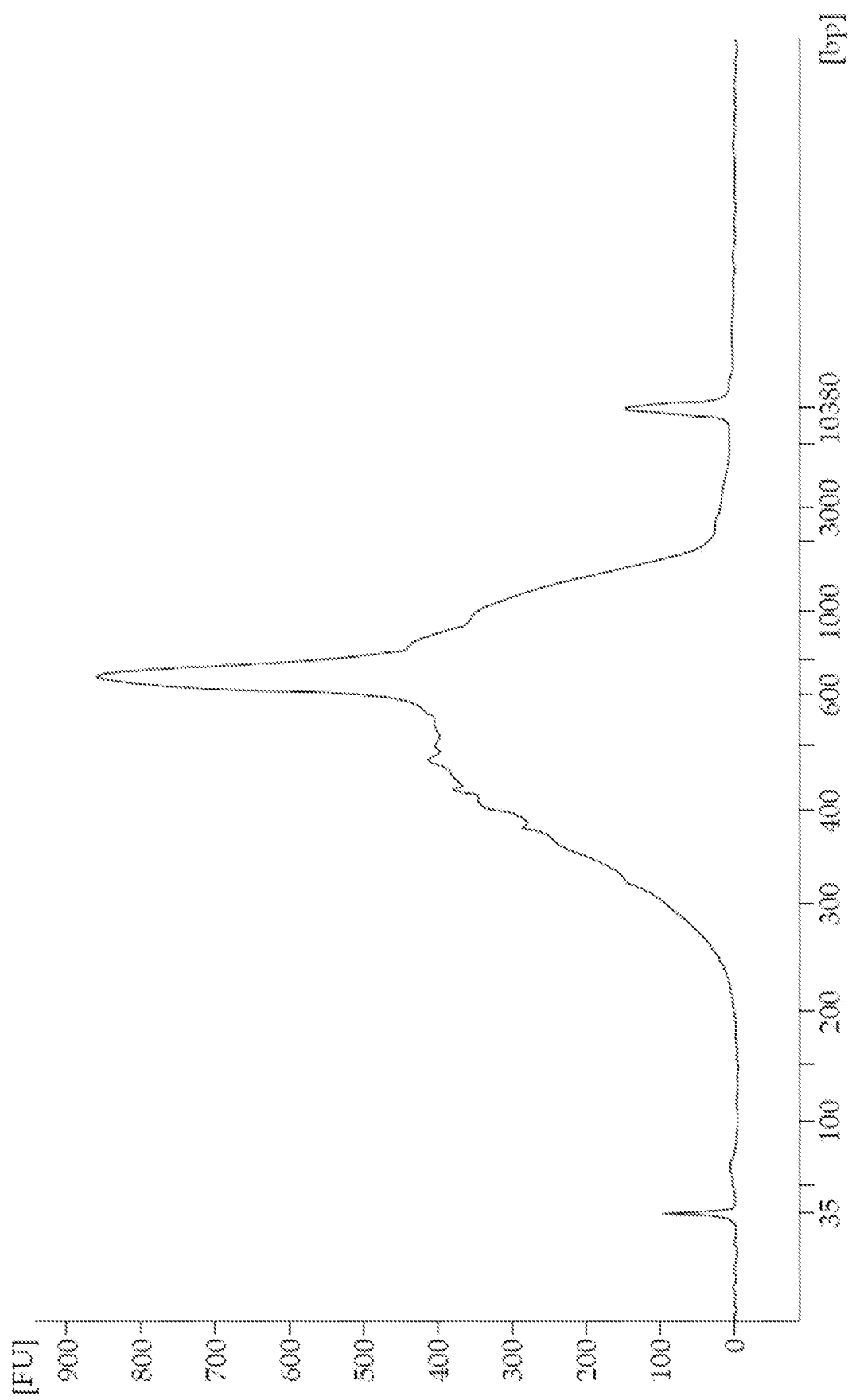
FIG. 8 depicts a non-limiting exemplary bioanalyzer trace generated according to the methods provided herein.
Figure 9B:
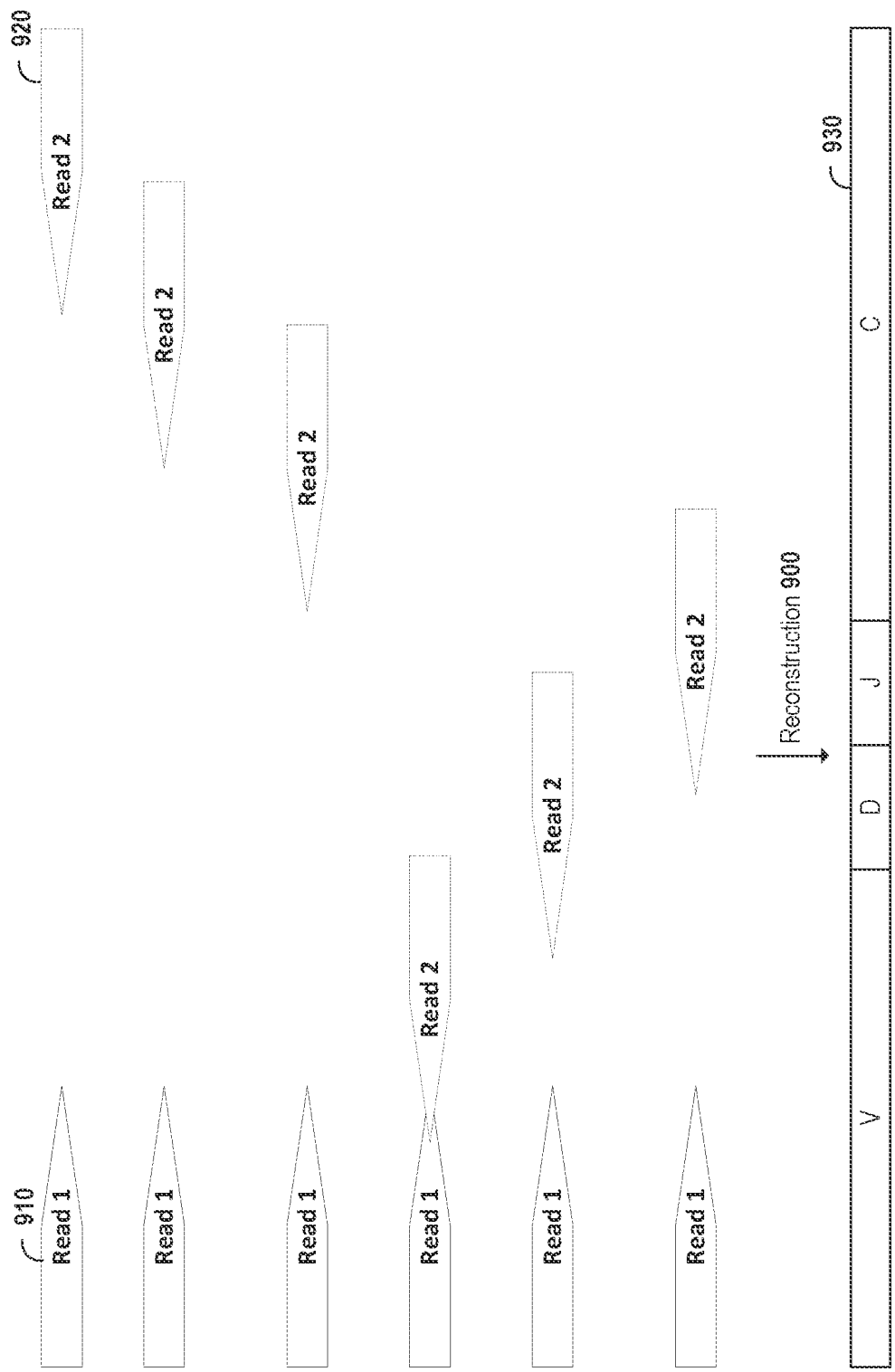

FIG. 7 is a schematic illustration of a non-limiting exemplary workflow of performing full-length expression profiling. The method can comprise random priming on a TCR/BCR enriched PCR product. The TCR/BCR enriched PCR product can be the product of an amplification of the extended barcoded nucleic acid molecules provided herein (e.g., a first plurality of barcoded amplicons). The TCR/BCR enriched PCR product can be the result of amplifying a plurality of extended barcoded nucleic acid molecules using a target-specific primer capable of hybridizing to a sequence of the nucleic acid target and a primer comprising a first universal sequence. The performance of random priming can generate shorter products. Sense strand priming and antisense strand priming can yield random priming extension products. The method can comprise performing PCR3. PCR3 amplification of sense strand products containing cell barcodes and UMI can generate a sequencing library. However, there is no amplification of anti-sense strand products without cell barcodes and UMI. Depending on the binding site of the random primer, a range of extension products can be generated. FIG. 8 depicts a non-limiting exemplary bioanalyzer trace generated according to the methods provided herein. Accordingly, there is provided herein a means to get longer reads of the V region (in order to identify the VDJ of a particular sample). The Illumina reads from the C region, and the normal read length is about 150 bp, which yields sequencing data to the end of V (if starting with the extended barcoded nucleic acid molecule provided herein). The PCR3 primers can add sequencing adapters (e.g., P5 and P7) and sample index (e.g., i5, i7) via overhangs. The method can comprise sequencing and bioinformatically reconstructing full-length V(D)J (e.g., aligning the plurality of sequencing reads as depicted in FIG. 9B). In some embodiments, the methods provided herein both identify the nucleic acid target (e.g. V(D)J-containing transcripts) and count the number of copies of said nucleic acid target.

There are provided, in some embodiments, compositions, methods, systems, and kits for obtaining full-length nucleic acid target (e.g., transcript) information. In some embodiments, the extended barcoded nucleic acid molecules generated according to the methods provided herein are employed as a template for performing random priming and extension. In some embodiments, the extended barcoded nucleic acid molecules are amplified (e.g., with a target specific primer and a primer comprising a first universal sequence) to generate a first plurality of barcoded amplicons. In some embodiments, the first plurality of barcoded amplicons are used as a template for performing random priming and extension (e.g., using randomers comprising a second universal sequence, or a complement thereof) to generate plurality of extension products. The random primers can bind to different locations along the coding sequence of all transcripts and extend to generate a plurality of extension products (e.g., a linearly amplified products). The extension products can comprise cDNA which is of varying length depending on the binding site of random primer. The extension product can be amplified with sequencing library amplification primers to generate a second plurality of barcoded amplicons. Sequencing library amplification can comprise using library forward and reverse primers adding sequencing adapters and/or library indices via overhangs. Library amplification can add sequencing adapters (e.g., P5 and P7 sequence) and sample index (e.g., i5, i7) via overhangs in a library forward primer and a library reverse primer. The methods can comprise obtaining the sequence information of the second plurality of barcoded amplicons (or products thereof). The second plurality of barcoded amplicons can be sequenced and subjected to downstream methods of the disclosure. Paired-end sequencing using to generate 150 bp×2 sequencing reads can reveal the cell label, unique molecular index, poly(A) tail, and/or gene (or a partial sequence of the gene) on read 1, the gene (or a partial sequence of the gene and/or poly(A) tail on read 2, and the sample index on index 1 read. Obtaining the sequence information of the second plurality of barcoded amplicons (or products thereof) can comprise obtaining sequencing data comprising a plurality of sequencing reads of the second plurality of barcoded amplicons (or products thereof). The method can comprise generating an full-length sequence of the nucleic acid target by aligning each of the plurality of sequencing reads.

The methods of the disclosure can be used for identifying VDJ regions of B cell receptors (BCR), T cell receptors (TCR), and antibodies. VDJ recombination, also known as somatic recombination, is a mechanism of genetic recombination in the early stages of immunoglobulin (Ig) (e.g., BCR) and T cell receptor (TCR) production of the immune system. VDJ recombination can nearly randomly combine Variable (V), Diverse (D) and Joining (J) gene segments. Because of its randomness in choosing different genes, it is able to diversely encode proteins to match antigens from bacteria, viruses, parasites, dysfunctional cells such as tumor cells and pollens.

The VDJ region can comprise a large 3 Mb locus comprising variable (V) genes, diversity (D) genes and joining (J) genes. These are the segments that can participate in VDJ recombination. There can be constant genes which may not undergo VDJ recombination. The first event in the VDJ recombination of this locus can be that one of the D genes rearranges to one of the J genes. Following this, one of the V genes can be appended to this DJ rearrangement to form the functional VDJ rearranged gene that then codes for the variable segment of the heavy chain protein. Both of these steps can be catalyzed by recombinase enzymes, which can delete out the intervening DNA.

This recombination process takes place in a stepwise fashion in progenitor B cells to produce the diversity required for the antibody repertoire. Each B cell may only produce one antibody (e.g., BCR). This specificity can be achieved by allelic exclusion such that functional rearrangement of one allele signals to prevent further recombination of the second allele.

In some embodiments, the sample comprises an immune cell. An immune cell can include, for example, T cell, B cell, lymphoid stem cell, myeloid progenitor cell, lymphocyte, granulocyte, B-cell progenitor, T cell progenitor, Natural Killer cell, Tc cell, Th cell, plasma cell, memory cell, neutrophil, eosinophil, basophil, mast cell, monocyte, dendritic cell and/or macrophage, or any combination thereof.

A T cell can be a T cell clone, which can refer to T cells derived from a single T cell or those having identical TCRs. A T cell can be part of a T cell line which can include T cell clones and mixed populations of T cells with different TCRs all of which may recognize the same target (e.g., antigen, tumor, virus). T cells can be obtained from a number of sources, including peripheral blood mononuclear cells, bone marrow, lymph node tissue, spleen tissue, and tumors. T cells can be obtained from a unit of blood collected from a subject, such as using the Ficoll separation. Cells from the circulating blood of an individual can be obtained by apheresis or leukapheresis. The apheresis product can comprise lymphocytes, including T cells, monocytes, granulocytes, B cells, other nucleated white blood cells, red blood cells, and platelets. The cells can be washed and resuspended in media to isolate the cell of interest.

T cells can be isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, T cells can be isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. Immune cells (e.g., T cells and B cells) can be antigen specific (e.g., specific for a tumor).

In some embodiments, the cell can be an antigen-presenting cell (APC), such as a B cell, an activated B cell from a lymph node, a lymphoblastoid cell, a resting B-cell, or a neoplastic B cell, e.g. from a lymphoma. An APC can refer to a B-cell or a follicular dendritic cell expressing at least one of the BCRC proteins on its surface.

The methods of the disclosure can be used to trace the molecular phenotype of single T cells. Different subtypes of T cells can be distinguished by expression of different molecular markers. T cells express a unique T cell receptor (TCR) from a diverse repertoire of TCRs. In most T cells, the TCR can be composed of a heterodimer of a α and a β chain; each functional chain can be a product of somatic DNA recombination events during T cell development, allowing the expression of over a million different TCRs in a single individual. TCRs can be used to define the identity of individual T cells, allowing for lineage tracing for T cell clonal expansion during an immune response. The immunological methods of the disclosure can be used in a variety of ways, including but not limited to, identifying unique TCRα and TCRβ chain pairing in single T cells, quantifying TCR and marker expression at the single cell level, identifying TCR diversity in an individual, characterizing the TCR repertoire expressed in different T cell populations, determining functionality of the alpha and beta chain alleles of the TCR, and identifying clonal expansion of T cells during immune response.

T-Cell Receptor Chain Pairing

T-cell receptors (TCRs) are recognition molecules present on the surface of T lymphocytes. The T-cell receptors found on the surface of T-cells can be comprised of two glycoprotein subunits which are referred to as the alpha and beta chains. Both chains can comprise a molecular weight of about 40 kDa and possess a variable and a constant domain. The genes which encode the alpha and beta chains can be organized in libraries of V, D and J regions from which the genes are formed by genetic rearrangement. TCRs can recognize antigen which is presented by an antigen presenting cell as a part of a complex with a specific self-molecule encoded by a histocompatibility gene. The most potent histocompatibility genes are known as the major histocompatibility complex (MHC). The complex which is recognized by T-cell receptors, therefore, consists of and MHC/peptide ligand.

In some embodiments, the methods, devices, and systems of the disclosure can be used for T cell receptor sequencing and pairing. The methods, devices, and systems of the disclosure can be used for sequencing T-cell receptor alpha and beta chains, pairing alpha and beta chains, and/or determining the functional copy of T-cell receptor alpha chains. A single cell can be contained in a single partition (e.g., well) with a single solid support (e.g., bead). The cell can be lysed. The bead can comprise a stochastic label that can bind to a specific location within an alpha and/or beta chain of a TCR. The TCR alpha and beta molecules associated with solid support can be subjected to the molecular biology methods of the disclosure, including reverse transcription, amplification, and sequencing. TCR alpha and beta chains that comprise the same cellular label can be considered to be from the same single cell, thereby pairing alpha and beta chains of the TCR.

Heavy and Light Chain Pairing in Antibody Repertoires

The methods devices and systems of the disclosure can be used for heavy and light chain pairing of BCR receptors and antibodies. The methods of the present disclosure allow for the repertoire of immune receptors and antibodies in an individual organism or population of cells to be determined. The methods of the present disclosure may aid in determining pairs of polypeptide chains that make up immune receptors. B cells and T cells each express immune receptors; B cells express immunoglobulins and BCRs, and T cells express T cell receptors (TCRs). Both types of immune receptors can comprise two polypeptide chains. Immunoglobulins can comprise variable heavy (VH) and variable light (VL) chains. There can be two types of TCRs: one consisting of an alpha and a beta chain, and one consisting of a delta and a gamma chain. Polypeptides in an immune receptor can comprise constant region and a variable region. Variable regions can result from recombination and end joint rearrangement of gene fragments on the chromosome of a B or T cell. In B cells additional diversification of variable regions can occur by somatic hypermutation.

The immune system has a large repertoire of receptors, and any given receptor pair expressed by a lymphocyte can be encoded by a pair of separate, unique transcripts. Knowing the sequences of pairs of immune receptor chains expressed in a single cell can be used to ascertain the immune repertoire of a given individual or population of cells.

In some embodiments, the methods, devices, and systems of the disclosure can be used for antibody sequencing and pairing. The methods, devices, and systems of the disclosure can be used for sequencing antibody heavy and light chains (e.g., in B cells), and/or pairing the heavy and light chains. A single cell can be contained in a single partition (e.g., well) with a single solid support (e.g., bead). The cell can be lysed.

The bead can comprise a stochastic label that can bind to a specific location within a heavy and/or light chain of an antibody (e.g., in a B cell). The heavy and light chain molecules associated with solid support can be subjected to the molecular biology methods of the disclosure, including reverse transcription, amplification, and sequencing. Antibody heavy and light chains that comprise the same cellular label can be considered to be from the same single cell, thereby pairing heavy and light chains of the antibody.

Methods of Full-Length Expression Profiling

There are provided, in some embodiments, methods of labeling nucleic acid targets in a sample. In some embodiments, the method comprises: contacting copies of a nucleic acid target with a plurality of oligonucleotide barcodes, wherein each oligonucleotide barcode comprises a first universal sequence, a molecular label (e.g., a first molecular label), and a target-binding region capable of hybridizing to the nucleic acid target; generating a plurality of barcoded nucleic acid molecules each comprising the target-binding region and a complement of the target-binding region; hybridizing the complement of the target-binding region of each barcoded nucleic acid molecule with the target-binding region of one or more of: (i) an oligonucleotide barcode of the plurality of oligonucleotide barcodes, (ii) the barcoded nucleic acid molecule itself, and (iii) a different barcoded nucleic acid molecule of the plurality of barcoded nucleic acid molecules; extending 3'-ends of the plurality of barcoded nucleic acid molecules to generate a plurality of extended barcoded nucleic acid molecules each comprising the first molecular label and a second molecular label; amplifying the plurality of extended barcoded nucleic acid molecules using a target-specific primer capable of hybridizing to a sequence of the nucleic acid target and a primer comprising the first universal sequence, thereby generating a first plurality of barcoded amplicons comprising the sequence of the nucleic acid target, or a portion thereof; hybridizing random primers to the first plurality of barcoded amplicons and extending the random primers to generate a plurality of extension products, wherein the random primers comprise a second universal sequence, or a complement thereof; and amplifying the plurality of extension products using primers capable of hybridizing to the first universal sequence and the second universal sequence, or complements thereof, thereby generating a second plurality of barcoded amplicons. In some embodiments, the method comprises: determining the copy number of the nucleic acid target in the sample based on the number of first molecular labels with distinct sequences, second molecular labels with distinct sequences, or a combination thereof, associated with the second plurality of barcoded amplicons, or products thereof. In some embodiments, the first universal sequence and the second universal sequence are the same. In some embodiments, the first universal sequence and the second universal sequence are different.

There are provided, in some embodiments, methods of determining the numbers of nucleic acid targets in a sample. In some embodiments, the method comprises: contacting copies of a nucleic acid target with a plurality of oligonucleotide barcodes, wherein each oligonucleotide barcode comprises a first universal sequence, a molecular label (e.g., a first molecular label), and a target-binding region capable of hybridizing to the nucleic acid target; generating a plurality of barcoded nucleic acid molecules each comprising the target-binding region and a complement of the target-binding region; hybridizing the complement of the target-binding region of each barcoded nucleic acid molecule with the target-binding region of one or more of: (i) an oligonucleotide barcode of the plurality of oligonucleotide barcodes, (ii) the barcoded nucleic acid molecule itself, and (iii) a different barcoded nucleic acid molecule of the plurality of barcoded nucleic acid molecules; extending 3'-ends of the plurality of barcoded nucleic acid molecules to generate a plurality of extended barcoded nucleic acid molecules each comprising the first molecular label and a second molecular label; amplifying the plurality of extended barcoded nucleic acid molecules using a target-specific primer capable of hybridizing to a sequence of the nucleic acid target and a primer comprising the first universal sequence, thereby generating a first plurality of barcoded amplicons comprising the sequence of the nucleic acid target, or a portion thereof; hybridizing random primers to the first plurality of barcoded amplicons and extending the random primers to generate a plurality of extension products, wherein the random primers comprise a second universal sequence, or a complement thereof; amplifying the plurality of extension products using primers capable of hybridizing to the first universal sequence and the second universal sequence, or complements thereof, thereby generating a second plurality of barcoded amplicons; and determining the copy number of the nucleic acid target in the sample based on the number of first molecular labels with distinct sequences, second molecular labels with distinct sequences, or a combination thereof, associated with the second plurality of barcoded amplicons, or products thereof.

Determining the copy number of the nucleic acid target in the sample can comprise: (a) determining the copy number of the nucleic acid target in the sample based on the number of second molecular labels with distinct sequences associated with the second plurality of barcoded amplicons, or products thereof, and/or (b) determining the copy number of the nucleic acid target in the sample based on the number of first molecular labels with distinct sequences associated with the second plurality of barcoded amplicons, or products thereof. In some embodiments, the method comprises: denaturing the plurality of barcoded nucleic acid molecules prior to hybridizing the complement of the target-binding region of each barcoded nucleic acid molecule with the target-binding region of: (i) an oligonucleotide barcode of the plurality of oligonucleotide barcodes, (ii) the barcoded nucleic acid molecule itself, and/or (iii) a different barcoded nucleic acid molecule of the plurality of barcoded nucleic acid molecules.

The method can comprise denaturing the plurality of extended barcoded nucleic acid molecules prior to amplifying the plurality of extended barcoded nucleic acid molecules. The sequence of each of the plurality of nucleic acid targets can comprise a subsequence of each of the plurality of nucleic acid targets. The sequence of the nucleic acid target in the plurality of barcoded nucleic acid molecules can comprise a subsequence of the nucleic acid target. In some embodiments, the first molecular label is hybridized to the second molecular label after extending the 3'-ends of the plurality of barcoded nucleic acid molecules. The extended barcoded nucleic acid molecules can each comprise the first molecular label, the second molecular label, the target-binding region, and the complement of the target-binding region. In some embodiments, the complement of the target-binding region is complementary to a portion of the target-binding region. The target-binding region can comprise a gene-specific sequence, a poly(dT) sequence, or both.

Generating a plurality of barcoded nucleic acid molecules each comprising the target-binding region and a complement of the target-binding region can comprise: (i) barcoding copies of a nucleic acid target in a sample using the plurality of oligonucleotide barcodes to generate a plurality of barcoded nucleic acid molecules each comprising a sequence complementary to at least a portion of the nucleic acid target, a first molecular label, and the target-binding region; and (ii) attaching an oligonucleotide comprising a complement of the target binding region to the plurality of barcoded nucleic acid molecules to generate a plurality of barcoded nucleic acid molecules each comprising the target-binding region and a complement of the target-binding region.

Generating a plurality of barcoded nucleic acid molecules each comprising the target-binding region and a complement of the target-binding region can comprise: (i) barcoding copies of a nucleic acid target in a sample using the plurality of oligonucleotide barcodes to generate a plurality of barcoded nucleic acid molecules each comprising a sequence complementary to at least a portion of the nucleic acid target, a first molecular label, and the target-binding region; (ii) amplifying the plurality of barcoded nucleic acid molecules to generate a plurality of amplified barcoded nucleic acid molecules; and (iii) attaching an oligonucleotide comprising a complement of the target binding region to plurality of amplified barcoded nucleic acid molecules to generate a plurality of barcoded nucleic acid molecules each comprising the target-binding region and a complement of the target-binding region.

Barcoding copies of a nucleic acid target in a sample can comprise extending the plurality of oligonucleotide barcodes hybridized to the copies of the nucleic acid target to generate the plurality of barcoded nucleic acid molecules. Extending the plurality of oligonucleotide barcodes hybridized to the copies of the nucleic acid target can comprise reverse transcribing the copies of the nucleic acid target hybridized to the plurality of oligonucleotide barcodes. Attaching the oligonucleotide comprising the complement of the target binding region can comprise ligating the oligonucleotide comprising the complement of the target binding region to the plurality of barcoded nucleic acid molecules and/or amplified barcoded nucleic acid molecules. In some embodiments, the target-binding region comprises a poly(dT) sequence, and wherein attaching the oligonucleotide comprising the complement of the target binding region comprises adding a plurality of adenosine monophosphates to the plurality of barcoded nucleic acid molecules and/or amplified barcoded nucleic acid molecules using a terminal deoxynucleotidyl transferase. Generating a plurality of barcoded nucleic acid molecules each comprising the target-binding region and a complement of the target-binding region can comprise: extending the plurality of oligonucleotide barcodes hybridized to the copies of the nucleic acid target in the presence of a reverse transcriptase and a template switch oligonucleotide comprising the target-binding region, or a portion thereof, to generate a plurality of barcoded nucleic acid molecules each comprising a sequence complementary to at least a portion of the nucleic acid target, a first molecular label, the target-binding region, and a complement of the target-binding region. In some embodiments, extending 3'-ends of the plurality of barcoded nucleic acid molecules comprises extending 3'-ends of the plurality of barcoded nucleic acid molecules using a DNA polymerase lacking at least one of 5' to 3' exonuclease activity and 3' to 5' exonuclease activity. In some embodiments, the DNA polymerase comprises a Klenow Fragment.

The number of cycles of random priming and extension can be different in different implementations. In some embodiments, the number of cycles of random priming and extension can comprise, or comprise about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, or a number or a range between any two of these values, cycles of random priming and extension. In some embodiments, the number of cycles of random priming and extension can comprise at least, or at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100, cycles of random priming and extension. Extending the random primers hybridized to the first plurality of barcoded amplicons can comprise using a DNA polymerase lacking at least one of 5' to 3' exonuclease activity and 3' to 5' exonuclease activity (e.g., a Klenow Fragment). In some embodiment, the extension enzyme is Klenow or Klenow exo-.

The random primers can comprise a random sequence of nucleotides. The random sequence of nucleotides can be about 4 to about 30 nucleotides in length. In some embodiments, said random sequence of nucleotides is 6 or 9 nucleotides in length. The random sequence of nucleotides can have different lengths in different implementations. In some embodiments, the random sequence of nucleotides within the random primers is, or is about, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, or a number or a range between any two of these values, nucleotides in length. In some embodiments, the random sequence of nucleotides within the random primers is at least, or is at most, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, nucleotides in length. The random primers can have different concentrations during the random priming step in different implementations. In some embodiments, the random primer is at least, or is at most, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 128, or a number or a range between any two of these values, uM in concentration during the random priming.

Hybridizing the complement of the target-binding region of a barcoded nucleic acid molecule with the target-binding region of the barcoded nucleic acid molecule itself can comprise intramolecular hybridization of the target-binding region and the complement of the target-binding region within a barcoded nucleic acid molecule to form a stem loop. In some embodiments, the second molecular label is the complement of the first molecular label.

Hybridizing the complement of the target-binding region of a barcoded nucleic acid molecule with the target-binding region of an oligonucleotide barcode of the plurality of oligonucleotide barcodes can comprise intermolecular hybridization of the complement of the target-binding region of a barcoded nucleic acid molecule with the target-binding region of an oligonucleotide barcode of the plurality of oligonucleotide barcodes. In some embodiments, the second molecular label is a different from the first molecular label, and wherein the second molecular label is not a complement of the first molecular label. In some embodiments, the method comprises extending the 3' ends of the oligonucleotide barcodes hybridized to the complement of the target-binding region of the barcoded nucleic acid molecule to generate a plurality of extended barcoded nucleic acid molecules each comprising a complement of the first molecular label and a second molecular label. In some embodiments, the sequence of the second molecular label is different from the sequence of the first molecular label, wherein the wherein the second molecular label is not a complement of the first molecular label.

Hybridizing the complement of the target-binding region of a barcoded nucleic acid molecule with the target-binding region of a different barcoded nucleic acid molecule of the plurality of barcoded nucleic acid molecules can comprise intermolecular hybridization of the complement of the target-binding region of a barcoded nucleic acid molecule with the target-binding region of a different barcoded nucleic acid molecule of the plurality of barcoded nucleic acid molecules. In some embodiments, the sequence of the second molecular label is different from the sequence of the first molecular label, and wherein the second molecular label is not a complement of the first molecular label.

In some embodiments, the methods comprise the addition (e.g., by a template switching reaction) of a complement of a target-binding region to an end (e.g., the 3' end) of a barcoded nucleic acid molecule. In some embodiments, the method comprises i) intramolecular hybridization and/or ii) intermolecular hybridization of the target-binding region of an oligonucleotide barcode (or a product thereof, such as, for example, another barcoded nucleic acid molecule, or an amplicon thereof) followed by extension to generate an extended barcoded nucleic acid molecule. An extended barcoded nucleic acid molecule can be barcoded on both the 3' and the 5' end. In some embodiments, intramolecular hybridization of a barcoded molecule forms hairpin loops with capture mRNA transcripts on 3' poly(dT) capture beads. mRNA molecules can be captured onto beads via the poly(A) tail binding to the target-binding region of an oligonucleotide barcode. Following hybridization, template switching can be used to attach a poly(dA) tail at the 5' end of the captured transcript. The new poly(dA) tail can then hybridize to free capture oligonucleotides (e.g., barcodes, such as stochastic barcodes) on the same bead. After extension, the mRNA molecules can be barcoded on both the 3' and the 5' end. This allows generation of both 3' and 5' barcoded transcripts that can be sequenced on, for example, the Illumina sequencing platform. Access to barcoded 5' sequence can allow detection of the variable region of T-cell receptor (TCR) and B-cell receptor (BCR), as well as splice variants and sequence variations that occur in the 5' ends of the transcripts.

Figure 6A:
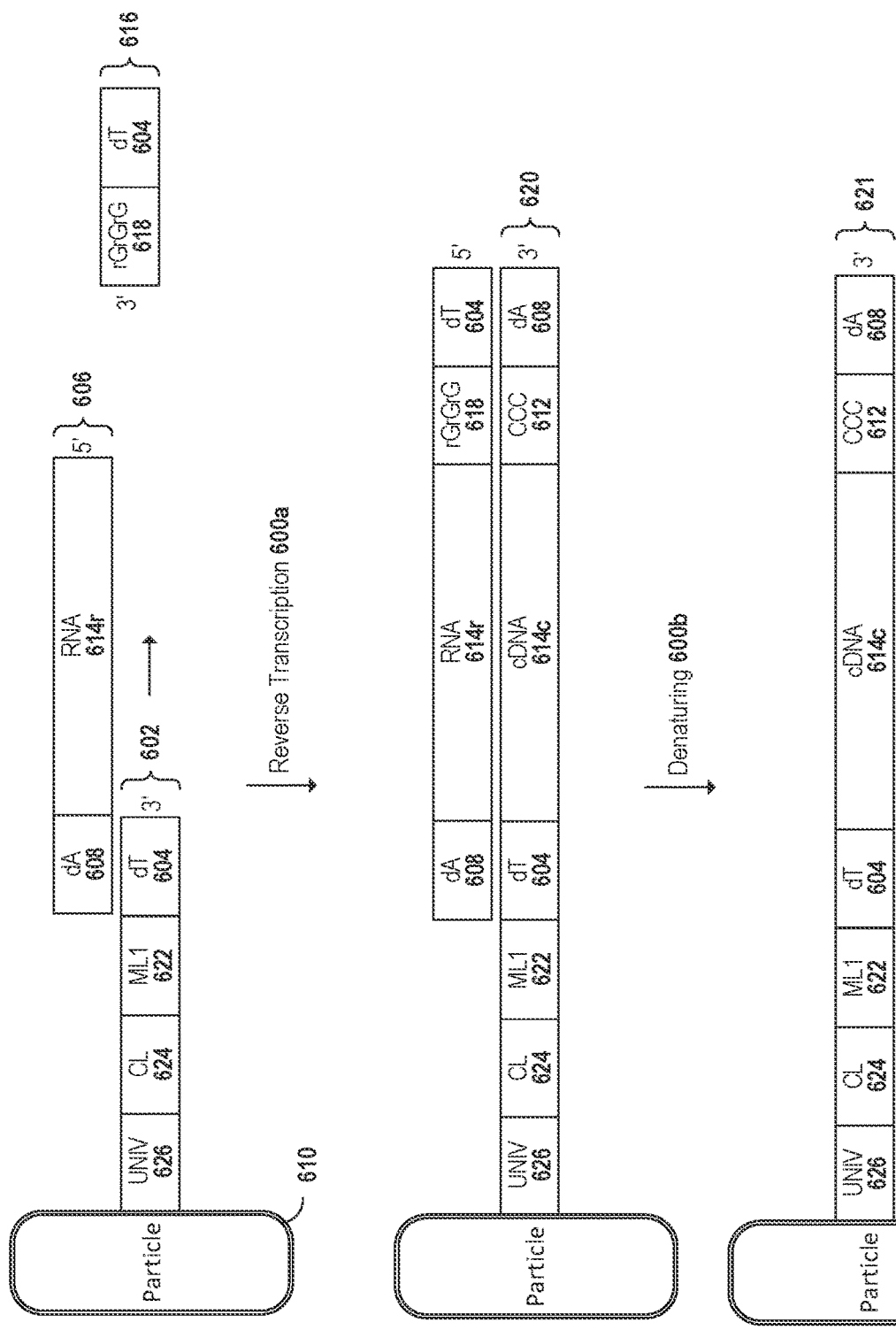
FIGS. 6A-6O show schematic illustrations of non-limiting exemplary workflows of determining the full-length sequence of a nucleic acid target (e.g., an immune receptor mRNA).
Figure 6B:
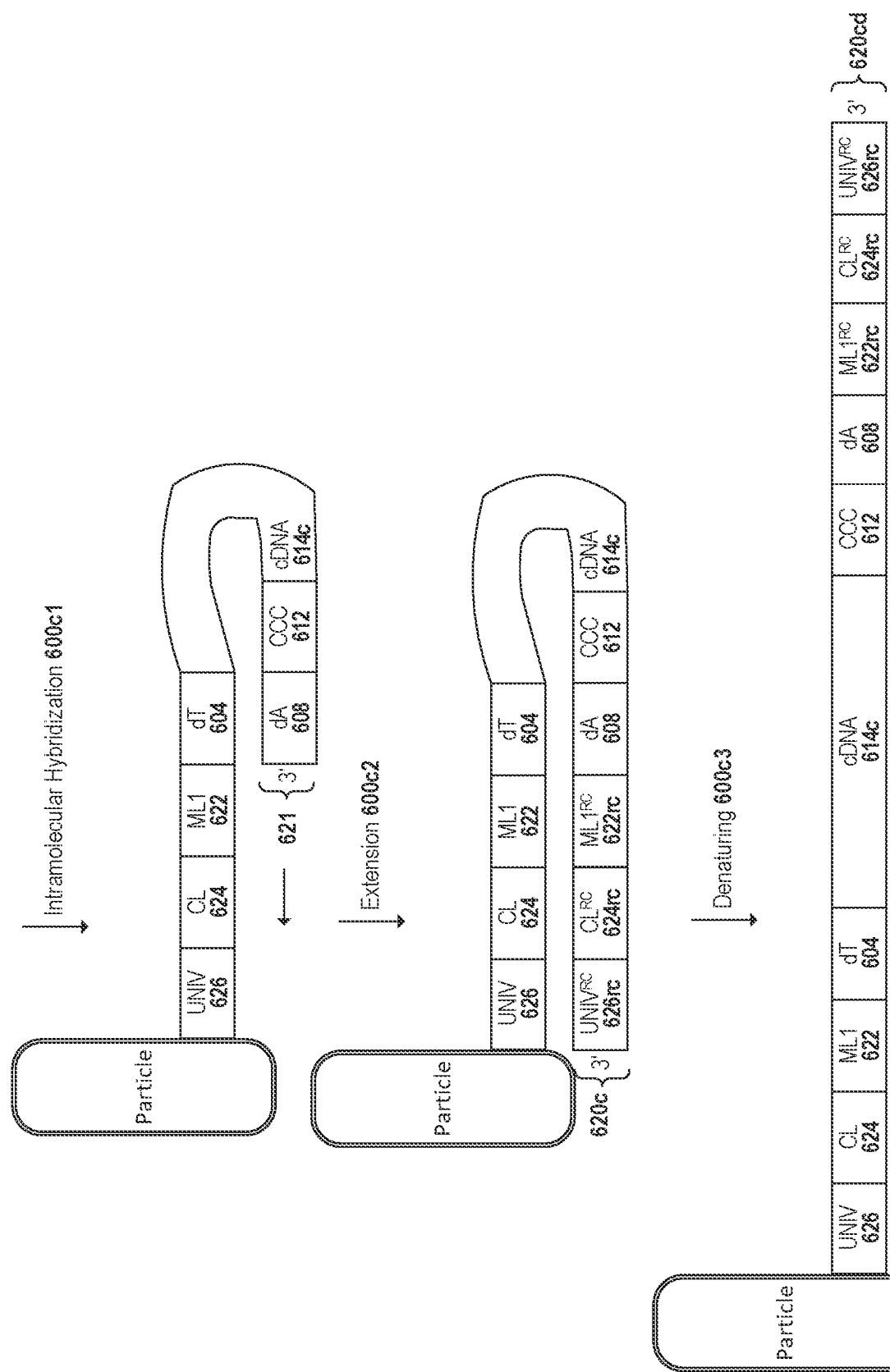
Figure 6C:
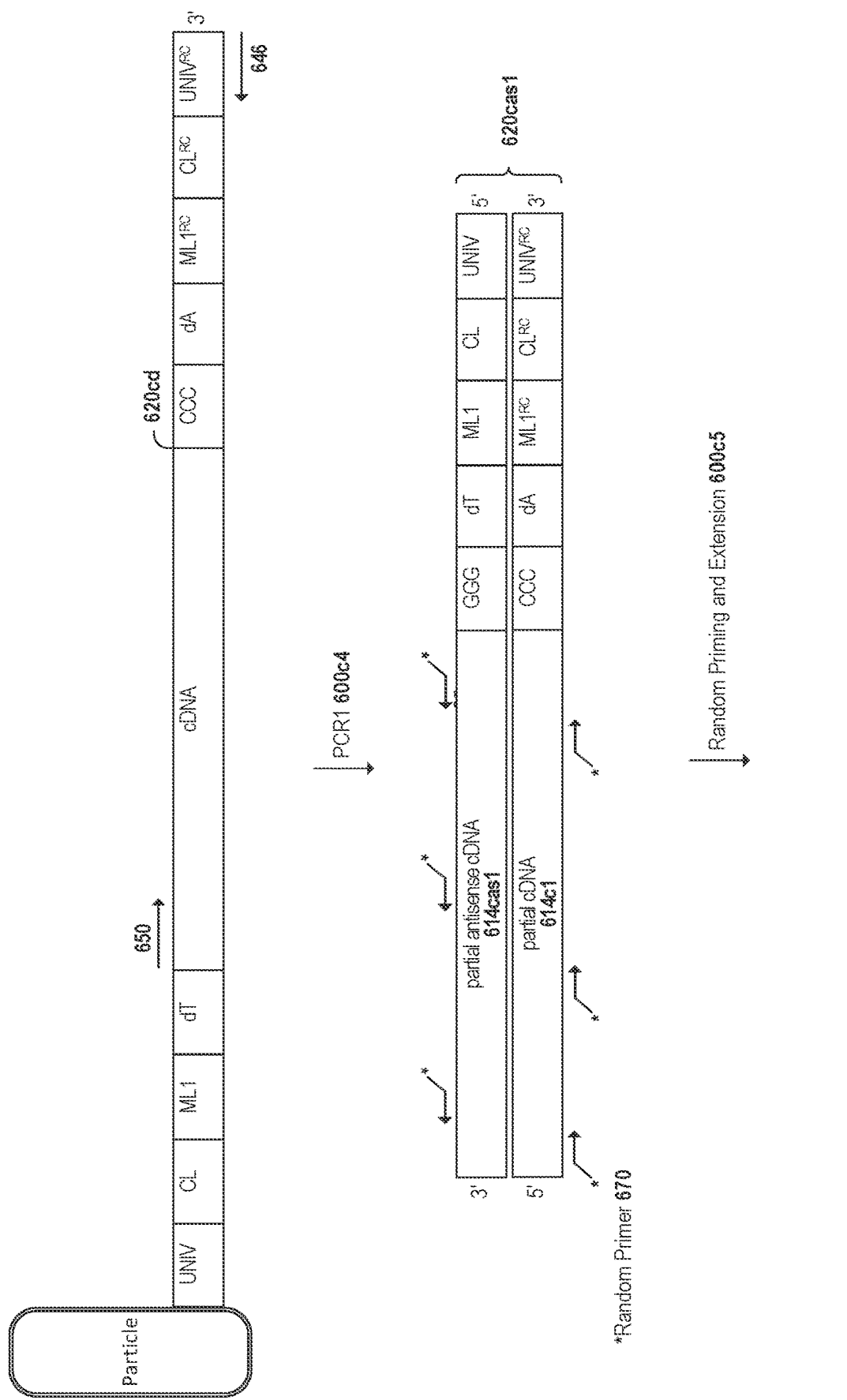
Figure 6D:
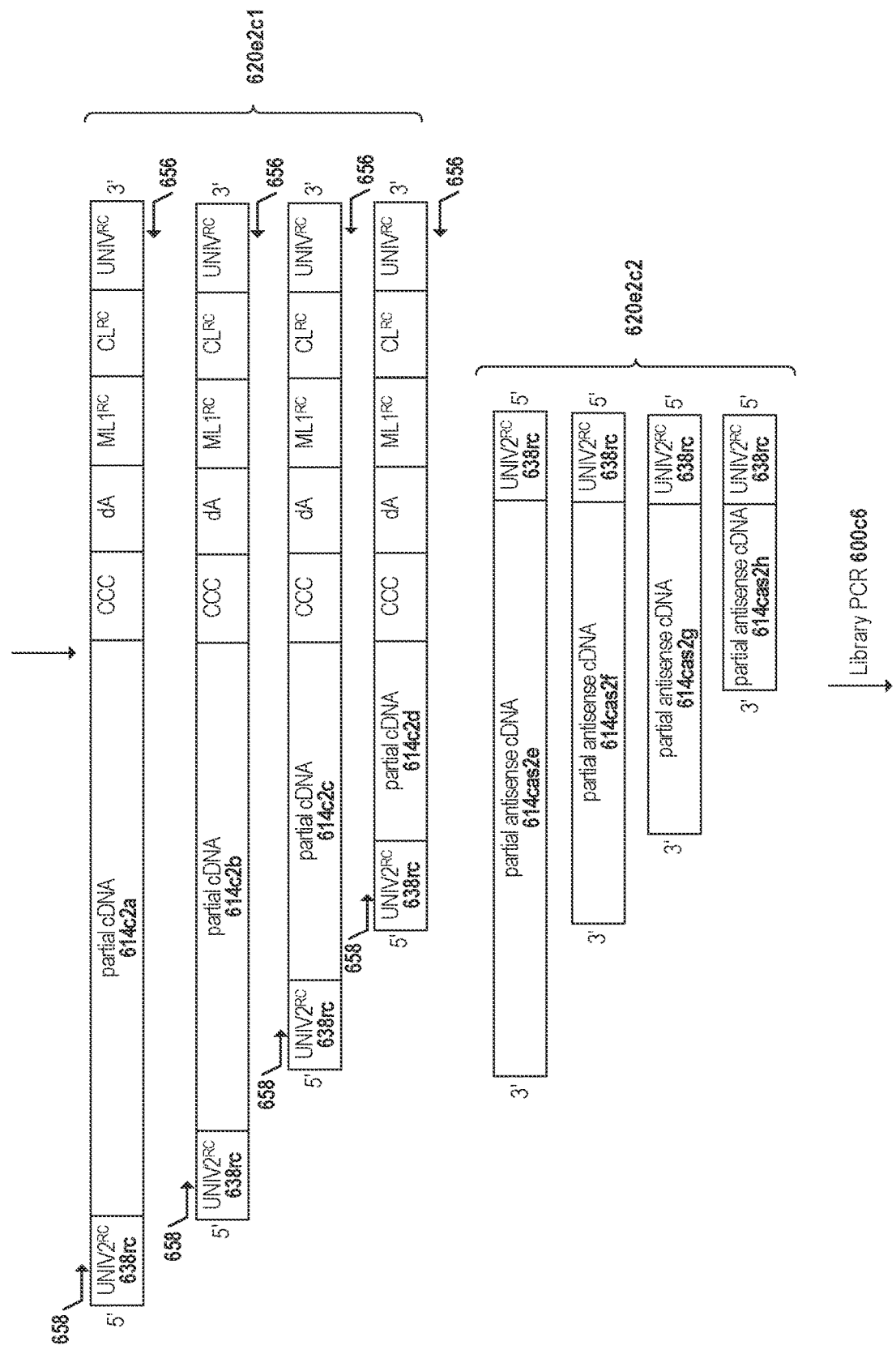
Figure 6E:
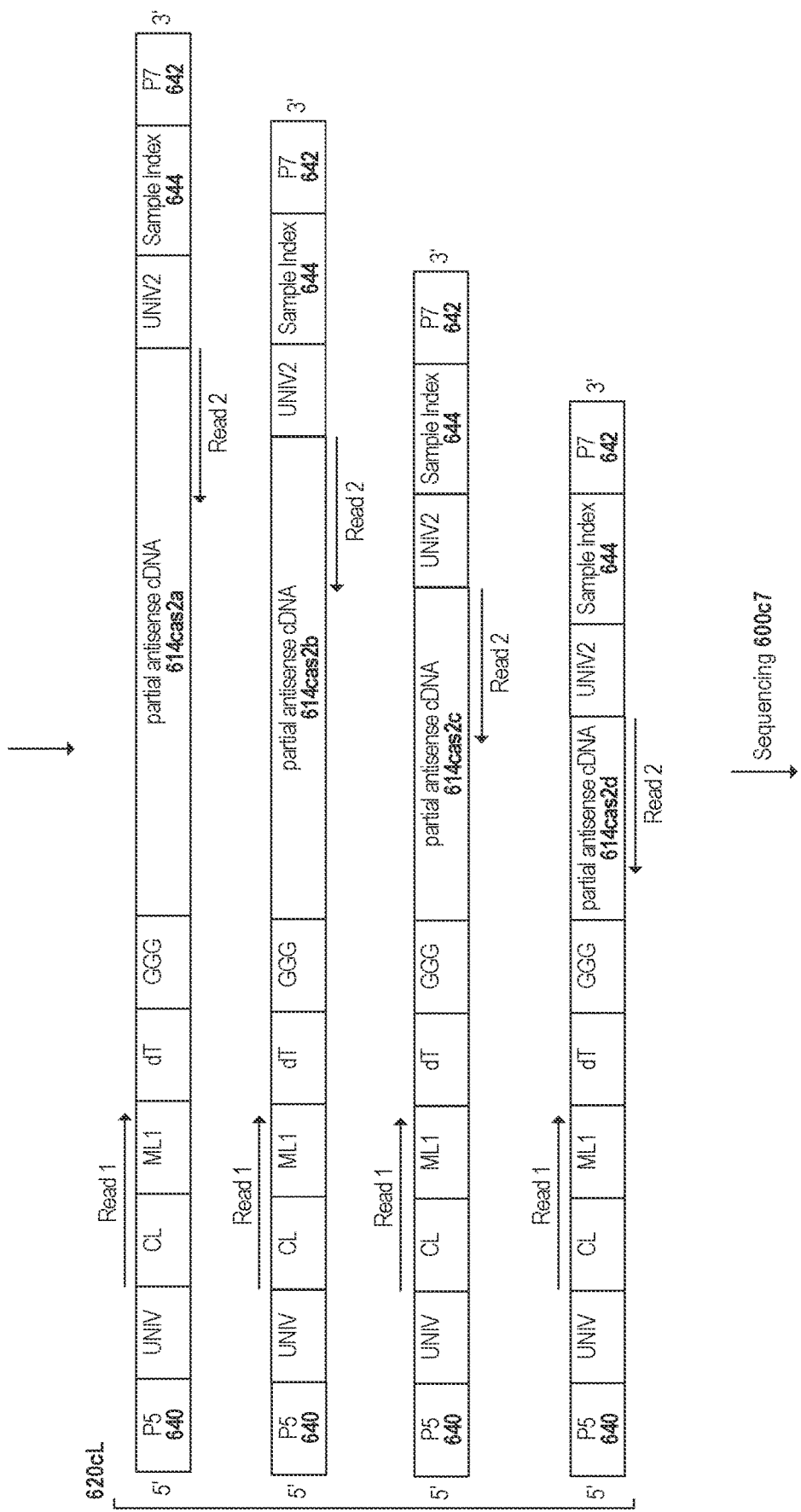
Figure 6F:
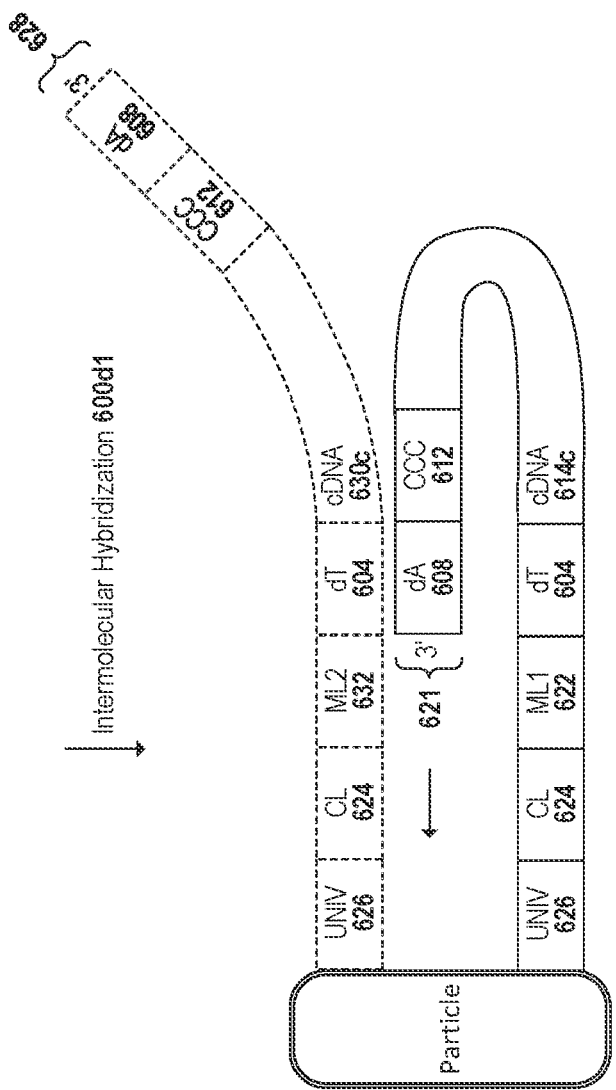
Figure 6G:
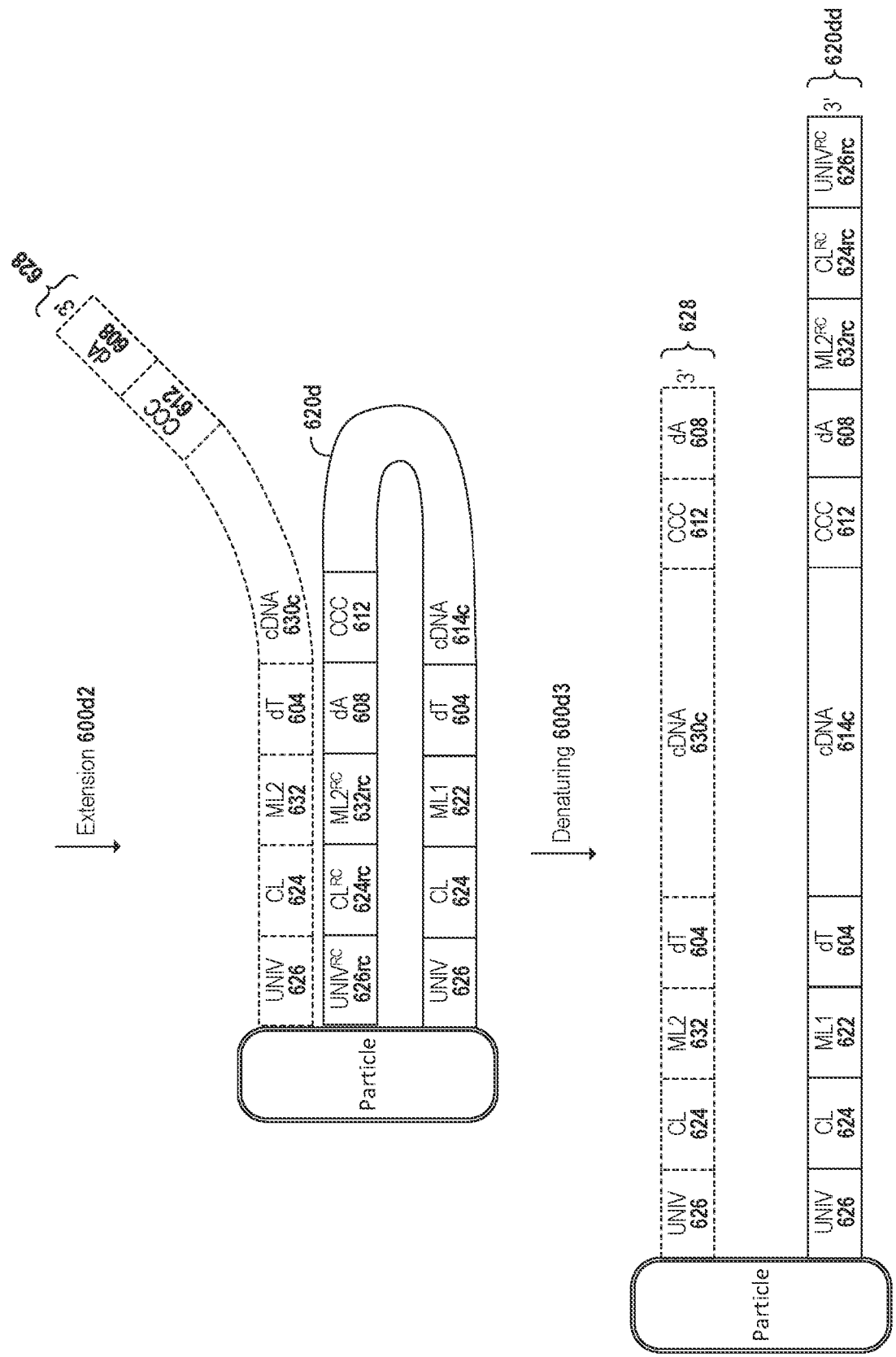
Figure 6H:
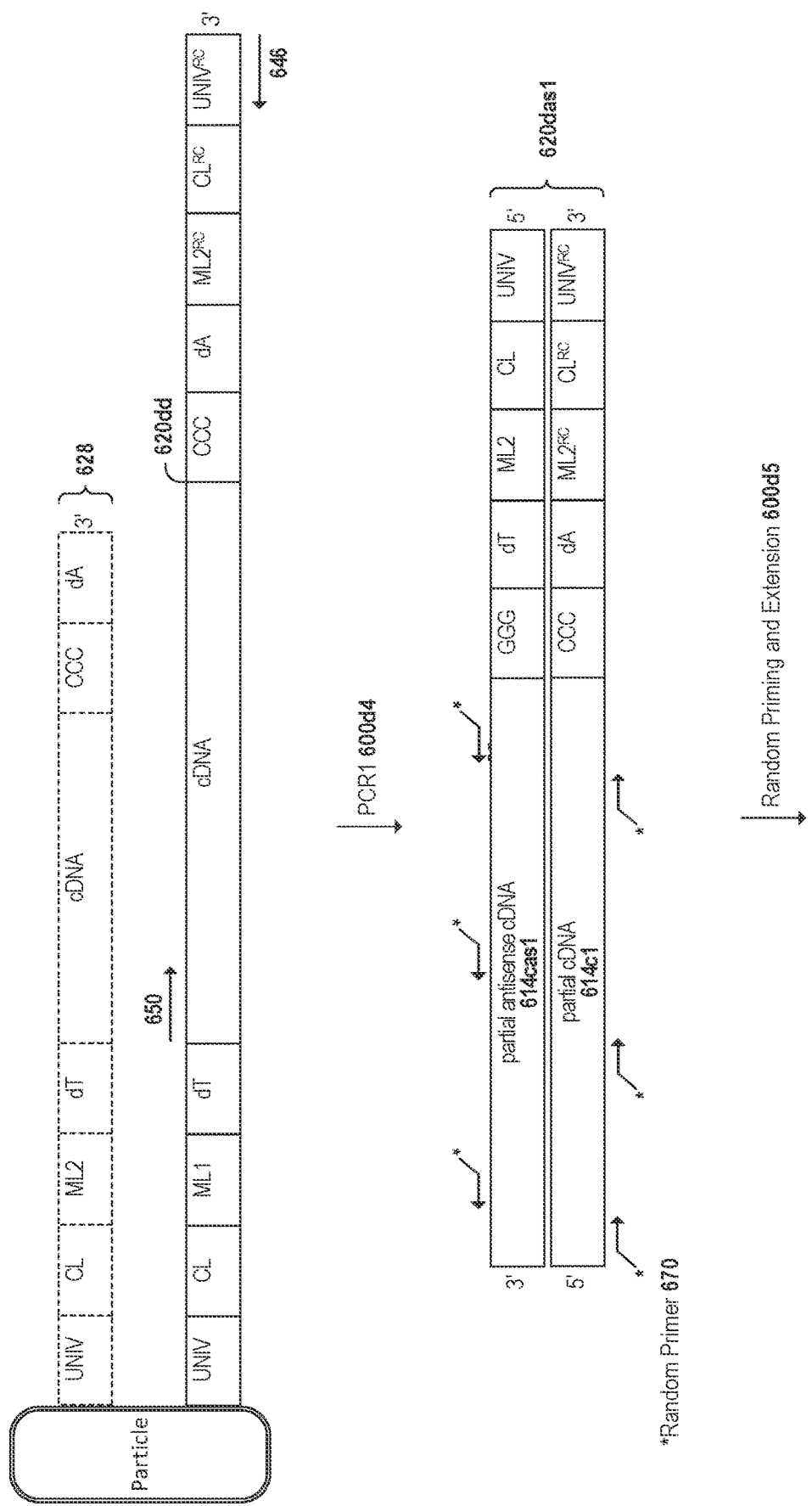
Figure 6I:
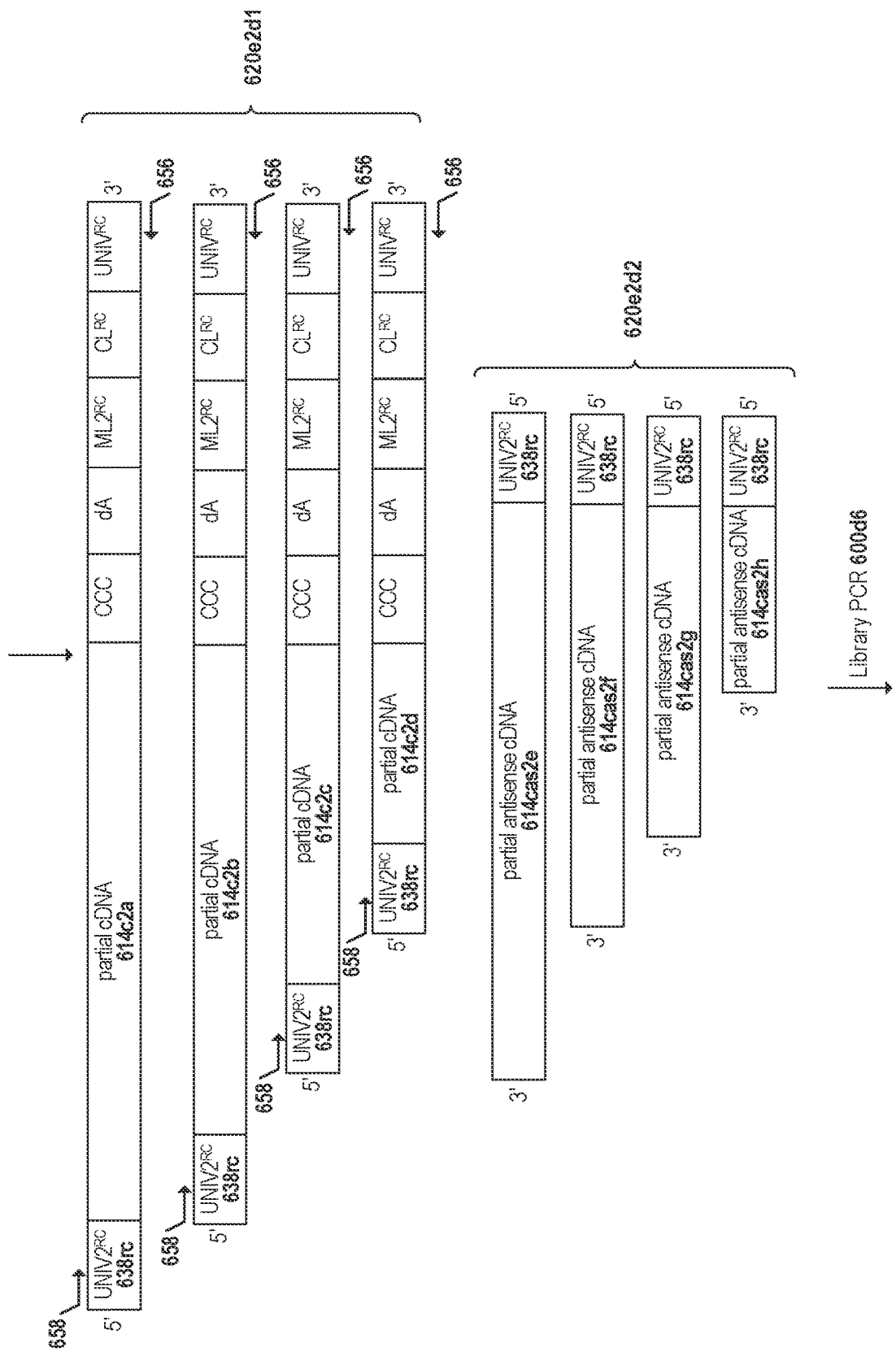
Figure 6J:
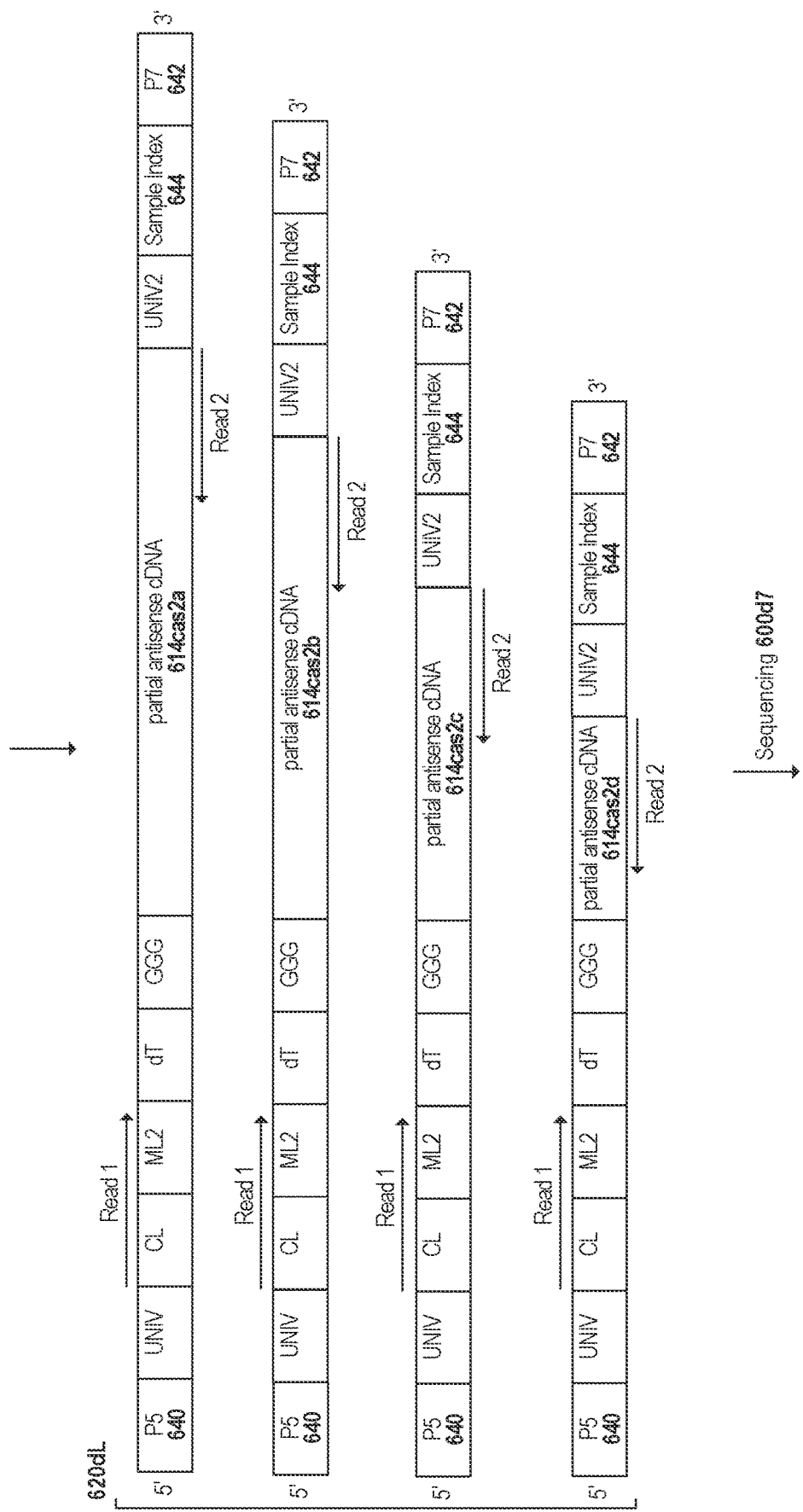
Figure 6K:
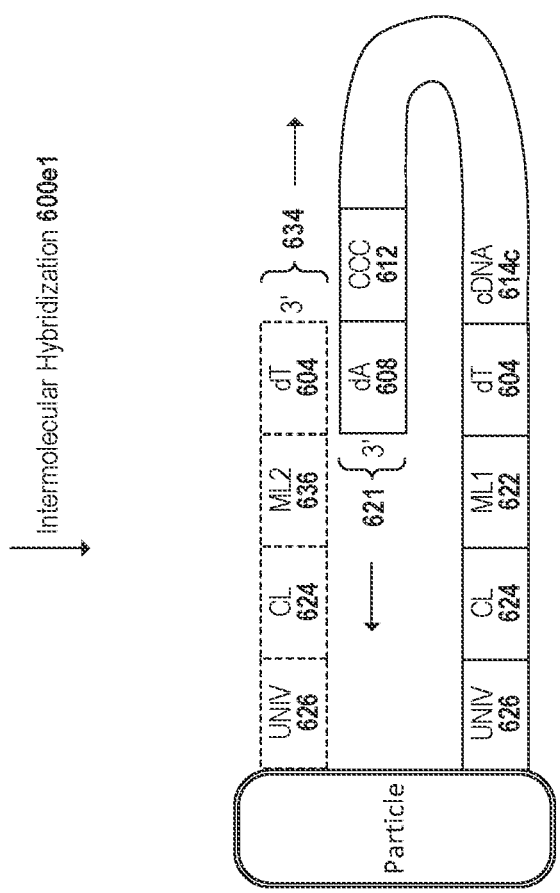
Figure 6L:
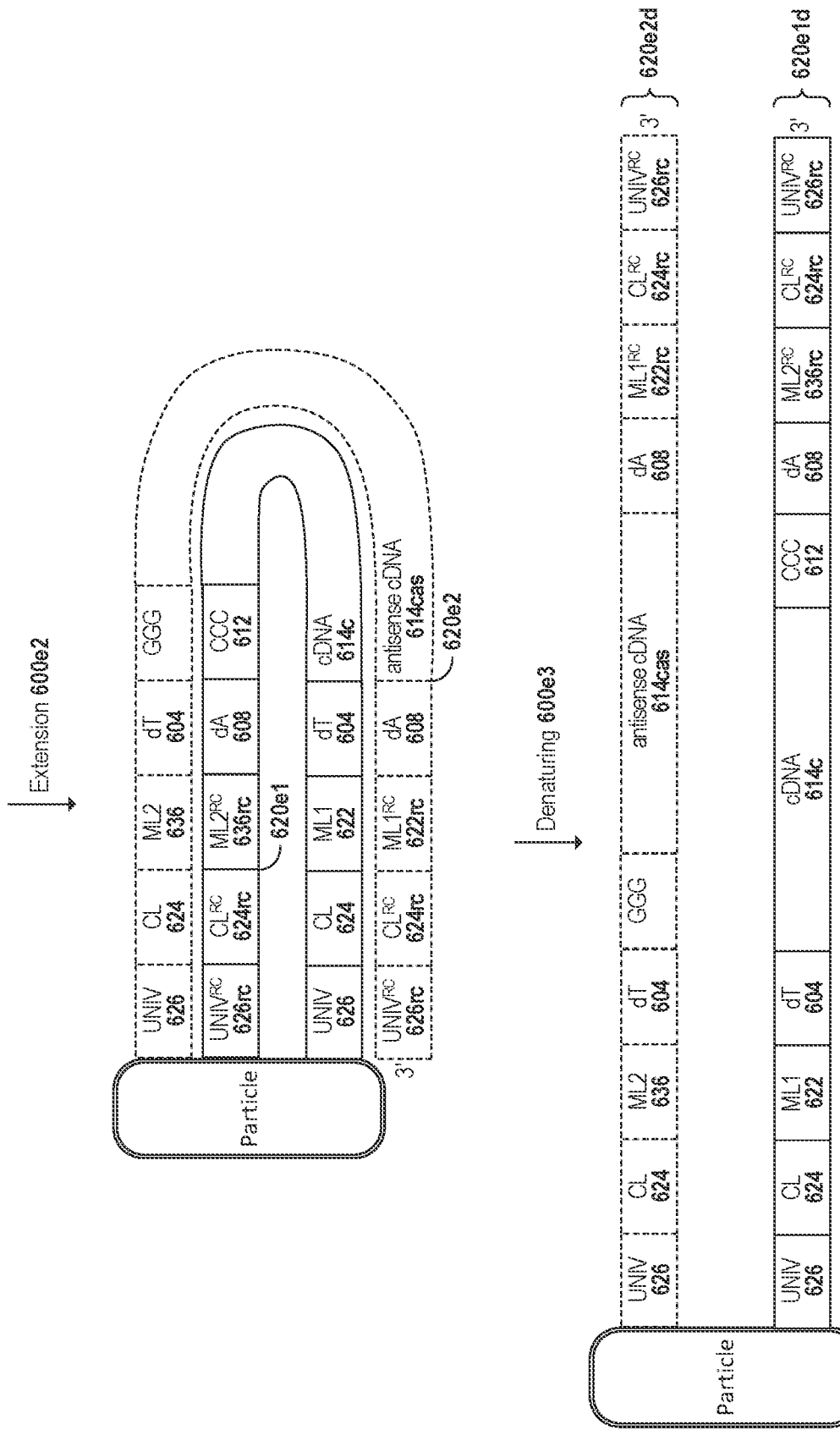
Figure 6M:
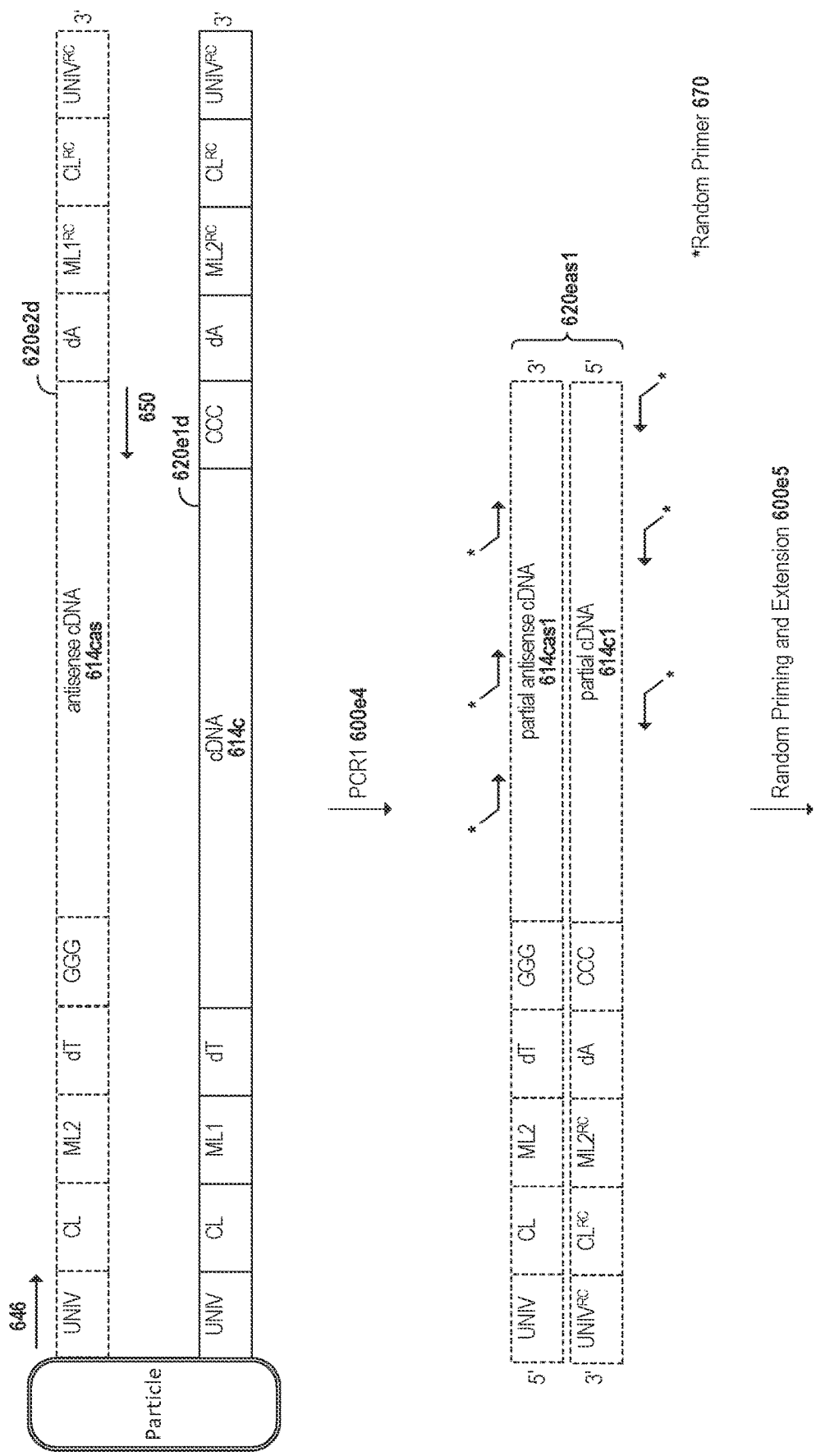
Figure 6N:
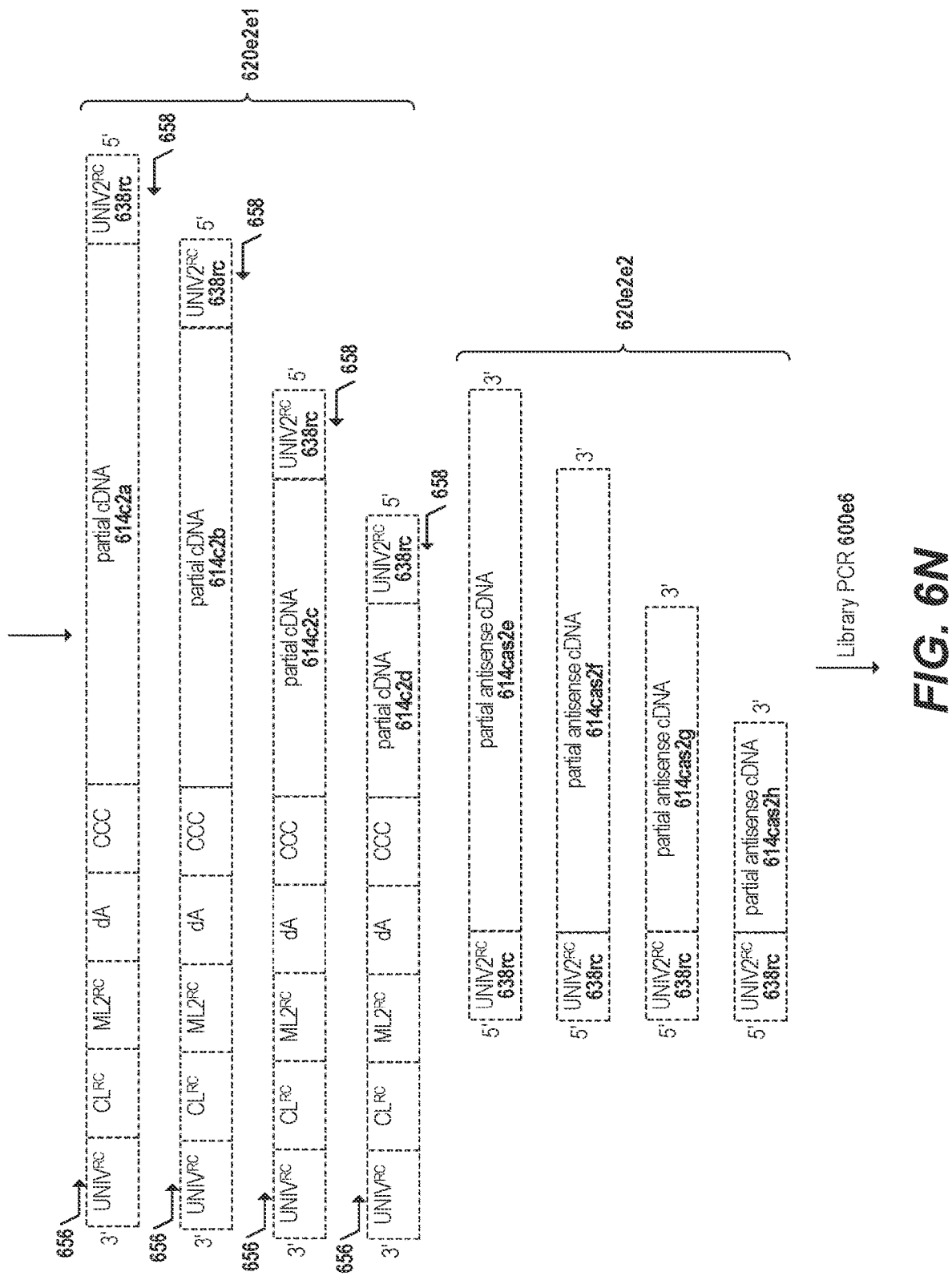
Figure 6O:
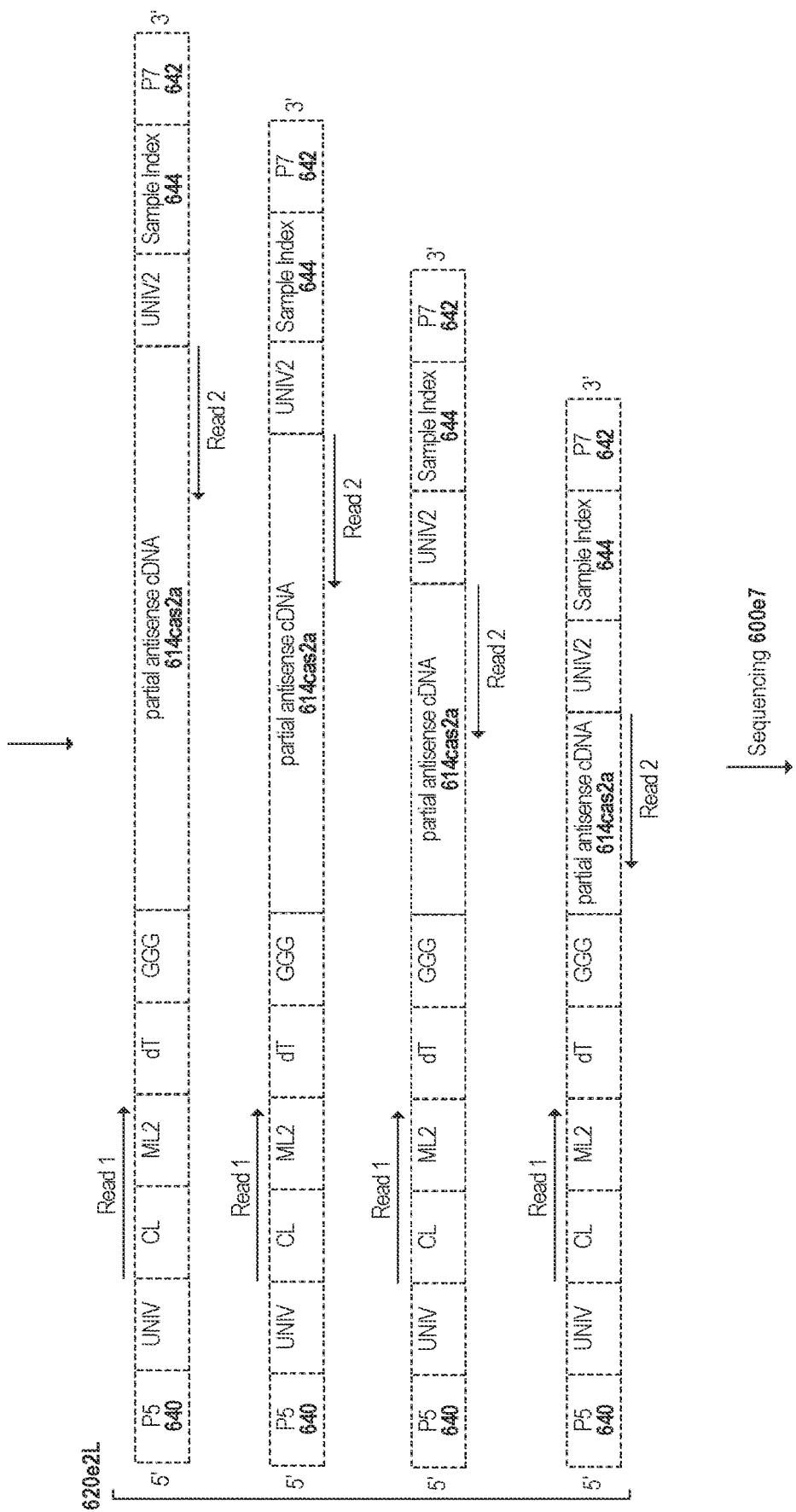

FIGS. 6A-6O show schematic illustrations of non-limiting exemplary workflows of determining the full-length sequences of a nucleic acid target (e.g., the V(D)J region of an immune receptor) using 5' barcoding and/or 3' barcoding. BD® Rhapsody™ beads are solid barcoded beads that maintains integrity through a wide range of physical and chemical manipulations. Following poly(A) capture of mRNA on the beads, reverse transcription and template switching can be performed to add a poly(dA) tail to the 3' end of the barcoded cDNA. The added poly(dA) tail allows the bead-bound cDNA to self-hybridize to oligo(dT) regions of barcodes (e.g., stochastic barcodes) on the same bead, forming a bridge-loop structure. Klenow extension of the bridge-loop can generate a new barcoded cDNA molecule that came from the same mRNA transcript, with the opposite orientation as the first barcoded cDNA, allowing both 3' and 5' ends to the molecular barcode to be linked.

The method disclosed herein can allow 3'-based and/or 5'-based full-length sequence determination. This method can enable provide flexibility to sequence determination. In some embodiments, the method can enable immune repertoire profiling of both T cells and B cells on a Rhapsody™ system, for samples such as mouse and human samples, without changing protocol or product configuration aside from primers used. In some embodiments, 3' and/or 5'-based full-length gene expression profiling of V(D)J can be performed. In some embodiments, both phenotypic markers and V(D)J sequence of T cell and B cells in single cell platforms can be investigated. In some embodiments, both 3' and 5' information of their transcripts can be captured in a single experiment. The methods disclosed herein can allow V(D)J detection of both T cells and B cells (e.g., hypermutation).

The methods and systems described herein can be used with methods and systems using antibodies associated with (e.g., attached to or conjugated with) oligonucleotides (also referred to herein as AbOs or AbOligos). Embodiments of using AbOs to determine protein expression profiles in single cells and tracking sample origins have been described in U.S. patent application Ser. No. 15/715,028, published as U.S. Patent Application Publication No. 2018/0088112, and U.S. patent application Ser. No. 15/937,713; the content of each is incorporated by reference herein in its entirety. In some embodiments, the method disclosed herein allows full-length V(D)J profiling of T cells and B cells, 3' targeted, 5' targeted, 3' whole transcriptome amplification (WTA), 5' WTA, protein expression profiling with AbO, and/or sample multiplexing on a single experiment.

Template-Switching Reactions

FIGS. 6A-6O show schematic illustrations of non-limiting exemplary workflows of determining the full-length sequences of a nucleic acid target (e.g., the V(D)J region of an immune receptor) using 5' barcoding and/or 3' barcoding. A barcode (e.g., a stochastic barcode, an oligonucleotide barcode 602) can comprise a target binding region (e.g., a poly(dT) 604) that can bind to nucleic acid targets (e.g., poly-adenylated RNA transcripts 606) via a poly(dA) tail 608, or other nucleic acid targets, for labeling or barcoding (e.g., unique labeling). The target-binding region can comprise a gene-specific sequence, an oligo(dT) sequence, a random multimer, or any combination thereof. In some embodiments the barcode is associated with a solid support (e.g., a particle 610). A plurality of barcodes 602 can be associated with particle 610. In some embodiments, the particle is a bead. The bead can be a polymeric bead, for example a deformable bead or a gel bead, functionalized with barcodes or stochastic barcodes (such as gel beads from 10× Genomics (San Francisco, Calif.)). In some implementation, a gel bead can comprise a polymer-based gels. Gel beads can be generated, for example, by encapsulating one or more polymeric precursors into droplets. Upon exposure of the polymeric precursors to an accelerator (e.g., tetramethylethylenediamine (TEMED)), a gel bead may be generated.

FIG. 6A depicts a non-limiting exemplary embodiment of reverse transcription reaction 600a. During reverse transcription 600a, upon reaching the end of the oligonucleotide barcode 602, the terminal transferase activity of an enzyme (e.g., a reverse transcriptase, such as a Moloney murine leukemia virus (MMLV)) adds a few additional nucleotides (e.g., deoxycytidine, CCC 612) to the 3' end of the newly synthesized cDNA sequence strand 614c (the antisense sequence of RNA sequence 614r). These CCC bases 612 can function as an anchoring site of the template switch oligonucleotide (e.g., template switching oligonucleotide) 616, which comprises a sequence complementary to the tailed sequence (e.g., rGrGrG 618). The template switch oligonucleotide 616 can comprise at least part of the target binding region 604. Upon base pairing between the rGrGrG 618 and the appended deoxycytidine stretch 612, the enzyme "switches" template strands, from oligonucleotide barcode 602 to the template switch oligonucleotide 616, and continues replication to the 5' end of the template switch oligonucleotide 616. Thus, the resulting first strand labelled cDNA (e.g., barcoded nucleic acid molecule 620) contains a reverse complement sequence of the template switch oligonucleotide 616 and thus can comprise the complement (e.g., reverse complement) of the target binding region (e.g., poly(dA) 608). The barcoded nucleic acid molecule 620 can comprise cDNA 614c (the reverse complementary sequence of RNA sequence 614r). The reaction can be performed in the presence of one or more additives configured to reduce secondary structure (e.g., ethylene glycol). The barcoded nucleic acid molecule 620 can also comprise a number of labels. The oligonucleotide barcode 602 can include first molecular label (ML1) 622 and a sample label (e.g, partition label, cell label (CL) 624) for labeling the transcripts 606 and tracking sample origins of the RNA transcripts 606 (or nucleic acid targets, such as for example, antibody oligonucleotides, whether associated with antibodies or have dissociated from antibodies), respectively, along with one or more additional sequences flanking the first molecular label 622/cell label 624 region of each barcode 602 for subsequent reactions, such as, for example, a first universal sequence 626 (e.g., Read 1 sequence). The repertoire of sequences of the molecular labels in the oligonucleotide barcodes per sample can be sufficiently large for stochastic labeling of RNA transcripts. In some embodiments, the sample label is a partition label. In some embodiments, the sample label is a cell label. The barcoded nucleic acid molecule 620 can undergo a denaturing step 600b (e.g., denaturing), thereby generating single-stranded barcoded nucleic acid molecule 621.

In some embodiments, the first molecular label is hybridized to the second molecular label after extending the 3'-ends of the plurality of barcoded nucleic acid molecules. In some embodiments, the extended barcoded nucleic acid molecules each comprise the first molecular label, the second molecular label, the target-binding region, and the complement of the target-binding region. In some embodiments, the complement of the target-binding region is complementary to a portion of the target-binding region. In some embodiments, the target-binding region comprises a gene-specific sequence. In some embodiments, the target-binding region comprises a poly(dT) sequence.

The term "template switching" can refer to the ability of a reverse transcriptase to switch from an initial nucleic acid sequence template to the 3' end of a new nucleic acid sequence template having little or no complementarity to the 3' end of the nucleic acid synthesized from the initial template. An example of template switching is the ability of a reverse transcriptase to switch from an initial nucleic acid sequence template/primer substrate to the 3' end of a new nucleic acid sequence template having little or no complementary to the 3' end of the nucleic acid primer strand. Template switching allows, e.g., a DNA copy to be prepared using a reverse transcriptase that switches from an initial nucleic acid sequence template to the 3' end of a new nucleic acid sequence template having little or no complementarity to the 3' end of the DNA synthesized from the initial template, thereby allowing the synthesis of a continuous product DNA that directly links an adaptor sequence to a target oligonucleotide sequence without ligation. Template switching can comprise ligation of adaptor, homopolymer tailing (e.g., polyadenylation), random primer, or an oligonucleotide that the polymerase can associate with. In any of the above-mentioned embodiments, template switching may be used to introduce a target-binding region or the complement thereof.

In some embodiments, the reverse transcriptase is capable of terminal transferase activity. In some embodiments, the template switch oligonucleotide comprises one or more 3' ribonucleotides. In some embodiments, the template switch oligonucleotide comprises three 3' ribonucleotides. The 3' ribonucleotides can comprise guanine. In some embodiments, the reverse transcriptase comprises a viral reverse transcriptase. In some embodiments, the viral reverse transcriptase is a murine leukemia virus (MLV) reverse transcriptase or a Moloney murine leukemia virus (MMLV) reverse transcriptase.

The complement of a target-binding region can comprise the reverse complementary sequence of the target-binding region or can comprise the complementary sequence of the target-binding region. The complement of a molecular label can comprise a reverse complementary sequence of the molecular label or can comprise a complementary sequence of the molecular label. In some embodiments, the plurality of barcoded nucleic acid molecules can comprise barcoded deoxyribonucleic acid (DNA) molecules and/or barcoded ribonucleic acid (RNA) molecules. In some embodiments, the nucleic acid target comprises a nucleic acid molecule (e.g., ribonucleic acid (RNA), messenger RNA (mRNA), microRNA, small interfering RNA (siRNA), RNA degradation product, RNA comprising a poly(A) tail, or any combination thereof). In some embodiments, the mRNA encodes an immune receptor. The nucleic acid target can comprise a cellular component binding reagent. In some embodiments, the nucleic acid molecule is associated with the cellular component binding reagent. The method can comprise dissociating the nucleic acid molecule and the cellular component binding reagent. In some embodiments, at least 10 of the plurality of oligonucleotide barcodes comprise different molecular label sequences. Each molecular label of the plurality of oligonucleotide barcodes can comprise at least 6 nucleotides.

In some embodiments, the plurality of oligonucleotide barcodes are associated with a solid support. The plurality of oligonucleotide barcodes associated with the same solid support can each comprise an identical sample label. Each sample label of the plurality of oligonucleotide barcodes can comprise at least 6 nucleotides. The plurality of oligonucleotide barcodes can each comprise a cell label. Each cell label of the plurality of oligonucleotide barcodes can comprise at least 6 nucleotides. Oligonucleotide barcodes associated with the same solid support can comprise the same cell label. Oligonucleotide barcodes associated with different solid supports can comprise different cell labels. The plurality of extended barcoded nucleic acid molecules can each comprise a cell label and a complement of the cell label. The complement of the cell label can comprise a reverse complementary sequence of the cell label or a complementary sequence of the cell label. The method can comprise extending the plurality of oligonucleotide barcodes hybridized to the copies of the nucleic acid target in the presence of one or more of ethylene glycol, polyethylene glycol, 1,2-propanediol, dimethyl sulfoxide (DMSO), glycerol, formamide, 7-deaza-GTP, acetamide, tetramethylammonium chloride salt, betaine, or any combination thereof. In some embodiments, the solid support can comprise a synthetic particle. In some embodiments, the solid support can comprise a planar surface.

The sample can comprise a single cell, and the method can comprise associating a synthetic particle comprising the plurality of the oligonucleotide barcodes with the single cell in the sample. The method can comprise lysing the single cell after associating the synthetic particle with the single cell. Lysing the single cell can comprise heating the sample, contacting the sample with a detergent, changing the pH of the sample, or any combination thereof. In some embodiments, the synthetic particle and the single cell are in the same well. In some embodiments, the synthetic particle and the single cell are in the same droplet. In some embodiments, at least one of the plurality of oligonucleotide barcodes is immobilized on the synthetic particle. In some embodiments, at least one of the plurality of oligonucleotide barcodes is partially immobilized on the synthetic particle. At least one of the plurality of oligonucleotide barcodes can be enclosed in the synthetic particle. In some embodiments, at least one of the plurality of oligonucleotide barcodes is partially enclosed in the synthetic particle. In some embodiments, the synthetic particle is disruptable. The synthetic particle can comprise a bead. The bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The synthetic particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. In some embodiments, the synthetic particle can comprise a disruptable hydrogel particle. Each of the plurality of oligonucleotide barcodes can comprise a linker functional group, the synthetic particle can comprise a solid support functional group, and/or the support functional group and the linker functional group can be associated with each other. In some embodiments, the linker functional group and the support functional group are individually selected from the group consisting of C6, biotin, streptavidin, primary amine(s), aldehyde(s), ketone(s), and any combination thereof.

Intramolecular Hybridization of Barcoded Nucleic Acid Molecules

In some embodiments, hybridizing the complement of the target-binding region of a barcoded nucleic acid molecule with the target-binding region of the barcoded nucleic acid molecule itself comprises intramolecular hybridization of the target-binding region and the complement of the target-binding region within a barcoded nucleic acid molecule to form a stem loop. In some embodiments, the second molecular label is the complement of the first molecular label.

The workflow can comprise intramolecular hybridization of a single-stranded barcoded nucleic acid molecule 621 as depicted in the non-limiting exemplary FIG. 6B schematic illustrations. The workflow can comprise intramolecular hybridization 600c1 of the target-binding region 604 and the complement of the target-binding region 608 within a single-stranded barcoded nucleic acid molecule 621 to form a stem loop. The workflow can comprise extending 600c2 the 3'-end of the stem loop of single-stranded barcoded nucleic acid molecule 621 to generate extended barcoded nucleic acid molecule 620c. The extended barcoded nucleic acid molecule 620c can comprise a complement (e.g., reverse complement) of the first molecular label 622rc, a complement (e.g., reverse complement) of the cell label 624rc, and/or a complement (e.g., reverse complement) of the first universal sequence 626rc. The workflow can comprise denaturing 600c3 the extended barcoded nucleic acid molecule 620c to generate a single-stranded extended barcoded nucleic acid molecule 620cd. In some embodiments, intermolecular hybridization 600c1 and/or extending 600c2 is performed in the presence of a high salt buffer and/or PEG. In some embodiments, extension is performed using a DNA polymerase lacking at least one of 5' to 3' exonuclease activity and 3' to 5' exonuclease activity (e.g., a Klenow Fragment).

Single-stranded extended barcoded nucleic acid molecule 620cd can comprise a barcode (e.g., a cell label and a molecular label) on both the 5' end and 3' end of a target nucleic acid molecule (e.g., transcript), thereby enabling more extensive analysis of the target nucleic acid molecule as compared to an analysis of a target nucleic acid molecule with only one barcode on one end with regards to sequence identification, transcript counting, alternative splicing analysis, mutation screening, and/or full-length sequencing. Single-stranded extended barcoded nucleic acid molecule 620cd can serve as a template for one or more extension reactions (e.g., random priming and extension) and/or amplification reactions (e.g., PCR), such as, for example, the non-limiting exemplary scheme depicted in FIGS. 6C-6E. The amplification(s) can comprise target-specific (e.g., gene-specific) cDNA amplification. For example, single-stranded extended barcoded nucleic acid molecule 620cd can undergo a first round of amplification ("PCR1") 600c4 employing a universal oligonucleotide primer 646 comprising a sequence of the first universal sequence (or a complement thereof) and a target-specific primer (e.g., target-specific primer 650), thereby producing a first plurality of amplicons 620cas1 each comprising a molecular label (e.g., a first molecular label), a cell label, a first universal sequence and partial antisense cDNA 614cas1 (the length of which depends on the binding site of target-specific primer 650 within the cDNA 614c). PCR1 600c4 can comprise 1-30 cycles (e.g., 15 cycles).

The workflow can comprise a random priming and extension 600c5. Random primers 670 can be hybridized the first plurality of barcoded amplicons 620cas1 and the random primers 670 can be extended to generate a plurality of extension products 620e2c1 and 620e2c2. Random primers 670 can include overhangs, which can include, or be, for example, a second universal sequence 638 (or a complement thereof, e.g., reverse complement 638rc) (e.g., Read 2 sequence, a universal PCR handle). Extension products 620*e*2*c*1 can comprise a first universal sequence, a second universal sequence, a cell label, and a molecule label (e.g., a first molecular label), or complements thereof. Extension products 620*e*2*c*1 can comprise, for example, partial cDNA 614*c*2*a*, 614*c*2*b*, 614*c*2*c*, and 614*c*2*d* (the length of each of which depends on the binding site of random primer 670 within the partial cDNA). Extension products 620*e*2*c*2 can comprise a second universal sequence (or a complement thereof). Extension products 620*e*2*c*2 can comprise, for example, partial antisense cDNA 614*cas*2*e*, 614*cas*2*f*, 614*cas*2*g*, and 614*cas*2*h* (the length of each of which depends on the binding site of random primer 670 within the partial cDNA).

The workflow can comprise library amplification ("Library PCR") 600*c*6. Library PCR 600*c*6 can comprise library amplification of extension products 620*e*2*c*1 with sequencing library amplification primers 656 and 658. Sequencing library amplification primers 656 can 658 can anneal to first universal sequence 626 and second universal sequence 638 (or complements thereof), respectively. Library PCR 600*c*6 can add sequencing adapters (e.g., P5 640 and P7 642) and sample index 644 (e.g., i5, i7) via overhangs in sequencing library amplification primers 656 and 658. Library PCR amplicons 620*c*L (e.g., second plurality of barcoded amplicons) can comprise a range of cDNA lengths (e.g., partial antisense cDNA 614*cas*2*a*, 614*cas*2*b*, 614*cas*2*c*, 614*cas*2*d*) that can collectively encompass some or all of the mRNA sequence of the nucleic acid target. Library amplicons 620*c*L can be sequenced and subjected to downstream methods of the disclosure. Sequencing 600*c*7 using 150 bp×2 sequencing can reveal the cell label, unique molecular label and/or gene (or a partial sequence of the gene) on read 1, the gene (or a partial sequence of the gene) on read 2, and the sample index on index 1 read and/or index 2 read. Library PCR 600*c*6 can comprise 1-30 cycles (e.g., 15 cycles). The method can comprise the bioinformatic reconstruction 900 of the full-length sequence of the nucleic acid target (e.g., immune receptor mRNA 930) by aligning the plurality of Read 1 910 and Read 2 920 reads as depicted in FIG. 9B.

In some embodiments, 3' and/or 5'-based full-length expression profiling of the V(D)J region of an immune receptor can be performed. In some embodiments, both phenotypic markers and immune receptor V(D)J sequence(s) of T cells and/or B cells in single cell platforms can be investigated. The method disclosed herein can allow V(D)J detection of both T cells and B cells (e.g., hypermutation). In some embodiments, both the 3' and 5' regions of extended barcoded nucleic acid molecule 620*cd* are amplified. In some embodiments, only the 5' region of extended barcoded nucleic acid molecule 620*cd* is amplified. In some embodiments, only the 3' region of extended barcoded nucleic acid molecule 620*cd* is amplified. In some embodiments one or more of the amplification reactions comprises multiplex PCR. For example, both the 3' and 5' regions of extended barcoded nucleic acid molecule 620*cd* can be amplified simultaneously (e.g., multiplex PCR). In some embodiments the workflow comprises multiplex PCR employing a panel of target-specific PCR1 primers. In some embodiments, the targets comprise BCRs, TCRs, and/or immune-related transcripts.

Intermolecular Hybridization of Barcoded Nucleic Acid Molecules with Barcoded Nucleic Acid Molecules In some embodiments, hybridizing the complement of the target-binding region of a barcoded nucleic acid molecule with the target-binding region of a different barcoded nucleic acid molecule of the plurality of barcoded nucleic acid molecules comprises intermolecular hybridization of the complement of the target-binding region of a barcoded nucleic acid molecule with the target-binding region of a different barcoded nucleic acid molecule of the plurality of barcoded nucleic acid molecules. In some embodiments, the sequence of the second molecular label is different from the sequence of the first molecular label, and wherein the second molecular label is not a complement of the first molecular label.

The workflow can comprise intermolecular hybridization of single-stranded barcoded nucleic acid molecule 621 with a distinct barcoded nucleic acid molecule 628 as depicted in the non-limiting exemplary FIGS. 6F-6G schematic illustrations. Distinct barcoded nucleic acid molecule 628 can comprise cDNA 630*c*, second molecular label 632, cell label 624, and first universal sequence 626. The sequence of second molecular label 632 of barcoded nucleic acid molecule 628 can be different from the sequence of the first molecular label 622 of single-stranded barcoded nucleic acid molecule 621 (e.g., not a complement). The target-binding region 604, cell label 624 and/or first universal sequence 626 of barcoded nucleic acid molecule 628 can be the same as (or a complement thereof) the target-binding region 604, cell label 624 and/or first universal sequence 626 of single-stranded barcoded nucleic acid molecule 621. The workflow can comprise, in some embodiments, intermolecular hybridization 600*d*1 of the complement of the target-binding region 608 of single-stranded barcoded nucleic acid molecule 621 with the target-binding region 604 of barcoded nucleic acid molecule 628. The workflow can comprise extending 600*d*2 the 3'-end of single-stranded barcoded nucleic acid molecule 621 to generate extended barcoded nucleic acid molecule 620*d*. The extended barcoded nucleic acid molecule 620*d* can comprise a complement (e.g., reverse complement) of the second molecular label 632*rc*, a complement (e.g., reverse complement) of the cell label 624*rc*, and/or a complement (e.g., reverse complement) of the first universal sequence 626*rc*. The workflow can comprise denaturing 600*d*3 the extended barcoded nucleic acid molecule 620*d* to generate a single-stranded extended barcoded nucleic acid molecule 620*dd*. In some embodiments, intermolecular hybridization 600*d*1 and/or extending 600*d*2 is performed in the presence of a high salt buffer and/or PEG. In some embodiments, extension is performed using a DNA polymerase lacking at least one of 5' to 3' exonuclease activity and 3' to 5' exonuclease activity (e.g., a Klenow Fragment).

Single-stranded extended barcoded nucleic acid molecule 620*dd* can comprise a barcode (e.g., a cell label and a molecular label) on both the 5' end and 3' end of a target nucleic acid molecule (e.g., transcript), thereby enabling more extensive analysis of the target nucleic acid molecule as compared to an analysis of a target nucleic acid molecule with only one barcode on one end with regards to sequence identification, transcript counting, alternative splicing analysis, mutation screening, and/or full-length sequencing. Single-stranded extended barcoded nucleic acid molecule 620*dd* can serve as a template for one or more extension reactions (e.g., random priming and extension) and/or amplification reactions (e.g., PCR), such as, for example, the non-limiting exemplary scheme depicted in FIGS. 6H-6J. The amplification(s) can comprise target-specific (e.g., gene-specific) cDNA amplification. For example, single-stranded extended barcoded nucleic acid molecule 620*dd* can undergo a first round of amplification ("PCR1") 600*d*4 employing a universal oligonucleotide primer 646 comprising a sequence of the first universal sequence (or a complement thereof) and a target-specific primer (e.g., target-specific primer 650), thereby producing a first plurality of amplicons 620das1 each comprising a molecular label (e.g., a second molecular label), a cell label, a first universal sequence and partial antisense cDNA 614cas1 (the length of which depends on the binding site of target-specific primer 650 within the cDNA 614c). PCR1 600d4 can comprise 1-30 cycles (e.g., 15 cycles).

The workflow can comprise a random priming and extension 600d5. Random primers 670 can be hybridized the first plurality of barcoded amplicons 620das1 and the random primers 670 can be extended to generate a plurality of extension products 620e2d1 and 620e2d2. Random primers 670 can include overhangs, which can include, or be, for example, a second universal sequence 638 (or a complement thereof, e.g., reverse complement 638rc) (e.g., Read 2 sequence, a universal PCR handle). Extension products 620e2d1 can comprise a first universal sequence, a second universal sequence, a cell label, and a molecule label (e.g., a first molecular label), or complements thereof. Extension products 620e2d1 can comprise, for example, partial cDNA 614c2a, 614c2b, 614c2c, and 614c2d (the length of each of which depends on the binding site of random primer 670 within the partial cDNA). Extension products 620e2d2 can comprise a second universal sequence (or a complement thereof). Extension products 620e2d2 can comprise, for example, partial antisense cDNA 614cas2e, 614cas2f, 614cas2g, and 614cas2h (the length of each of which depends on the binding site of random primer 670 within the partial cDNA).

The workflow can comprise library amplification ("Library PCR") 600d6. Library PCR 600d6 can comprise library amplification of extension products 620e2d1 with sequencing library amplification primers 656 and 658. Sequencing library amplification primers 656 can 658 can anneal to first universal sequence 626 and second universal sequence 638 (or complements thereof), respectively. Library PCR 600d6 can add sequencing adapters (e.g., P5 640 and P7 642) and sample index 644 (e.g., i5, i7) via overhangs in sequencing library amplification primers 656 and 658. Library PCR amplicons 620dL (e.g., second plurality of barcoded amplicons) can comprise a range of cDNA lengths (e.g., partial antisense cDNA 614cas2a, 614cas2b, 614cas2c, 614cas2d) that can collectively encompass some or all of the mRNA sequence of the nucleic acid target. Library amplicons 620dL can be sequenced and subjected to downstream methods of the disclosure. Sequencing 600d7 using 150 bp×2 sequencing can reveal the cell label, unique molecular label and/or gene (or a partial sequence of the gene) on read 1, the gene (or a partial sequence of the gene) on read 2, and the sample index on index 1 read and/or index 2 read. Library PCR 600d6 can comprise 1-30 cycles (e.g., 15 cycles). The method can comprise the bioinformatic reconstruction 900 of the full-length sequence of the nucleic acid target (e.g., immune receptor mRNA 930) by aligning the plurality of Read 1 910 and Read 2 920 reads as depicted in FIG. 9B.

In some embodiments, 3' and/or 5'-based full-length expression profiling of the V(D)J region of an immune receptor can be performed. In some embodiments, both phenotypic markers and immune receptor V(D)J sequence(s) of T cells and/or B cells in single cell platforms can be investigated. The method disclosed herein can allow V(D)J detection of both T cells and B cells (e.g., hypermutation). In some embodiments, both the 3' and 5' regions of extended barcoded nucleic acid molecule 620dd are amplified. In some embodiments, only the 5' region of extended barcoded nucleic acid molecule 620dd is amplified. In some embodiments, only the 3' region of extended barcoded nucleic acid molecule 620dd is amplified. In some embodiments one or more of the amplification reactions comprises multiplex PCR. For example, both the 3' and 5' regions of extended barcoded nucleic acid molecule 620dd can be amplified simultaneously (e.g., multiplex PCR). In some embodiments the workflow comprises multiplex PCR employing a panel of target-specific PCR1 primers. In some embodiments, the targets comprise BCRs, TCRs, and/or immune-related transcripts.

Intermolecular Hybridization of Barcoded Nucleic Acid Molecules with Oligonucleotide Barcodes In some embodiments, hybridizing the complement of the target-binding region of a barcoded nucleic acid molecule with the target-binding region of an oligonucleotide barcode of the plurality of oligonucleotide barcodes comprises intermolecular hybridization of the complement of the target-binding region of a barcoded nucleic acid molecule with the target-binding region of an oligonucleotide barcode of the plurality of oligonucleotide barcodes. In some embodiments, the second molecular label is a different from the first molecular label, and wherein the second molecular label is not a complement of the first molecular label. In some embodiments, the method comprises extending the 3' ends of the oligonucleotide barcodes hybridized to the complement of the target-binding region of the barcoded nucleic acid molecule to generate a plurality of extended barcoded nucleic acid molecules each comprising a complement of the first molecular label and a second molecular label. In some embodiments, the sequence of the second molecular label is different from the sequence of the first molecular label, wherein the wherein the second molecular label is not a complement of the first molecular label.

The workflow can comprise intermolecular hybridization of single-stranded barcoded nucleic acid molecule 621 with distinct oligonucleotide barcode 634 as depicted in the non-limiting exemplary FIGS. 6K-6L schematic illustrations. Distinct oligonucleotide barcode 634 can comprise second molecular label 636, cell label 624, and first universal sequence 626. The sequence of second molecular label 636 of oligonucleotide barcode 634 can be different from the sequence of the first molecular label 622 of single-stranded barcoded nucleic acid molecule 621 (e.g., not a complement). The target-binding region 604, cell label 624 and/or first universal sequence 626 of oligonucleotide barcode 634 can be the same as (or a complement thereof) the target-binding region 604, cell label 624 and/or first universal sequence 626 of single-stranded barcoded nucleic acid molecule 621. The workflow can comprise, in some embodiments, intermolecular hybridization 600e1 of the complement of the target-binding region 608 of single-stranded barcoded nucleic acid molecule 621 with the target-binding region 604 of oligonucleotide barcode 634. The workflow can comprise extending 600e2 the 3'-end of single-stranded barcoded nucleic acid molecule 621 to generate extended barcoded nucleic acid molecule 620e1. The extended barcoded nucleic acid molecule 620e1 can comprise a complement (e.g., reverse complement) of the second molecular label 636rc, a complement (e.g., reverse complement) of the cell label 624rc, a complement (e.g., reverse complement) of the first universal sequence 626rc, and/or cDNA 614c. The workflow can comprise denaturing 600e3 the extended barcoded nucleic acid molecule 620e1 to generate a single-stranded extended barcoded nucleic acid molecule 620e1d. The workflow can comprise extending 600e2 the 3'-end of oligonucleotide barcode 634 to generate extended barcoded nucleic acid molecule 620e2. The extended barcoded nucleic acid molecule 620e2 can comprise a complement (e.g., reverse complement) of the first molecular label 622rc, a complement (e.g., reverse complement) of the cell label 624rc, a complement (e.g., reverse complement) of the first universal sequence 626rc, and/or antisense cDNA 614cas. The workflow can comprise denaturing 600e3 the extended barcoded nucleic acid molecule 620e2 to generate a single-stranded extended barcoded nucleic acid molecule 620e2d. In some embodiments, intermolecular hybridization 600e1 and/or extending 600e2 is performed in the presence of a high salt buffer and/or PEG. In some embodiments, extension is performed using a DNA polymerase lacking at least one of 5' to 3' exonuclease activity and 3' to 5' exonuclease activity (e.g., a Klenow Fragment).

Single-stranded extended barcoded nucleic acid molecule 620e1d and single-stranded extended barcoded nucleic acid molecule 620e2d can comprise a barcode (e.g., a cell label and a molecular label) on both the 5' end and 3' end of a target nucleic acid molecule (e.g., transcript), thereby enabling more extensive analysis of the target nucleic acid molecule as compared to an analysis of a target nucleic acid molecule with only one barcode on one end with regards to sequence identification, transcript counting, alternative splicing analysis, mutation screening, and/or full-length sequencing. Single-stranded extended barcoded nucleic acid molecule 620e1d and single-stranded extended barcoded nucleic acid molecule 620e2d can serve as a template for one or more extension reactions (e.g., random priming and extension) and/or amplification reactions (e.g., PCR) such as, for example, the non-limiting exemplary scheme depicted in FIGS. 6M-6O. The amplification(s) can comprise target-specific (e.g., gene-specific) cDNA amplification. For example, single-stranded extended barcoded nucleic acid molecule 620e2d can undergo a first round of amplification ("PCR1") 600e4 employing a universal oligonucleotide primer 646 comprising a sequence of the first universal sequence (or a complement thereof) and a target-specific primer (e.g., target-specific primer 650), thereby producing a first plurality of amplicons 620eas1 each comprising a molecular label (e.g., a second molecular label), a cell label, a first universal sequence and partial antisense cDNA 614cas1 (the length of which depends on the binding site of target-specific primer 650 within the cDNA 614cas). PCR1 600e4 can comprise 1-30 cycles (e.g., 15 cycles).

The workflow can comprise a random priming and extension 600e5. Random primers 670 can be hybridized the first plurality of barcoded amplicons and the random primers 670 can be extended to generate a plurality of extension products 620e2e1 and 620e2e2. Random primers 670 can include overhangs, which can include, or be, for example, a second universal sequence 638 (or a complement thereof, e.g., reverse complement 638rc) (e.g., Read 2 sequence, a universal PCR handle). Extension products 620e2l can comprise a first universal sequence, a second universal sequence, a cell label, and a molecule label (e.g., a first molecular label), or complements thereof. Extension products 620e2e1 can comprise, for example, partial cDNA 614c2a, 614c2b, 614c2c, and 614c2d (the length of each of which depends on the binding site of random primer 670 within the partial cDNA). Extension products 620e2e2 can comprise a second universal sequence (or a complement thereof). Extension products 620e2e2 can comprise, for example, partial antisense cDNA 614cas2e, 614cas2f, 614cas2g, and 614cas2h (the length of each of which depends on the binding site of random primer 670 within the partial cDNA).

The workflow can comprise library amplification ("Library PCR") 600e6. Library PCR 600e6 can comprise library amplification of extension products 620e2e1 with sequencing library amplification primers 656 and 658. Sequencing library amplification primers 656 can 658 can anneal to first universal sequence 626 and second universal sequence 638 (or complements thereof), respectively. Library PCR 600e6 can add sequencing adapters (e.g., P5 640 and P7 642) and sample index 644 (e.g., i5, i7) via overhangs in sequencing library amplification primers 656 and 658. Library PCR amplicons 620e2L (e.g., second plurality of barcoded amplicons) can comprise a range of cDNA lengths (e.g., partial antisense cDNA 614cas2a, 614cas2b, 614cas2c, 614cas2d) that can collectively encompass some or all of the mRNA sequence of the nucleic acid target. Library amplicons 620e2L can be sequenced and subjected to downstream methods of the disclosure. Sequencing 600e7 using 150 bp×2 sequencing can reveal the cell label, unique molecular label and/or gene (or a partial sequence of the gene) on read 1, the gene (or a partial sequence of the gene) on read 2, and the sample index on index 1 read and/or index 2 read. Library PCR 600e6 can comprise 1-30 cycles (e.g., 15 cycles). The method can comprise the bioinformatic reconstruction 900 of the full-length sequence of the nucleic acid target (e.g., immune receptor mRNA 930) by aligning the plurality of Read 1 910 and Read 2 920 reads as depicted in FIG. 9B.

In some embodiments, 3' and/or 5'-based full-length expression profiling of the V(D)J region of an immune receptor can be performed. In some embodiments, both phenotypic markers and immune receptor V(D)J sequence(s) of T cells and/or B cells in single cell platforms can be investigated. The method disclosed herein can allow V(D)J detection of both T cells and B cells (e.g., hypermutation). In some embodiments, both the 3' and 5' regions of extended barcoded nucleic acid molecule(s) 620e1d and/or 620e2d are amplified. In some embodiments, only the 5' region of extended barcoded nucleic acid molecule(s) 620e1d and/or 620e2d are amplified. In some embodiments, only the 3' region of extended barcoded nucleic acid molecule(s) 620e1d and/or 620e2d are amplified. In some embodiments one or more of the amplification reactions comprises multiplex PCR. For example, both the 3' and 5' regions of extended barcoded nucleic acid molecule(s) 620e1d and/or 620e2d can be amplified simultaneously (e.g., multiplex PCR). In some embodiments the workflow comprises multiplex PCR employing a panel of target-specific PCR1 primers. In some embodiments, the targets comprise BCRs, TCRs, and/or immune-related transcripts.

Immune Repertoire Profiling

There are provided, in some embodiments, methods for full-length expression profiling of the V(D)J region of immune receptors. In some embodiments, the sample comprises a single cell. In some embodiments, the sample comprises a plurality of cells, a plurality of single cells, a tissue, a tumor sample, or any combination thereof. A single cell can comprise an immune cell. In some embodiments, the immune cell is a B cell or a T cell. In some embodiments, a single cell can comprise a circulating tumor cell. In some embodiments, each oligonucleotide barcode can comprise a first universal sequence. In some embodiments, the plurality of extended barcoded nucleic acid molecules comprises a first universal sequence and a complement of the first universal sequence. Amplifying the plurality of extended barcoded nucleic acid molecules can comprise using a target-specific primer capable of hybridizing to a sequence of the nucleic acid target and a primer comprising the first universal sequence. In some such embodiments, the target-specific primer specifically hybridizes to an immune receptor. For example, the target-specific primer can specifically hybridize to a constant region of an immune receptor, a variable region of an immune receptor, a diversity region of an immune receptor, the junction of a variable region and diversity region of an immune receptor, or any combination thereof. The immune receptor can be a T cell receptor (TCR) and/or a B cell receptor (BCR) receptor. The TCR can comprise TCR alpha chain, TCR beta chain, TCR gamma chain, TCR delta chain, or any combination thereof. The BCR can comprise BCR heavy chain and/or BCR light chain.

The method can comprise obtaining sequence information of the second plurality of barcoded amplicons, or products thereof. In some embodiments, obtaining the sequence information comprises attaching sequencing adaptors to the second plurality of barcoded amplicons, or products thereof. Amplifying the plurality of extension products can comprise adding sequences of binding sites of sequencing primers and/or sequencing adaptors, complimentary sequences thereof, and/or portions thereof, to the plurality of extension products. The sequencing adaptors can comprise the P5 sequence, the P7 sequence, a complimentary sequence thereof, or a portion thereof. The sequencing primers can comprise a Read 1 sequencing primer, a Read 2 sequencing primer, a complimentary sequence thereof, or a portion thereof.

Obtaining the sequence information can comprise obtaining the sequence information of the BCR light chain and the BCR heavy chain of a single cell. The sequence information of the BCR light chain and the BCR heavy chain can comprise the sequence of the complementarity determining region 1 (CDR1), the CDR2, the CDR3, or any combination thereof, of the BCR light chain and/or the BCR heavy chain. The method can comprise pairing the BCR light chain and the BCR heavy chain of the single cell based on the obtained sequence information. The sample can comprise a plurality of single cells, and the method can comprise pairing the BCR light chain and the BCR heavy chain of at least 50% of the single cells based on the obtained sequence information. In some embodiments, the percentage of single cells of a sample wherein the BCR light chain and the BCR heavy chain are paired according the methods provided herein can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of single cells of a sample wherein the BCR light chain and the BCR heavy chain are paired according the methods provided herein can be at least, or at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

Obtaining the sequence information can comprise obtaining the sequence information of the TCR alpha chain and the TCR beta chain of a single cell. In some embodiments, the sequence information of the TCR alpha chain and the TCR beta chain can comprise the sequence of the complementarity determining region 1 (CDR1), the CDR2, the CDR3, or any combination thereof, of the TCR alpha chain and/or the TCR beta chain. In some embodiments, the method can comprise pairing the TCR alpha chain and the TCR beta chain of the single cell based on the obtained sequence information. In some embodiments, the sample can comprise a plurality of single cells, and the method can comprise pairing the TCR alpha chain and the TCR beta chain of at least 50% of the single cells based on the obtained sequence information. In some embodiments, the percentage of single cells of a sample wherein the TCR alpha chain and the TCR beta chain are paired according the methods provided herein can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of single cells of a sample wherein the TCR alpha chain and the TCR beta chain are paired according the methods provided herein can be at least, or at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

Obtaining the sequence information can comprise obtaining the sequence information of the TCR gamma chain and the TCR delta chain of a single cell. The sequence information of the TCR gamma chain and the TCR delta chain can comprise the sequence of the complementarity determining region 1 (CDR1), the CDR2, the CDR3, or any combination thereof, of the TCR gamma chain and/or the TCR delta chain. The method can comprise pairing the TCR gamma chain and the TCR delta chain of the single cell based on the obtained sequence information. The sample can comprise a plurality of single cells, and the method can comprise pairing the TCR gamma chain and the TCR delta chain of at least 50% of the single cells based on the obtained sequence information. In some embodiments, the percentage of single cells of a sample wherein the TCR delta chain and the TCR gamma chain are paired according the methods provided herein can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of single cells of a sample wherein the TCR delta chain and the TCR gamma chain are paired according the methods provided herein can be at least, or at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

Obtaining sequence information of the second plurality of barcoded amplicons, or products thereof, can comprise: obtaining sequencing data comprising a plurality of sequencing reads of the second plurality of barcoded amplicons, or products thereof, wherein each of the plurality of sequencing reads comprise (1) a cell label sequence, (2) a molecular label sequence, and/or (3) a subsequence of the nucleic acid target. In some embodiments, the method comprises: for each unique cell label sequence, which indicates a single cell of the sample: aligning each of the plurality of sequencing reads of the nucleic acid target to generate an aligned sequence of the nucleic acid target. As depicted in FIG. 9B, sequencing data can comprise a plurality of sequencing reads, such as, for example Read 1 910 and Read 2 920 reads. In some embodiments, as a result of the random priming step, Read 1 910 and/or Read 2 920 reads can collectively encompass the entire nucleic acid target (e.g., immune receptor transcript). The method can comprise the bioinformatic reconstruction 900 of the full-length sequence of the nucleic acid target (e.g., immune receptor mRNA 930) by aligning the plurality of Read 1 910 and Read 2 920. Advantageously, the compositions and methods provided herein can provide both identification and counting of nucleic acid targets (e.g., V(D)J-containing transcripts).

In some embodiments, the aligned sequence of the nucleic acid target comprises at least 50% of the cDNA sequence of the nucleic acid target, at least 70% of the cDNA sequence of the nucleic acid target, at least 90% of the cDNA sequence of the nucleic acid target, or the full length of the cDNA sequence of the nucleic acid target. In some embodiments, the aligned sequence of the nucleic acid target can be, or be about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values, of the cDNA sequence of the nucleic acid target. In some embodiments, the aligned sequence of the nucleic acid target can be at least, or at most, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the cDNA sequence of the nucleic acid target. The nucleic acid target can be an immune receptor.

In some embodiments, the aligned sequence of the nucleic acid target comprises the complementarity determining region 1 (CDR1), the complementarity determining region 2 (CDR2), the complementarity determining region 3 (CDR3), the variable region, the full length of the variable region, or a combination thereof. The aligned sequence of the nucleic acid target can comprise the variable region, the diversity region, the junction of a variable region diversity region and/or the constant region, or any combination thereof. In some embodiments, the method does not comprise fragmentation, tagmentation, or both.

Kits for Obtaining Full-Length Information of Nucleic Acid Targets

Disclosed herein include kits. In some embodiments, the kit comprises: a plurality of oligonucleotide barcodes, wherein each of the plurality of oligonucleotide barcodes comprises a molecular label and a target-binding region, and wherein at least 10 of the plurality of oligonucleotide barcodes comprise different molecular label sequences; a reverse transcriptase; a template switching oligonucleotide comprising the target-binding region, or a portion thereof; and a DNA polymerase lacking at least one of 5' to 3' exonuclease activity and 3' to 5' exonuclease activity. Disclosed herein include kits. In some embodiments, the kit comprises: a plurality of oligonucleotide barcodes, wherein each of the plurality of oligonucleotide barcodes comprises a molecular label and a target-binding region, and wherein at least 10 of the plurality of oligonucleotide barcodes comprise different molecular label sequences; a terminal deoxynucleotidyl transferase; and a DNA polymerase lacking at least one of 5' to 3' exonuclease activity and 3' to 5' exonuclease activity.

The kit can comprise random primers. The random primers can comprise a random sequence of nucleotides. The random sequence of nucleotides can be about 4 to about 30 nucleotides in length. In some embodiments, the DNA polymerase comprises a Klenow Fragment. In some embodiments, the reverse transcriptase comprises a viral reverse transcriptase. In some embodiments, the viral reverse transcriptase is a murine leukemia virus (MLV) reverse transcriptase. In some embodiments, the viral reverse transcriptase is a Moloney murine leukemia virus (MMLV) reverse transcriptase. In some embodiments, the template switch oligonucleotide comprises one or more 3' ribonucleotides, for example three 3' ribonucleotides. In some embodiments, the 3' ribonucleotides comprise guanine. In some embodiments, the kit comprises one or more of ethylene glycol, polyethylene glycol, 1,2-propanediol, dimethyl sulfoxide (DMSO), glycerol, formamide, 7-deaza-GTP, acetamide, tetramethylammonium chloride salt, betaine, or any combination thereof In some embodiments, the kit comprises a buffer. In some embodiments, the kit comprises a cartridge. In some embodiments, the kit comprises one or more reagents for a reverse transcription reaction. In some embodiments, the kit comprises one or more reagents for an amplification reaction. In some embodiments, the target-binding region comprises a gene-specific sequence, an oligo(dT) sequence, a random multimer, or any combination thereof. In some embodiments, the oligonucleotide barcode comprises an identical sample label and/or an identical cell label In some embodiments, each sample label and/or cell label of the plurality of oligonucleotide barcodes comprise at least 6 nucleotides. In some embodiments, each molecular label of the plurality of oligonucleotide barcodes comprises at least 6 nucleotides. In some embodiments, at least one of the plurality of oligonucleotide barcodes is immobilized on the synthetic particle. In some embodiments, at least one of the plurality of oligonucleotide barcodes is partially immobilized on the synthetic particle. In some embodiments, at least one of the plurality of oligonucleotide barcodes is enclosed in the synthetic particle. In some embodiments, at least one of the plurality of oligonucleotide barcodes is partially enclosed in the synthetic particle. In some embodiments, the synthetic particle is disruptable. In some embodiments, the synthetic particle comprises a bead, for example a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. In some embodiments, the synthetic particle comprises a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. In some embodiments, the synthetic particle comprises a disruptable hydrogel particle. In some embodiments, each of the plurality of oligonucleotide barcodes comprises a linker functional group, the synthetic particle comprises a solid support functional group, and/or the support functional group and the linker functional group are associated with each other. In some embodiments, the linker functional group and the support functional group are individually selected from the group consisting of C6, biotin, streptavidin, primary amine(s), aldehyde(s), ketone(s), and any combination thereof.

EXAMPLES

Some aspects of the embodiments described herein are disclosed in further detail in the following examples, which are not in any way intended to limit the scope of the present disclosure.

Example 1

Random Priming-Based Determination of Full-Length V(D)J Sequences

Figure 10A:
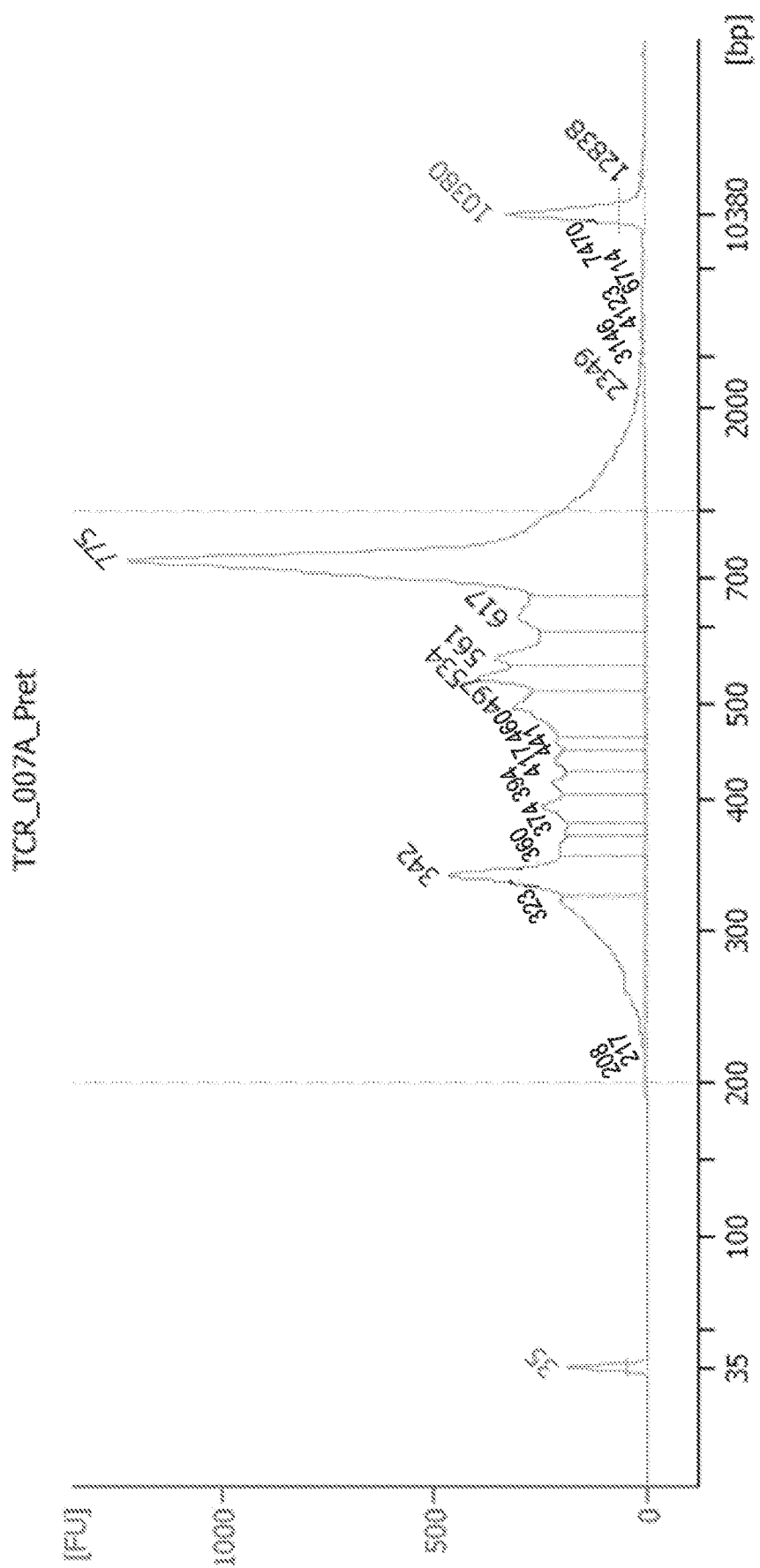
FIGS. 10A-10D depict data related to the random priming-based methods provided herein. Bioanalyzer traces of TCR products (FIGS. 10A-10B) and BCR products (FIGS. 10C-10D) obtained with a random-priming based approach provided herein (FIGS. 10A and 10C) as compared to a currently available method (FIGS. 10B and 10D) are shown.
Figure 10B:
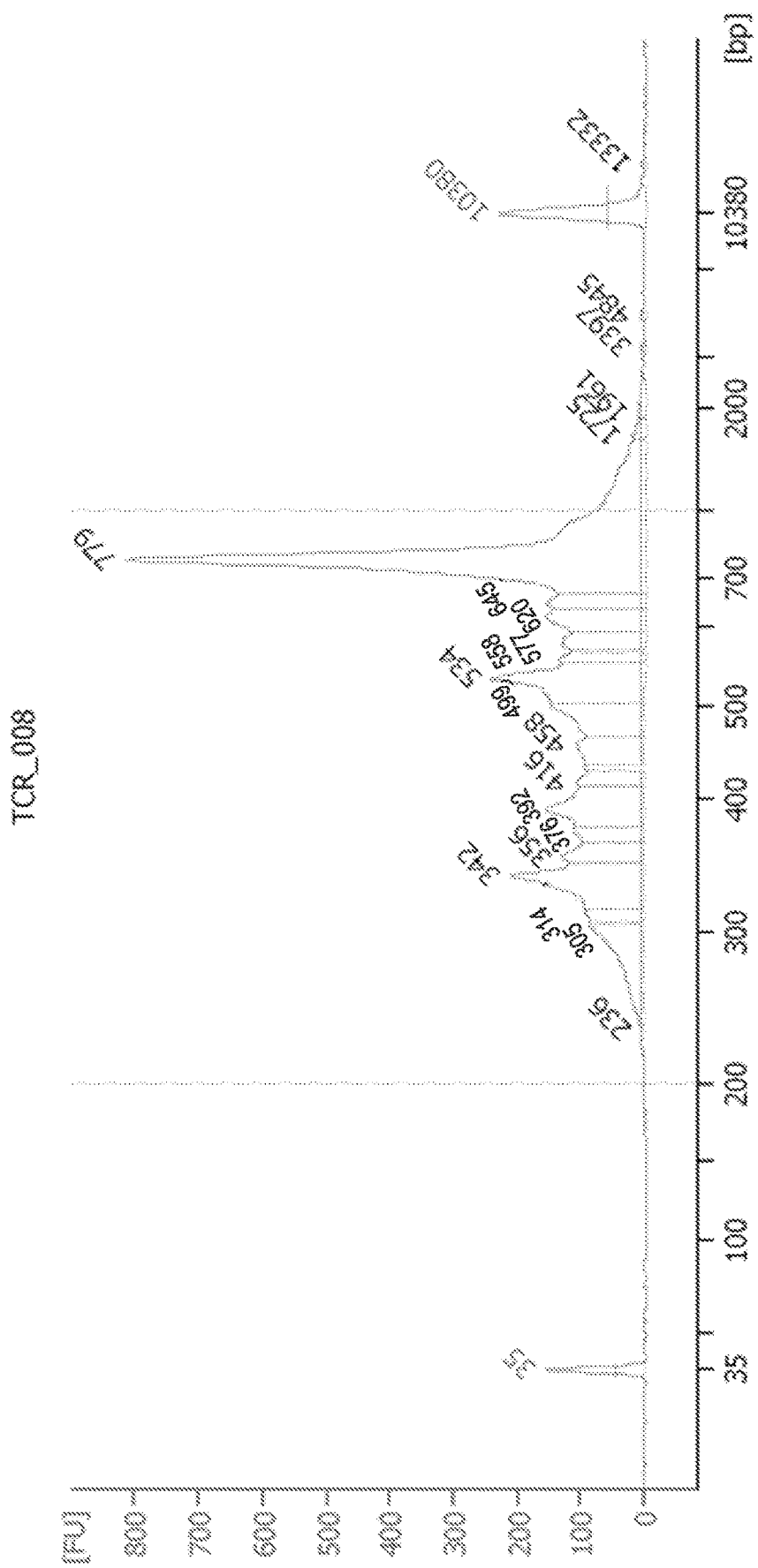
Figure 10C:
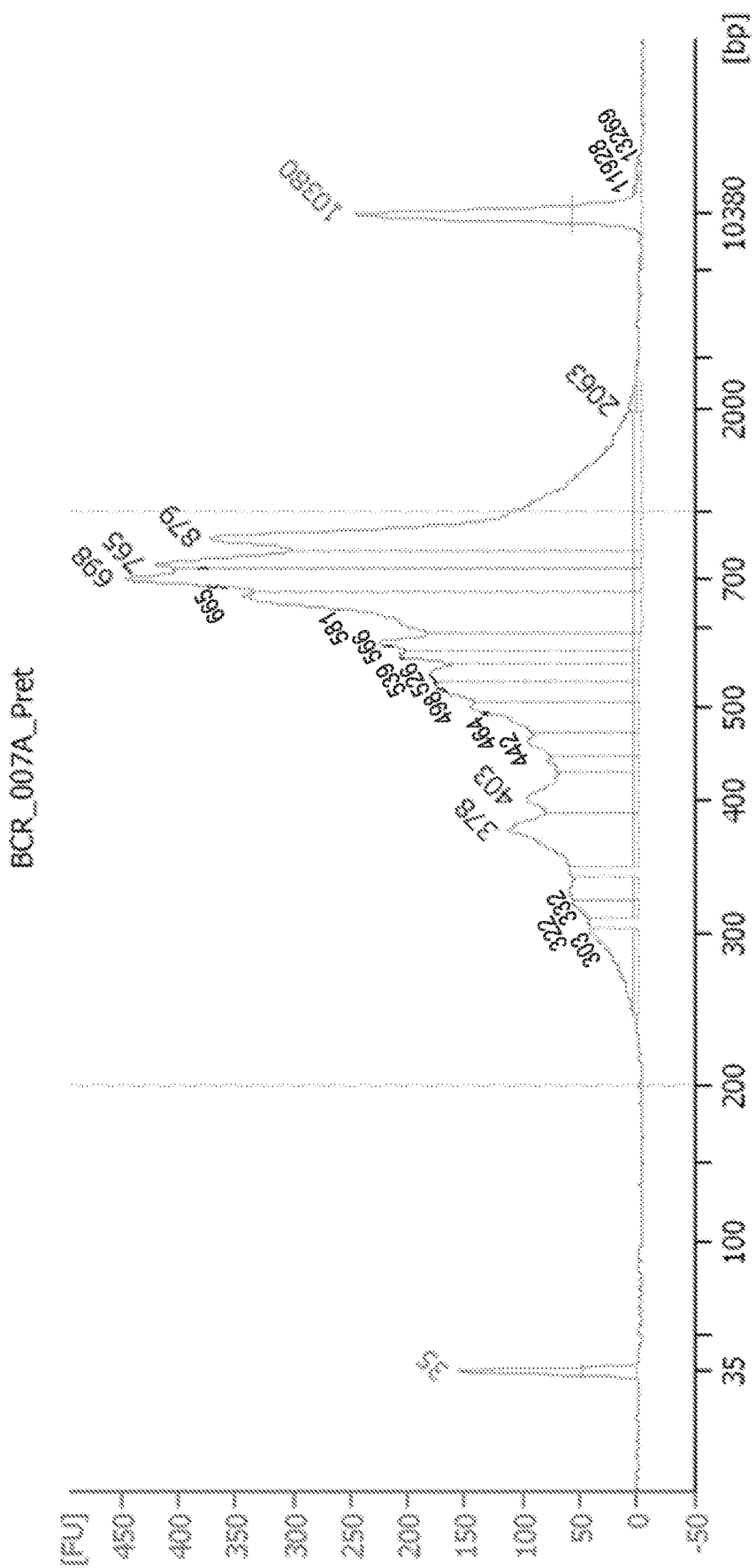
Figure 10D:
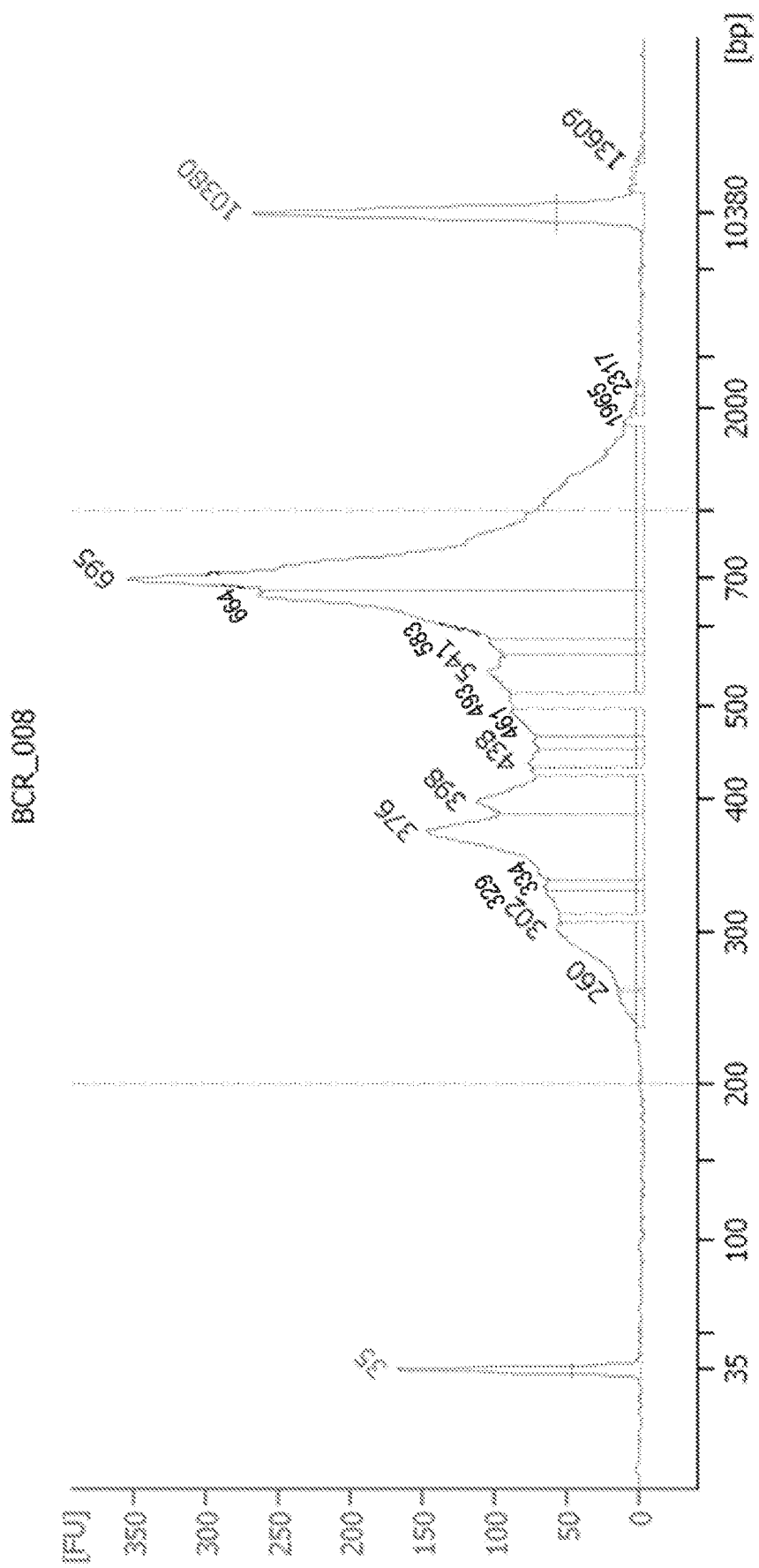
Figures 11A, 11B:
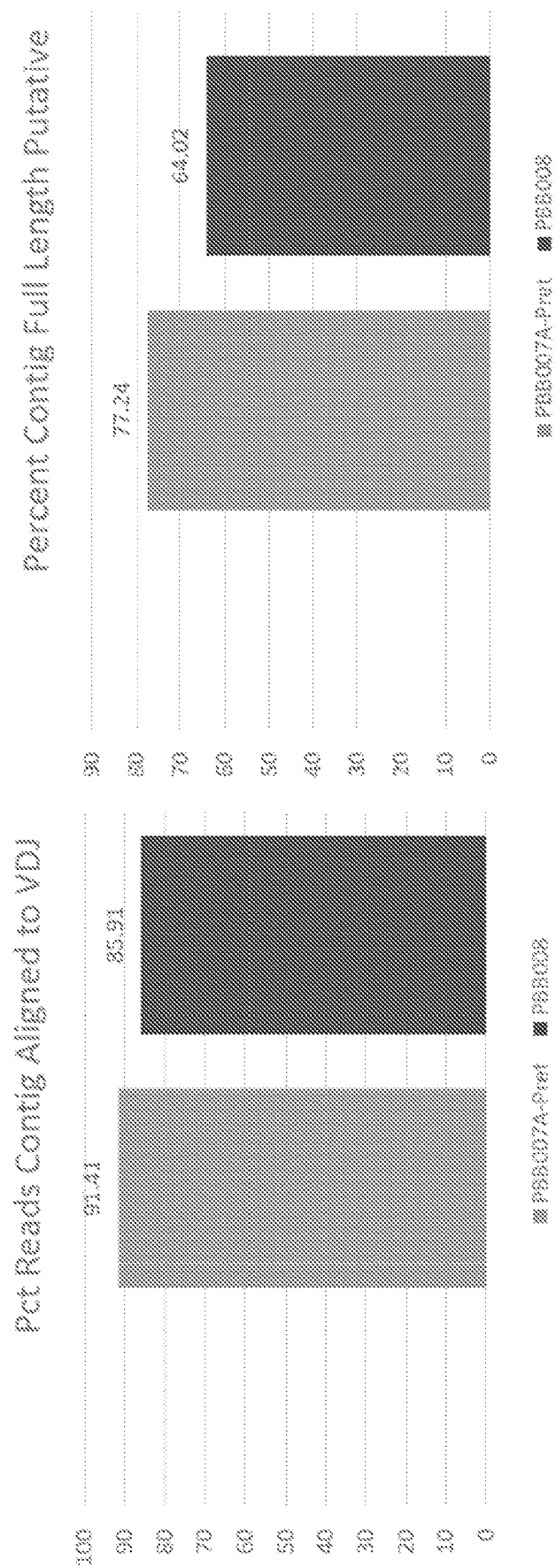
FIGS. 11A-11B depict data related to the random priming-based methods provided herein. The percentage of VDJ sequences that are full-length (FIG. 11B) and come from cells (FIG. 11A) is shown for a random-priming based approach provided herein (-Pret) as compared to a currently available method.

This example demonstrates the random priming-based methods for full-length expression profiling of nucleic acid targets (e.g., V(D)J-containing transcripts) provided herein. As seen in the bioanalyzer traces of TCR products (FIGS. 10A-10B) and BCR products (FIGS. 10C-10D), smaller fragments are obtained with a random-priming based approach provided herein (FIGS. 10A and 10C) as compared to a currently available method (FIGS. 10B and 10D). Next, sequencing was performed to determine the percentage of VDJ sequences that are full-length (FIG. 11B) and come from cells (FIG. 11A). Of the reads that aligned to VDJ, were successfully assembled into a contig, and that contig is a valid VDJ sequence (has CDR3), the percentage shown in FIG. 11A relates to the number of those reads that come from putative cells. In putative cells, for the contigs that were identified as dominant, the percentage of them that are full-length is shown in FIG. 11B. Full-length was determined by whether that contig has sequence identified for all major parts of the chain: FR1, CDR1, FR2, CDR2, FR3, CDR3, FR4. Furthermore, as shown in FIGS. 12A-12D, full-length paired chains are found in the correct cell types (BCR in B cells, TCR in T cells), with BCR pairing (FIGS. 12A-12B) and TCR pairing (FIGS. 12C-12D) obtained with a random-priming based approach provided herein (FIGS. 12A and 12C) superior to a currently available method (FIGS. 12B and 12D). These results provide proof-of-principle for the random-priming based methods and compositions provided herein.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory

What is claimed is:

1. A method for labeling nucleic acid targets in a sample, comprising:
    contacting copies of a nucleic acid target with a plurality of oligonucleotide barcodes, wherein each oligonucleotide barcode comprises a first universal sequence, a molecular label, and a target-binding region capable of hybridizing to the nucleic acid target;
    generating a plurality of barcoded nucleic acid molecules each comprising the target-binding region and a complement of the target-binding region;
    hybridizing the complement of the target-binding region of each barcoded nucleic acid molecule with the target-binding region of one or more of:
        (i) an oligonucleotide barcode of the plurality of oligonucleotide barcodes,
        (ii) the barcoded nucleic acid molecule itself, and
        (iii) a different barcoded nucleic acid molecule of the plurality of barcoded nucleic acid molecules;
    extending 3'-ends of the plurality of barcoded nucleic acid molecules to generate a plurality of extended barcoded nucleic acid molecules each comprising the first molecular label and a second molecular label;
    amplifying the plurality of extended barcoded nucleic acid molecules using a target-specific primer capable of hybridizing to a sequence of the nucleic acid target and a primer comprising the first universal sequence, thereby generating a first plurality of barcoded amplicons comprising the sequence of the nucleic acid target, or a portion thereof;
    hybridizing random primers to the first plurality of barcoded amplicons and extending the random primers to generate a plurality of extension products, wherein the random primers comprise a second universal sequence, or a complement thereof; and
    amplifying the plurality of extension products using primers capable of hybridizing to the first universal sequence and the second universal sequence, or complements thereof, thereby generating a second plurality of barcoded amplicons.

2. The method of claim 1, comprising: determining the copy number of the nucleic acid target in the sample based on the number of first molecular labels with distinct sequences, second molecular labels with distinct sequences, or a combination thereof, associated with the second plurality of barcoded amplicons, or products thereof.

3. The method of claim 2, wherein determining the copy number of the nucleic acid target in the sample comprises:
    (a) determining the copy number of the nucleic acid target in the sample based on the number of second molecular labels with distinct sequences associated with the second plurality of barcoded amplicons, or products thereof, and/or
    (b) determining the copy number of the nucleic acid target in the sample based on the number of first molecular labels with distinct sequences associated with the second plurality of barcoded amplicons, or products thereof.

4. The method of claim 1, the method comprising denaturing the plurality of barcoded nucleic acid molecules prior to hybridizing the complement of the target-binding region of each barcoded nucleic acid molecule with the target-binding region of: (i) an oligonucleotide barcode of the plurality of oligonucleotide barcodes, (ii) the barcoded nucleic acid molecule itself, and/or (iii) a different barcoded nucleic acid molecule of the plurality of barcoded nucleic acid molecules.

5. The method of claim 1, wherein the extended barcoded nucleic acid molecules each comprise the first molecular label, the second molecular label, the target-binding region, and the complement of the target-binding region.

6. The method of claim 1, wherein generating a plurality of barcoded nucleic acid molecules each comprising the target-binding region and a complement of the target-binding region comprises:
extending the plurality of oligonucleotide barcodes hybridized to the copies of the nucleic acid target in the presence of a reverse transcriptase and a template switch oligonucleotide comprising the target-binding region, or a portion thereof, to generate a plurality of barcoded nucleic acid molecules each comprising a sequence complementary to at least a portion of the nucleic acid target, a first molecular label, the target-binding region, and a complement of the target-binding region.

7. The method of claim 6, wherein the template switch oligonucleotide comprises one or more 3' ribonucleotides, wherein the 3' ribonucleotides comprise guanine.

8. The method of claim 1, wherein hybridizing the complement of the target-binding region of a barcoded nucleic acid molecule with the target-binding region of the barcoded nucleic acid molecule itself comprises intramolecular hybridization of the target-binding region and the complement of the target-binding region within a barcoded nucleic acid molecule to form a stem loop, wherein the second molecular label is the complement of the first molecular label.

9. The method of claim 1, wherein hybridizing the complement of the target-binding region of a barcoded nucleic acid molecule with the target-binding region of an oligonucleotide barcode of the plurality of oligonucleotide barcodes comprises intermolecular hybridization of the complement of the target-binding region of a barcoded nucleic acid molecule with the target-binding region of an oligonucleotide barcode of the plurality of oligonucleotide barcodes.

10. The method of claim 9, wherein the second molecular label is a different from the first molecular label, and wherein the second molecular label is not a complement of the first molecular label.

11. The method of claim 9, comprising extending the 3' ends of the oligonucleotide barcodes hybridized to the complement of the target-binding region of the barcoded nucleic acid molecule to generate a plurality of extended barcoded nucleic acid molecules each comprising a complement of the first molecular label and a second molecular label.

12. The method of claim 11, wherein the sequence of the second molecular label is different from the sequence of the first molecular label, wherein the wherein the second molecular label is not a complement of the first molecular label.

13. The method of claim 1, wherein hybridizing the complement of the target-binding region of a barcoded nucleic acid molecule with the target-binding region of a different barcoded nucleic acid molecule of the plurality of barcoded nucleic acid molecules comprises intermolecular hybridization of the complement of the target-binding region of a barcoded nucleic acid molecule with the target-binding region of a different barcoded nucleic acid molecule of the plurality of barcoded nucleic acid molecules, wherein the sequence of the second molecular label is different from the sequence of the first molecular label, and wherein the second molecular label is not a complement of the first molecular label.

14. The method of claim 1, wherein the target-specific primer specifically hybridizes to a constant region of an immune receptor, a variable region of an immune receptor, a diversity region of an immune receptor, the junction of a variable region and diversity region of an immune receptor, or a combination thereof, wherein the immune receptor is a T cell receptor (TCR) and/or a B cell receptor (BCR) receptor, wherein the TCR comprises TCR alpha chain, TCR beta chain, TCR gamma chain, TCR delta chain, or any combination thereof, and wherein the BCR receptor comprises BCR heavy chain and/or BCR light chain.

15. The method of claim 1, comprising obtaining sequence information of the second plurality of barcoded amplicons, or products thereof, wherein obtaining sequence information of the second plurality of barcoded amplicons, or products thereof, comprises:
obtaining sequencing data comprising a plurality of sequencing reads of the second plurality of barcoded amplicons, or products thereof,
wherein each of the plurality of sequencing reads comprise (1) a cell label sequence, (2) a molecular label sequence, and/or (3) a subsequence of the nucleic acid target.

16. The method of claim 15, comprising:
for each unique cell label sequence, which indicates a single cell of the sample:
aligning each of the plurality of sequencing reads of the nucleic acid target to generate an aligned sequence of the nucleic acid target.

17. The method of claim 16, wherein the aligned sequence of the nucleic acid target comprises at least 50% of the cDNA sequence of the nucleic acid target, at least 70% of the cDNA sequence of the nucleic acid target, at least 90% of the cDNA sequence of the nucleic acid target, or the full length of the cDNA sequence of the nucleic acid target.

18. The method of claim 1, wherein the nucleic acid target is an immune receptor, and wherein the immune receptor comprises BCR light chain, BCR heavy chain, TCR alpha chain, TCR beta chain, TCR gamma chain, TCR delta chain, or any combination thereof.

19. The method of claim 16, wherein the aligned sequence of the nucleic acid target comprises the complementarity determining region 1 (CDR1), the complementarity determining region 2 (CDR2), the complementarity determining region 3 (CDR3), the variable region, the full length of the variable region, or a combination thereof.

20. The method of claim 16, wherein the aligned sequence of the nucleic acid target comprises the variable region, the diversity region, the junction of a variable region diversity region and/or the constant region, or any combination thereof.

21. The method of claim 16, wherein obtaining the sequence information comprises obtaining the sequence information of the BCR light chain and the BCR heavy chain of a single cell, and wherein the sequence information of the BCR light chain and the BCR heavy chain comprises the sequence of the complementarity determining region 1 (CDR1), the CDR2, the CDR3, or any combination thereof, of the BCR light chain and/or the BCR heavy chain.

22. The method of claim 21, the method comprising pairing the BCR light chain and the BCR heavy chain of the single cell based on the obtained sequence information.

23. The method of claim 22, wherein the sample comprises a plurality of single cells, the method comprising pairing the BCR light chain and the BCR heavy chain of at least 50% of said single cells based on the obtained sequence information.

24. The method of claim 16, wherein obtaining the sequence information comprises obtaining the sequence information of the TCR alpha chain and the TCR beta chain of a single cell, and wherein the sequence information of the TCR alpha chain and the TCR beta chain comprises the sequence of the complementarity determining region 1 (CDR1), the CDR2, the CDR3, or any combination thereof, of the TCR alpha chain and/or the TCR beta chain.

25. The method of claim 24, the method comprising pairing the TCR alpha chain and the TCR beta chain of the single cell based on the obtained sequence information.

26. The method of claim 25, wherein the sample comprises a plurality of single cells, the method comprising pairing the TCR alpha chain and the TCR beta chain of at least 50% of said single cells based on the obtained sequence information.

27. The method of claim 16, wherein obtaining the sequence information comprises obtaining the sequence information of the TCR gamma chain and the TCR delta chain of a single cell, wherein the sequence information of the TCR gamma chain and the TCR delta chain comprises the sequence of the complementarity determining region 1 (CDR1), the CDR2, the CDR3, or any combination thereof, of the TCR gamma chain and/or the TCR delta chain.

28. The method of claim 27, the method comprising pairing the TCR gamma chain and the TCR delta chain of the single cell based on the obtained sequence information.

29. The method of claim 28, wherein the sample comprises a plurality of single cells, the method comprising pairing the TCR gamma chain and the TCR delta chain of at least 50% of said single cells based on the obtained sequence information.

* * * * *